US012545926B2

(12) United States Patent
Zhou et al.

(10) Patent No.: US 12,545,926 B2
(45) Date of Patent: Feb. 10, 2026

(54) NUCLEIC ACID MOLECULES FOR CONFERRING INSECTICIDAL PROPERTIES IN PLANTS

(71) Applicant: SYNGENTA CROP PROTECTION AG, Basel (CH)

(72) Inventors: Ailing Zhou, Research Triangle Park, NC (US); Kasimalai Azhakanandam, Research Triangle Park, NC (US); Jared Conville, Research Triangle Park, NC (US); Yan Zhang, Research Triangle Park, NC (US)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 18/289,473

(22) PCT Filed: May 3, 2022

(86) PCT No.: PCT/US2022/027372

§ 371 (c)(1),
(2) Date: Nov. 3, 2023

(87) PCT Pub. No.: WO2022/235606

PCT Pub. Date: Nov. 10, 2022

(65) Prior Publication Data

US 2024/0240199 A1 Jul. 18, 2024

Related U.S. Application Data

(60) Provisional application No. 63/183,672, filed on May 4, 2021.

(51) Int. Cl.
*C07K 14/325* (2006.01)
*C12N 15/82* (2006.01)
*C12Q 1/6895* (2018.01)

(52) U.S. Cl.
CPC ........ *C12N 15/8286* (2013.01); *C07K 14/325* (2013.01); *C12Q 1/6895* (2013.01); *C12Q 2600/13* (2013.01)

(58) Field of Classification Search
CPC C12N 15/8286; C07K 14/325; C12Q 1/6895; C12Q 2600/13
See application file for complete search history.

(56) References Cited

U.S. PATENT DOCUMENTS 12,203,091 B2 * 1/2025 Chae .................... C07K 14/325

FOREIGN PATENT DOCUMENTS

WO 2018111553 6/2018
WO WO-2018111553 A1 * 6/2018 ............. A01N 37/46
WO 2020176412 9/2020

OTHER PUBLICATIONS

Li et al (2024) Bt Research. 15(1):42-52. (Year: 2024).*
(Continued)

*Primary Examiner* — Anne Kubelik
*Assistant Examiner* — Victoria L Deleo
(74) *Attorney, Agent, or Firm* — Destiny Davenport

(57) ABSTRACT

The present disclosure is related to a nucleic acid sequence which confers expression of insecticidal proteins when introduced into a cell, as well as related compositions and methods of use thereof. In some aspects, the disclosure provides a plant comprising the nucleic acid sequence.

30 Claims, 1 Drawing Sheet

Specification includes a Sequence Listing.

(56) References Cited

OTHER PUBLICATIONS

Srivastava et al (2017) Plant Cell, Tissue and Organ Culture. 129:153-160. (Year: 2017).*

International Search Report mailed on Sep. 28, 2022 cited in International Application No. PCT/US2022/027372 filed May 3, 2022.

* cited by examiner

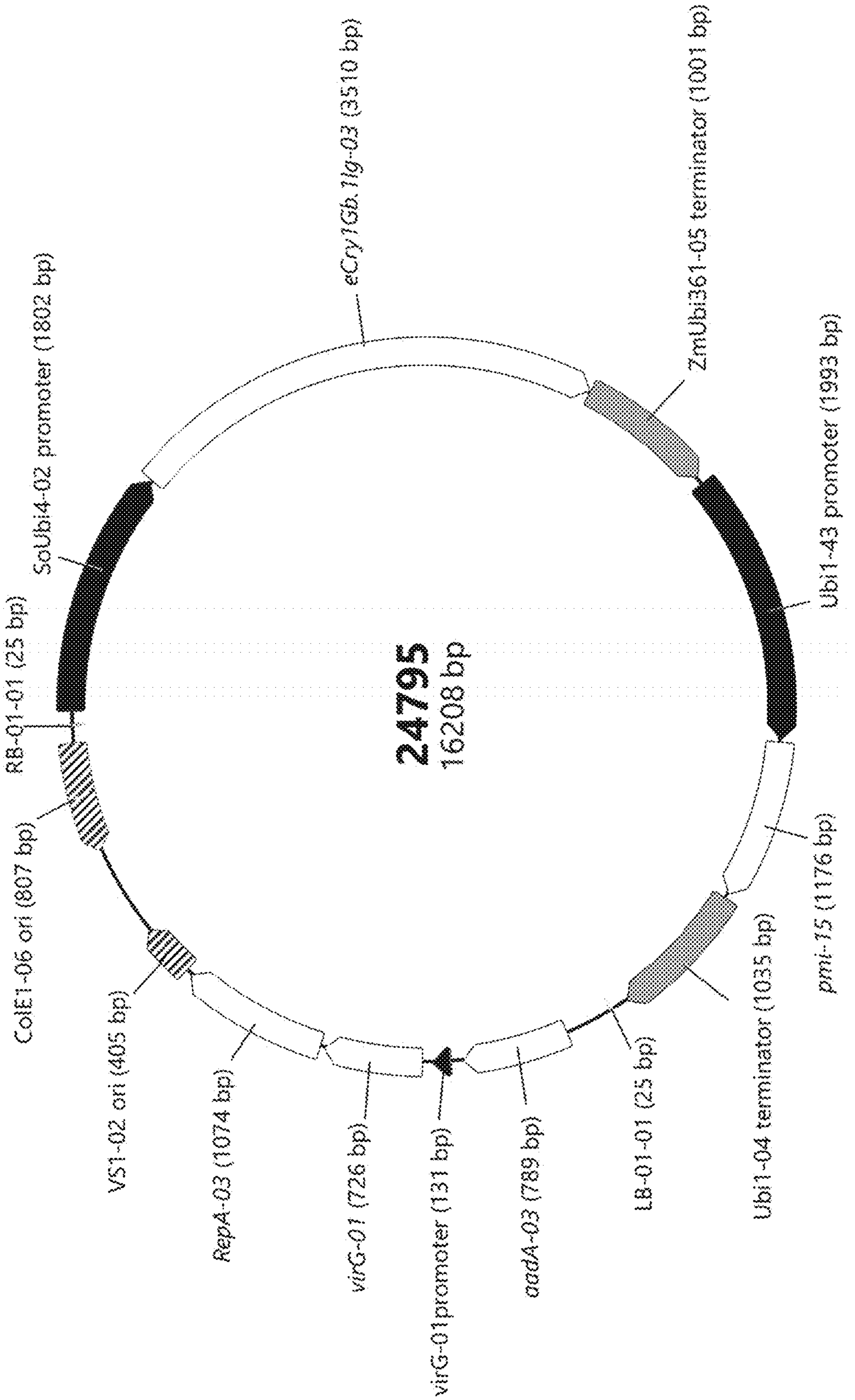
24795
16208 bp
SoUbi4-02 promoter (1802 bp)
eCry1Gb.1Ig-03 (3510 bp)
ZmUbi361-05 terminator (1001 bp)
Ubi1-43 promoter (1993 bp)
pmi-15 (1176 bp)
Ubi1-04 terminator (1035 bp)
LB-01-01 (25 bp)
aadA-03 (789 bp)
virG-01promoter (131 bp)
virG-01 (726 bp)
RepA-03 (1074 bp)
VS1-02 ori (405 bp)
ColE1-06 ori (807 bp)
RB-01-01 (25 bp)

SEQUENCE LISTING

<160> NUMBER OF SEQ ID NOS: 75

<210> SEQ ID NO 1
<211> LENGTH: 10641
<212> TYPE: DNA
<213> ORGANISM: Artificial sequence
<220> FEATURE:
<223> OTHER INFORMATION: Synthetic polynucleotide

<400> SEQUENCE: 1
gaattcatta tgtggtctag gtaggttcta tatataagaa aacttgaaat gttctaaaaa 60
aaaattcaag cccatgcatg attgaagcaa acggtatagc aacggtgtta acctgatcta 120
gtgatctctt gcaatcctta acggccacct accgcaggta gcaaacggcg tccccctcct 180
cgatatctcc gcggcgacct ctggcttttt ccgcggaatt gcgcggtggg gacggattcc 240
acgagaccgc gacgcaaccg cctctcgccg ctgggcccca caccgctcgg tgccgtagcc 300
tcacgggact ctttctccct cctcccccgt tataaattgg cttcatcccc tccttgcctc 360
atccatccaa atcccagtcc ccaatcccat cccttcgtag gagaaattca tcgaagctaa 420
gcgaatcctc gcgatcctct caaggtactg cgagttttcg atccccctct cgacccctcg 480
tatgtttgtg tttgtcgtag cgtttgatta ggtatgcttt ccctgtttgt gttcgtcgta 540
gcgtttgatt aggtatgctt tccctgttcg tgttcatcgt agtgtttgat taggtcgtgt 600
gaggcgatgg cctgctcgcg tccttcgatc tgtagtcgat ttgcgggtcg tggtgtagat 660
ctgcgggctg tgatgaagtt atttggtgtg atctgctcgc ctgattctgc gggttggctc 720
gagtagatat gatggttgga ccggttggtt cgtttaccgc gctagggttg ggctgggatg 780
atgttgcatg cgccgttgcg cgtgatcccg cagcaggact tgcgtttgat tgccagatct 840
cgttacgatt atgtgatttg gtttggactt tttagatctg tagcttctgc ttatgtgcca 900
gatgcgccta ctgctcatat gcctgatgat aatcataaat ggctgtggaa ctaactagtt 960
gattgcggag tcatgtatca gctacaggtg tagggactag ctacaggtgt agggacttgc 1020
gtctaattgt ttggtccttt actcatgttg caattatgca atttagttta gattgtttgt 1080
tccactcatc taggctgtaa aagggacact gcttagattg ctgtttaatc tttttagtag 1140
attatattat attggtaact tattacccct attacatgcc atacgtgact tctgctcatg 1200
cctgatgata atcatagatc actgtggaat taattagttg attgttgaat catgtttcat 1260
gtacatacca cggcacaatt gcttagttcc ttaacaaatg caaattttac tgatccatgt 1320
atgatttgcg tggttctcta atgtgaaata ctatagctac ttgttagtaa gaatcaggtt 1380
cgtatgctta atgctgtatg tgccttctgc tcatgcctga tgataatcat atatcactgg 1440
aattaattag ttgatcgttt aatcatatat caagtacata ccatgccaca atttttagtc 1500
acttaaccca tgcagattga actggtccct gcatgttttg ctaaattgtt ctattctgat 1560
tagaccatat atcatgtatt ttttttggt aatggttctc ttattttaaa tgctatatag 1620
ttctggtact tgttagaaag atctgcttca tagtttagtt gcctatccct cgaattagga 1680
tgctgagcag ctgatcctat agctttgttt catgtatcaa ttcttttgtg ttcaacagtc 1740
agtttttgtt agattcattg taacttatgg tcgcttactc ttctggtcct caatgcttgc 1800
agggatccta aaccatggag atcaacaacc agaaccagtg cgtgccgtac aactgcctta 1860
acaaccccga gtccgagatc ctgaacgtgg ccatcttctc cagcgagcag gtcgcggaga 1920
tccacctcaa gatcacgcgc ctgatcctcg agaacttcct gccgggcggc tccttcgctt 1980
tcggcctgtt cgacctcatc tggggcatct tcaacgagga ccagtggagc gcgttcctca 2040

```
ggcaggtgga ggagctgatc aaccagcgca tcacggagtt cgccaggggc caggctatcc   2100
agcggctggt gggcttcggc aggtcctacg acgagtacat cctggccctc aaggagtggg   2160
agaacgaccc cgacaacccg gccagcaagg agcgcgtgag gacccgcttc aggaccaccg   2220
acgacgctct cctgacgggc gtccccctca tggctatccc gggcttcgag ctggccaccc   2280
tctcggtgta cgctcagtcg gccaacctgc acctcgccct cctgcgggac gctgtgttct   2340
tcggcgagag gtggggcctg acccagacga acatcaacga cctctactcc aggctgaaga   2400
acagcatccg cgactacacg aaccactgcg tgcgcttcta caacatcggc ctgggcaacc   2460
tcaacgtcat caggccggag tactaccgct tccagaggga gctgaccatc agcgtgctgg   2520
acctcgtcgc cctgttcccc aactacgaca tccgcacgta cccgatccca accaagtccc   2580
agctcacgag ggagatctac accgacccga tcatctcgcc gggcgcccag gccggctaca   2640
ccctgcagga cgtcctgagg gagccccacc tgatggactt cctgaacagg ctcatcatct   2700
acaccggcga gtacaggggc atcaggcact gggcgggcca cgaggtggag tccagcagga   2760
cgggcatgat gaccaacatc cgcttcccgc tctacggcac cgcggccacg gccgagccaa   2820
cccgcttcat cacgccgtcc accttccccg gcctgaacct cttctacagg accctgtcgg   2880
ctcccatctt ccgcgacgag ccgggcgcga acatcatcat ccgctacagg acctccctcg   2940
tggagggcgt cggcttcatc cagccgaaca acggcgagca gctgtaccgc gtgaggggca   3000
cgctggacag cctggaccag ctcccactgg agggcgagtc cagcctcacc gagtactcgc   3060
acaggctgtg ccacgtcagg ttcgcccaga gcctcaggaa cgcggagccc ctggactacg   3120
ccagggtgcc catgttcagc tggacccaca ggtcggctac ccccaccaac accatcgacc   3180
cagacgtgat cacgcagatc ccgctcgtca aggcccacac cctgcagtcg ggcaccaccg   3240
tggtcaaggg ccccggcttc acgggcggcg acatcctgag gaggacctcc ggcggcccat   3300
tcgccttcag caacgtcaac ctcgactgga acctgtccca gcgctacagg gcgcgcatca   3360
ggtacgccag caccacgaac ctgcgcatgt atgtgaccat cgcgggcgag aggatcttcg   3420
ccggccagtt caacaagacg atgaacaccg gcgacccgct caccttccag tccttcagct   3480
acgcgacgat cgacaccgcc ttcacgttcc ccacgaaggc ctccagcctg accgtgggcg   3540
ccgacacctt ctccagcggc aacgaggtct acgtggaccg cttcgagctg atcccggtga   3600
cggcgacctt cgaggccgag tacgacctgg agaaggccca gaaggcggtc aacgccctct   3660
tcacctccag caaccagatc ggcctgaaga cggacgtgac cgactaccac atcgacaagg   3720
tgtccaacct cgtcgagtgc ctgagcgacg agttctgcct cgacgagaag agggagctgt   3780
ccgagaaggt caagcacgcc aagcgcctct gcgacgagag gaacctcctg caggacccga   3840
acttcagggg aatcaaccgc cagccggaca ggggctggag gggcagcacc gacatcacca   3900
tccagggcgg cgacgacgtg ttcaaggaga actacgtcac gctcccgggc accttcgacg   3960
agtgctaccc cacgtacctg taccagaaga tcgacgagtc caagctcaag gcctacaccc   4020
gctacgagct gaggggatac atcgaggaca gccaggacct cgagatctac ctgatccgct   4080
acaacgcgaa gcacgagacg gtgaacgtcc ccggcacggg ctccctgtgg cccctctcgg   4140
ctcagtcgcc gatcggcaag tgcggcgagc ccaacaggtg cgccacccac ctcgagtgga   4200
acccggacct ggactgctcc tgccgggacg gcgagaagtg cgctcaccac tcccaccact   4260
tcagcctgga catcgacgtg ggctgcacgg acctcaacga ggacctgggc gtgtgggtca   4320
tcttcaaaat caagacgcag gacggccacg ctaggctggg caacctcgag ttcctggagg   4380
```

```
agaagccgct ggtgggcgag gctctggcca gggtcaagag ggcggagaag aagtggcgcg   4440
acaagaggga gaagctggag ctggagacga acatcgtcta caaggaggcc aagaagtccg   4500
tggacgcgct cttcgtcaac agccagtacg acaggctgca ggcggacacc aacatcgcca   4560
tcatccacgc cgcggacaag cgcgtgcact ccatcaggga ggcctacctc cccgagctga   4620
gcgtgatccc gggcgtcaac gctgccatct tcgaggagct ggagggccgc atcttcaccg   4680
cctactccct gtacgacgcg aggaacgtca tcaagaacgg cgacttcaac aacggcctca   4740
gctgctggaa cgtgaagggc cacgtggacg tcgaggagca gaacaaccac cgctcggtgc   4800
tggtggtccc cgagtgggag gctgaggtca gccaggaggt gcgcgtctgc ccgggcaggg   4860
gatacatcct ccgcgtgacc gcgtacaagg agggctacgg cgagggctgc gtcacgatcc   4920
acgagatcga ggacaacacc gacgagctga agttctccaa ctgcgtggag gaggagatct   4980
acccgaacaa cacggtcacc tgcaacgact acacggccac ccaggaggag tacgagggca   5040
cgtacacgtc gaggaacagg ggctacgacg gcgcttacga gtccaacagc tcggtgccgg   5100
ccgactacgc tagcgcgtac gaggagaagg cctacacgga cggccgcagg gacaacacct   5160
gcgagtcgaa caggggctac ggcgactaca cgccgctccc ggccggctac gtgaccaagg   5220
agctggagta cttcccggag acggacaagg tctggatcga gatcggcgag acggagggca   5280
ccttcatcgt ggactcagtc gagctgctgc tcatggagga gtaggagctc gccaacagtc   5340
gttgaagctg ctgctgtatc tgggttatct agtgtctctg cctttgccca aggatagtgc   5400
tgtctttcaa agtatttgta tcgtttgtgt cgtgagtcgt gactgagctg gtttcaagga   5460
ccagttgtgt tctcgttacc caaaactatc gtgcgaccgc atatggctta atcatgaata   5520
aatgttgttt gaatttaaac tattcgctga atattgttgt tttttgtcat gtcagttaat   5580
gttactaaat tggttgcctt ctaatttttg tttactggtg tttgtcgcac cttatctttt   5640
tactgtatgt ttacttcagg ttctggcagt ctcatttttt gtgactagtt aaaacttaca   5700
gctaaaaaaa tgcagttttt aattttaatt tgaagtttga ttagagctat tgatacccgg   5760
accatcaggt taggttagtt gtgcatagaa tcataaatat taatcatgtt ttctatgaat   5820
taagtcaaac ttgaaagtct ggctgaatat agtttctatg aatcatattg atatacatgt   5880
ttgattattt gttttgctat tagctattta ctttggtgaa tctatatagg cttatgcaga   5940
accttttttt ttgttctata tatccatatc ctagtactca gtagctctat gttttctgga   6000
gactagtggc ttgctttttc gtatgtctaa ttttttgctt gaccattgca aaacaaaaat   6060
tacctagtgt aatctctttt tataataatc ttgtaatgcg tctacctata ggtcaaagta   6120
ggttttgttt ggaaccctta gagctaactg ttagctagtt gataaattat tagctgagtt   6180
aagctagcta atgaactagt tttgatatta gctgaggatg tttgaaacct aataattatt   6240
ttttattagc taactatact aaattttagt agagagattc caaacaggag ttaacatggg   6300
atcagattgg ctatgcgttt gcaatcccat actaattagc taacggaccg ctaattagct   6360
aacgatcgct taattaagct tgcatgcctg cagtgcagcg tgacccggtc gtgcccctct   6420
ctagagataa tgagcattgc atgtctaagt tataaaaaat taccacatat ttttttttgtc  6480
acacttgttt gaagtgcagt ttatctatct ttatacatat atttaaactt tactctacga   6540
ataatataat ctatagtact acaataatat cagtgtttta gagaatcata taaatgaaca   6600
gttagacatg gtctaaagga caattgagta ttttgacaac aggactctac agttttatct   6660
ttttagtgtg catgtgttct cctttttttt tgcaaatagc ttcacctata taatacttca   6720
tccattttat tagtacatcc atttagggtt tagggttaat ggtttttata gactaatttt   6780
```

```
tttagtacat ctattttatt ctattttagc ctctaaatta agaaaactaa aactctattt   6840
tagttttttt atttaataat ttagatataa aatagaataa aataaagtga ctaaaaatta   6900
aacaaatacc ctttaagaaa ttaaaaaaac taaggaaaca tttttcttgt ttcgagtaga   6960
taatgccagc ctgttaaacg ccgccgacga gtctaacgga caccaaccag cgaaccagca   7020
gcgtcgcgtc gggccaagcg aagcagacgg cacggcatct ctgtcgctgc ctctggaccc   7080
ctctcgagag ttccgctcca ccgttggact tgctccgctg tcggcatcca gaaattgcgt   7140
ggcggagcgg cagacgtgag ccggcacggc aggcggcctc ctcctcctct cacggcaccg   7200
gcagctacgg gggattcctt tcccaccgct ccttcgcttt cccttcctcg cccgccgtaa   7260
taaatagaca cccccctccac accctctttc cccaacctcg tgttgttcgg agcgcacaca   7320
cacacaacca gatctccccc aaatccaccc gtcggcacct ccgcttcaag gtacgccgct   7380
cgtcctcccc ccccccccct ctctaccttc tctagatcgg cgttccggtc catagttagg   7440
gcccggtagt tctacttctg ttcatgtttg tgttagatcc gtgtttgtgt tagatccgtg   7500
ctgttagcgt tcgtacacgg atgcgacctg tacgtcagac acgttctgat tgctaacttg   7560
ccagtgtttc tctttgggga atcctgggat ggctctagcc gttccgcaga cgggatcgat   7620
ttcatgattt tttttgtttc gttgcatagg gtttggtttg ccctttttcct ttatttcaat   7680
atatgccgtg cacttgtttg tcgggtcatc ttttcatgct tttttttgtc ttggttgtga   7740
tgatgtggtc tggttgggcg gtcgttctag atcggagtag aattctgttt caaactacct   7800
ggtggattta ttaattttgg atctgtatgt gtgtgccata catattcata gttacgaatt   7860
gaagatgatg gatggaaata tcgatctagg ataggtatac atgttgatgc gggttttact   7920
gatgcatata cagagatgct tttgttcgc ttggttgtga tgatgtggtg tggttgggcg   7980
gtcgttcatt cgttctagat cggagtagaa tactgtttca aactacctgg tgtatttatt   8040
aattttggaa ctgtatgtgt gtgtcataca tcttcatagt tacgagttta agatggatgg   8100
aaatatcgat ctaggatagg tatacatgtt gatgtgggtt ttactgatgc atatacatga   8160
tggcatatgc agcatctatt catatgctct aaccttgagt acctatctat tataataaac   8220
aagtatgttt tataattatt ttgatcttga tatacttgga tgatggcata tccagcagct   8280
atatctggat ttttttagcc ctgccttcat acgctattta tttgcttggt actgtttctt   8340
ttgtcgttgc tcaccctgtt gtttggtgtt acttctgcag ggatctccga tcatgcaaaa   8400
actcattaac tcagtgcaaa actatgcctg gggcagcaaa acggcgttga ctgaacttta   8460
cggtatggaa aatccgtcca gccagccgat ggccgagctg tggatgggcg cacatccgaa   8520
aagcagttca cgagtgcaga atgccgccgg agatatcgtt tcactgcgtg atgtgattga   8580
gagtgataaa tcgactctgc tcggagaggc cgttgccaaa cgctttggcg aactgccttt   8640
cctgttcaaa gtattatgcg cagcacagcc actctccatt caggttcatc caaacaaaca   8700
caattctgaa atcggttttg ccaaagaaaa tgccgcaggt atcccgatgg atgccgccga   8760
gcgtaactat aaagatccta accacaagcc ggagctggtt tttgcgctga cgcctttcct   8820
tgcgatgaac gcgtttcgtg aattttccga gattgtctcc ctactccagc cggtcgcagg   8880
tgcacatccg gcgattgctc actttttaca acagcctgat gccgaacgtt taagcgaact   8940
gttcgccagc ctgttgaata tgcagggtga agaaaaatcc cgcgcgctgg cgattttaaa   9000
atcggccctc gatagccagc agggtgaacc gtggcaaacg attcgtttaa tttctgaatt   9060
ttacccggaa gacagcggtc tgttctcccc gctattgctg aatgtggtga aattgaaccc   9120
```

```
tggcgaagcg atgttcctgt tcgctgaaac accgcacgct tacctgcaag gcgtggcgct   9180

ggaagtgatg gcaaactccg ataacgtgct gcgtgcgggt ctgacgccta aatacattga   9240

tattccggaa ctggttgcca atgtgaaatt cgaagccaaa ccggctaacc agttgttgac   9300

ccagccggtg aaacaaggtg cagaactgga cttcccgatt ccagtggacg attttgcctt   9360

ctcgctgcac gaccttagtg ataaagaaac caccattagc cagcagagtg ccgccatttt   9420

gttctgcgtc gaaggcgatg caacgttgtg gaaaggttct cagcagttac agcttaaacc   9480

gggtgaatca gcgtttattg ccgccaacga atcaccggtg actgtcaaag gccacggccg   9540

tttagcgcgt gtttacaaca agctgtaaga gcttactgaa aaaattaaca tctcttgcta   9600

agctgggtca tgggtcgttt aagctgccga tgtgcctgcg tcgtctggtg ccctctctcc   9660

atatggaggt tgtcaaagta tctgctgttc gtgtcatgag tcgtgtcagt gttggtttaa   9720

taatggaccg gttgtgttgt gtgtgcgtac tacccagaac tatgacaaat catgaataag   9780

tttgatgttt gaaattaaag cctgtgctca ttatgttctg tctttcagtt gtctcctaat   9840

atttgcctcc aggtactggc tatctaccgt ttcttactta ggaggtgttt gaatgcacta   9900

aaactaatag ttagtggcta aaattagtta aaacatccaa acaccatagc taatagttga   9960

actattagct atttttggaa aattagttaa tagtgaggta gttatttgtt agctagctaa  10020

ttcaactaac aatttttagc caactaacaa ttagtttcag tgcattcaaa caccccctta  10080

atgttaacgt ggttctatct accgtctcct aatatatggt tgattgttcg gtttgttgct  10140

atgctattgg gttctgattg ctgctagttc ttgctgaatc cagaagttct cgtagtatag  10200

ctcagattca tattatttat ttgagtgata agtgatccag gttattacta tgttagctag  10260

gtttttttta caaggataaa ttatctgtga tcataattct tatgaaagct ttatgtttcc  10320

tggaggcagt ggcatgcaat gcatgacagc aacttgatca caccagctga ggtagatacg  10380

gtaacaaggt tcttaaatct gttcaccaaa tcattggaga acacacatac acattcttgc  10440

cagtcttggt tagagaaatt tcatgacaaa atgccaaagc tgtcttgact cttcactttt  10500

ggccatgagt cgtgacttag tttggtttaa tggaccggtt ctcctagctt gttctactca  10560

aaactgttgt tgatgcgaat aagttgtgat ggttgatctc tggattttgt tttgctctca  10620

atagtggacg agattagata g                                             10641
```

<210> SEQ ID NO 2
<211> LENGTH: 16208
<212> TYPE: DNA
<213> ORGANISM: Artificial sequence
<220> FEATURE:
<223> OTHER INFORMATION: Synthetic polynucleotide

<400> SEQUENCE: 2

```
attcctgtgg ttggcatgca catacaaatg gacgaacgga taaacctttt cacgcccttt     60

taaatatccg attattctaa taaacgctct tttctcttag gtttacccgc caatatatcc    120

tgtcaaacac tgatagttta aactggcact agcctaacgg tgttgactaa ctaggccgct    180

tccctaatta gctaacccgg gggcgcgccg ggacccgaat tcattatgtg gtctaggtag    240

gttctatata taagaaaact tgaaatgttc taaaaaaaaa ttcaagccca tgcatgattg    300

aagcaaacgg tatagcaacg gtgttaacct gatctagtga tctcttgcaa tccttaacgg    360

ccacctaccg caggtagcaa acggcgtccc cctcctcgat atctccgcgg cgacctctgg    420

ctttttccgc ggaattgcgc ggtggggacg gattccacga gaccgcgacg caaccgcctc    480

tcgccgctgg gccccacacc gctcggtgcc gtagcctcac gggactcttt ctccctcctc    540
```

```
ccccgttata aattggcttc atcccctcct tgcctcatcc atccaaatcc cagtccccaa    600
tcccatccct tcgtaggaga aattcatcga agctaagcga atcctcgcga tcctctcaag    660
gtactgcgag ttttcgatcc ccctctcgac ccctcgtatg tttgtgtttg tcgtagcgtt    720
tgattaggta tgctttccct gtttgtgttc gtcgtagcgt ttgattaggt atgctttccc    780
tgttcgtgtt catcgtagtg tttgattagg tcgtgtgagg cgatggcctg ctcgcgtcct    840
tcgatctgta gtcgatttgc gggtcgtggt gtagatctgc gggctgtgat gaagttattt    900
ggtgtgatct gctcgcctga ttctgcgggt tggctcgagt agatatgatg gttggaccgg    960
ttggttcgtt taccgcgcta gggttgggct gggatgatgt tgcatgcgcc gttgcgcgtg   1020
atcccgcagc aggacttgcg tttgattgcc agatctcgtt acgattatgt gatttggttt   1080
ggacttttta gatctgtagc ttctgcttat gtgccagatg cgcctactgc tcatatgcct   1140
gatgataatc ataaatggct gtggaactaa ctagttgatt gcggagtcat gtatcagcta   1200
caggtgtagg gactagctac aggtgtaggg acttgcgtct aattgtttgg tcctttactc   1260
atgttgcaat tatgcaattt agtttagatt gtttgttcca ctcatctagg ctgtaaaagg   1320
gacactgctt agattgctgt ttaatctttt tagtagatta tattatattg gtaacttatt   1380
acccctatta catgccatac gtgacttctg ctcatgcctg atgataatca tagatcactg   1440
tggaattaat tagttgattg ttgaatcatg tttcatgtac ataccacggc acaattgctt   1500
agttccttaa caaatgcaaa ttttactgat ccatgtatga tttgcgtggt tctctaatgt   1560
gaaatactat agctacttgt tagtaagaat caggttcgta tgcttaatgc tgtatgtgcc   1620
ttctgctcat gcctgatgat aatcatatat cactggaatt aattagttga tcgtttaatc   1680
atatatcaag tacataccat gccacaattt ttagtcactt aacccatgca gattgaactg   1740
gtccctgcat gttttgctaa attgttctat tctgattaga ccatatatca tgtatttttt   1800
tttggtaatg gttctcttat tttaaatgct atatagttct ggtacttgtt agaaagatct   1860
gcttcatagt ttagttgcct atccctcgaa ttaggatgct gagcagctga tcctatagct   1920
ttgtttcatg tatcaattct tttgtgttca acagtcagtt tttgttagat tcattgtaac   1980
ttatggtcgc ttactcttct ggtcctcaat gcttgcaggg atcctaaacc atggagatca   2040
acaaccagaa ccagtgcgtg ccgtacaact gccttaacaa ccccgagtcc gagatcctga   2100
acgtggccat cttctccagc gagcaggtcg cggagatcca cctcaagatc acgcgcctga   2160
tcctcgagaa cttcctgccg ggcggctcct tcgctttcgg cctgttcgac ctcatctggg   2220
gcatcttcaa cgaggaccag tggagcgcgt tcctcaggca ggtggaggag ctgatcaacc   2280
agcgcatcac ggagttcgcc aggggccagg ctatccagcg gctggtgggc ttcggcaggt   2340
cctacgacga gtacatcctg gccctcaagg agtgggagaa cgaccccgac aacccggcca   2400
gcaaggagcg cgtgaggacc cgcttcagga ccaccgacga cgctctcctg acgggcgtcc   2460
ccctcatggc tatcccgggc ttcgagctgg ccaccctctc ggtgtacgct cagtcggcca   2520
acctgcacct cgccctcctg cgggacgctg tgttcttcgg cgagaggtgg ggcctgaccc   2580
agacgaacat caacgacctc tactccaggc tgaagaacag catccgcgac tacacgaacc   2640
actgcgtgcg cttctacaac atcggcctgg gcaacctcaa cgtcatcagg ccggagtact   2700
accgcttcca gagggagctg accatcagcg tgctggacct cgtcgccctg ttccccaact   2760
acgacatccg cacgtacccg atcccaacca agtcccagct cacgagggag atctacaccg   2820
acccgatcat ctcgccgggc gcccaggccg gctacaccct gcaggacgtc ctgagggagc   2880
```

cccacctgat ggacttcctg aacaggctca tcatctacac cggcgagtac aggggcatca 2940
ggcactgggc gggccacgag gtggagtcca gcaggacggg catgatgacc aacatccgct 3000
tcccgctcta cggcaccgcg gccacggccg agccaacccg cttcatcacg ccgtccacct 3060
tccccggcct gaacctcttc tacaggaccc tgtcggctcc catcttccgc gacgagccgg 3120
gcgcgaacat catcatccgc tacaggacct ccctcgtgga gggcgtcggc ttcatccagc 3180
cgaacaacgg cgagcagctg taccgcgtga ggggcacgct ggacagcctg gaccagctcc 3240
cactggaggg cgagtccagc ctcaccgagt actcgcacag gctgtgccac gtcaggttcg 3300
cccagagcct caggaacgcg gagcccctgg actacgccag ggtgcccatg ttcagctgga 3360
cccacaggtc ggctaccccc accaacacca tcgacccaga cgtgatcacg cagatcccgc 3420
tcgtcaaggc ccacaccctg cagtcgggca ccaccgtggt caagggcccc ggcttcacgg 3480
gcggcgacat cctgaggagg acctccggcg gcccattcgc cttcagcaac gtcaacctcg 3540
actggaacct gtcccagcgc tacagggcgc gcatcaggta cgccagcacc acgaacctgc 3600
gcatgtatgt gaccatcgcg ggcgagagga tcttcgccgg ccagttcaac aagacgatga 3660
acaccggcga cccgctcacc ttccagtcct tcagctacgc gacgatcgac accgccttca 3720
cgttccccac gaaggcctcc agcctgaccg tgggcgccga caccttctcc agcggcaacg 3780
aggtctacgt ggaccgcttc gagctgatcc cggtgacggc gaccttcgag gccgagtacg 3840
acctggagaa ggcccagaag gcggtcaacg ccctcttcac ctccagcaac cagatcggcc 3900
tgaagacgga cgtgaccgac taccacatcg acaaggtgtc caacctcgtc gagtgcctga 3960
gcgacgagtt ctgcctcgac gagaagaggg agctgtccga gaaggtcaag cacgccaagc 4020
gcctctgcga cgagaggaac ctcctgcagg acccgaactt caggggaatc aaccgccagc 4080
cggacagggg ctggaggggc agcaccgaca tcaccatcca gggcggcgac gacgtgttca 4140
aggagaacta cgtcacgctc ccgggcacct tcgacgagtg ctaccccacg tacctgtacc 4200
agaagatcga cgagtccaag ctcaaggcct acacccgcta cgagctgagg ggatacatcg 4260
aggacagcca ggacctcgag atctacctga tccgctacaa cgcgaagcac gagacggtga 4320
acgtccccgg cacgggctcc ctgtggcccc tctcggctca gtcgccgatc ggcaagtgcg 4380
gcgagcccaa caggtgcgcc acccacctcg agtggaaccc ggacctggac tgctcctgcc 4440
gggacggcga gaagtgcgct caccactccc accacttcag cctggacatc gacgtgggct 4500
gcacggacct caacgaggac ctgggcgtgt gggtcatctt caaaatcaag acgcaggacg 4560
gccacgctag gctgggcaac ctcgagttcc tggaggagaa gccgctggtg ggcgaggctc 4620
tggccagggt caagagggcg gagaagaagt ggcgcgacaa gagggagaag ctggagctgg 4680
agacgaacat cgtctacaag gaggccaaga agtccgtgga cgcgctcttc gtcaacagcc 4740
agtacgacag gctgcaggcg gacaccaaca tcgccatcat ccacgccgcg gacaagcgcg 4800
tgcactccat cagggaggcc tacctccccg agctgagcgt gatcccgggc gtcaacgctg 4860
ccatcttcga ggagctggag ggccgcatct tcaccgccta ctccctgtac gacgcgagga 4920
acgtcatcaa gaacggcgac ttcaacaacg gcctcagctg ctggaacgtg aagggccacg 4980
tggacgtcga ggagcagaac aaccaccgct cggtgctggt ggtccccgag tgggaggctg 5040
aggtcagcca ggaggtgcgc gtctgcccgg gcaggggata catcctccgc gtgaccgcgt 5100
acaaggaggg ctacggcgag ggctgcgtca cgatccacga gatcgaggac aacaccgacg 5160
agctgaagtt ctccaactgc gtggaggagg agatctaccc gaacaacacg gtcacctgca 5220
acgactacac ggccacccag gaggagtacg agggcacgta cacgtcgagg aacaggggct 5280

```
acgacggcgc ttacgagtcc aacagctcgg tgccggccga ctacgctagc gcgtacgagg   5340
agaaggccta cacggacggc cgcagggaca acacctgcga gtcgaacagg ggctacggcg   5400
actacacgcc gctcccggcc ggctacgtga ccaaggagct ggagtacttc ccggagacgg   5460
acaaggtctg gatcgagatc ggcgagacgg agggcacctt catcgtggac tcagtcgagc   5520
tgctgctcat ggaggagtag gagctcgcca acagtcgttg aagctgctgc tgtatctggg   5580
ttatctagtg tctctgcctt tgcccaagga tagtgctgtc tttcaaagta tttgtatcgt   5640
ttgtgtcgtg agtcgtgact gagctggttt caaggaccag ttgtgttctc gttacccaaa   5700
actatcgtgc gaccgcatat ggcttaatca tgaataaatg ttgtttgaat ttaaactatt   5760
cgctgaatat tgttgttttt tgtcatgtca gttaatgtta ctaaattggt tgccttctaa   5820
tttttgttta ctggtgtttg tcgcacctta tctttttact gtatgtttac ttcaggttct   5880
ggcagtctca tttttttgtga ctagttaaaa cttacagcta aaaaaatgca gtttttaatt   5940
ttaatttgaa gtttgattag agctattgat acccggacca tcaggttagg ttagttgtgc   6000
atagaatcat aaatattaat catgttttct atgaattaag tcaaacttga aagtctggct   6060
gaatatagtt tctatgaatc atattgatat acatgtttga ttatttgttt tgctattagc   6120
tatttacttt ggtgaatcta tataggctta tgcagaacct tttttttgt tctatatatc   6180
catatcctag tactcagtag ctctatgttt tctggagact agtggcttgc tttttcgtat   6240
gtctaatttt ttgcttgacc attgcaaaac aaaaattacc tagtgtaatc tctttttata   6300
ataatcttgt aatgcgtcta cctataggtc aaagtaggtt ttgtttggaa cccttagagc   6360
taactgttag ctagttgata aattattagc tgagttaagc tagctaatga actagttttg   6420
atattagctg aggatgtttg aaacctaata attattttt attagctaac tatactaaat   6480
tttagtagag agattccaaa caggagttaa catgggatca gattggctat gcgtttgcaa   6540
tcccatacta attagctaac ggaccgctaa ttagctaacg atcgcttaat taagcttgca   6600
tgcctgcagt gcagcgtgac ccggtcgtgc ccctctctag agataatgag cattgcatgt   6660
ctaagttata aaaaattacc acatattttt tttgtcacac ttgtttgaag tgcagtttat   6720
ctatctttat acatatattt aaactttact ctacgaataa tataatctat agtactacaa   6780
taatatcagt gttttagaga atcatataaa tgaacagtta gacatggtct aaaggacaat   6840
tgagtatttt gacaacagga ctctacagtt ttatcttttt agtgtgcatg tgttctcctt   6900
tttttttgca aatagcttca cctatataat acttcatcca ttttattagt acatccattt   6960
agggtttagg gttaatggtt tttatagact aattttttta gtacatctat tttattctat   7020
tttagcctct aaattaagaa aactaaaact ctattttagt ttttttattt aataatttag   7080
atataaaata gaataaaata aagtgactaa aaattaaaca aataccottt aagaaattaa   7140
aaaaactaag gaaacatttt tcttgtttcg agtagataat gccagcctgt taaacgccgc   7200
cgacgagtct aacggacacc aaccagcgaa ccagcagcgt cgcgtcgggc caagcgaagc   7260
agacggcacg gcatctctgt cgctgcctct ggacccctct cgagagttcc gctccaccgt   7320
tggacttgct ccgctgtcgg catccagaaa ttgcgtggcg gagcggcaga cgtgagccgg   7380
cacggcaggc ggcctcctcc tcctctcacg gcaccggcag ctacgggga ttcctttccc    7440
accgctcctt cgctttccct tcctcgcccg ccgtaataaa tagacacccc ctccacaccc   7500
tctttcccca acctcgtgtt gttcggagcg cacacacaca caaccagatc tcccccaaat   7560
ccacccgtcg gcacctccgc ttcaaggtac gccgctcgtc ctcccccccc cccctctct    7620
```

-continued

```
accttctcta gatcggcgtt ccggtccata gttagggccc ggtagttcta cttctgttca   7680
tgtttgtgtt agatccgtgt ttgtgttaga tccgtgctgt tagcgttcgt acacggatgc   7740
gacctgtacg tcagacacgt tctgattgct aacttgccag tgtttctctt tggggaatcc   7800
tgggatggct ctagccgttc cgcagacggg atcgatttca tgattttttt tgtttcgttg   7860
catagggttt ggtttgccct tttcctttat ttcaatatat gccgtgcact tgtttgtcgg   7920
gtcatctttt catgcttttt tttgtcttgg ttgtgatgat gtggtctggt tgggcggtcg   7980
ttctagatcg gagtagaatt ctgtttcaaa ctacctggtg gatttattaa ttttggatct   8040
gtatgtgtgt gccatacata ttcatagtta cgaattgaag atgatggatg gaaatatcga   8100
tctaggatag gtatacatgt tgatgcgggt tttactgatg catatacaga gatgcttttt   8160
gttcgcttgg ttgtgatgat gtggtgtggt tgggcggtcg ttcattcgtt ctagatcgga   8220
gtagaatact gtttcaaact acctggtgta tttattaatt ttggaactgt atgtgtgtgt   8280
catacatctt catagttacg agtttaagat ggatggaaat atcgatctag gataggtata   8340
catgttgatg tgggttttac tgatgcatat acatgatggc atatgcagca tctattcata   8400
tgctctaacc ttgagtacct atctattata ataaacaagt atgttttata attattttga   8460
tcttgatata cttggatgat ggcatatcca gcagctatat ctggattttt ttagccctgc   8520
cttcatacgc tatttatttg cttggtactg tttcttttgt cgttgctcac cctgttgttt   8580
ggtgttactt ctgcagggat ctccgatcat gcaaaaactc attaactcag tgcaaaacta   8640
tgcctggggc agcaaaacgg cgttgactga actttacggt atggaaaatc cgtccagcca   8700
gccgatggcc gagctgtgga tgggcgcaca tccgaaaagc agttcacgag tgcagaatgc   8760
cgccggagat atcgtttcac tgcgtgatgt gattgagagt gataaatcga ctctgctcgg   8820
agaggccgtt gccaaacgct ttggcgaact gcctttcctg ttcaaagtat tatgcgcagc   8880
acagccactc tccattcagg ttcatccaaa caaacacaat tctgaaatcg gttttgccaa   8940
agaaaatgcc gcaggtatcc cgatggatgc cgccgagcgt aactataaag atcctaacca   9000
caagccggag ctggtttttg cgctgacgcc tttccttgcg atgaacgcgt ttcgtgaatt   9060
ttccgagatt gtctccctac tccagccggt cgcaggtgca catccggcga ttgctcactt   9120
tttacaacag cctgatgccg aacgtttaag cgaactgttc gccagcctgt tgaatatgca   9180
gggtgaagaa aaatcccgcg cgctggcgat tttaaaatcg gccctcgata gccagcaggg   9240
tgaaccgtgg caaacgattc gtttaatttc tgaattttac ccggaagaca gcggtctgtt   9300
ctccccgcta ttgctgaatg tggtgaaatt gaaccctggc gaagcgatgt tcctgttcgc   9360
tgaaacaccg cacgcttacc tgcaaggcgt ggcgctggaa gtgatggcaa actccgataa   9420
cgtgctgcgt gcgggtctga cgcctaaata cattgatatt ccggaactgg ttgccaatgt   9480
gaaattcgaa gccaaaccgg ctaaccagtt gttgacccag ccggtgaaac aaggtgcaga   9540
actggacttc ccgattccag tggacgattt tgccttctcg ctgcacgacc ttagtgataa   9600
agaaaccacc attagccagc agagtgccgc cattttgttc tgcgtcgaag gcgatgcaac   9660
gttgtggaaa ggttctcagc agttacagct taaaccgggt gaatcagcgt ttattgccgc   9720
caacgaatca ccggtgactg tcaaaggcca cggccgttta gcgcgtgttt acaacaagct   9780
gtaagagctt actgaaaaaa ttaacatctc ttgctaagct gggtcatggg tcgtttaagc   9840
tgccgatgtg cctgcgtcgt ctggtgccct ctctccatat ggaggttgtc aaagtatctg   9900
ctgttcgtgt catgagtcgt gtcagtgttg gtttaataat ggaccggttg tgttgtgtgt   9960
gcgtactacc cagaactatg acaaatcatg aataagtttg atgtttgaaa ttaaagcctg  10020
```

```
tgctcattat gttctgtctt tcagttgtct cctaatattt gcctccaggt actggctatc  10080
taccgtttct tacttaggag gtgtttgaat gcactaaaac taatagttag tggctaaaat  10140
tagttaaaac atccaaacac catagctaat agttgaacta ttagctattt ttggaaaatt  10200
agttaatagt gaggtagtta tttgttagct agctaattca actaacaatt tttagccaac  10260
taacaattag tttcagtgca ttcaaacacc cccttaatgt taacgtggtt ctatctaccg  10320
tctcctaata tatggttgat tgttcggttt gttgctatgc tattgggttc tgattgctgc  10380
tagttcttgc tgaatccaga agttctcgta gtatagctca gattcatatt atttatttga  10440
gtgataagtg atccaggtta ttactatgtt agctaggttt tttttacaag gataaattat  10500
ctgtgatcat aattcttatg aaagctttat gtttcctgga ggcagtggca tgcaatgcat  10560
gacagcaact tgatcacacc agctgaggta gatacggtaa caaggttctt aaatctgttc  10620
accaaatcat tggagaacac acatacacat tcttgccagt cttggttaga gaaatttcat  10680
gacaaaatgc caaagctgtc ttgactcttc acttttggcc atgagtcgtg acttagtttg  10740
gtttaatgga ccggttctcc tagcttgttc tactcaaaac tgttgttgat gcgaataagt  10800
tgtgatggtt gatctctgga ttttgttttg ctctcaatag tggacgagat tagatagcct  10860
gcaggcccgg gggcgcgccc taattagcta acggccagga tcgccgcgtg agcctttagc  10920
aactagctag attaattaac gcaatctgtt attaagttgt ctaagcgtca atttgtttac  10980
accacaatat atcctgccac cagccagcca acagctcccc gaccggcagc tcggcacaaa  11040
atcaccactc gatacaggca gcccatcaga attaattctc atgtttgaca gcttatcatc  11100
gactgcacgg tgcaccaatg cttctggcgt caggcagcca tcggaagctg tggtatggct  11160
gtgcaggtcg taaatcactg cataattcgt gtcgctcaag gcgcactccc gttctggata  11220
atgttttttg cgccgacatc ataacggttc tggcaaatat tctgaaatga gctgttgaca  11280
attaatcatc cggctcgtat aatgtgtgga attgtgagcg gataacaatt tcacacagga  11340
aacagaccat gagggaagcg ttgatcgccg aagtatcgac tcaactatca gaggtagttg  11400
gcgtcatcga gcgccatctc gaaccgacgt tgctggccgt acatttgtac ggctccgcag  11460
tggatggcgg cctgaagcca cacagtgata ttgatttgct ggttacggtg accgtaaggc  11520
ttgatgaaac aacgcggcga gctttgatca acgacctttt ggaaacttcg gcttcccctg  11580
gagagagcga gattctccgc gctgtagaag tcaccattgt tgtgcacgac gacatcattc  11640
cgtggcgtta tccagctaag cgcgaactgc aatttggaga atggcagcgc aatgacattc  11700
ttgcaggtat cttcgagcca gccacgatcg acattgatct ggctatcttg ctgacaaaag  11760
caagagaaca tagcgttgcc ttggtaggtc cagcggcgga ggaactcttt gatccggttc  11820
ctgaacagga tctatttgag gcgctaaatg aaaccttaac gctatggaac tcgccgcccg  11880
actgggctgg cgatgagcga aatgtagtgc ttacgttgtc ccgcatttgg tacagcgcag  11940
taaccggcaa aatcgcgccg aaggatgtcg ctgccgactg ggcaatggag cgcctgccgg  12000
cccagtatca gcccgtcata cttgaagcta ggcaggctta tcttggacaa gaagatcgct  12060
tggcctcgcg cgcagatcag ttggaagaat ttgttcacta cgtgaaaggc gagatcacca  12120
aagtagtcgg caaataaagc tctagtggat ctccgtaccc agggatctgg ctcgcggcgg  12180
acgcacgacg ccggggcgag accataggcg atctcctaaa tcaatagtag ctgtaacctc  12240
gaagcgtttc acttgtaaca acgattgaga atttttgtca taaaattgaa atacttggtt  12300
cgcatttttg tcatccgcgg tcagccgcaa ttctgacgaa ctgcccattt agctggagat  12360
```

-continued

```
gattgtacat ccttcacgtg aaaatttctc aagcgctgtg aacaagggtt cagattttag  12420
attgaaaggt gagccgttga aacacgttct tcttgtcgat gacgacgtcg ctatgcggca  12480
tcttattatt gaatacctta cgatccacgc cttcaaagtg accgcggtag ccgacagcac  12540
ccagttcaca agagtactct cttccgcgac ggtcgatgtc gtggttgttg atctagattt  12600
aggtcgtgaa gatgggctcg agatcgttcg taatctggcg gcaaagtctg atattccaat  12660
cataattatc agtggcgacc gccttgagga gacggataaa gttgttgcac tcgagctagg  12720
agcaagtgat tttatcgcta agccgttcag tatcagagag tttctagcac gcattcgggt  12780
tgccttgcgc gtgcgcccca acgttgtccg ctccaaagac cgacggtctt tttgttttac  12840
tgactggaca cttaatctca ggcaacgtcg cttgatgtcc gaagctggcg gtgaggtgaa  12900
acttacggca ggtgagttca atcttctcct cgcgttttta gagaaacccc gcgacgttct  12960
atcgcgcgag caacttctca ttgccagtcg agtacgcgac gaggaggttt atgacaggag  13020
tatagatgtt ctcatttga ggctgcgccg caaacttgag gcagatccgt caagccctca  13080
actgataaaa acagcaagag gtgccggtta tttctttgac gcggacgtgc aggtttcgca  13140
cggggggacg atggcagcct gagccaattc ccagatcccc gaggaatcgg cgtgagcggt  13200
cgcaaaccat ccggcccggt acaaatcggc gcggcgctgg gtgatgacct ggtggagaag  13260
ttgaaggccg cgcaggccgc ccagcggcaa cgcatcgagg cagaagcacg ccccggtgaa  13320
tcgtggcaag cggccgctga tcgaatccgc aaagaatccc ggcaaccgcc ggcagccggt  13380
gcgccgtcga ttaggaagcc gcccaagggc gacgagcaac cagatttttt cgttccgatg  13440
ctctatgacg tgggcacccg cgatagtcgc agcatcatgg acgtggccgt tttccgtctg  13500
tcgaagcgtg accgacgagc tggcgaggtg atccgctacg agcttccaga cgggcacgta  13560
gaggtttccg cagggccggc cggcatggcc agtgtgtggg attacgacct ggtactgatg  13620
gcggtttccc atctaaccga atccatgaac cgataccggg aagggaaggg agacaagccc  13680
ggccgcgtgt tccgtccaca cgttgcggac gtactcaagt tctgccggcg agccgatggc  13740
ggaaagcaga aagacgacct ggtagaaacc tgcattcggt taaacaccac gcacgttgcc  13800
atgcagcgta cgaagaaggc caagaacggc cgcctggtga cggtatccga gggtgaagcc  13860
ttgattagcc gctacaagat cgtaaagagc gaaaccgggc ggccggagta catcgagatc  13920
gagctggctg attggatgta ccgcgagatc acagaaggca agaacccgga cgtgctgacg  13980
gttcaccccg attacttttt gatcgatccc ggcatcggcc gttttctcta ccgcctggca  14040
cgccgcgccg caggcaaggc agaagccaga tggttgttca agacgatcta cgaacgcagt  14100
ggcagcgccg gagagttcaa gaagttctgt ttcaccgtgc gcaagctgat cgggtcaaat  14160
gacctgccgg agtacgattt gaaggaggag gcggggcagg ctggcccgat cctagtcatg  14220
cgctaccgca acctgatcga gggcgaagca tccgccggtt cctaatgtac ggagcagatg  14280
ctagggcaaa ttgccctagc aggggaaaaa ggtcgaaaag gtctctttcc tgtggatagc  14340
acgtacattg ggaacccaaa gccgtacatt gggaaccgga acccgtacat tgggaaccca  14400
aagccgtaca ttgggaaccg gtcacacatg taagtgactg atataaaaga gaaaaaaggc  14460
gatttttccg cctaaaactc tttaaaactt attaaaactc ttaaaacccg cctggcctgt  14520
gcataactgt ctggccagcg cacagccgaa gagctgcaaa aagcgcctac ccttcggtcg  14580
ctgcgctccc tacgccccgc cgcttcgcgt cggcctatcg cggccgctgg ccgctcaaaa  14640
atggctggcc tacggccagg caatctacca gggcgcggac aagccgcgcc gtcgccactc  14700
gaccgccggc gctgaggtct gcctcgtgaa gaaggtgttg ctgactcata ccaggcctga  14760
```

atcgccccat catccagcca gaaagtgagg gagccacggt tgatgagagc tttgttgtag 14820
gtggaccagt tggtgatttt gaacttttgc tttgccacgg aacggtctgc gttgtcggga 14880
agatgcgtga tctgatcctt caactcagca aaagttcgat ttattcaaca aagccgccgt 14940
cccgtcaagt cagcgtaatg ctctgccagt gttacaacca attaaccaat tctgattaga 15000
aaaactcatc gagcatcaaa tgaaactgca atttattcat atcaggatta tcaataccat 15060
atttttgaaa aagccgtttc tgtaatgaag gagaaaactc accgaggcag ttccatagga 15120
tggcaagatc ctggtatcgg tctgcgattc cgactcgtcc aacatcaata caacctatta 15180
atttcccctc gtcaaaaata aggttatcaa gtgagaaatc accatgagtg acgactgaat 15240
ccggtgagaa tggcaaaagc tctgcattaa tgaatcggcc aacgcgcggg gagaggcggt 15300
ttgcgtattg ggcgctcttc cgcttcctcg ctcactgact cgctgcgctc ggtcgttcgg 15360
ctgcggcgag cggtatcagc tcactcaaag gcggtaatac ggttatccac agaatcaggg 15420
gataacgcag gaaagaacat gtgagcaaaa ggccagcaaa aggccaggaa ccgtaaaaag 15480
gccgcgttgc tggcgttttt ccataggctc cgcccccctg acgagcatca caaaaatcga 15540
cgctcaagtc agaggtggcg aaacccgaca ggactataaa gataccaggc gtttccccct 15600
ggaagctccc tcgtgcgctc tcctgttccg accctgccgc ttaccggata cctgtccgcc 15660
tttctccctt cgggaagcgt ggcgctttct catagctcac gctgtaggta tctcagttcg 15720
gtgtaggtcg ttcgctccaa gctgggctgt gtgcacgaac cccccgttca gcccgaccgc 15780
tgcgccttat ccggtaacta tcgtcttgag tccaacccgg taagacacga cttatcgcca 15840
ctggcagcag ccactggtaa caggattagc agagcgaggt atgtaggcgg tgctacagag 15900
ttcttgaagt ggtggcctaa ctacggctac actagaagaa cagtatttgg tatctgcgct 15960
ctgctgaagc cagttacctt cggaaaaaga gttggtagct cttgatccgg caaacaaacc 16020
accgctggta gcggtggttt ttttgtttgc aagcagcaga ttacgcgcag aaaaaaagga 16080
tctcaagaag atcctttgat cttttctacg gggtctgacg ctcagtggaa cgaaaactca 16140
cgttaaggga ttttggtcat gagattatca aaaaggatct tcacctagat ccttttgatc 16200
cggaatta 16208

<210> SEQ ID NO 3
<211> LENGTH: 3510
<212> TYPE: DNA
<213> ORGANISM: Artificial sequence
<220> FEATURE:
<223> OTHER INFORMATION: Synthetic polynucleotide

<400> SEQUENCE: 3
atggagatca acaaccagaa ccagtgcgtg ccgtacaact gccttaacaa ccccgagtcc 60
gagatcctga acgtggccat cttctccagc gagcaggtcg cggagatcca cctcaagatc 120
acgcgcctga tcctcgagaa cttcctgccg ggcggctcct tcgctttcgg cctgttcgac 180
ctcatctggg gcatcttcaa cgaggaccag tggagcgcgt tcctcaggca ggtggaggag 240
ctgatcaacc agcgcatcac ggagttcgcc aggggccagg ctatccagcg gctggtgggc 300
ttcggcaggt cctacgacga gtacatcctg gccctcaagg agtgggagaa cgaccccgac 360
aacccggcca gcaaggagcg cgtgaggacc cgcttcagga ccaccgacga cgctctcctg 420
acgggcgtcc ccctcatggc tatcccgggc ttcgagctgg ccaccctctc ggtgtacgct 480
cagtcggcca acctgcacct cgccctcctg cgggacgctg tgttcttcgg cgagaggtgg 540

```
ggcctgaccc agacgaacat caacgacctc tactccaggc tgaagaacag catccgcgac    600
tacacgaacc actgcgtgcg cttctacaac atcggcctgg gcaacctcaa cgtcatcagg    660
ccggagtact accgcttcca gagggagctg accatcagcg tgctggacct cgtcgccctg    720
ttccccaact acgacatccg cacgtacccg atcccaacca agtcccagct cacgagggag    780
atctacaccg acccgatcat ctcgccgggc gcccaggccg gctacaccct gcaggacgtc    840
ctgagggagc cccacctgat ggacttcctg aacaggctca tcatctacac cggcgagtac    900
aggggcatca ggcactgggc gggccacgag gtggagtcca gcaggacggg catgatgacc    960
aacatccgct tcccgctcta cggcaccgcg gccacggccg agccaacccg cttcatcacg   1020
ccgtccacct tccccggcct gaacctcttc tacaggaccc tgtcggctcc catcttccgc   1080
gacgagccgg gcgcgaacat catcatccgc tacaggacct ccctcgtgga gggcgtcggc   1140
ttcatccagc cgaacaacgg cgagcagctg taccgcgtga ggggcacgct ggacagcctg   1200
gaccagctcc cactggaggg cgagtccagc ctcaccgagt actcgcacag gctgtgccac   1260
gtcaggttcg cccagagcct caggaacgcg gagcccctgg actacgccag ggtgcccatg   1320
ttcagctgga cccacaggtc ggctaccccc accaacacca tcgacccaga cgtgatcacg   1380
cagatcccgc tcgtcaaggc ccacaccctg cagtcgggca ccaccgtggt caagggcccc   1440
ggcttcacgg gcggcgacat cctgaggagg acctccggcg gcccattcgc cttcagcaac   1500
gtcaacctcg actggaacct gtcccagcgc tacagggcgc gcatcaggta cgccagcacc   1560
acgaacctgc gcatgtatgt gaccatcgcg ggcgagagga tcttcgccgg ccagttcaac   1620
aagacgatga acaccggcga cccgctcacc ttccagtcct tcagctacgc gacgatcgac   1680
accgccttca cgttccccac gaaggcctcc agcctgaccg tgggcgccga caccttctcc   1740
agcggcaacg aggtctacgt ggaccgcttc gagctgatcc cggtgacggc gaccttcgag   1800
gccgagtacg acctggagaa ggcccagaag gcggtcaacg ccctcttcac ctccagcaac   1860
cagatcggcc tgaagacgga cgtgaccgac taccacatcg acaaggtgtc caacctcgtc   1920
gagtgcctga gcgacgagtt ctgcctcgac gagaagaggg agctgtccga gaaggtcaag   1980
cacgccaagc gcctctgcga cgagaggaac ctcctgcagg acccgaactt caggggaatc   2040
aaccgccagc cggacagggg ctggaggggc agcaccgaca tcaccatcca gggcggcgac   2100
gacgtgttca aggagaacta cgtcacgctc ccgggcacct tcgacgagtg ctaccccacg   2160
tacctgtacc agaagatcga cgagtccaag ctcaaggcct acacccgcta cgagctgagg   2220
ggatacatcg aggacagcca ggacctcgag atctacctga tccgctacaa cgcgaagcac   2280
gagacggtga acgtccccgg cacgggctcc ctgtggcccc tctcggctca gtcgccgatc   2340
ggcaagtgcg gcgagcccaa caggtgcgcc acccacctcg agtggaaccc ggacctggac   2400
tgctcctgcc gggacggcga gaagtgcgct caccactccc accacttcag cctggacatc   2460
gacgtgggct gcacggacct caacgaggac ctgggcgtgt gggtcatctt caaaatcaag   2520
acgcaggacg gccacgctag gctgggcaac ctcgagttcc tggaggagaa gccgctggtg   2580
ggcgaggctc tggccagggt caagagggcg gagaagaagt ggcgcgacaa gagggagaag   2640
ctggagctgg agacgaacat cgtctacaag gaggccaaga agtccgtgga cgcgctcttc   2700
gtcaacagcc agtacgacag gctgcaggcg gacaccaaca tcgccatcat ccacgccgcg   2760
gacaagcgcg tgcactccat cagggaggcc tacctccccg agctgagcgt gatcccgggc   2820
gtcaacgctg ccatcttcga ggagctggag ggccgcatct tcaccgccta ctccctgtac   2880
gacgcgagga acgtcatcaa gaacggcgac ttcaacaacg gcctcagctg ctggaacgtg   2940
```

```
aagggccacg tggacgtcga ggagcagaac aaccaccgct cggtgctggt ggtccccgag   3000

tgggaggctg aggtcagcca ggaggtgcgc gtctgcccgg gcaggggata catcctccgc   3060

gtgaccgcgt acaaggaggg ctacggcgag ggctgcgtca cgatccacga gatcgaggac   3120

aacaccgacg agctgaagtt ctccaactgc gtggaggagg agatctaccc gaacaacacg   3180

gtcacctgca acgactacac ggccacccag gaggagtacg agggcacgta cacgtcgagg   3240

aacaggggct acgacggcgc ttacgagtcc aacagctcgg tgccggccga ctacgctagc   3300

gcgtacgagg agaaggccta cacggacggc cgcagggaca acacctgcga gtcgaacagg   3360

ggctacggcg actacacgcc gctcccggcc ggctacgtga ccaaggagct ggagtacttc   3420

ccggagacgg acaaggtctg gatcgagatc ggcgagacgg agggcacctt catcgtggac   3480

tcagtcgagc tgctgctcat ggaggagtag                                    3510
```

```
<210> SEQ ID NO 4
<211> LENGTH: 1169
<212> TYPE: PRT
<213> ORGANISM: Artificial sequence
<220> FEATURE:
<223> OTHER INFORMATION: Synthetic polypeptide

<400> SEQUENCE: 4

Met Glu Ile Asn Asn Gln Asn Gln Cys Val Pro Tyr Asn Cys Leu Asn
1               5                   10                  15

Asn Pro Glu Ser Glu Ile Leu Asn Val Ala Ile Phe Ser Ser Glu Gln
            20                  25                  30

Val Ala Glu Ile His Leu Lys Ile Thr Arg Leu Ile Leu Glu Asn Phe
        35                  40                  45

Leu Pro Gly Gly Ser Phe Ala Phe Gly Leu Phe Asp Leu Ile Trp Gly
    50                  55                  60

Ile Phe Asn Glu Asp Gln Trp Ser Ala Phe Leu Arg Gln Val Glu Glu
65                  70                  75                  80

Leu Ile Asn Gln Arg Ile Thr Glu Phe Ala Arg Gly Gln Ala Ile Gln
                85                  90                  95

Arg Leu Val Gly Phe Gly Arg Ser Tyr Asp Glu Tyr Ile Leu Ala Leu
            100                 105                 110

Lys Glu Trp Glu Asn Asp Pro Asp Asn Pro Ala Ser Lys Glu Arg Val
        115                 120                 125

Arg Thr Arg Phe Arg Thr Thr Asp Asp Ala Leu Leu Thr Gly Val Pro
    130                 135                 140

Leu Met Ala Ile Pro Gly Phe Glu Leu Ala Thr Leu Ser Val Tyr Ala
145                 150                 155                 160

Gln Ser Ala Asn Leu His Leu Ala Leu Leu Arg Asp Ala Val Phe Phe
                165                 170                 175

Gly Glu Arg Trp Gly Leu Thr Gln Thr Asn Ile Asn Asp Leu Tyr Ser
            180                 185                 190

Arg Leu Lys Asn Ser Ile Arg Asp Tyr Thr Asn His Cys Val Arg Phe
        195                 200                 205

Tyr Asn Ile Gly Leu Gly Asn Leu Asn Val Ile Arg Pro Glu Tyr Tyr
    210                 215                 220

Arg Phe Gln Arg Glu Leu Thr Ile Ser Val Leu Asp Leu Val Ala Leu
225                 230                 235                 240

Phe Pro Asn Tyr Asp Ile Arg Thr Tyr Pro Ile Pro Thr Lys Ser Gln
                245                 250                 255
```

```
Leu Thr Arg Glu Ile Tyr Thr Asp Pro Ile Ile Ser Pro Gly Ala Gln
            260                 265                 270

Ala Gly Tyr Thr Leu Gln Asp Val Leu Arg Glu Pro His Leu Met Asp
        275                 280                 285

Phe Leu Asn Arg Leu Ile Ile Tyr Thr Gly Glu Tyr Arg Gly Ile Arg
    290                 295                 300

His Trp Ala Gly His Glu Val Glu Ser Ser Arg Thr Gly Met Met Thr
305                 310                 315                 320

Asn Ile Arg Phe Pro Leu Tyr Gly Thr Ala Ala Thr Ala Glu Pro Thr
                325                 330                 335

Arg Phe Ile Thr Pro Ser Thr Phe Pro Gly Leu Asn Leu Phe Tyr Arg
            340                 345                 350

Thr Leu Ser Ala Pro Ile Phe Arg Asp Glu Pro Gly Ala Asn Ile Ile
        355                 360                 365

Ile Arg Tyr Arg Thr Ser Leu Val Glu Gly Val Gly Phe Ile Gln Pro
    370                 375                 380

Asn Asn Gly Glu Gln Leu Tyr Arg Val Arg Gly Thr Leu Asp Ser Leu
385                 390                 395                 400

Asp Gln Leu Pro Leu Glu Gly Glu Ser Ser Leu Thr Glu Tyr Ser His
                405                 410                 415

Arg Leu Cys His Val Arg Phe Ala Gln Ser Leu Arg Asn Ala Glu Pro
            420                 425                 430

Leu Asp Tyr Ala Arg Val Pro Met Phe Ser Trp Thr His Arg Ser Ala
        435                 440                 445

Thr Pro Thr Asn Thr Ile Asp Pro Asp Val Ile Thr Gln Ile Pro Leu
    450                 455                 460

Val Lys Ala His Thr Leu Gln Ser Gly Thr Thr Val Val Lys Gly Pro
465                 470                 475                 480

Gly Phe Thr Gly Gly Asp Ile Leu Arg Arg Thr Ser Gly Gly Pro Phe
                485                 490                 495

Ala Phe Ser Asn Val Asn Leu Asp Trp Asn Leu Ser Gln Arg Tyr Arg
            500                 505                 510

Ala Arg Ile Arg Tyr Ala Ser Thr Thr Asn Leu Arg Met Tyr Val Thr
        515                 520                 525

Ile Ala Gly Glu Arg Ile Phe Ala Gly Gln Phe Asn Lys Thr Met Asn
    530                 535                 540

Thr Gly Asp Pro Leu Thr Phe Gln Ser Phe Ser Tyr Ala Thr Ile Asp
545                 550                 555                 560

Thr Ala Phe Thr Phe Pro Thr Lys Ala Ser Ser Leu Thr Val Gly Ala
                565                 570                 575

Asp Thr Phe Ser Ser Gly Asn Glu Val Tyr Val Asp Arg Phe Glu Leu
            580                 585                 590

Ile Pro Val Thr Ala Thr Phe Glu Ala Glu Tyr Asp Leu Glu Lys Ala
        595                 600                 605

Gln Lys Ala Val Asn Ala Leu Phe Thr Ser Ser Asn Gln Ile Gly Leu
    610                 615                 620

Lys Thr Asp Val Thr Asp Tyr His Ile Asp Lys Val Ser Asn Leu Val
625                 630                 635                 640

Glu Cys Leu Ser Asp Glu Phe Cys Leu Asp Glu Lys Arg Glu Leu Ser
                645                 650                 655

Glu Lys Val Lys His Ala Lys Arg Leu Cys Asp Glu Arg Asn Leu Leu
            660                 665                 670

Gln Asp Pro Asn Phe Arg Gly Ile Asn Arg Gln Pro Asp Arg Gly Trp
```

```
        675                 680                 685

Arg Gly Ser Thr Asp Ile Thr Ile Gln Gly Gly Asp Asp Val Phe Lys
    690                 695                 700

Glu Asn Tyr Val Thr Leu Pro Gly Thr Phe Asp Glu Cys Tyr Pro Thr
705                 710                 715                 720

Tyr Leu Tyr Gln Lys Ile Asp Glu Ser Lys Leu Lys Ala Tyr Thr Arg
                725                 730                 735

Tyr Glu Leu Arg Gly Tyr Ile Glu Asp Ser Gln Asp Leu Glu Ile Tyr
            740                 745                 750

Leu Ile Arg Tyr Asn Ala Lys His Glu Thr Val Asn Val Pro Gly Thr
        755                 760                 765

Gly Ser Leu Trp Pro Leu Ser Ala Gln Ser Pro Ile Gly Lys Cys Gly
    770                 775                 780

Glu Pro Asn Arg Cys Ala Thr His Leu Glu Trp Asn Pro Asp Leu Asp
785                 790                 795                 800

Cys Ser Cys Arg Asp Gly Glu Lys Cys Ala His His Ser His His Phe
                805                 810                 815

Ser Leu Asp Ile Asp Val Gly Cys Thr Asp Leu Asn Glu Asp Leu Gly
            820                 825                 830

Val Trp Val Ile Phe Lys Ile Lys Thr Gln Asp Gly His Ala Arg Leu
        835                 840                 845

Gly Asn Leu Glu Phe Leu Glu Glu Lys Pro Leu Val Gly Glu Ala Leu
    850                 855                 860

Ala Arg Val Lys Arg Ala Glu Lys Lys Trp Arg Asp Lys Arg Glu Lys
865                 870                 875                 880

Leu Glu Leu Glu Thr Asn Ile Val Tyr Lys Glu Ala Lys Lys Ser Val
                885                 890                 895

Asp Ala Leu Phe Val Asn Ser Gln Tyr Asp Arg Leu Gln Ala Asp Thr
            900                 905                 910

Asn Ile Ala Ile Ile His Ala Ala Asp Lys Arg Val His Ser Ile Arg
        915                 920                 925

Glu Ala Tyr Leu Pro Glu Leu Ser Val Ile Pro Gly Val Asn Ala Ala
    930                 935                 940

Ile Phe Glu Glu Leu Glu Gly Arg Ile Phe Thr Ala Tyr Ser Leu Tyr
945                 950                 955                 960

Asp Ala Arg Asn Val Ile Lys Asn Gly Asp Phe Asn Asn Gly Leu Ser
                965                 970                 975

Cys Trp Asn Val Lys Gly His Val Asp Val Glu Glu Gln Asn Asn His
            980                 985                 990

Arg Ser Val Leu Val Val Pro Glu  Trp Glu Ala Glu Val  Ser Gln Glu
        995                 1000                1005

Val Arg  Val Cys Pro Gly Arg  Gly Tyr Ile Leu Arg  Val Thr Ala
    1010                 1015                 1020

Tyr Lys  Glu Gly Tyr Gly Glu  Gly Cys Val Thr Ile  His Glu Ile
    1025                 1030                 1035

Glu Asp  Asn Thr Asp Glu Leu  Lys Phe Ser Asn Cys  Val Glu Glu
    1040                 1045                 1050

Glu Ile  Tyr Pro Asn Asn Thr  Val Thr Cys Asn Asp  Tyr Thr Ala
    1055                 1060                 1065

Thr Gln  Glu Glu Tyr Glu Gly  Thr Tyr Thr Ser Arg  Asn Arg Gly
    1070                 1075                 1080

Tyr Asp  Gly Ala Tyr Glu Ser  Asn Ser Ser Val Pro  Ala Asp Tyr
    1085                 1090                 1095
```

```
Ala Ser  Ala Tyr Glu Glu Lys  Ala Tyr Thr Asp Gly  Arg Arg Asp
    1100                1105                1110

Asn Thr  Cys Glu Ser Asn Arg  Gly Tyr Gly Asp Tyr  Thr Pro Leu
    1115                1120                1125

Pro Ala  Gly Tyr Val Thr Lys  Glu Leu Glu Tyr Phe  Pro Glu Thr
    1130                1135                1140

Asp Lys  Val Trp Ile Glu Ile  Gly Glu Thr Glu Gly  Thr Phe Ile
    1145                1150                1155

Val Asp  Ser Val Glu Leu Leu  Leu Met Glu Glu
    1160                1165


<210> SEQ ID NO 5
<211> LENGTH: 1176
<212> TYPE: DNA
<213> ORGANISM: Artificial sequence
<220> FEATURE:
<223> OTHER INFORMATION: Synthetic polynucleotide

<400> SEQUENCE: 5

atgcaaaaac tcattaactc agtgcaaaac tatgcctggg gcagcaaaac ggcgttgact     60

gaactttacg gtatggaaaa tccgtccagc cagccgatgg ccgagctgtg gatgggcgca    120

catccgaaaa gcagttcacg agtgcagaat gccgccggag atatcgtttc actgcgtgat    180

gtgattgaga gtgataaatc gactctgctc ggagaggccg ttgccaaacg ctttggcgaa    240

ctgcctttcc tgttcaaagt attatgcgca gcacagccac tctccattca ggttcatcca    300

aacaaacaca attctgaaat cggttttgcc aaagaaaatg ccgcaggtat cccgatggat    360

gccgccgagc gtaactataa agatcctaac cacaagccgg agctggtttt tgcgctgacg    420

cctttccttg cgatgaacgc gtttcgtgaa ttttccgaga ttgtctccct actccagccg    480

gtcgcaggtg cacatccggc gattgctcac tttttacaac agcctgatgc cgaacgttta    540

agcgaactgt tcgccagcct gttgaatatg cagggtgaag aaaaatcccg cgcgctggcg    600

attttaaaat cggccctcga tagccagcag ggtgaaccgt ggcaaacgat tcgtttaatt    660

tctgaatttt acccggaaga cagcggtctg ttctccccgc tattgctgaa tgtggtgaaa    720

ttgaaccctg gcgaagcgat gttcctgttc gctgaaacac cgcacgctta cctgcaaggc    780

gtggcgctgg aagtgatggc aaactccgat aacgtgctgc gtgcgggtct gacgcctaaa    840

tacattgata ttccggaact ggttgccaat gtgaaattcg aagccaaacc ggctaaccag    900

ttgttgaccc agccggtgaa acaaggtgca gaactggact tcccgattcc agtggacgat    960

tttgccttct cgctgcacga ccttagtgat aaagaaacca ccattagcca gcagagtgcc   1020

gccattttgt tctgcgtcga aggcgatgca acgttgtgga aaggttctca gcagttacag   1080

cttaaaccgg gtgaatcagc gtttattgcc gccaacgaat caccggtgac tgtcaaaggc   1140

cacggccgtt tagcgcgtgt ttacaacaag ctgtaa                             1176


<210> SEQ ID NO 6
<211> LENGTH: 391
<212> TYPE: PRT
<213> ORGANISM: Artificial sequence
<220> FEATURE:
<223> OTHER INFORMATION: Synthetic polypeptide

<400> SEQUENCE: 6

Met Gln Lys Leu Ile Asn Ser Val Gln Asn Tyr Ala Trp Gly Ser Lys
1               5                   10                  15
```

```
Thr Ala Leu Thr Glu Leu Tyr Gly Met Glu Asn Pro Ser Ser Gln Pro
            20                  25                  30

Met Ala Glu Leu Trp Met Gly Ala His Pro Lys Ser Ser Ser Arg Val
        35                  40                  45

Gln Asn Ala Ala Gly Asp Ile Val Ser Leu Arg Asp Val Ile Glu Ser
    50                  55                  60

Asp Lys Ser Thr Leu Leu Gly Glu Ala Val Ala Lys Arg Phe Gly Glu
65                  70                  75                  80

Leu Pro Phe Leu Phe Lys Val Leu Cys Ala Ala Gln Pro Leu Ser Ile
                85                  90                  95

Gln Val His Pro Asn Lys His Asn Ser Glu Ile Gly Phe Ala Lys Glu
            100                 105                 110

Asn Ala Ala Gly Ile Pro Met Asp Ala Ala Glu Arg Asn Tyr Lys Asp
        115                 120                 125

Pro Asn His Lys Pro Glu Leu Val Phe Ala Leu Thr Pro Phe Leu Ala
    130                 135                 140

Met Asn Ala Phe Arg Glu Phe Ser Glu Ile Val Ser Leu Leu Gln Pro
145                 150                 155                 160

Val Ala Gly Ala His Pro Ala Ile Ala His Phe Leu Gln Gln Pro Asp
                165                 170                 175

Ala Glu Arg Leu Ser Glu Leu Phe Ala Ser Leu Leu Asn Met Gln Gly
            180                 185                 190

Glu Glu Lys Ser Arg Ala Leu Ala Ile Leu Lys Ser Ala Leu Asp Ser
        195                 200                 205

Gln Gln Gly Glu Pro Trp Gln Thr Ile Arg Leu Ile Ser Glu Phe Tyr
    210                 215                 220

Pro Glu Asp Ser Gly Leu Phe Ser Pro Leu Leu Leu Asn Val Val Lys
225                 230                 235                 240

Leu Asn Pro Gly Glu Ala Met Phe Leu Phe Ala Glu Thr Pro His Ala
                245                 250                 255

Tyr Leu Gln Gly Val Ala Leu Glu Val Met Ala Asn Ser Asp Asn Val
            260                 265                 270

Leu Arg Ala Gly Leu Thr Pro Lys Tyr Ile Asp Ile Pro Glu Leu Val
        275                 280                 285

Ala Asn Val Lys Phe Glu Ala Lys Pro Ala Asn Gln Leu Leu Thr Gln
    290                 295                 300

Pro Val Lys Gln Gly Ala Glu Leu Asp Phe Pro Ile Pro Val Asp Asp
305                 310                 315                 320

Phe Ala Phe Ser Leu His Asp Leu Ser Asp Lys Glu Thr Thr Ile Ser
                325                 330                 335

Gln Gln Ser Ala Ala Ile Leu Phe Cys Val Glu Gly Asp Ala Thr Leu
            340                 345                 350

Trp Lys Gly Ser Gln Gln Leu Gln Leu Lys Pro Gly Glu Ser Ala Phe
        355                 360                 365

Ile Ala Ala Asn Glu Ser Pro Val Thr Val Lys Gly His Gly Arg Leu
    370                 375                 380

Ala Arg Val Tyr Asn Lys Leu
385                 390
```

<210> SEQ ID NO 7
<211> LENGTH: 1176
<212> TYPE: DNA
<213> ORGANISM: Artificial sequence
<220> FEATURE:
<223> OTHER INFORMATION: Synthetic polynucleotide

<400> SEQUENCE: 7
atgcaaaaac tcattaactc agtgcaaaac tatgcctggg gcagcaaaac ggcgttgact 60
gaactttacg gtatggaaaa tccgtccagc cagccgatgg ccgagctgtg gatgggcgca 120
catccgaaaa gcagttcacg agtgcagaat gccgccggag atatcgtttc actgcgtgat 180
gtgattgaga gtgataaatc gactctgctc ggagaggccg ttgccaaacg ctttggcgaa 240
ctgcctttcc tgttcaaagt attgtgcgca gcacagccac tctccattca ggttcatcca 300
aacaaacaca attctgaaat cggttttgcc aaagaaaatg ccgcaggtat cccgatggat 360
gccgccgagc gtaactataa agatcctaac cacaagccgg agctggtttt tgcgctgacg 420
cctttccttg cgatgaacgc gtttcgtgaa ttttccgaga ttgtctccct actccagccg 480
gtcgcaggtg cacatccggc gattgctcac tttttacaac agcctgatgc cgaacgttta 540
agcgaactgt tcgccagcct gttgaatatg cagggtgaag aaaaatcccg cgcgctggcg 600
attttaaaat cggccctcga tagccagcag ggtgaaccgt ggcaaacgat tcgtttaatt 660
tctgaatttt acccggaaga cagcggtctg ttctccccgc tattgctgaa tgtggtgaaa 720
ttgaaccctg gcgaagcgat gttcctgttc gctgaaacac cgcacgctta cctgcaaggc 780
gtggcgctgg aagtgatggc aaactccgat aacgtgctgc gtgcgggtct gacgcctaaa 840
tacattgata ttccggaact ggttgccaat gtgaaattcg aagccaaacc ggctaaccag 900
ttgttgaccc agccggtgaa acaaggtgca gaactggact tcccgattcc agtggacgat 960
tttgccttct cgctgcacga ccttagtgat aaagaaacca ccattagcca gcagagtgcc 1020
gccattttgt tctgcgtcga aggcgatgca acgttgtgga aaggttctca gcagttacag 1080
cttaaaccgg gtgaatcagc gtttattgcc gccaacgaat caccggtgac tgtcaaaggc 1140
cacggccgtt tagcgcgtgt ttacaacaag ctgtaa 1176

<210> SEQ ID NO 8
<211> LENGTH: 10641
<212> TYPE: DNA
<213> ORGANISM: Artificial sequence
<220> FEATURE:
<223> OTHER INFORMATION: Synthetic polynucleotide

<400> SEQUENCE: 8
gaattcatta tgtggtctag gtaggttcta tatataagaa aacttgaaat gttctaaaaa 60
aaaattcaag cccatgcatg attgaagcaa acggtatagc aacggtgtta acctgatcta 120
gtgatctctt gcaatcctta acggccacct accgcaggta gcaaacggcg tccccctcct 180
cgatatctcc gcggcgacct ctggcttttt ccgcggaatt gcgcggtggg gacggattcc 240
acgagaccgc gacgcaaccg cctctcgccg ctgggcccca caccgctcgg tgccgtagcc 300
tcacgggact ctttctccct cctcccccgt tataaattgg cttcatcccc tccttgcctc 360
atccatccaa atcccagtcc ccaatcccat cccttcgtag gagaaattca tcgaagctaa 420
gcgaatcctc gcgatcctct caaggtactg cgagttttcg atccccctct cgacccctcg 480
tatgtttgtg tttgtcgtag cgtttgatta ggtatgcttt ccctgtttgt gttcgtcgta 540
gcgtttgatt aggtatgctt tccctgttcg tgttcatcgt agtgtttgat taggtcgtgt 600
gaggcgatgg cctgctcgcg tccttcgatc tgtagtcgat ttgcgggtcg tggtgtagat 660
ctgcgggctg tgatgaagtt atttggtgtg atctgctcgc ctgattctgc gggttggctc 720
gagtagatat gatggttgga ccggttggtt cgtttaccgc gctagggttg ggctgggatg 780

-continued

```
atgttgcatg cgccgttgcg cgtgatcccg cagcaggact tgcgtttgat tgccagatct    840
cgttacgatt atgtgatttg gtttggactt tttagatctg tagcttctgc ttatgtgcca    900
gatgcgccta ctgctcatat gcctgatgat aatcataaat ggctgtggaa ctaactagtt    960
gattgcggag tcatgtatca gctacaggtg tagggactag ctacaggtgt agggacttgc   1020
gtctaattgt ttggtccttt actcatgttg caattatgca atttagttta gattgtttgt   1080
tccactcatc taggctgtaa aagggacact gcttagattg ctgtttaatc tttttagtag   1140
attatattat attggtaact tattacccct attacatgcc atacgtgact tctgctcatg   1200
cctgatgata atcatagatc actgtggaat taattagttg attgttgaat catgtttcat   1260
gtacatacca cggcacaatt gcttagttcc ttaacaaatg caaattttac tgatccatgt   1320
atgatttgcg tggttctcta atgtgaaata ctatagctac ttgttagtaa gaatcaggtt   1380
cgtatgctta atgctgtatg tgccttctgc tcatgcctga tgataatcat atatcactgg   1440
aattaattag ttgatcgttt aatcatatat caagtacata ccatgccaca atttttagtc   1500
acttaaccca tgcagattga actggtccct gcatgttttg ctaaattgtt ctattctgat   1560
tagaccatat atcatgtatt ttttttggt aatggttctc ttattttaaa tgctatatag   1620
ttctggtact tgttagaaag atctgcttca tagtttagtt gcctatccct cgaattagga   1680
tgctgagcag ctgatcctat agctttgttt catgtatcaa ttcttttgtg ttcaacagtc   1740
agtttttgtt agattcattg taacttatgg tcgcttactc ttctggtcct caatgcttgc   1800
agggatccta aaccatggag atcaacaacc agaaccagtg cgtgccgtac aactgcctta   1860
acaaccccga gtccgagatc ctgaacgtgg ccatcttctc cagcgagcag gtcgcggaga   1920
tccacctcaa gatcacgcgc ctgatcctcg agaacttcct gccgggcggc tccttcgctt   1980
tcggcctgtt cgacctcatc tggggcatct tcaacgagga ccagtggagc gcgttcctca   2040
ggcaggtgga ggagctgatc aaccagcgca tcacggagtt cgccaggggc caggctatcc   2100
agcggctggt gggcttcggc aggtcctacg acgagtacat cctggccctc aaggagtggg   2160
agaacgaccc cgacaacccg gccagcaagg agcgcgtgag gacccgcttc aggaccaccg   2220
acgacgctct cctgacgggc gtccccctca tggctatccc gggcttcgag ctggccaccc   2280
tctcggtgta cgctcagtcg gccaacctgc acctcgccct cctgcgggac gctgtgttct   2340
tcggcgagag gtggggcctg acccagacga acatcaacga cctctactcc aggctgaaga   2400
acagcatccg cgactacacg aaccactgcg tgcgcttcta caacatcggc ctgggcaacc   2460
tcaacgtcat caggccggag tactaccgct tccagaggga gctgaccatc agcgtgctgg   2520
acctcgtcgc cctgttcccc aactacgaca tccgcacgta cccgatccca accaagtccc   2580
agctcacgag ggagatctac accgacccga tcatctcgcc gggcgcccag gccggctaca   2640
ccctgcagga cgtcctgagg gagccccacc tgatggactt cctgaacagg ctcatcatct   2700
acaccggcga gtacaggggc atcaggcact gggcgggcca cgaggtggag tccagcagga   2760
cgggcatgat gaccaacatc cgcttcccgc tctacggcac cgcggccacg gccgagccaa   2820
cccgcttcat cacgccgtcc accttccccg gcctgaacct cttctacagg accctgtcgg   2880
ctcccatctt ccgcgacgag ccgggcgcga acatcatcat ccgctacagg acctccctcg   2940
tggagggcgt cggcttcatc cagccgaaca acggcgagca gctgtaccgc gtgaggggca   3000
cgctggacag cctggaccag ctcccactgg agggcgagtc cagcctcacc gagtactcgc   3060
acaggctgtg ccacgtcagg ttcgcccaga gcctcaggaa cgcggagccc ctggactacg   3120
ccagggtgcc catgttcagc tggacccaca ggtcggctac ccccaccaac accatcgacc   3180
```

```
cagacgtgat cacgcagatc ccgctcgtca aggcccacac cctgcagtcg ggcaccaccg   3240
tggtcaaggg ccccggcttc acgggcggcg acatcctgag gaggacctcc ggcggcccat   3300
tcgccttcag caacgtcaac ctcgactgga acctgtccca gcgctacagg gcgcgcatca   3360
ggtacgccag caccacgaac ctgcgcatgt atgtgaccat cgcgggcgag aggatcttcg   3420
ccggccagtt caacaagacg atgaacaccg gcgacccgct caccttccag tccttcagct   3480
acgcgacgat cgacaccgcc ttcacgttcc ccacgaaggc ctccagcctg accgtgggcg   3540
ccgacacctt ctccagcggc aacgaggtct acgtggaccg cttcgagctg atcccggtga   3600
cggcgacctt cgaggccgag tacgacctgg agaaggccca gaaggcggtc aacgccctct   3660
tcacctccag caaccagatc ggcctgaaga cggacgtgac cgactaccac atcgacaagg   3720
tgtccaacct cgtcgagtgc ctgagcgacg agttctgcct cgacgagaag agggagctgt   3780
ccgagaaggt caagcacgcc aagcgcctct gcgacgagag gaacctcctg caggacccga   3840
acttcagggg aatcaaccgc cagccggaca ggggctggag gggcagcacc gacatcacca   3900
tccagggcgg cgacgacgtg ttcaaggaga actacgtcac gctcccgggc accttcgacg   3960
agtgctaccc cacgtacctg taccagaaga tcgacgagtc caagctcaag gcctacaccc   4020
gctacgagct gaggggatac atcgaggaca gccaggacct cgagatctac ctgatccgct   4080
acaacgcgaa gcacgagacg gtgaacgtcc ccggcacggg ctccctgtgg cccctctcgg   4140
ctcagtcgcc gatcggcaag tgcggcgagc ccaacaggtg cgccacccac ctcgagtgga   4200
acccggacct ggactgctcc tgccgggacg gcgagaagtg cgctcaccac tcccaccact   4260
tcagcctgga catcgacgtg ggctgcacgg acctcaacga ggacctgggc gtgtgggtca   4320
tcttcaaaat caagacgcag gacggccacg ctaggctggg caacctcgag ttcctggagg   4380
agaagccgct ggtgggcgag gctctggcca gggtcaagag ggcggagaag aagtggcgcg   4440
acaagaggga gaagctggag ctggagacga acatcgtcta caaggaggcc aagaagtccg   4500
tggacgcgct cttcgtcaac agccagtacg acaggctgca ggcggacacc aacatcgcca   4560
tcatccacgc cgcggacaag cgcgtgcact ccatcaggga ggcctacctc cccgagctga   4620
gcgtgatccc gggcgtcaac gctgccatct tcgaggagct ggagggccgc atcttcaccg   4680
cctactccct gtacgacgcg aggaacgtca tcaagaacgg cgacttcaac aacggcctca   4740
gctgctggaa cgtgaagggc cacgtggacg tcgaggagca gaacaaccac cgctcggtgc   4800
tggtggtccc cgagtgggag gctgaggtca gccaggaggt gcgcgtctgc ccgggcaggg   4860
gatacatcct ccgcgtgacc gcgtacaagg agggctacgg cgagggctgc gtcacgatcc   4920
acgagatcga ggacaacacc gacgagctga agttctccaa ctgcgtggag gaggagatct   4980
acccgaacaa cacggtcacc tgcaacgact acacggccac ccaggaggag tacgagggca   5040
cgtacacgtc gaggaacagg ggctacgacg gcgcttacga gtccaacagc tcggtgccgg   5100
ccgactacgc tagcgcgtac gaggagaagg cctacacgga cggccgcagg gacaacacct   5160
gcgagtcgaa caggggctac ggcgactaca cgccgctccc ggccggctac gtgaccaagg   5220
agctggagta cttcccggag acggacaagg tctggatcga gatcggcgag acggagggca   5280
ccttcatcgt ggactcagtc gagctgctgc tcatggagga gtaggagctc gccaacagtc   5340
gttgaagctg ctgctgtatc tgggttatct agtgtctctg cctttgccca aggatagtgc   5400
tgtctttcaa agtatttgta tcgtttgtgt cgtgagtcgt gactgagctg gtttcaagga   5460
ccagttgtgt tctcgttacc caaaactatc gtgcgaccgc atatggctta atcatgaata   5520
```

aatgttgttt gaatttaaac tattcgctga atattgttgt tttttgtcat gtcagttaat 5580
gttactaaat tggttgcctt ctaatttttg tttactggtg tttgtcgcac cttatctttt 5640
tactgtatgt ttacttcagg ttctggcagt ctcatttttt gtgactagtt aaaacttaca 5700
gctaaaaaaa tgcagttttt aattttaatt tgaagtttga ttagagctat tgatacccgg 5760
accatcaggt taggttagtt gtgcatagaa tcataaatat taatcatgtt ttctatgaat 5820
taagtcaaac ttgaaagtct ggctgaatat agtttctatg aatcatattg atatacatgt 5880
ttgattattt gttttgctat tagctattta ctttggtgaa tctatatagg cttatgcaga 5940
accttttttt ttgttctata tatccatatc ctagtactca gtagctctat gttttctgga 6000
gactagtggc ttgctttttc gtatgtctaa tttttttgctt gaccattgca aaacaaaaat 6060
tacctagtgt aatctctttt tataataatc ttgtaatgcg tctacctata ggtcaaagta 6120
ggttttgttt ggaaccctta gagctaactg ttagctagtt gataaattat tagctgagtt 6180
aagctagcta atgaactagt tttgatatta gctgaggatg tttgaaacct aataattatt 6240
ttttattagc taactatact aaattttagt agagagattc caaacaggag ttaacatggg 6300
atcagattgg ctatgcgttt gcaatcccat actaattagc taacggaccg ctaattagct 6360
aacgatcgct taattaagct tgcatgcctg cagtgcagcg tgacccggtc gtgcccctct 6420
ctagagataa tgagcattgc atgtctaagt tataaaaaat taccacatat ttttttgtc 6480 acacttgttt gaagtgcagt ttatctatct ttatacatat atttaaactt tactctacga 6540
ataatataat ctatagtact acaataatat cagtgtttta gagaatcata taaatgaaca 6600
gttagacatg gtctaaagga caattgagta ttttgacaac aggactctac agttttatct 6660
ttttagtgtg catgtgttct ccttttttt tgcaaatagc ttcacctata taatacttca 6720
tccattttat tagtacatcc atttagggtt tagggttaat ggtttttata gactaatttt 6780
tttagtacat ctattttatt ctattttagc ctctaaatta agaaaactaa aactctattt 6840 tagtttttt atttaataat ttagatataa aatagaataa aataaagtga ctaaaaatta 6900
aacaaatacc ctttaagaaa ttaaaaaaac taaggaaaca tttttcttgt ttcgagtaga 6960
taatgccagc ctgttaaacg ccgccgacga gtctaacgga caccaaccag cgaaccagca 7020
gcgtcgcgtc gggccaagcg aagcagacgg cacggcatct ctgtcgctgc ctctggaccc 7080
ctctcgagag ttccgctcca ccgttggact tgctccgctg tcggcatcca gaaattgcgt 7140
ggcggagcgg cagacgtgag ccggcacggc aggcggcctc ctcctcctct cacggcaccg 7200
gcagctacgg gggattcctt tcccaccgct ccttcgcttt cccttcctcg cccgccgtaa 7260
taaatagaca cccccctccac accctctttc cccaacctcg tgttgttcgg agcgcacaca 7320
cacacaacca gatctccccc aaatccaccc gtcggcacct ccgcttcaag gtacgccgct 7380
cgtcctcccc cccccccct ctctaccttc tctagatcgg cgttccggtc catagttagg 7440
gcccggtagt tctacttctg ttcatgtttg tgttagatcc gtgtttgtgt tagatccgtg 7500
ctgttagcgt tcgtacacgg atgcgacctg tacgtcagac acgttctgat tgctaacttg 7560
ccagtgtttc tctttgggga atcctgggat ggctctagcc gttccgcaga cgggatcgat 7620
ttcatgattt tttttgtttc gttgcatagg gtttggtttg cccttttcct ttatttcaat 7680
atatgccgtg cacttgtttg tcgggtcatc ttttcatgct tttttttgtc ttggttgtga 7740
tgatgtggtc tggttgggcg gtcgttctag atcggagtag aattctgttt caaactacct 7800
ggtggattta ttaattttgg atctgtatgt gtgtgccata catattcata gttacgaatt 7860
gaagatgatg gatggaaata tcgatctagg ataggtatac atgttgatgc gggttttact 7920

```
gatgcatata cagagatgct ttttgttcgc ttggttgtga tgatgtggtg tggttgggcg   7980
gtcgttcatt cgttctagat cggagtagaa tactgtttca aactacctgg tgtatttatt   8040
aattttggaa ctgtatgtgt gtgtcataca tcttcatagt tacgagttta agatggatgg   8100
aaatatcgat ctaggatagg tatacatgtt gatgtgggtt ttactgatgc atatacatga   8160
tggcatatgc agcatctatt catatgctct aaccttgagt acctatctat tataataaac   8220
aagtatgttt tataattatt ttgatcttga tatacttgga tgatggcata tccagcagct   8280
atatctggat ttttttagcc ctgccttcat acgctattta tttgcttggt actgtttctt   8340
ttgtcgttgc tcaccctgtt gtttggtgtt acttctgcag ggatctccga tcatgcaaaa   8400
actcattaac tcagtgcaaa actatgcctg gggcagcaaa acggcgttga ctgaacttta   8460
cggtatggaa aatccgtcca gccagccgat ggccgagctg tggatgggcg cacatccgaa   8520
aagcagttca cgagtgcaga atgccgccgg agatatcgtt tcactgcgtg atgtgattga   8580
gagtgataaa tcgactctgc tcggagaggc cgttgccaaa cgctttggcg aactgccttt   8640
cctgttcaaa gtattgtgcg cagcacagcc actctccatt caggttcatc caaacaaaca   8700
caattctgaa atcggttttg ccaaagaaaa tgccgcaggt atcccgatgg atgccgccga   8760
gcgtaactat aaagatccta accacaagcc ggagctggtt tttgcgctga cgcctttcct   8820
tgcgatgaac gcgtttcgtg aattttccga gattgtctcc ctactccagc cggtcgcagg   8880
tgcacatccg gcgattgctc actttttaca acagcctgat gccgaacgtt taagcgaact   8940
gttcgccagc ctgttgaata tgcagggtga agaaaaatcc cgcgcgctgg cgattttaaa   9000
atcggccctc gatagccagc agggtgaacc gtggcaaacg attcgtttaa tttctgaatt   9060
ttacccggaa gacagcggtc tgttctcccc gctattgctg aatgtggtga aattgaaccc   9120
tggcgaagcg atgttcctgt tcgctgaaac accgcacgct tacctgcaag gcgtggcgct   9180
ggaagtgatg gcaaactccg ataacgtgct gcgtgcgggt ctgacgccta aatacattga   9240
tattccggaa ctggttgcca atgtgaaatt cgaagccaaa ccggctaacc agttgttgac   9300
ccagccggtg aaacaaggtg cagaactgga cttcccgatt ccagtggacg attttgcctt   9360
ctcgctgcac gaccttagtg ataaagaaac caccattagc cagcagagtg ccgccatttt   9420
gttctgcgtc gaaggcgatg caacgttgtg gaaaggttct cagcagttac agcttaaacc   9480
gggtgaatca gcgtttattg ccgccaacga atcaccggtg actgtcaaag gccacggccg   9540
tttagcgcgt gtttacaaca agctgtaaga gcttactgaa aaaattaaca tctcttgcta   9600
agctgggtca tgggtcgttt aagctgccga tgtgcctgcg tcgtctggtg ccctctctcc   9660
atatggaggt tgtcaaagta tctgctgttc gtgtcatgag tcgtgtcagt gttggtttaa   9720
taatggaccg gttgtgttgt gtgtgcgtac tacccagaac tatgacaaat catgaataag   9780
tttgatgttt gaaattaaag cctgtgctca ttatgttctg tctttcagtt gtctcctaat   9840
atttgcctcc aggtactggc tatctaccgt ttcttactta ggaggtgttt gaatgcacta   9900
aaactaatag ttagtggcta aaattagtta aaacatccaa acaccatagc taatagttga   9960
actattagct atttttggaa aattagttaa tagtgaggta gttatttgtt agctagctaa  10020
ttcaactaac aatttttagc caactaacaa ttagtttcag tgcattcaaa caccccctta  10080
atgttaacgt ggttctatct accgtctcct aatatatggt tgattgttcg gtttgttgct  10140
atgctattgg gttctgattg ctgctagttc ttgctgaatc cagaagttct cgtagtatag  10200
ctcagattca tattatttat ttgagtgata agtgatccag gttattacta tgttagctag  10260
```

```
gttttttta caaggataaa ttatctgtga tcataattct tatgaaagct ttatgtttcc  10320

tggaggcagt ggcatgcaat gcatgacagc aacttgatca caccagctga ggtagatacg  10380

gtaacaaggt tcttaaatct gttcaccaaa tcattggaga acacacatac acattcttgc  10440

cagtcttggt tagagaaatt tcatgacaaa atgccaaagc tgtcttgact cttcactttt  10500

ggccatgagt cgtgacttag tttggtttaa tggaccggtt ctcctagctt gttctactca  10560

aaactgttgt tgatgcgaat aagttgtgat ggttgatctc tggattttgt tttgctctca  10620

atagtggacg agattagata g                                            10641
```

```
<210> SEQ ID NO 9
<211> LENGTH: 10641
<212> TYPE: DNA
<213> ORGANISM: Artificial sequence
<220> FEATURE:
<223> OTHER INFORMATION: Synthetic polynucleotide

<400> SEQUENCE: 9

gaattcatta tgtggtctag gtaggttcta tatataagaa aacttgaaat gttctaaaaa     60

aaaattcaag cccatgcatg attgaagcaa acggtatagc aacggtgtta acctgatcta    120

gtgatctctt gcaatcctta acggccacct accgcaggta gcaaacggcg tccccctcct    180

cgatatctcc gcggcgacct ctggcttttt ccgcggaatt gcgcggtggg gacggattcc    240

acgagaccgc gacgcaaccg cctctcgccg ctgggcccca caccgctcgg tgccgtagcc    300

tcacgggact ctttctccct cctcccccgt tataaattgg cttcatcccc tccttgcctc    360

atccatccaa atcccagtcc ccaatcccat cccttcgtag gagaaattca tcgaagctaa    420

gcgaatcctc gcgatcctct caaggtactg cgagttttcg atccccctct cgacccctcg    480

tatgtttgtg tttgtcgtag cgtttgatta ggtatgcttt ccctgtttgt gttcgtcgta    540

gcgtttgatt aggtatgctt tccctgttcg tgttcatcgt agtgtttgat taggtcgtgt    600

gaggcgatgg cctgctcgcg tccttcgatc tgtagtcgat ttgcgggtcg tggtgtagat    660

ctgcgggctg tgatgaagtt atttggtgtg atctgctcgc ctgattctgc tggttggctc    720

gagtagatat gatggttgga ccggttggtt cgtttaccgc gctagggttg ggctgggatg    780

atgttgcatg cgccgttgcg cgtgatcccg cagcaggact tgcgtttgat tgccagatct    840

cgttacgatt atgtgatttg gtttggactt tttagatctg tagcttctgc ttatgtgcca    900

gatgcgccta ctgctcatat gcctgatgat aatcataaat ggctgtggaa ctaactagtt    960

gattgcggag tcatgtatca gctacaggtg tagggactag ctacaggtgt agggacttgc   1020

gtctaattgt ttggtccttt actcatgttg caattatgca atttagttta gattgtttgt   1080

tccactcatc taggctgtaa aagggacact gcttagattg ctgtttaatc tttttagtag   1140

attatattat attggtaact tattacccct attacatgcc atacgtgact tctgctcatg   1200

cctgatgata atcatagatc actgtggaat taattagttg attgttgaat catgtttcat   1260

gtacatacca cggcacaatt gcttagttcc ttaacaaatg caaattttac tgatccatgt   1320

atgatttgcg tggttctcta atgtgaaata ctatagctac ttgttagtaa gaatcaggtt   1380

cgtatgctta atgctgtatg tgccttctgc tcatgcctga tgataatcat atatcactgg   1440

aattaattag ttgatcgttt aatcatatat caagtacata ccatgccaca atttttagtc   1500

acttaaccca tgcagattga actggtccct gcatgttttg ctaaattgtt ctattctgat   1560

tagaccatat atcatgtatt ttttttggt aatggttctc ttattttaaa tgctatatag    1620

ttctggtact tgttagaaag atctgcttca tagtttagtt gcctatccct cgaattagga   1680
```

```
tgctgagcag ctgatcctat agctttgttt catgtatcaa ttcttttgtg ttcaacagtc   1740
agtttttgtt agattcattg taacttatgg tcgcttactc ttctggtcct caatgcttgc   1800
agggatccta aaccatggag atcaacaacc agaaccagtg cgtgccgtac aactgcctta   1860
acaaccccga gtccgagatc ctgaacgtgg ccatcttctc cagcgagcag gtcgcggaga   1920
tccacctcaa gatcacgcgc ctgatcctcg agaacttcct gccgggcggc tccttcgctt   1980
tcggcctgtt cgacctcatc tggggcatct tcaacgagga ccagtggagc gcgttcctca   2040
ggcaggtgga ggagctgatc aaccagcgca tcacggagtt cgccaggggc caggctatcc   2100
agcggctggt gggcttcggc aggtcctacg acgagtacat cctggccctc aaggagtggg   2160
agaacgaccc cgacaacccg gccagcaagg agcgcgtgag gacccgcttc aggaccaccg   2220
acgacgctct cctgacgggc gtccccctca tggctatccc gggcttcgag ctggccaccc   2280
tctcggtgta cgctcagtcg gccaacctgc acctcgccct cctgcgggac gctgtgttct   2340
tcggcgagag gtggggcctg acccagacga acatcaacga cctctactcc aggctgaaga   2400
acagcatccg cgactacacg aaccactgcg tgcgcttcta caacatcggc ctgggcaacc   2460
tcaacgtcat caggccggag tactaccgct tccagaggga gctgaccatc agcgtgctgg   2520
acctcgtcgc cctgttcccc aactacgaca tccgcacgta cccgatccca accaagtccc   2580
agctcacgag ggagatctac accgacccga tcatctcgcc gggcgcccag gccggctaca   2640
ccctgcagga cgtcctgagg gagccccacc tgatggactt cctgaacagg ctcatcatct   2700
acaccggcga gtacaggggc atcaggcact gggcgggcca cgaggtggag tccagcagga   2760
cgggcatgat gaccaacatc cgcttcccgc tctacggcac cgcggccacg gccgagccaa   2820
cccgcttcat cacgccgtcc accttccccg gcctgaacct cttctacagg accctgtcgg   2880
ctcccatctt ccgcgacgag ccgggcgcga acatcatcat ccgctacagg acctccctcg   2940
tggagggcgt cggcttcatc cagccgaaca acggcgagca gctgtaccgc gtgaggggca   3000
cgctggacag cctggaccag ctcccactgg agggcgagtc cagcctcacc gagtactcgc   3060
acaggctgtg ccacgtcagg ttcgcccaga gcctcaggaa cgcggagccc ctggactacg   3120
ccagggtgcc catgttcagc tggacccaca ggtcggctac ccccaccaac accatcgacc   3180
cagacgtgat cacgcagatc ccgctcgtca aggcccacac cctgcagtcg ggcaccaccg   3240
tggtcaaggg ccccggcttc acgggcggcg acatcctgag gaggacctcc ggcggcccat   3300
tcgccttcag caacgtcaac ctcgactgga acctgtccca gcgctacagg gcgcgcatca   3360
ggtacgccag caccacgaac ctgcgcatgt atgtgaccat cgcgggcgag aggatcttcg   3420
ccggccagtt caacaagacg atgaacaccg gcgacccgct caccttccag tccttcagct   3480
acgcgacgat cgacaccgcc ttcacgttcc ccacgaaggc ctccagcctg accgtgggcg   3540
ccgacacctt ctccagcggc aacgaggtct acgtggaccg cttcgagctg atcccggtga   3600
cggcgacctt cgaggccgag tacgacctgg agaaggccca gaaggcggtc aacgccctct   3660
tcacctccag caaccagatc ggcctgaaga cggacgtgac cgactaccac atcgacaagg   3720
tgtccaacct cgtcgagtgc ctgagcgacg agttctgcct cgacgagaag agggagctgt   3780
ccgagaaggt caagcacgcc aagcgcctct gcgacgagag gaacctcctg caggacccga   3840
acttcagggg aatcaaccgc cagccggaca ggggctggag gggcagcacc gacatcacca   3900
tccagggcgg cgacgacgtg ttcaaggaga actacgtcac gctcccgggc accttcgacg   3960
agtgctaccc cacgtacctg taccagaaga tcgacgagtc caagctcaag gcctacaccc   4020
```

```
gctacgagct gaggggatac atcgaggaca gccaggacct cgagatctac ctgatccgct   4080
acaacgcgaa gcacgagacg gtgaacgtcc ccggcacggg ctccctgtgg cccctctcgg   4140
ctcagtcgcc gatcggcaag tgcggcgagc ccaacaggtg cgccacccac ctcgagtgga   4200
acccggacct ggactgctcc tgccgggacg gcgagaagtg cgctcaccac tcccaccact   4260
tcagcctgga catcgacgtg ggctgcacgg acctcaacga ggacctgggc gtgtgggtca   4320
tcttcaaaat caagacgcag gacggccacg ctaggctggg caacctcgag ttcctggagg   4380
agaagccgct ggtgggcgag gctctggcca gggtcaagag ggcggagaag aagtggcgcg   4440
acaagaggga gaagctggag ctggagacga acatcgtcta caaggaggcc aagaagtccg   4500
tggacgcgct cttcgtcaac agccagtacg acaggctgca ggcggacacc aacatcgcca   4560
tcatccacgc cgcggacaag cgcgtgcact ccatcaggga ggcctacctc cccgagctga   4620
gcgtgatccc gggcgtcaac gctgccatct tcgaggagct ggagggccgc atcttcaccg   4680
cctactccct gtacgacgcg aggaacgtca tcaagaacgg cgacttcaac aacggcctca   4740
gctgctggaa cgtgaagggc cacgtggacg tcgaggagca gaacaaccac cgctcggtgc   4800
tggtggtccc cgagtgggag gctgaggtca gccaggaggt gcgcgtctgc ccgggcaggg   4860
gatacatcct ccgcgtgacc gcgtacaagg agggctacgg cgagggctgc gtcacgatcc   4920
acgagatcga ggacaacacc gacgagctga agttctccaa ctgcgtggag gaggagatct   4980
acccgaacaa cacggtcacc tgcaacgact acacggccac ccaggaggag tacgagggca   5040
cgtacacgtc gaggaacagg ggctacgacg gcgcttacga gtccaacagc tcggtgccgg   5100
ccgactacgc tagcgcgtac gaggagaagg cctacacgga cggccgcagg gacaacacct   5160
gcgagtcgaa caggggctac ggcgactaca cgccgctccc ggccggctac gtgaccaagg   5220
agctggagta cttcccggag acggacaagg tctggatcga gatcggcgag acggagggca   5280
ccttcatcgt ggactcagtc gagctgctgc tcatggagga gtaggagctc gccaacagtc   5340
gttgaagctg ctgctgtatc tgggttatct agtgtctctg cctttgccca aggatagtgc   5400
tgtctttcaa agtatttgta tcgtttgtgt cgtgagtcgt gactgagctg gtttcaagga   5460
ccagttgtgt tctcgttacc caaaactatc gtgcgaccgc atatggctta atcatgaata   5520
aatgttgttt gaatttaaac tattcgctga atattgttgt tttttgtcat gtcagttaat   5580
gttactaaat tggttgcctt ctaatttttg tttactggtg tttgtcgcac cttatctttt   5640
tactgtatgt ttacttcagg ttctggcagt ctcatttttt gtgactagtt aaaacttaca   5700
gctaaaaaaa tgcagttttt aattttaatt tgaagtttga ttagagctat tgatacccgg   5760
accatcaggt taggttagtt gtgcatagaa tcataaatat taatcatgtt ttctatgaat   5820
taagtcaaac ttgaaagtct ggctgaatat agtttctatg aatcatattg atatacatgt   5880
ttgattattt gttttgctat tagctattta ctttggtgaa tctatatagg cttatgcaga   5940
accttttttt ttgttctata tatccatatc ctagtactca gtagctctat gttttctgga   6000
gactagtggc ttgctttttc gtatgtctaa ttttttgctt gaccattgca aaacaaaaat   6060
tacctagtgt aatctctttt tataataatc ttgtaatgcg tctacctata ggtcaaagta   6120
ggttttgttt ggaaccctta gagctaactg ttagctagtt gataaattat tagctgagtt   6180
aagctagcta atgaactagt tttgatatta gctgaggatg tttgaaacct aataattatt   6240
ttttattagc taactatact aaattttagt agagagattc caaacaggag ttaacatggg   6300
atcagattgg ctatgcgttt gcaatcccat actaattagc taacggaccg ctaattagct   6360
aacgatcgct taattaagct tgcatgcctg cagtgcagcg tgacccggtc gtgcccctct   6420
```

ctagagataa tgagcattgc atgtctaagt tataaaaaat taccacatat ttttttgtc 6480
acacttgttt gaagtgcagt ttatctatct ttatacatat atttaaactt tactctacga 6540
ataatataat ctatagtact acaataatat cagtgtttta gagaatcata taaatgaaca 6600
gttagacatg gtctaaagga caattgagta ttttgacaac aggactctac agttttatct 6660
ttttagtgtg catgtgttct cctttttttt tgcaaatagc ttcacctata taatacttca 6720
tccattttat tagtacatcc atttagggtt tagggttaat ggtttttata gactaatttt 6780
tttagtacat ctattttatt ctattttagc ctctaaatta agaaaactaa aactctattt 6840
tagttttttt atttaataat ttagatataa aatagaataa aataaagtga ctaaaaatta 6900
aacaaatacc ctttaagaaa ttaaaaaaac taaggaaaca tttttcttgt ttcgagtaga 6960
taatgccagc ctgttaaacg ccgccgacga gtctaacgga caccaaccag cgaaccagca 7020
gcgtcgcgtc gggccaagcg aagcagacgg cacggcatct ctgtcgctgc ctctggaccc 7080
ctctcgagag ttccgctcca ccgttggact tgctccgctg tcggcatcca gaaattgcgt 7140
ggcggagcgg cagacgtgag ccggcacggc aggcggcctc ctcctcctct cacggcaccg 7200
gcagctacgg gggattcctt tcccaccgct ccttcgcttt cccttcctcg cccgccgtaa 7260
taaatagaca ccccctccac accctctttc cccaacctcg tgttgttcgg agcgcacaca 7320
cacacaacca gatctccccc aaatccaccc gtcggcacct ccgcttcaag gtacgccgct 7380
cgtcctcccc cccccccct ctctaccttc tctagatcgg cgttccggtc catagttagg 7440
gcccggtagt tctacttctg ttcatgtttg tgttagatcc gtgtttgtgt tagatccgtg 7500
ctgttagcgt tcgtacacgg atgcgacctg tacgtcagac acgttctgat tgctaacttg 7560
ccagtgtttc tctttgggga atcctgggat ggctctagcc gttccgcaga cgggatcgat 7620
ttcatgattt tttttgtttc gttgcatagg gtttggtttg ccctttttcct ttatttcaat 7680
atatgccgtg cacttgtttg tcgggtcatc ttttcatgct ttttttgtc ttggttgtga 7740
tgatgtggtc tggttgggcg gtcgttctag atcggagtag aattctgttt caaactacct 7800
ggtggattta ttaattttgg atctgtatgt gtgtgccata catattcata gttacgaatt 7860
gaagatgatg gatggaaata tcgatctagg ataggtatac atgttgatgc gggttttact 7920
gatgcatata cagagatgct tttgttcgc ttggttgtga tgatgtggtg tggttgggcg 7980
gtcgttcatt cgttctagat cggagtagaa tactgtttca aactacctgg tgtatttatt 8040
aattttggaa ctgtatgtgt gtgtcataca tcttcatagt tacgagttta agatggatgg 8100
aaatatcgat ctaggatagg tatacatgtt gatgtgggtt ttactgatgc atatacatga 8160
tggcatatgc agcatctatt catatgctct aaccttgagt acctatctat tataataaac 8220
aagtatgttt tataattatt ttgatcttga tatacttgga tgatggcata tccagcagct 8280
atatctggat ttttttagcc ctgccttcat acgctattta tttgcttggt actgtttctt 8340
ttgtcgttgc tcaccctgtt gtttggtgtt acttctgcag ggatctccga tcatgcaaaa 8400
actcattaac tcagtgcaaa actatgcctg gggcagcaaa acggcgttga ctgaacttta 8460
cggtatggaa aatccgtcca gccagccgat ggccgagctg tggatgggcg cacatccgaa 8520
aagcagttca cgagtgcaga atgccgccgg agatatcgtt tcactgcgtg atgtgattga 8580
gagtgataaa tcgactctgc tcggagaggc cgttgccaaa cgctttggcg aactgccttt 8640
cctgttcaaa gtattatgcg cagcacagcc actctccatt caggttcatc caaacaaaca 8700
caattctgaa atcggttttg ccaaagaaaa tgccgcaggt atcccgatgg atgccgccga 8760
gcgtaactat aaagatccta accacaagcc ggagctggtt tttgcgctga cgcctttcct 8820
tgcgatgaac gcgtttcgtg aattttccga gattgtctcc ctactccagc cggtcgcagg 8880
tgcacatccg gcgattgctc actttttaca acagcctgat gccgaacgtt taagcgaact 8940
gttcgccagc ctgttgaata tgcagggtga agaaaaatcc cgcgcgctgg cgattttaaa 9000
atcggccctc gatagccagc agggtgaacc gtggcaaacg attcgtttaa tttctgaatt 9060
ttacccggaa gacagcggtc tgttctcccc gctattgctg aatgtggtga aattgaaccc 9120
tggcgaagcg atgttcctgt tcgctgaaac accgcacgct tacctgcaag gcgtggcgct 9180
ggaagtgatg gcaaactccg ataacgtgct gcgtgcgggt ctgacgccta aatacattga 9240
tattccggaa ctggttgcca atgtgaaatt cgaagccaaa ccggctaacc agttgttgac 9300
ccagccggtg aaacaaggtg cagaactgga cttcccgatt ccagtggacg attttgcctt 9360
ctcgctgcac gaccttagtg ataaagaaac caccattagc cagcagagtg ccgccatttt 9420
gttctgcgtc gaaggcgatg caacgttgtg gaaaggttct cagcagttac agcttaaacc 9480
gggtgaatca gcgtttattg ccgccaacga atcaccggtg actgtcaaag gccacggccg 9540
tttagcgcgt gtttacaaca agctgtaaga gcttactgaa aaaattaaca tctcttgcta 9600
agctgggtca tgggtcgttt aagctgccga tgtgcctgcg tcgtctggtg ccctctctcc 9660
atatggaggt tgtcaaagta tctgctgttc gtgtcatgag tcgtgtcagt gttggtttaa 9720
taatggaccg gttgtgttgt gtgtgcgtac tacccagaac tatgacaaat catgaataag 9780
tttgatgttt gaaattaaag cctgtgctca ttatgttctg tctttcagtt gtctcctaat 9840
atttgcctcc aggtactggc tatctaccgt ttcttactta ggaggtgttt gaatgcacta 9900
aaactaatag ttagtggcta aaattagtta aaacatccaa acaccatagc taatagttga 9960
actattagct atttttggaa aattagttaa tagtgaggta gttatttgtt agctagctaa 10020
ttcaactaac aatttttagc caactaacaa ttagtttcag tgcattcaaa cacccccctta 10080 atgttaacgt ggttctatct accgtctcct aatatatggt tgattgttcg gtttgttgct 10140
atgctattgg gttctgattg ctgctagttc ttgctgaatc cagaagttct cgtagtatag 10200
ctcagattca tattatttat ttgagtgata agtgatccag gttattacta tgttagctag 10260 gttttttttta caaggataaa ttatctgtga tcataattct tatgaaagct ttatgtttcc 10320
tggaggcagt ggcatgcaat gcatgacagc aacttgatca caccagctga ggtagatacg 10380
gtaacaaggt tcttaaatct gttcaccaaa tcattggaga acacacatac acattcttgc 10440
cagtcttggt tagagaaatt tcatgacaaa atgccaaagc tgtcttgact cttcactttt 10500
ggccatgagt cgtgacttag tttggtttaa tggaccggtt ctcctagctt gttctactca 10560
aaactgttgt tgatgcgaat aagttgtgat ggttgatctc tggattttgt tttgctctca 10620
atagtggacg agattagata g 10641

<210> SEQ ID NO 10
<211> LENGTH: 10640
<212> TYPE: DNA
<213> ORGANISM: Artificial sequence
<220> FEATURE:
<223> OTHER INFORMATION: Synthetic polynucleotide

<400> SEQUENCE: 10
gaattcatta tgtggtctag gtaggttcta tatataagaa aacttgaaat gttctaaaaa 60
aaaattcaag cccatgcatg attgaagcaa acggtatagc aacggtgtta acctgatcta 120
gtgatctctt gcaatcctta acggccacct accgcaggta gcaaacggcg tccccctcct 180

```
cgatatctcc gcggcgacct ctggcttttt ccgcggaatt gcgcggtggg gacggattcc    240
acgagaccgc gacgcaaccg cctctcgccg ctgggcccca caccgctcgg tgccgtagcc    300
tcacgggact ctttctccct cctccccgtt ataaattggc ttcatcccct ccttgcctca    360
tccatccaaa tcccagtccc caatcccatc ccttcgtagg agaaattcat cgaagctaag    420
cgaatcctcg cgatcctctc aaggtactgc gagttttcga tccccctctc gacccctcgt    480
atgtttgtgt ttgtcgtagc gtttgattag gtatgctttc cctgtttgtg ttcgtcgtag    540
cgtttgatta ggtatgcttt ccctgttcgt gttcatcgta gtgtttgatt aggtcgtgtg    600
aggcgatggc ctgctcgcgt ccttcgatct gtagtcgatt tgcgggtcgt ggtgtagatc    660
tgcgggctgt gatgaagtta tttggtgtga tctgctcgcc tgattctgct ggttggctcg    720
agtagatatg atggttggac cggttggttc gtttaccgcg ctagggttgg gctgggatga    780
tgttgcatgc gccgttgcgc gtgatcccgc agcaggactt gcgtttgatt gccagatctc    840
gttacgatta tgtgatttgg tttggacttt ttagatctgt agcttctgct tatgtgccag    900
atgcgcctac tgctcatatg cctgatgata atcataaatg gctgtggaac taactagttg    960
attgcggagt catgtatcag ctacaggtgt agggactagc tacaggtgta gggacttgcg   1020
tctaattgtt tggtccttta ctcatgttgc aattatgcaa tttagtttag attgtttgtt   1080
ccactcatct aggctgtaaa agggacactg cttagattgc tgtttaatct ttttagtaga   1140
ttatattata ttggtaactt attacccta ttacatgcca tacgtgactt ctgctcatgc    1200
ctgatgataa tcatagatca ctgtggaatt aattagttga ttgttgaatc atgtttcatg   1260
tacataccac ggcacaattg cttagttcct taacaaatgc aaattttact gatccatgta   1320
tgatttgcgt ggttctctaa tgtgaaatac tatagctact tgttagtaag aatcaggttc   1380
gtatgcttaa tgctgtatgt gccttctgct catgcctgat gataatcata tatcactgga   1440
attaattagt tgatcgttta atcatatatc aagtacatac catgccacaa tttttagtca   1500
cttaacccat gcagattgaa ctggtccctg catgttttgc taaattgttc tattctgatt   1560
agaccatata tcatgtattt ttttttggta atggttctct tattttaaat gctatatagt   1620
tctggtactt gttagaaaga tctgcttcat agtttagttg cctatccctc gaattaggat   1680
gctgagcagc tgatcctata gctttgtttc atgtatcaat tcttttgtgt tcaacagtca   1740
gtttttgtta gattcattgt aacttatggt cgcttactct tctggtcctc aatgcttgca   1800
gggatcctaa accatggaga tcaacaacca gaaccagtgc gtgccgtaca actgccttaa   1860
caaccccgag tccgagatcc tgaacgtggc catcttctcc agcgagcagg tcgcggagat   1920
ccacctcaag atcacgcgcc tgatcctcga gaacttcctg ccgggcggct ccttcgcttt   1980
cggcctgttc gacctcatct ggggcatctt caacgaggac cagtggagcg cgttcctcag   2040
gcaggtggag gagctgatca accagcgcat cacggagttc gccaggggcc aggctatcca   2100
gcggctggtg ggcttcggca ggtcctacga cgagtacatc ctggccctca aggagtggga   2160
gaacgacccc gacaacccgg ccagcaagga gcgcgtgagg acccgcttca ggaccaccga   2220
cgacgctctc ctgacgggcg tcccccctcat ggctatcccg ggcttcgagc tggccaccct   2280
ctcggtgtac gctcagtcgg ccaacctgca cctcgccctc ctgcgggacg ctgtgttctt   2340
cggcgagagg tggggcctga cccagacgaa catcaacgac ctctactcca ggctgaagaa   2400
cagcatccgc gactacacga accactgcgt gcgcttctac aacatcggcc tgggcaacct   2460
caacgtcatc aggccggagt actaccgctt ccagagggag ctgaccatca gcgtgctgga   2520
```

-continued

```
cctcgtcgcc ctgttcccca actacgacat ccgcacgtac ccgatcccaa ccaagtccca   2580
gctcacgagg gagatctaca ccgacccgat catctcgccg ggcgcccagg ccggctacac   2640
cctgcaggac gtcctgaggg agccccacct gatggacttc ctgaacaggc tcatcatcta   2700
caccggcgag tacaggggca tcaggcactg ggcgggccac gaggtggagt ccagcaggac   2760
gggcatgatg accaacatcc gcttcccgct ctacggcacc gcggccacgg ccgagccaac   2820
ccgcttcatc acgccgtcca ccttccccgg cctgaacctc ttctacagga ccctgtcggc   2880
tcccatcttc cgcgacgagc cgggcgcgaa catcatcatc cgctacagga cctccctcgt   2940
ggagggcgtc ggcttcatcc agccgaacaa cggcgagcag ctgtaccgcg tgaggggcac   3000
gctggacagc ctggaccagc tcccactgga gggcgagtcc agcctcaccg agtactcgca   3060
caggctgtgc cacgtcaggt tcgcccagag cctcaggaac gcggagcccc tggactacgc   3120
cagggtgccc atgttcagct ggacccacag gtcggctacc cccaccaaca ccatcgaccc   3180
agacgtgatc acgcagatcc cgctcgtcaa ggcccacacc ctgcagtcgg gcaccaccgt   3240
ggtcaagggc cccggcttca cgggcggcga catcctgagg aggacctccg gcggcccatt   3300
cgccttcagc aacgtcaacc tcgactggaa cctgtcccag cgctacaggg cgcgcatcag   3360
gtacgccagc accacgaacc tgcgcatgta tgtgaccatc gcgggcgaga ggatcttcgc   3420
cggccagttc aacaagacga tgaacaccgg cgacccgctc accttccagt ccttcagcta   3480
cgcgacgatc gacaccgcct tcacgttccc cacgaaggcc tccagcctga ccgtgggcgc   3540
cgacaccttc tccagcggca acgaggtcta cgtggaccgc ttcgagctga tcccggtgac   3600
ggcgaccttc gaggccgagt acgacctgga gaaggcccag aaggcggtca acgccctctt   3660
cacctccagc aaccagatcg gcctgaagac ggacgtgacc gactaccaca tcgacaaggt   3720
gtccaacctc gtcgagtgcc tgagcgacga gttctgcctc gacgagaaga gggagctgtc   3780
cgagaaggtc aagcacgcca agcgcctctg cgacgagagg aacctcctgc aggacccgaa   3840
cttcagggga atcaaccgcc agccggacag gggctggagg ggcagcaccg acatcaccat   3900
ccagggcggc gacgacgtgt tcaaggagaa ctacgtcacg ctcccgggca ccttcgacga   3960
gtgctacccc acgtacctgt accagaagat cgacgagtcc aagctcaagg cctacacccg   4020
ctacgagctg aggggataca tcgaggacag ccaggacctc gagatctacc tgatccgcta   4080
caacgcgaag cacgagacgg tgaacgtccc cggcacgggc tccctgtggc ccctctcggc   4140
tcagtcgccg atcggcaagt gcggcgagcc caacaggtgc gccacccacc tcgagtggaa   4200
cccggacctg gactgctcct gccgggacgg cgagaagtgc gctcaccact cccaccactt   4260
cagcctggac atcgacgtgg gctgcacgga cctcaacgag gacctgggcg tgtgggtcat   4320
cttcaaaatc aagacgcagg acggccacgc taggctgggc aacctcgagt tcctggagga   4380
gaagccgctg gtgggcgagg ctctggccag ggtcaagagg gcggagaaga agtggcgcga   4440
caagagggag aagctggagc tggagacgaa catcgtctac aaggaggcca agaagtccgt   4500
ggacgcgctc ttcgtcaaca gccagtacga caggctgcag gcggacacca acatcgccat   4560
catccacgcc gcggacaagc gcgtgcactc catcagggag gcctacctcc ccgagctgag   4620
cgtgatcccg ggcgtcaacg ctgccatctt cgaggagctg gagggccgca tcttcaccgc   4680
ctactccctg tacgacgcga ggaacgtcat caagaacggc gacttcaaca acggcctcag   4740
ctgctggaac gtgaagggcc acgtggacgt cgaggagcag aacaaccacc gctcggtgct   4800
ggtggtcccc gagtgggagg ctgaggtcag ccaggaggtg cgcgtctgcc cgggcagggg   4860
atacatcctc cgcgtgaccg cgtacaagga gggctacggc gagggctgcg tcacgatcca   4920
```

```
cgagatcgag gacaacaccg acgagctgaa gttctccaac tgcgtggagg aggagatcta   4980
cccgaacaac acggtcacct gcaacgacta cacggccacc caggaggagt acgagggcac   5040
gtacacgtcg aggaacaggg gctacgacgg cgcttacgag tccaacagct cggtgccggc   5100
cgactacgct agcgcgtacg aggagaaggc ctacacggac ggccgcaggg acaacacctg   5160
cgagtcgaac aggggctacg gcgactacac gccgctcccg gccggctacg tgaccaagga   5220
gctggagtac ttcccggaga cggacaaggt ctggatcgag atcggcgaga cggagggcac   5280
cttcatcgtg gactcagtcg agctgctgct catggaggag taggagctcg ccaacagtcg   5340
ttgaagctgc tgctgtatct gggttatcta gtgtctctgc ctttgcccaa ggatagtgct   5400
gtctttcaaa gtatttgtat cgtttgtgtc gtgagtcgtg actgagctgg tttcaaggac   5460
cagttgtgtt ctcgttaccc aaaactatcg tgcgaccgca tatggcttaa tcatgaataa   5520
atgttgtttg aatttaaact attcgctgaa tattgttgtt ttttgtcatg tcagttaatg   5580
ttactaaatt ggttgccttc taatttttgt ttactggtgt ttgtcgcacc ttatcttttt   5640
actgtatgtt tacttcaggt tctggcagtc tcatttttttg tgactagtta aaacttacag   5700
ctaaaaaaat gcagtttttta attttaattt gaagtttgat tagagctatt gatacccgga   5760
ccatcaggtt aggttagttg tgcatagaat cataaatatt aatcatgttt tctatgaatt   5820
aagtcaaact tgaaagtctg gctgaatata gtttctatga atcatattga tatacatgtt   5880
tgattatttg ttttgctatt agctatttac tttggtgaat ctatataggc ttatgcagaa   5940
cctttttttt tgttctatat atccatatcc tagtactcag tagctctatg ttttctggag   6000
actagtggct tgctttttcg tatgtctaat tttttgcttg accattgcaa aacaaaaatt   6060
acctagtgta atctcttttt ataataatct tgtaatgcgt ctacctatag gtcaaagtag   6120
gttttgtttg gaacccttag agctaactgt tagctagttg ataaattatt agctgagtta   6180
agctagctaa tgaactagtt ttgatattag ctgaggatgt ttgaaaccta ataattattt   6240
tttattagct aactatacta aattttagta gagagattcc aaacaggagt taacatggga   6300
tcagattggc tatgcgtttg caatcccata ctaattagct aacggaccgc taattagcta   6360
acgatcgctt aattaagctt gcatgcctgc agtgcagcgt gacccggtcg tgcccctctc   6420
tagagataat gagcattgca tgtctaagtt ataaaaaatt accacatatt tttttttgtca   6480
cacttgtttg aagtgcagtt tatctatctt tatacatata tttaaacttt actctacgaa   6540
taatataatc tatagtacta caataatatc agtgttttag agaatcatat aaatgaacag   6600
ttagacatgg tctaaaggac aattgagtat tttgacaaca ggactctaca gttttatctt   6660
tttagtgtgc atgtgttctc cttttttttt gcaaatagct tcacctatat aatacttcat   6720
ccattttatt agtacatcca tttagggttt agggttaatg gtttttatag actaattttt   6780
ttagtacatc tattttattc tattttagcc tctaaattaa gaaaactaaa actctatttt   6840
agttttttta tttaataatt tagatataaa atagaataaa ataaagtgac taaaaattaa   6900
acaaataccc tttaagaaat taaaaaaact aaggaaacat ttttcttgtt tcgagtagat   6960
aatgccagcc tgttaaacgc cgccgacgag tctaacggac accaaccagc gaaccagcag   7020
cgtcgcgtcg ggccaagcga agcagacggc acggcatctc tgtcgctgcc tctggacccc   7080
tctcgagagt tccgctccac cgttggactt gctccgctgt cggcatccag aaattgcgtg   7140
gcggagcggc agacgtgagc cggcacggca ggcggcctcc tcctcctctc acggcaccgg   7200
cagctacggg ggattccttt cccaccgctc cttcgctttc ccttcctcgc ccgccgtaat   7260
```

-continued aaatagacac cccctccaca ccctctttcc ccaacctcgt gttgttcgga gcgcacacac 7320
acacaaccag atctccccca aatccacccg tcggcacctc cgcttcaagg tacgccgctc 7380
gtcctccccc cccccccctc tctaccttct ctagatcggc gttccggtcc atagttaggg 7440
cccggtagtt ctacttctgt tcatgtttgt gttagatccg tgtttgtgtt agatccgtgc 7500
tgttagcgtt cgtacacgga tgcgacctgt acgtcagaca cgttctgatt gctaacttgc 7560
cagtgtttct ctttggggaa tcctgggatg gctctagccg ttccgcagac gggatcgatt 7620
tcatgatttt ttttgtttcg ttgcataggg tttggtttgc ccttttcctt tatttcaata 7680
tatgccgtgc acttgtttgt cgggtcatct tttcatgctt ttttttgtct tggttgtgat 7740
gatgtggtct ggttgggcgg tcgttctaga tcggagtaga attctgtttc aaactacctg 7800
gtggatttat taattttgga tctgtatgtg tgtgccatac atattcatag ttacgaattg 7860
aagatgatgg atggaaatat cgatctagga taggtataca tgttgatgcg ggttttactg 7920
atgcatatac agagatgctt tttgttcgct tggttgtgat gatgtggtgt ggttgggcgg 7980
tcgttcattc gttctagatc ggagtagaat actgtttcaa actacctggt gtatttatta 8040
attttggaac tgtatgtgtg tgtcatacat cttcatagtt acgagtttaa gatggatgga 8100
aatatcgatc taggataggt atacatgttg atgtgggttt tactgatgca tatacatgat 8160
ggcatatgca gcatctattc atatgctcta accttgagta cctatctatt ataataaaca 8220
agtatgtttt ataattattt tgatcttgat atacttggat gatggcatat ccagcagcta 8280
tatctggatt tttttagccc tgccttcata cgctatttat ttgcttggta ctgtttcttt 8340
tgtcgttgct caccctgttg tttggtgtta cttctgcagg gatctccgat catgcaaaaa 8400
ctcattaact cagtgcaaaa ctatgcctgg ggcagcaaaa cggcgttgac tgaactttac 8460
ggtatggaaa atccgtccag ccagccgatg gccgagctgt ggatgggcgc acatccgaaa 8520
agcagttcac gagtgcagaa tgccgccgga gatatcgttt cactgcgtga tgtgattgag 8580
agtgataaat cgactctgct cggagaggcc gttgccaaac gctttggcga actgcctttc 8640
ctgttcaaag tattatgcgc agcacagcca ctctccattc aggttcatcc aaacaaacac 8700
aattctgaaa tcggttttgc caaagaaaat gccgcaggta tcccgatgga tgccgccgag 8760
cgtaactata aagatcctaa ccacaagccg gagctggttt ttgcgctgac gcctttcctt 8820
gcgatgaacg cgtttcgtga attttccgag attgtctccc tactccagcc ggtcgcaggt 8880
gcacatccgg cgattgctca ctttttacaa cagcctgatg ccgaacgttt aagcgaactg 8940
ttcgccagcc tgttgaatat gcagggtgaa gaaaaatccc gcgcgctggc gattttaaaa 9000
tcggccctcg atagccagca gggtgaaccg tggcaaacga ttcgtttaat ttctgaattt 9060
tacccggaag acagcggtct gttctccccg ctattgctga atgtggtgaa attgaaccct 9120
ggcgaagcga tgttcctgtt cgctgaaaca ccgcacgctt acctgcaagg cgtggcgctg 9180
gaagtgatgg caaactccga taacgtgctg cgtgcgggtc tgacgcctaa atacattgat 9240
attccggaac tggttgccaa tgtgaaattc gaagccaaac cggctaacca gttgttgacc 9300
cagccggtga aacaaggtgc agaactggac ttcccgattc cagtggacga ttttgccttc 9360
tcgctgcacg accttagtga taaagaaacc accattagcc agcagagtgc cgccattttg 9420
ttctgcgtcg aaggcgatgc aacgttgtgg aaaggttctc agcagttaca gcttaaaccg 9480
ggtgaatcag cgtttattgc cgccaacgaa tcaccggtga ctgtcaaagg ccacggccgt 9540
ttagcgcgtg tttacaacaa gctgtaagag cttactgaaa aaattaacat ctcttgctaa 9600
gctgggtcat gggtcgttta agctgccgat gtgcctgcgt cgtctggtgc cctctctcca 9660
tatggaggtt gtcaaagtat ctgctgttcg tgtcatgagt cgtgtcagtg ttggtttaat 9720
aatggaccgg ttgtgttgtg tgtgcgtact acccagaact atgacaaatc atgaataagt 9780
ttgatgtttg aaattaaagc ctgtgctcat tatgttctgt ctttcagttg tctcctaata 9840
tttgcctcca ggtactggct atctaccgtt tcttacttag gaggtgtttg aatgcactaa 9900
aactaatagt tagtggctaa aattagttaa aacatccaaa caccatagct aatagttgaa 9960
ctattagcta tttttggaaa attagttaat agtgaggtag ttatttgtta gctagctaat 10020
tcaactaaca atttttagcc aactaacaat tagtttcagt gcattcaaac accccttaa 10080
tgttaacgtg gttctatcta ccgtctccta atatatggtt gattgttcgg tttgttgcta 10140
tgctattggg ttctgattgc tgctagttct tgctgaatcc agaagttctc gtagtatagc 10200
tcagattcat attatttatt tgagtgataa gtgatccagg ttattactat gttagctagg 10260
tttttttac aaggataaat tatctgtgat cataattctt atgaaagctt tatgtttcct 10320
ggaggcagtg gcatgcaatg catgacagca acttgatcac accagctgag gtagatacgg 10380
taacaaggtt cttaaatctg ttcaccaaat cattggagaa cacacataca cattcttgcc 10440
agtcttggtt agagaaattt catgacaaaa tgccaaagct gtcttgactc ttcacttttg 10500
gccatgagtc gtgacttagt ttggtttaat ggaccggttc tcctagcttg ttctactcaa 10560
aactgttgtt gatgcgaata agttgtgatg gttgatctct ggattttgtt ttgctctcaa 10620
tagtggacga gattagatag 10640

<210> SEQ ID NO 11
<211> LENGTH: 10642
<212> TYPE: DNA
<213> ORGANISM: Artificial sequence
<220> FEATURE:
<223> OTHER INFORMATION: Synthetic polynucleotide

<400> SEQUENCE: 11
gaattcatta tgtggtctag gtaggttcta tatataagaa aacttgaaat gttctaaaaa 60
aaaattcaag cccatgcatg attgaagcaa acggtatagc aacggtgtta acctgatcta 120
gtgatctctt gcaatcctta acggccacct accgcaggta gcaaacggcg tccccctcct 180
cgatatctcc gcggcgacct ctggcttttt ccgcggaatt gcgcggtggg gacggattcc 240
acgagaccgc gacgcaaccg cctctcgccg ctgggcccca caccgctcgg tgccgtagcc 300
tcacgggact ctttctccct cctcccccgt tataaattgg cttcatcccc tccttgcctc 360
atccatccaa atcccagtcc ccaatcccat cccttcgtag gagaaattca tcgaagctaa 420
gcgaatcctc gcgatcctct caaggtactg cgagttttcg atccccctct cgacccctcg 480
tatgtttgtg tttgtcgtag cgtttgatta ggtatgcttt ccctgtttgt gttcgtcgta 540
gcgtttgatt aggtatgctt tccctgttcg tgttcatcgt agtgtttgat taggtcgtgt 600
gaggcgatgg cctgctcgcg tccttcgatc tgtagtcgat ttgcgggtcg tggtgtagat 660
ctgcgggctg tgatgaagtt atttggtgtg atctgctcgc ctgattctgc tggttggctc 720
gagtagatat gatggttgga ccggttggtt cgtttaccgc gctagggttg ggctgggatg 780
atgttgcatg cgccgttgcg cgtgatcccg cagcaggact tgcgtttgat tgccagatct 840
cgttacgatt atgtgatttg gtttggactt tttagatctg tagcttctgc ttatgtgcca 900
gatgcgccta ctgctcatat gcctgatgat aatcataaat ggctgtggaa ctaactagtt 960
gattgcggag tcatgtatca gctacaggtg tagggactag ctacaggtgt agggacttgc 1020

-continued

```
gtctaattgt ttggtccttt actcatgttg caattatgca atttagttta gattgtttgt   1080
tccactcatc taggctgtaa aagggacact gcttagattg ctgtttaatc tttttagtag   1140
attatattat attggtaact tattacccct attacatgcc atacgtgact tctgctcatg   1200
cctgatgata atcatagatc actgtggaat taattagttg attgttgaat catgtttcat   1260
gtacatacca cggcacaatt gcttagttcc ttaacaaatg caaattttac tgatccatgt   1320
atgatttgcg tggttctcta atgtgaaata ctatagctac ttgttagtaa gaatcaggtt   1380
cgtatgctta atgctgtatg tgccttctgc tcatgcctga tgataatcat atatcactgg   1440
aattaattag ttgatcgttt aatcatatat caagtacata ccatgccaca atttttagtc   1500
acttaaccca tgcagattga actggtccct gcatgttttg ctaaattgtt ctattctgat   1560
tagaccatat atcatgtatt ttttttggt aatggttctc ttattttaaa tgctatatag   1620
ttctggtact tgttagaaag atctgcttca tagtttagtt gcctatccct cgaattagga   1680
tgctgagcag ctgatcctat agctttgttt catgtatcaa ttcttttgtg ttcaacagtc   1740
agtttttgtt agattcattg taacttatgg tcgcttactc ttctggtcct caatgcttgc   1800
agggatccta aaccatggag atcaacaacc agaaccagtg cgtgccgtac aactgcctta   1860
acaaccccga gtccgagatc ctgaacgtgg ccatcttctc cagcgagcag gtcgcggaga   1920
tccacctcaa gatcacgcgc ctgatcctcg agaacttcct gccgggcggc tccttcgctt   1980
tcggcctgtt cgacctcatc tggggcatct tcaacgagga ccagtggagc gcgttcctca   2040
ggcaggtgga ggagctgatc aaccagcgca tcacggagtt cgccaggggc caggctatcc   2100
agcggctggt gggcttcggc aggtcctacg acgagtacat cctggccctc aaggagtggg   2160
agaacgaccc cgacaacccg gccagcaagg agcgcgtgag gacccgcttc aggaccaccg   2220
acgacgctct cctgacgggc gtccccctca tggctatccc gggcttcgag ctggccaccc   2280
tctcggtgta cgctcagtcg gccaacctgc acctcgccct cctgcgggac gctgtgttct   2340
tcggcgagag gtggggcctg acccagacga acatcaacga cctctactcc aggctgaaga   2400
acagcatccg cgactacacg aaccactgcg tgcgcttcta caacatcggc ctgggcaacc   2460
tcaacgtcat caggccggag tactaccgct tccagaggga gctgaccatc agcgtgctgg   2520
acctcgtcgc cctgttcccc aactacgaca tccgcacgta cccgatccca accaagtccc   2580
agctcacgag ggagatctac accgacccga tcatctcgcc gggcgcccag gccggctaca   2640
ccctgcagga cgtcctgagg gagccccacc tgatggactt cctgaacagg ctcatcatct   2700
acaccggcga gtacaggggc atcaggcact gggcgggcca cgaggtggag tccagcagga   2760
cgggcatgat gaccaacatc cgcttcccgc tctacggcac cgcggccacg gccgagccaa   2820
cccgcttcat cacgccgtcc accttccccg gcctgaacct cttctacagg accctgtcgg   2880
ctcccatctt ccgcgacgag ccgggcgcga acatcatcat ccgctacagg acctccctcg   2940
tggagggcgt cggcttcatc cagccgaaca acggcgagca gctgtaccgc gtgaggggca   3000
cgctggacag cctggaccag ctcccactgg agggcgagtc cagcctcacc gagtactcgc   3060
acaggctgtg ccacgtcagg ttcgcccaga gcctcaggaa cgcggagccc ctggactacg   3120
ccagggtgcc catgttcagc tggacccaca ggtcggctac cccaccaac accatcgacc   3180
cagacgtgat cacgcagatc ccgctcgtca aggcccacac cctgcagtcg ggcaccaccg   3240
tggtcaaggg ccccggcttc acgggcggcg acatcctgag gaggacctcc ggcggcccat   3300
tcgccttcag caacgtcaac ctcgactgga acctgtccca gcgctacagg gcgcgcatca   3360
ggtacgccag caccacgaac ctgcgcatgt atgtgaccat cgcgggcgag aggatcttcg   3420
```

ccggccagtt caacaagacg atgaacaccg gcgacccgct caccttccag tccttcagct 3480
acgcgacgat cgacaccgcc ttcacgttcc ccacgaaggc ctccagcctg accgtgggcg 3540
ccgacacctt ctccagcggc aacgaggtct acgtggaccg cttcgagctg atcccggtga 3600
cggcgacctt cgaggccgag tacgacctgg agaaggccca gaaggcggtc aacgccctct 3660
tcacctccag caaccagatc ggcctgaaga cggacgtgac cgactaccac atcgacaagg 3720
tgtccaacct cgtcgagtgc ctgagcgacg agttctgcct cgacgagaag agggagctgt 3780
ccgagaaggt caagcacgcc aagcgcctct gcgacgagag gaacctcctg caggacccga 3840
acttcagggg aatcaaccgc cagccggaca ggggctggag gggcagcacc gacatcacca 3900
tccagggcgg cgacgacgtg ttcaaggaga actacgtcac gctcccgggc accttcgacg 3960
agtgctaccc cacgtacctg taccagaaga tcgacgagtc caagctcaag gcctacaccc 4020
gctacgagct gaggggatac atcgaggaca gccaggacct cgagatctac ctgatccgct 4080
acaacgcgaa gcacgagacg gtgaacgtcc ccggcacggg ctccctgtgg cccctctcgg 4140
ctcagtcgcc gatcggcaag tgcggcgagc ccaacaggtg cgccacccac ctcgagtgga 4200
acccggacct ggactgctcc tgccgggacg gcgagaagtg cgctcaccac tcccaccact 4260
tcagcctgga catcgacgtg ggctgcacgg acctcaacga ggacctgggc gtgtgggtca 4320
tcttcaaaat caagacgcag gacggccacg ctaggctggg caacctcgag ttcctggagg 4380
agaagccgct ggtgggcgag gctctggcca gggtcaagag ggcggagaag aagtggcgcg 4440
acaagaggga gaagctggag ctggagacga acatcgtcta caaggaggcc aagaagtccg 4500
tggacgcgct cttcgtcaac agccagtacg acaggctgca ggcggacacc aacatcgcca 4560
tcatccacgc cgcggacaag cgcgtgcact ccatcaggga ggcctacctc cccgagctga 4620
gcgtgatccc gggcgtcaac gctgccatct tcgaggagct ggagggccgc atcttcaccg 4680
cctactccct gtacgacgcg aggaacgtca tcaagaacgg cgacttcaac aacggcctca 4740
gctgctggaa cgtgaagggc cacgtggacg tcgaggagca gaacaaccac cgctcggtgc 4800
tggtggtccc cgagtgggag gctgaggtca gccaggaggt gcgcgtctgc ccgggcaggg 4860
gatacatcct ccgcgtgacc gcgtacaagg agggctacgg cgagggctgc gtcacgatcc 4920
acgagatcga ggacaacacc gacgagctga agttctccaa ctgcgtggag gaggagatct 4980
acccgaacaa cacggtcacc tgcaacgact acacggccac ccaggaggag tacgagggca 5040
cgtacacgtc gaggaacagg ggctacgacg gcgcttacga gtccaacagc tcggtgccgg 5100
ccgactacgc tagcgcgtac gaggagaagg cctacacgga cggccgcagg gacaacacct 5160
gcgagtcgaa caggggctac ggcgactaca cgccgctccc ggccggctac gtgaccaagg 5220
agctggagta cttcccggag acggacaagg tctggatcga gatcggcgag acggagggca 5280
ccttcatcgt ggactcagtc gagctgctgc tcatggagga gtaggagctc gccaacagtc 5340
gttgaagctg ctgctgtatc tgggttatct agtgtctctg cctttgccca aggatagtgc 5400
tgtctttcaa agtatttgta tcgtttgtgt cgtgagtcgt gactgagctg gtttcaagga 5460
ccagttgtgt tctcgttacc caaaactatc gtgcgaccgc atatggctta atcatgaata 5520
aatgttgttt gaatttaaac tattcgctga atattgttgt tttttgtcat gtcagttaat 5580
gttactaaat tggttgcctt ctaatttttg tttactggtg tttgtcgcac cttatctttt 5640
tactgtatgt ttacttcagg ttctggcagt ctcatttttt gtgactagtt aaaacttaca 5700
gctaaaaaaa tgcagttttt aattttaatt tgaagtttga ttagagctat tgatacccgg 5760
accatcaggt taggttagtt gtgcatagaa tcataaatat taatcatgtt ttctatgaat 5820
taagtcaaac ttgaaagtct ggctgaatat agtttctatg aatcatattg atatacatgt 5880
ttgattattt gttttgctat tagctattta ctttggtgaa tctatatagg cttatgcaga 5940
accttttttt ttgttctata tatccatatc ctagtactca gtagctctat gttttctgga 6000
gactagtggc ttgctttttc gtatgtctaa tttttgctt gaccattgca aaacaaaaat 6060
tacctagtgt aatctctttt tataataatc ttgtaatgcg tctacctata ggtcaaagta 6120
ggttttgttt ggaaccctta gagctaactg ttagctagtt gataaattat tagctgagtt 6180
aagctagcta atgaactagt tttgatatta gctgaggatg tttgaaacct aataattatt 6240
ttttattagc taactatact aaattttagt agagagattc caaacaggag ttaacatggg 6300
atcagattgg ctatgcgttt gcaatcccat actaattagc taacggaccg ctaattagct 6360
aacgatcgct taattaagct tgcatgcctg cagtgcagcg tgacccggtc gtgcccctct 6420
ctagagataa tgagcattgc atgtctaagt tataaaaaat taccacatat tttttttgtc 6480
acacttgttt gaagtgcagt ttatctatct ttatacatat atttaaactt tactctacga 6540
ataatataat ctatagtact acaataatat cagtgtttta gagaatcata taaatgaaca 6600
gttagacatg gtctaaagga caattgagta ttttgacaac aggactctac agttttatct 6660
ttttagtgtg catgtgttct cctttttttt tgcaaatagc ttcacctata taatacttca 6720
tccattttat tagtacatcc atttagggtt tagggttaat ggtttttata gactaatttt 6780
tttagtacat ctattttatt ctattttagc ctctaaatta agaaaactaa aactctattt 6840
tagtttttt atttaataat ttagatataa aatagaataa aataaagtga ctaaaaatta 6900
aacaaatacc ctttaagaaa ttaaaaaaac taaggaaaca tttttcttgt ttcgagtaga 6960
taatgccagc ctgttaaacg ccgccgacga gtctaacgga caccaaccag cgaaccagca 7020
gcgtcgcgtc gggccaagcg aagcagacgg cacggcatct ctgtcgctgc ctctggaccc 7080
ctctcgagag ttccgctcca ccgttggact tgctccgctg tcggcatcca gaaattgcgt 7140
ggcggagcgg cagacgtgag ccggcacggc aggcggcctc ctcctcctct cacggcaccg 7200
gcagctacgg gggattcctt tcccaccgct ccttcgcttt cccttcctcg cccgccgtaa 7260
taaatagaca cccccctcca caccctcttt ccccaacctc gtgttgttcg gagcgcacac 7320
acacacaacc agatctcccc caaatccacc cgtcggcacc tccgcttcaa ggtacgccgc 7380
tcgtcctccc cccccccccc tctctacctt ctctagatcg gcgttccggt ccatagttag 7440
ggcccggtag ttctacttct gttcatgttt gtgttagatc cgtgtttgtg ttagatccgt 7500
gctgttagcg ttcgtacacg gatgcgacct gtacgtcaga cacgttctga ttgctaactt 7560
gccagtgttt ctctttgggg aatcctggga tggctctagc cgttccgcag acgggatcga 7620
tttcatgatt ttttttgttt cgttgcatag ggtttggttt gcccttttcc tttatttcaa 7680
tatatgccgt gcacttgttt gtcgggtcat cttttcatgc ttttttttgt cttggttgtg 7740
atgatgtggt ctggttgggc ggtcgttcta gatcggagta gaattctgtt tcaaactacc 7800
tggtggattt attaatttg gatctgtatg tgtgtgccat acatattcat agttacgaat 7860
tgaagatgat ggatggaaat atcgatctag gataggtata catgttgatg cgggttttac 7920
tgatgcatat acagagatgc tttttgttcg cttggttgtg atgatgtggt gtggttgggc 7980
ggtcgttcat tcgttctaga tcggagtaga atactgtttc aaactacctg gtgtatttat 8040
taattttgga actgtatgtg tgtgtcatac atcttcatag ttacgagttt aagatggatg 8100
gaaatatcga tctaggatag gtatacatgt tgatgtgggt tttactgatg catatacatg 8160
atggcatatg cagcatctat tcatatgctc taaccttgag tacctatcta ttataataaa 8220
caagtatgtt ttataattat tttgatcttg atatacttgg atgatggcat atccagcagc 8280
tatatctgga tttttttagc cctgccttca tacgctattt atttgcttgg tactgtttct 8340
tttgtcgttg ctcaccctgt tgtttggtgt tacttctgca gggatctccg atcatgcaaa 8400
aactcattaa ctcagtgcaa aactatgcct ggggcagcaa aacggcgttg actgaacttt 8460
acggtatgga aaatccgtcc agccagccga tggccgagct gtggatgggc gcacatccga 8520
aaagcagttc acgagtgcag aatgccgccg gagatatcgt ttcactgcgt gatgtgattg 8580
agagtgataa atcgactctg ctcggagagg ccgttgccaa acgctttggc gaactgcctt 8640
tcctgttcaa agtattatgc gcagcacagc cactctccat tcaggttcat ccaaacaaac 8700
acaattctga aatcggtttt gccaaagaaa atgccgcagg tatcccgatg gatgccgccg 8760
agcgtaacta taaagatcct aaccacaagc cggagctggt tttgcgctg acgcctttcc 8820
ttgcgatgaa cgcgtttcgt gaattttccg agattgtctc cctactccag ccggtcgcag 8880
gtgcacatcc ggcgattgct cactttttac aacagcctga tgccgaacgt ttaagcgaac 8940
tgttcgccag cctgttgaat atgcagggtg aagaaaaatc ccgcgcgctg gcgattttaa 9000
aatcggccct cgatagccag cagggtgaac cgtggcaaac gattcgttta atttctgaat 9060
tttacccgga agacagcggt ctgttctccc cgctattgct gaatgtggtg aaattgaacc 9120
ctggcgaagc gatgttcctg ttcgctgaaa caccgcacgc ttacctgcaa ggcgtggcgc 9180
tggaagtgat ggcaaactcc gataacgtgc tgcgtgcggg tctgacgcct aaatacattg 9240
atattccgga actggttgcc aatgtgaaat tcgaagccaa accggctaac cagttgttga 9300
cccagccggt gaaacaaggt gcagaactgg acttcccgat tccagtggac gattttgcct 9360
tctcgctgca cgaccttagt gataaagaaa ccaccattag ccagcagagt gccgccattt 9420
tgttctgcgt cgaaggcgat gcaacgttgt ggaaaggttc tcagcagtta cagcttaaac 9480
cgggtgaatc agcgtttatt gccgccaacg aatcaccggt gactgtcaaa ggccacggcc 9540
gtttagcgcg tgtttacaac aagctgtaag agcttactga aaaaattaac atctcttgct 9600
aagctgggtc atgggtcgtt taagctgccg atgtgcctgc gtcgtctggt gccctctctc 9660
catatggagg ttgtcaaagt atctgctgtt cgtgtcatga gtcgtgtcag tgttggttta 9720
ataatggacc ggttgtgttg tgtgtgcgta ctacccagaa ctatgacaaa tcatgaataa 9780
gtttgatgtt tgaaattaaa gcctgtgctc attatgttct gtctttcagt tgtctcctaa 9840
tatttgcctc caggtactgg ctatctaccg tttcttactt aggaggtgtt tgaatgcact 9900
aaaactaata gttagtggct aaaattagtt aaaacatcca aacaccatag ctaatagttg 9960
aactattagc tatttttgga aaattagtta atagtgaggt agttatttgt tagctagcta 10020
attcaactaa caatttttag ccaactaaca attagtttca gtgcattcaa acaccccctt 10080
aatgttaacg tggttctatc taccgtctcc taatatatgg ttgattgttc ggtttgttgc 10140
tatgctattg ggttctgatt gctgctagtt cttgctgaat ccagaagttc tcgtagtata 10200
gctcagattc atattattta tttgagtgat aagtgatcca ggttattact atgttagcta 10260
ggtttttttt acaaggataa attatctgtg atcataattc ttatgaaagc tttatgtttc 10320
ctggaggcag tggcatgcaa tgcatgacag caacttgatc acaccagctg aggtagatac 10380
ggtaacaagg ttcttaaatc tgttcaccaa atcattggag aacacacata cacattcttg 10440
ccagtcttgg ttagagaaat ttcatgacaa aatgccaaag ctgtcttgac tcttcacttt 10500
tggccatgag tcgtgactta gtttggttta atggaccggt tctcctagct tgttctactc 10560
aaaactgttg ttgatgcgaa taagttgtga tggttgatct ctggattttg ttttgctctc 10620
aatagtggac gagattagat ag 10642

<210> SEQ ID NO 12
<211> LENGTH: 10642
<212> TYPE: DNA
<213> ORGANISM: Artificial sequence
<220> FEATURE:
<223> OTHER INFORMATION: Synthetic polynucleotide

<400> SEQUENCE: 12
gaattcatta tgtggtctag gtaggttcta tatataagaa aacttgaaat gttctaaaaa 60
aaaattcaag cccatgcatg attgaagcaa acggtatagc aacggtgtta acctgatcta 120
gtgatctctt gcaatcctta acggccacct accgcaggta gcaaacggcg tccccctcct 180
cgatatctcc gcggcgacct ctggcttttt ccgcggaatt gcgcggtggg gacggattcc 240
acgagaccgc gacgcaaccg cctctcgccg ctgggcccca caccgctcgg tgccgtagcc 300
tcacgggact ctttctccct cctcccccgt tataaattgg cttcatcccc tccttgcctc 360
atccatccaa atcccagtcc ccaatcccat cccttcgtag gagaaattca tcgaagctaa 420
gcgaatcctc gcgatcctct caaggtactg cgagttttcg atccccctct cgacccctcg 480
tatgtttgtg tttgtcgtag cgtttgatta ggtatgcttt ccctgtttgt gttcgtcgta 540
gcgtttgatt aggtatgctt tccctgttcg tgttcatcgt agtgtttgat taggtcgtgt 600
gaggcgatgg cctgctcgcg tccttcgatc tgtagtcgat ttgcgggtcg tggtgtagat 660
ctgcgggctg tgatgaagtt atttggtgtg atctgctcgc ctgattctgc tggttggctc 720
gagtagatat gatggttgga ccggttggtt cgtttaccgc gctagggttg ggctgggatg 780
atgttgcatg cgccgttgcg cgtgatcccg cagcaggact tgcgtttgat tgccagatct 840
cgttacgatt atgtgatttg gtttggactt tttagatctg tagcttctgc ttatgtgcca 900
gatgcgccta ctgctcatat gcctgatgat aatcataaat ggctgtggaa ctaactagtt 960
gattgcggag tcatgtatca gctacaggtg tagggactag ctacaggtgt agggacttgc 1020
gtctaattgt ttggtccttt actcatgttg caattatgca atttagttta gattgtttgt 1080
tccactcatc taggctgtaa aagggacact gcttagattg ctgtttaatc tttttagtag 1140
attatattat attggtaact tattacccct attacatgcc atacgtgact tctgctcatg 1200
cctgatgata atcatagatc actgtggaat taattagttg attgttgaat catgtttcat 1260
gtacatacca cggcacaatt gcttagttcc ttaacaaatg caaattttac tgatccatgt 1320
atgatttgcg tggttctcta atgtgaaata ctatagctac ttgttagtaa gaatcaggtt 1380
cgtatgctta atgctgtatg tgccttctgc tcatgcctga tgataatcat atatcactgg 1440
aattaattag ttgatcgttt aatcatatat caagtacata ccatgccaca atttttagtc 1500
acttaaccca tgcagattga actggtccct gcatgttttg ctaaattgtt ctattctgat 1560
tagaccatat atcatgtatt tttttttggt aatggttctc ttattttaaa tgctatatag 1620
ttctggtact tgttagaaag atctgcttca tagtttagtt gcctatccct cgaattagga 1680
tgctgagcag ctgatcctat agctttgttt catgtatcaa ttcttttgtg ttcaacagtc 1740
agtttttgtt agattcattg taacttatgg tcgcttactc ttctggtcct caatgcttgc 1800
agggatccta aaccatggag atcaacaacc agaaccagtg cgtgccgtac aactgcctta 1860
acaaccccga gtccgagatc ctgaacgtgg ccatcttctc cagcgagcag gtcgcggaga 1920

-continued

```
tccacctcaa gatcacgcgc ctgatcctcg agaacttcct gccgggcggc tccttcgctt   1980
tcggcctgtt cgacctcatc tggggcatct tcaacgagga ccagtggagc gcgttcctca   2040
ggcaggtgga ggagctgatc aaccagcgca tcacggagtt cgccaggggc caggctatcc   2100
agcggctggt gggcttcggc aggtcctacg acgagtacat cctggccctc aaggagtggg   2160
agaacgaccc cgacaacccg gccagcaagg agcgcgtgag gacccgcttc aggaccaccg   2220
acgacgctct cctgacgggc gtccccctca tggctatccc gggcttcgag ctggccaccc   2280
tctcggtgta cgctcagtcg gccaacctgc acctcgccct cctgcgggac gctgtgttct   2340
tcggcgagag gtggggcctg acccagacga acatcaacga cctctactcc aggctgaaga   2400
acagcatccg cgactacacg aaccactgcg tgcgcttcta caacatcggc ctgggcaacc   2460
tcaacgtcat caggccggag tactaccgct tccagaggga gctgaccatc agcgtgctgg   2520
acctcgtcgc cctgttcccc aactacgaca tccgcacgta cccgatccca accaagtccc   2580
agctcacgag ggagatctac accgacccga tcatctcgcc gggcgcccag gccggctaca   2640
ccctgcagga cgtcctgagg gagccccacc tgatggactt cctgaacagg ctcatcatct   2700
acaccggcga gtacaggggc atcaggcact gggcgggcca cgaggtggag tccagcagga   2760
cgggcatgat gaccaacatc cgcttcccgc tctacggcac cgcggccacg gccgagccaa   2820
cccgcttcat cacgccgtcc accttccccg gcctgaacct cttctacagg accctgtcgg   2880
ctcccatctt ccgcgacgag ccgggcgcga acatcatcat ccgctacagg acctccctcg   2940
tggagggcgt cggcttcatc cagccgaaca acggcgagca gctgtaccgc gtgaggggca   3000
cgctggacag cctggaccag ctcccactgg agggcgagtc cagcctcacc gagtactcgc   3060
acaggctgtg ccacgtcagg ttcgcccaga gcctcaggaa cgcggagccc ctggactacg   3120
ccagggtgcc catgttcagc tggacccaca ggtcggctac ccccaccaac accatcgacc   3180
cagacgtgat cacgcagatc ccgctcgtca aggcccacac cctgcagtcg ggcaccaccg   3240
tggtcaaggg ccccggcttc acgggcggcg acatcctgag gaggacctcc ggcggcccat   3300
tcgccttcag caacgtcaac ctcgactgga acctgtccca gcgctacagg gcgcgcatca   3360
ggtacgccag caccacgaac ctgcgcatgt atgtgaccat cgcgggcgag aggatcttcg   3420
ccggccagtt caacaagacg atgaacaccg gcgacccgct caccttccag tccttcagct   3480
acgcgacgat cgacaccgcc ttcacgttcc ccacgaaggc ctccagcctg accgtgggcg   3540
ccgacacctt ctccagcggc aacgaggtct acgtggaccg cttcgagctg atcccggtga   3600
cggcgacctt cgaggccgag tacgacctgg agaaggccca gaaggcggtc aacgccctct   3660
tcacctccag caaccagatc ggcctgaaga cggacgtgac cgactaccac atcgacaagg   3720
tgtccaacct cgtcgagtgc ctgagcgacg agttctgcct cgacgagaag agggagctgt   3780
ccgagaaggt caagcacgcc aagcgcctct gcgacgagag gaacctcctg caggacccga   3840
acttcagggg aatcaaccgc cagccggaca ggggctggag gggcagcacc gacatcacca   3900
tccagggcgg cgacgacgtg ttcaaggaga actacgtcac gctcccgggc accttcgacg   3960
agtgctaccc cacgtacctg taccagaaga tcgacgagtc caagctcaag gcctacaccc   4020
gctacgagct gaggggatac atcgaggaca gccaggacct cgagatctac ctgatccgct   4080
acaacgcgaa gcacgagacg gtgaacgtcc ccggcacggg ctccctgtgg cccctctcgg   4140
ctcagtcgcc gatcggcaag tgcggcgagc ccaacaggtg cgccacccac ctcgagtgga   4200
acccggacct ggactgctcc tgccgggacg gcgagaagtg cgctcaccac tcccaccact   4260
```

```
tcagcctgga catcgacgtg ggctgcacgg acctcaacga ggacctgggc gtgtgggtca   4320
tcttcaaaat caagacgcag gacggccacg ctaggctggg caacctcgag ttcctggagg   4380
agaagccgct ggtgggcgag gctctggcca gggtcaagag ggcggagaag aagtggcgcg   4440
acaagaggga gaagctggag ctggagacga acatcgtcta caaggaggcc aagaagtccg   4500
tggacgcgct cttcgtcaac agccagtacg acaggctgca ggcggacacc aacatcgcca   4560
tcatccacgc cgcggacaag cgcgtgcact ccatcaggga ggcctacctc cccgagctga   4620
gcgtgatccc gggcgtcaac gctgccatct tcgaggagct ggagggccgc atcttcaccg   4680
cctactccct gtacgacgcg aggaacgtca tcaagaacgg cgacttcaac aacggcctca   4740
gctgctggaa cgtgaagggc cacgtggacg tcgaggagca gaacaaccac cgctcggtgc   4800
tggtggtccc cgagtgggag gctgaggtca gccaggaggt gcgcgtctgc ccgggcaggg   4860
gatacatcct ccgcgtgacc gcgtacaagg agggctacgg cgagggctgc gtcacgatcc   4920
acgagatcga ggacaacacc gacgagctga agttctccaa ctgcgtggag gaggagatct   4980
acccgaacaa cacggtcacc tgcaacgact acacggccac ccaggaggag tacgagggca   5040
cgtacacgtc gaggaacagg ggctacgacg gcgcttacga gtccaacagc tcggtgccgg   5100
ccgactacgc tagcgcgtac gaggagaagg cctacacgga cggccgcagg gacaacacct   5160
gcgagtcgaa caggggctac ggcgactaca cgccgctccc ggccggctac gtgaccaagg   5220
agctggagta cttcccggag acggacaagg tctggatcga gatcggcgag acggagggca   5280
ccttcatcgt ggactcagtc gagctgctgc tcatggagga gtaggagctc gccaacagtc   5340
gttgaagctg ctgctgtatc tgggttatct agtgtctctg cctttgccca aggatagtgc   5400
tgtctttcaa agtatttgta tcgtttgtgt cgtgagtcgt gactgagctg gtttcaagga   5460
ccagttgtgt tctcgttacc caaaactatc gtgcgaccgc atatggctta atcatgaata   5520
aatgttgttt gaatttaaac tattcgctga atattgttgt tttttgtcat gtcagttaat   5580
gttactaaat tggttgcctt ctaatttttg tttactggtg tttgtcgcac cttatctttt   5640
tactgtatgt ttacttcagg ttctggcagt ctcatttttt gtgactagtt aaaacttaca   5700
gctaaaaaaa tgcagttttt aattttaatt tgaagtttga ttagagctat tgatacccgg   5760
accatcaggt taggttagtt gtgcatagaa tcataaatat taatcatgtt ttctatgaat   5820
taagtcaaac ttgaaagtct ggctgaatat agtttctatg aatcatattg atatacatgt   5880
ttgattattt gttttgctat tagctattta ctttggtgaa tctatatagg cttatgcaga   5940
accttttttt ttgttctata tatccatatc ctagtactca gtagctctat gttttctgga   6000
gactagtggc ttgctttttc gtatgtctaa tttttttgctt gaccattgca aaacaaaaat   6060
tacctagtgt aatctctttt tataataatc ttgtaatgcg tctacctata ggtcaaagta   6120
ggttttgttt ggaaccctta gagctaactg ttagctagtt gataaattat tagctgagtt   6180
aagctagcta atgaactagt tttgatatta gctgaggatg tttgaaacct aataattatt   6240
ttttattagc taactatact aaattttagt agagagattc caaacaggag ttaacatggg   6300
atcagattgg ctatgcgttt gcaatcccat actaattagc taacggaccg ctaattagct   6360
aacgatcgct taattaagct tgcatgcctg cagtgcagcg tgacccggtc gtgcccctct   6420
ctagagataa tgagcattgc atgtctaagt tataaaaaat taccacatat ttttttgtc    6480
acacttgttt gaagtgcagt ttatctatct ttatacatat atttaaactt tactctacga   6540
ataatataat ctatagtact acaataatat cagtgtttta gagaatcata taaatgaaca   6600
gttagacatg gtctaaagga caattgagta ttttgacaac aggactctac agttttatct   6660
```

ttttagtgtg catgtgttct cctttttttt tgcaaatagc ttcacctata taatacttca 6720
tccattttat tagtacatcc atttagggtt tagggttaat ggtttttata gactaatttt 6780
tttagtacat ctattttatt ctattttagc ctctaaatta agaaaactaa aactctattt 6840
tagttttttt atttaataat ttagatataa aatagaataa aataaagtga ctaaaaatta 6900
aacaaatacc ctttaagaaa ttaaaaaaac taaggaaaca tttttcttgt ttcgagtaga 6960
taatgccagc ctgttaaacg ccgccgacga gtctaacgga caccaaccag cgaaccagca 7020
gcgtcgcgtc gggccaagcg aagcagacgg cacggcatct ctgtcgctgc ctctggaccc 7080
ctctcgagag ttccgctcca ccgttggact tgctccgctg tcggcatcca gaaattgcgt 7140
ggcggagcgg cagacgtgag ccggcacggc aggcggcctc ctcctcctct cacggcaccg 7200
gcagctacgg gggattcctt tcccaccgct ccttcgcttt cccttcctcg cccgccgtaa 7260
taaatagaca ccccctccac accctctttc cccaacctcg tgttgttcgg agcgcacaca 7320
cacacaacca gatctccccc aaatccaccc gtcggcacct ccgcttcaag gtacgccgct 7380
cgtcctcccc cccccccccc tctctacctt ctctagatcg gcgttccggt ccatagttag 7440
ggcccggtag ttctacttct gttcatgttt gtgttagatc cgtgtttgtg ttagatccgt 7500
gctgttagcg ttcgtacacg gatgcgacct gtacgtcaga cacgttctga ttgctaactt 7560
gccagtgttt ctctttgggg aatcctggga tggctctagc cgttccgcag acgggatcga 7620
tttcatgatt ttttttgttt cgttgcatag ggtttggttt gcccttttcc tttatttcaa 7680
tatatgccgt gcacttgttt gtcgggtcat cttttcatgc ttttttttgt cttggttgtg 7740
atgatgtggt ctggttgggc ggtcgttcta gatcggagta gaattctgtt tcaaactacc 7800
tggtggattt attaattttg gatctgtatg tgtgtgccat acatattcat agttacgaat 7860
tgaagatgat ggatggaaat atcgatctag gataggtata catgttgatg cgggttttac 7920
tgatgcatat acagagatgc tttttgttcg cttggttgtg atgatgtggt gtggttgggc 7980
ggtcgttcat tcgttctaga tcggagtaga atactgtttc aaactacctg gtgtatttat 8040
taattttgga actgtatgtg tgtgtcatac atcttcatag ttacgagttt aagatggatg 8100
gaaatatcga tctaggatag gtatacatgt tgatgtgggt tttactgatg catatacatg 8160
atggcatatg cagcatctat tcatatgctc taaccttgag tacctatcta ttataataaa 8220
caagtatgtt ttataattat tttgatcttg atatacttgg atgatggcat atccagcagc 8280
tatatctgga tttttttagc cctgccttca tacgctattt atttgcttgg tactgtttct 8340
tttgtcgttg ctcaccctgt tgtttggtgt tacttctgca gggatctccg atcatgcaaa 8400
aactcattaa ctcagtgcaa aactatgcct ggggcagcaa aacggcgttg actgaacttt 8460
acggtatgga aaatccgtcc agccagccga tggccgagct gtggatgggc gcacatccga 8520
aaagcagttc acgagtgcag aatgccgccg gagatatcgt ttcactgcgt gatgtgattg 8580
agagtgataa atcgactctg ctcggagagg ccgttgccaa acgctttggc gaactgcctt 8640
tcctgttcaa agtattatgc gcagcacagc cactctccat tcaggttcat ccaaacaaac 8700
acaattctga aatcggtttt gccaaagaaa atgccgcagg tatcccgatg gatgccgccg 8760
agcgtaacta taaagatcct aaccacaagc cggagctggt tttgcgctg acgcctttcc 8820
ttgcgatgaa cgcgtttcgt gaattttccg agattgtctc cctactccag ccggtcgcag 8880
gtgcacatcc ggcgattgct cactttttac aacagcctga tgccgaacgt ttaagcgaac 8940
tgttcgccag cctgttgaat atgcagggtg aagaaaaatc ccgcgcgctg gcgattttaa 9000
aatcggccct cgatagccag cagggtgaac cgtggcaaac gattcgttta atttctgaat 9060
tttacccgga agacagcggt ctgttctccc cgctattgct gaatgtggtg aaattgaacc 9120
ctggcgaagc gatgttcctg ttcgctgaaa caccgcacgc ttacctgcaa ggcgtggcgc 9180
tggaagtgat ggcaaactcc gataacgtgc tgcgtgcggg tctgacgcct aaatacattg 9240
atattccgga actggttgcc aatgtgaaat tcgaagccaa accggctaac cagttgttga 9300
cccagccggt gaaacaaggt gcagaactgg acttcccgat tccagtggac gattttgcct 9360
tctcgctgca cgaccttagt gataaagaaa ccaccattag ccagcagagt gccgccattt 9420
tgttctgcgt cgaaggcgat gcaacgttgt ggaaaggttc tcagcagtta cagcttaaac 9480
cgggtgaatc agcgtttatt gccgccaacg aatcaccggt gactgtcaaa ggccacggcc 9540
gtttagcgcg tgtttacaac aagctgtaag agcttactga aaaaattaac atctcttgct 9600
aagctgggtc atgggtcgtt taagctgccg atgtgcctgc gtcgtctggt gccctctctc 9660
catatggagg ttgtcaaagt atctgctgtt cgtgtcatga gtcgtgtcag tgttggttta 9720
ataatggacc ggttgtgttg tgtgtgcgta ctacccagaa ctatgacaaa tcatgaataa 9780
gtttgatgtt tgaaattaaa gcctgtgctc attatgttct gtctttcagt tgtctcctaa 9840
tatttgcctc caggtactgg ctatctaccg tttcttactt aggaggtgtt tgaatgcact 9900
aaaactaata gttagtggct aaaattagtt aaaacatcca aacaccatag ctaatagttg 9960
aactattagc tatttttgga aaattagtta atagtgaggt agttatttgt tagctagcta 10020
attcaactaa caatttttag ccaactaaca attagtttca gtgcattcaa acaccccctt 10080
aatgttaacg tggttctatc taccgtctcc taatatatgg ttgattgttc ggtttgttgc 10140
tatgctattg ggttctgatt gctgctagtt cttgctgaat ccagaagttc tcgtagtata 10200
gctcagattc atattattta tttgagtgat aagtgatcca ggttattact atgttagcta 10260
ggtttttttt acaaggataa attatctgtg atcataattc ttatgaaagc tttatgtttc 10320
ctggaggcag tggcatgcaa tgcatgacag caacttgatc acaccagctg aggtagatac 10380
ggtaacaagg ttcttaaatc tgttcaccaa atcattggag aacacacata cacattcttg 10440
ccagtcttgg ttagagaaat ttcatgacaa aatgccaaag ctgtcttgac tcttcacttt 10500
tggccatgag tcgtgactta gtttggttta atggaccggt tctcctagct tgttctactc 10560
aaaactgttg ttgatgcgaa taagttgtga tggttgatct ctggattttg ttttgctctc 10620
aatagtggac gagattagat ag 10642

<210> SEQ ID NO 13
<211> LENGTH: 10642
<212> TYPE: DNA
<213> ORGANISM: Artificial sequence
<220> FEATURE:
<223> OTHER INFORMATION: Synthetic polynucleotide

<400> SEQUENCE: 13
gaattcatta tgtggtctag gtaggttcta tatataagaa aacttgaaat gttctaaaaa 60
aaaattcaag cccatgcatg attgaagcaa acggtatagc aacggtgtta acctgatcta 120
gtgatctctt gcaatcctta acggccacct accgcaggta gcaaacggcg tccccctcct 180
cgatatctcc gcggcgacct ctggcttttt ccgcggaatt gcgcggtggg gacggattcc 240
acgagaccgc gacgcaaccg cctctcgccg ctgggcccca caccgctcgg tgccgtagcc 300
tcacgggact ctttctccct cctcccccgt tataaattgg cttcatcccc tccttgcctc 360
atccatccaa atcccagtcc ccaatcccat cccttcgtag gagaaattca tcgaagctaa 420

```
gcgaatcctc gcgatcctct caaggtactg cgagttttcg atccccctct cgacccctcg    480
tatgtttgtg tttgtcgtag cgtttgatta ggtatgcttt ccctgtttgt gttcgtcgta    540
gcgtttgatt aggtatgctt tccctgttcg tgttcatcgt agtgtttgat taggtcgtgt    600
gaggcgatgg cctgctcgcg tccttcgatc tgtagtcgat ttgcgggtcg tggtgtagat    660
ctgcgggctg tgatgaagtt atttggtgtg atctgctcgc ctgattctgc tggttggctc    720
gagtagatat gatggttgga ccggttggtt cgtttaccgc gctagggttg ggctgggatg    780
atgttgcatg cgccgttgcg cgtgatcccg cagcaggact tgcgtttgat tgccagatct    840
cgttacgatt atgtgatttg gtttggactt tttagatctg tagcttctgc ttatgtgcca    900
gatgcgccta ctgctcatat gcctgatgat aatcataaat ggctgtggaa ctaactagtt    960
gattgcggag tcatgtatca gctacaggtg tagggactag ctacaggtgt agggacttgc   1020
gtctaattgt ttggtccttt actcatgttg caattatgca atttagttta gattgtttgt   1080
tccactcatc taggctgtaa aagggacact gcttagattg ctgtttaatc tttttagtag   1140
attatattat attggtaact tattacccct attacatgcc atacgtgact tctgctcatg   1200
cctgatgata atcatagatc actgtggaat taattagttg attgttgaat catgtttcat   1260
gtacatacca cggcacaatt gcttagttcc ttaacaaatg caaattttac tgatccatgt   1320
atgatttgcg tggttctcta atgtgaaata ctatagctac ttgttagtaa gaatcaggtt   1380
cgtatgctta atgctgtatg tgccttctgc tcatgcctga tgataatcat atatcactgg   1440
aattaattag ttgatcgttt aatcatatat caagtacata ccatgccaca atttttagtc   1500
acttaaccca tgcagattga actggtccct gcatgttttg ctaaattgtt ctattctgat   1560
tagaccatat atcatgtatt tttttttggt aatggttctc ttattttaaa tgctatatag   1620
ttctggtact tgttagaaag atctgcttca tagtttagtt gcctatccct cgaattagga   1680
tgctgagcag ctgatcctat agctttgttt catgtatcaa ttcttttgtg ttcaacagtc   1740
agtttttgtt agattcattg taacttatgg tcgcttactc ttctggtcct caatgcttgc   1800
agggatccta aaccatggag atcaacaacc agaaccagtg cgtgccgtac aactgcctta   1860
acaaccccga gtccgagatc ctgaacgtgg ccatcttctc cagcgagcag gtcgcggaga   1920
tccacctcaa gatcacgcgc ctgatcctcg agaacttcct gccgggcggc tccttcgctt   1980
tcggcctgtt cgacctcatc tggggcatct tcaacgagga ccagtggagc gcgttcctca   2040
ggcaggtgga ggagctgatc aaccagcgca tcacggagtt cgccaggggc caggctatcc   2100
agcggctggt gggcttcggc aggtcctacg acgagtacat cctggccctc aaggagtggg   2160
agaacgaccc cgacaacccg gccagcaagg agcgcgtgag gacccgcttc aggaccaccg   2220
acgacgctct cctgacgggc gtccccctca tggctatccc gggcttcgag ctggccaccc   2280
tctcggtgta cgctcagtcg gccaacctgc acctcgccct cctgcgggac gctgtgttct   2340
tcggcgagag gtggggcctg acccagacga acatcaacga cctctactcc aggctgaaga   2400
acagcatccg cgactacacg aaccactgcg tgcgcttcta caacatcggc ctgggcaacc   2460
tcaacgtcat caggccggag tactaccgct tccagaggga gctgaccatc agcgtgctgg   2520
acctcgtcgc cctgttcccc aactacgaca tccgcacgta cccgatccca accaagtccc   2580
agctcacgag ggagatctac accgacccga tcatctcgcc gggcgcccag gccggctaca   2640
ccctgcagga cgtcctgagg gagccccacc tgatggactt cctgaacagg ctcatcatct   2700
acaccggcga gtacaggggc atcaggcact gggcgggcca cgaggtggag tccagcagga   2760
```

-continued

```
cgggcatgat gaccaacatc cgcttcccgc tctacggcac cgcggccacg gccgagccaa   2820
cccgcttcat cacgccgtcc accttccccg gcctgaacct cttctacagg accctgtcgg   2880
ctcccatctt ccgcgacgag ccgggcgcga acatcatcat ccgctacagg acctccctcg   2940
tggagggcgt cggcttcatc cagccgaaca acggcgagca gctgtaccgc gtgaggggca   3000
cgctggacag cctggaccag ctcccactgg agggcgagtc cagcctcacc gagtactcgc   3060
acaggctgtg ccacgtcagg ttcgcccaga gcctcaggaa cgcggagccc ctggactacg   3120
ccagggtgcc catgttcagc tggacccaca ggtcggctac ccccaccaac accatcgacc   3180
cagacgtgat cacgcagatc ccgctcgtca aggcccacac cctgcagtcg ggcaccaccg   3240
tggtcaaggg ccccggcttc acgggcggcg acatcctgag gaggacctcc ggcggcccat   3300
tcgccttcag caacgtcaac ctcgactgga acctgtccca gcgctacagg gcgcgcatca   3360
ggtacgccag caccacgaac ctgcgcatgt atgtgaccat cgcgggcgag aggatcttcg   3420
ccggccagtt caacaagacg atgaacaccg gcgacccgct caccttccag tccttcagct   3480
acgcgacgat cgacaccgcc ttcacgttcc ccacgaaggc ctccagcctg accgtgggcg   3540
ccgacacctt ctccagcggc aacgaggtct acgtggaccg cttcgagctg atcccggtga   3600
cggcgacctt cgaggccgag tacgacctgg agaaggccca gaaggcggtc aacgccctct   3660
tcacctccag caaccagatc ggcctgaaga cggacgtgac cgactaccac atcgacaagg   3720
tgtccaacct cgtcgagtgc ctgagcgacg agttctgcct cgacgagaag agggagctgt   3780
ccgagaaggt caagcacgcc aagcgcctct gcgacgagag gaacctcctg caggacccga   3840
acttcagggg aatcaaccgc cagccggaca ggggctggag gggcagcacc gacatcacca   3900
tccagggcgg cgacgacgtg ttcaaggaga actacgtcac gctcccgggc accttcgacg   3960
agtgctaccc cacgtacctg taccagaaga tcgacgagtc caagctcaag gcctacaccc   4020
gctacgagct gaggggatac atcgaggaca gccaggacct cgagatctac ctgatccgct   4080
acaacgcgaa gcacgagacg gtgaacgtcc ccggcacggg ctccctgtgg cccctctcgg   4140
ctcagtcgcc gatcggcaag tgcggcgagc ccaacaggtg cgccacccac ctcgagtgga   4200
acccggacct ggactgctcc tgccgggacg gcgagaagtg cgctcaccac tcccaccact   4260
tcagcctgga catcgacgtg ggctgcacgg acctcaacga ggacctgggc gtgtgggtca   4320
tcttcaaaat caagacgcag gacggccacg ctaggctggg caacctcgag ttcctggagg   4380
agaagccgct ggtgggcgag gctctggcca gggtcaagag ggcggagaag aagtggcgcg   4440
acaagaggga gaagctggag ctggagacga acatcgtcta caaggaggcc aagaagtccg   4500
tggacgcgct cttcgtcaac agccagtacg acaggctgca ggcggacacc aacatcgcca   4560
tcatccacgc cgcggacaag cgcgtgcact ccatcaggga ggcctacctc cccgagctga   4620
gcgtgatccc gggcgtcaac gctgccatct tcgaggagct ggagggccgc atcttcaccg   4680
cctactccct gtacgacgcg aggaacgtca tcaagaacgg cgacttcaac aacggcctca   4740
gctgctggaa cgtgaagggc cacgtggacg tcgaggagca gaacaaccac cgctcggtgc   4800
tggtggtccc cgagtgggag gctgaggtca gccaggaggt gcgcgtctgc ccgggcaggg   4860
gatacatcct ccgcgtgacc gcgtacaagg agggctacgg cgagggctgc gtcacgatcc   4920
acgagatcga ggacaacacc gacgagctga agttctccaa ctgcgtggag gaggagatct   4980
acccgaacaa cacggtcacc tgcaacgact acacggccac ccaggaggag tacgagggca   5040
cgtacacgtc gaggaacagg ggctacgacg gcgcttacga gtccaacagc tcggtgccgg   5100
ccgactacgc tagcgcgtac gaggagaagg cctacacgga cggccgcagg gacaacacct   5160
```

gcgagtcgaa caggggctac ggcgactaca cgccgctccc ggccggctac gtgaccaagg 5220
agctggagta cttcccggag acggacaagg tctggatcga gatcggcgag acggagggca 5280
ccttcatcgt ggactcagtc gagctgctgc tcatggagga gtaggagctc gccaacagtc 5340
gttgaagctg ctgctgtatc tgggttatct agtgtctctg cctttgccca aggatagtgc 5400
tgtctttcaa agtatttgta tcgtttgtgt cgtgagtcgt gactgagctg gtttcaagga 5460
ccagttgtgt tctcgttacc caaaactatc gtgcgaccgc atatggctta atcatgaata 5520
aatgttgttt gaatttaaac tattcgctga atattgttgt tttttgtcat gtcagttaat 5580
gttactaaat tggttgcctt ctaatttttg tttactggtg tttgtcgcac cttatctttt 5640
tactgtatgt ttacttcagg ttctggcagt ctcatttttt gtgactagtt aaaacttaca 5700
gctaaaaaaa tgcagttttt aattttaatt tgaagtttga ttagagctat tgatacccgg 5760
accatcaggt taggttagtt gtgcatagaa tcataaatat taatcatgtt ttctatgaat 5820
taagtcaaac ttgaaagtct ggctgaatat agtttctatg aatcatattg atatacatgt 5880
ttgattattt gttttgctat tagctattta ctttggtgaa tctatatagg cttatgcaga 5940
accttttttt ttgttctata tatccatatc ctagtactca gtagctctat gttttctgga 6000
gactagtggc ttgctttttc gtatgtctaa tttttttgctt gaccattgca aaacaaaaat 6060
tacctagtgt aatctctttt tataataatc ttgtaatgcg tctacctata ggtcaaagta 6120
ggttttgttt ggaaccctta gagctaactg ttagctagtt gataaattat tagctgagtt 6180
aagctagcta atgaactagt tttgatatta gctgaggatg tttgaaacct aataattatt 6240
ttttattagc taactatact aaattttagt agagagattc caaacaggag ttaacatggg 6300
atcagattgg ctatgcgttt gcaatcccat actaattagc taacggaccg ctaattagct 6360
aacgatcgct taattaagct tgcatgcctg cagtgcagcg tgacccggtc gtgcccctct 6420
ctagagataa tgagcattgc atgtctaagt tataaaaaat taccacatat ttttttgtc 6480
acacttgttt gaagtgcagt ttatctatct ttatacatat atttaaactt tactctacga 6540
ataatataat ctatagtact acaataatat cagtgtttta gagaatcata taaatgaaca 6600
gttagacatg gtctaaagga caattgagta ttttgacaac aggactctac agttttatct 6660
ttttagtgtg catgtgttct cctttttttt tgcaaatagc ttcacctata taatacttca 6720
tccattttat tagtacatcc atttagggtt tagggttaat ggtttttata gactaatttt 6780
tttagtacat ctattttatt ctattttagc ctctaaatta agaaaactaa aactctattt 6840
tagttttttt atttaataat ttagatataa aatagaataa aataaagtga ctaaaaatta 6900
aacaaatacc ctttaagaaa ttaaaaaaac taaggaaaca tttttcttgt ttcgagtaga 6960
taatgccagc ctgttaaacg ccgccgacga gtctaacgga caccaaccag cgaaccagca 7020
gcgtcgcgtc gggccaagcg aagcagacgg cacggcatct ctgtcgctgc ctctggaccc 7080
ctctcgagag ttccgctcca ccgttggact tgctccgctg tcggcatcca gaaattgcgt 7140
ggcggagcgg cagacgtgag ccggcacggc aggcggcctc ctcctcctct cacggcaccg 7200
gcagctacgg gggattcctt tcccaccgct ccttcgcttt cccttcctcg cccgccgtaa 7260
taaatagaca cccccctccac accctctttc cccaacctcg tgttgttcgg agcgcacaca 7320
cacacaacca gatctccccc aaatccaccc gtcggcacct ccgcttcaag gtacgccgct 7380
cgtcctcccc cccccccct ctctaccttc tctagatcgg cgttccggtc catagttagg 7440
gcccggtagt tctacttctg ttcatgtttg tgttagatcc gtgtttgtgt tagatccgtg 7500

-continued

```
ctgttagcgt tcgtacacgg atgcgacctg tacgtcagac acgttctgat tgctaacttg   7560
ccagtgtttc tctttgggga atcctgggat ggctctagcc gttccgcaga cgggatcgat   7620
ttcatgattt tttttgtttc gttgcatagg gtttggtttg cccttttcct ttatttcaat   7680
atatgccgtg cacttgtttg tcgggtcatc ttttcatgct tttttttgtc ttggttgtga   7740
tgatgtggtc tggttgggcg gtcgttctag atcggagtag aattctgttt caaactacct   7800
ggtggattta ttaattttgg atctgtatgt gtgtgccata catattcata gttacgaatt   7860
gaagatgatg gatggaaata tcgatctagg ataggtatac atgttgatgc gggttttact   7920
gatgcatata cagagatgct tttgttcgc ttggttgtga tgatgtggtg tggttgggcg   7980
gtcgttcatt tcgttctaga tcggagtaga atactgtttc aaactacctg gtgtatttat   8040
taattttgga actgtatgtg tgtgtcatac atcttcatag ttacgagttt aagatggatg   8100
gaaatatcga tctaggatag gtatacatgt tgatgtgggt tttactgatg catatacatg   8160
atggcatatg cagcatctat tcatatgctc taaccttgag tacctatcta ttataataaa   8220
caagtatgtt ttataattat tttgatcttg atatacttgg atgatggcat atccagcagc   8280
tatatctgga ttttttagc cctgccttca tacgctattt atttgcttgg tactgtttct   8340
tttgtcgttg ctcaccctgt tgtttggtgt tacttctgca gggatctccg atcatgcaaa   8400
aactcattaa ctcagtgcaa aactatgcct ggggcagcaa aacggcgttg actgaacttt   8460
acggtatgga aaatccgtcc agccagccga tggccgagct gtggatgggc gcacatccga   8520
aaagcagttc acgagtgcag aatgccgccg gagatatcgt ttcactgcgt gatgtgattg   8580
agagtgataa atcgactctg ctcggagagg ccgttgccaa acgctttggc gaactgcctt   8640
tcctgttcaa agtattatgc gcagcacagc cactctccat tcaggttcat ccaaacaaac   8700
acaattctga aatcggtttt gccaaagaaa atgccgcagg tatcccgatg gatgccgccg   8760
agcgtaacta taaagatcct aaccacaagc cggagctggt tttgcgctg acgcctttcc   8820
ttgcgatgaa cgcgtttcgt gaattttccg agattgtctc cctactccag ccggtcgcag   8880
gtgcacatcc ggcgattgct cactttttac aacagcctga tgccgaacgt ttaagcgaac   8940
tgttcgccag cctgttgaat atgcagggtg aagaaaaatc ccgcgcgctg gcgattttaa   9000
aatcggccct cgatagccag cagggtgaac cgtggcaaac gattcgttta atttctgaat   9060
tttacccgga agacagcggt ctgttctccc cgctattgct gaatgtggtg aaattgaacc   9120
ctggcgaagc gatgttcctg ttcgctgaaa caccgcacgc ttacctgcaa ggcgtggcgc   9180
tggaagtgat ggcaaactcc gataacgtgc tgcgtgcggg tctgacgcct aaatacattg   9240
atattccgga actggttgcc aatgtgaaat tcgaagccaa accggctaac cagttgttga   9300
cccagccggt gaaacaaggt gcagaactgg acttcccgat tccagtggac gatttgcct   9360
tctcgctgca cgaccttagt gataaagaaa ccaccattag ccagcagagt gccgccattt   9420
tgttctgcgt cgaaggcgat gcaacgttgt ggaaaggttc tcagcagtta cagcttaaac   9480
cgggtgaatc agcgtttatt gccgccaacg aatcaccggt gactgtcaaa ggccacggcc   9540
gtttagcgcg tgtttacaac aagctgtaag agcttactga aaaaattaac atctcttgct   9600
aagctgggtc atgggtcgtt taagctgccg atgtgcctgc gtcgtctggt gccctctctc   9660
catatggagg ttgtcaaagt atctgctgtt cgtgtcatga gtcgtgtcag tgttggttta   9720
ataatggacc ggttgtgttg tgtgtgcgta ctacccagaa ctatgacaaa tcatgaataa   9780
gtttgatgtt tgaaattaaa gcctgtgctc attatgttct gtctttcagt tgtctcctaa   9840
tatttgcctc caggtactgg ctatctaccg tttcttactt aggaggtgtt tgaatgcact   9900
```

aaaactaata gttagtggct aaaattagtt aaaacatcca aacaccatag ctaatagttg 9960
aactattagc tatttttgga aaattagtta atagtgaggt agttatttgt tagctagcta 10020
attcaactaa caatttttag ccaactaaca attagtttca gtgcattcaa acacccccctt 10080 aatgttaacg tggttctatc taccgtctcc taatatatgg ttgattgttc ggtttgttgc 10140
tatgctattg ggttctgatt gctgctagtt cttgctgaat ccagaagttc tcgtagtata 10200
gctcagattc atattattta tttgagtgat aagtgatcca ggttattact atgttagcta 10260
ggtttttttt acaaggataa attatctgtg atcataattc ttatgaaagc tttatgtttc 10320
ctggaggcag tggcatgcaa tgcatgacag caacttgatc acaccagctg aggtagatac 10380
ggtaacaagg ttcttaaatc tgttcaccaa atcattggag aacacacata cacattcttg 10440
ccagtcttgg ttagagaaat ttcatgacaa aatgccaaag ctgtcttgac tcttcacttt 10500
tggccatgag tcgtgactta gtttggttta atggaccggt tctcctagct tgttctactc 10560
aaaactgttg ttgatgcgaa taagttgtga tggttgatct ctggattttg ttttgctctc 10620
aatagtggac gagattagat ag 10642

<210> SEQ ID NO 14
<211> LENGTH: 10641
<212> TYPE: DNA
<213> ORGANISM: Artificial sequence
<220> FEATURE:
<223> OTHER INFORMATION: Synthetic polynucleotide

<400> SEQUENCE: 14
gaattcatta tgtggtctag gtaggttcta tatataagaa aacttgaaat gttctaaaaa 60
aaaattcaag cccatgcatg attgaagcaa acggtatagc aacggtgtta acctgatcta 120
gtgatctctt gcaatcctta acggccacct accgcaggta gcaaacggcg tccccctcct 180
cgatatctcc gcggcgacct ctggcttttt ccgcggaatt gcgcggtggg gacggattcc 240
acgagaccgc gacgcaaccg cctctcgccg ctgggcccca caccgctcgg tgccgtagcc 300
tcacgggact ctttctccct cctccccgtt ataaattggc ttcatcccct ccttgcctca 360
tccatccaaa tcccagtccc caatcccatc ccttcgtagg agaaattcat cgaagctaag 420
cgaatcctcg cgatcctctc aaggtactgc gagttttcga tccccctctc gacccctcgt 480
atgtttgtgt ttgtcgtagc gtttgattag gtatgctttc cctgtttgtg ttcgtcgtag 540
cgtttgatta ggtatgcttt ccctgttcgt gttcatcgta gtgtttgatt aggtcgtgtg 600
aggcgatggc ctgctcgcgt ccttcgatct gtagtcgatt tgcgggtcgt ggtgtagatc 660
tgcgggctgt gatgaagtta tttggtgtga tctgctcgcc tgattctgct ggttggctcg 720
agtagatatg atggttggac cggttggttc gtttaccgcg ctagggttgg gctgggatga 780
tgttgcatgc gccgttgcgc gtgatcccgc agcaggactt gcgtttgatt gccagatctc 840
gttacgatta tgtgatttgg tttggacttt ttagatctgt agcttctgct tatgtgccag 900
atgcgcctac tgctcatatg cctgatgata atcataaatg gctgtggaac taactagttg 960
attgcggagt catgtatcag ctacaggtgt agggactagc tacaggtgta gggacttgcg 1020
tctaattgtt tggtccttta ctcatgttgc aattatgcaa tttagtttag attgtttgtt 1080
ccactcatct aggctgtaaa agggacactg cttagattgc tgtttaatct ttttagtaga 1140
ttatattata ttggtaactt attacccctta ttacatgcca tacgtgactt ctgctcatgc 1200
ctgatgataa tcatagatca ctgtggaatt aattagttga ttgttgaatc atgtttcatg 1260
tacataccac ggcacaattg cttagttcct taacaaatgc aaattttact gatccatgta 1320
tgatttgcgt ggttctctaa tgtgaaatac tatagctact tgttagtaag aatcaggttc 1380
gtatgcttaa tgctgtatgt gccttctgct catgcctgat gataatcata tatcactgga 1440
attaattagt tgatcgttta atcatatatc aagtacatac catgccacaa tttttagtca 1500
cttaacccat gcagattgaa ctggtccctg catgttttgc taaattgttc tattctgatt 1560
agaccatata tcatgtattt ttttttggta atggttctct tattttaaat gctatatagt 1620
tctggtactt gttagaaaga tctgcttcat agtttagttg cctatccctc gaattaggat 1680
gctgagcagc tgatcctata gctttgtttc atgtatcaat tcttttgtgt tcaacagtca 1740
gtttttgtta gattcattgt aacttatggt cgcttactct tctggtcctc aatgcttgca 1800
gggatcctaa accatggaga tcaacaacca gaaccagtgc gtgccgtaca actgccttaa 1860
caaccccgag tccgagatcc tgaacgtggc catcttctcc agcgagcagg tcgcggagat 1920
ccacctcaag atcacgcgcc tgatcctcga gaacttcctg ccgggcggct ccttcgcttt 1980
cggcctgttc gacctcatct ggggcatctt caacgaggac cagtggagcg cgttcctcag 2040
gcaggtggag gagctgatca accagcgcat cacggagttc gccaggggcc aggctatcca 2100
gcggctggtg ggcttcggca ggtcctacga cgagtacatc ctggccctca aggagtggga 2160
gaacgacccc gacaacccgg ccagcaagga gcgcgtgagg acccgcttca ggaccaccga 2220
cgacgctctc ctgacgggcg tccccctcat ggctatcccg ggcttcgagc tggccaccct 2280
ctcggtgtac gctcagtcgg ccaacctgca cctcgccctc ctgcgggacg ctgtgttctt 2340
cggcgagagg tggggcctga cccagacgaa catcaacgac ctctactcca ggctgaagaa 2400
cagcatccgc gactacacga accactgcgt gcgcttctac aacatcggcc tgggcaacct 2460
caacgtcatc aggccggagt actaccgctt ccagagggag ctgaccatca gcgtgctgga 2520
cctcgtcgcc ctgttcccca actacgacat ccgcacgtac ccgatcccaa ccaagtccca 2580
gctcacgagg gagatctaca ccgacccgat catctcgccg ggcgcccagg ccggctacac 2640
cctgcaggac gtcctgaggg agccccacct gatggacttc ctgaacaggc tcatcatcta 2700
caccggcgag tacaggggca tcaggcactg ggcgggccac gaggtggagt ccagcaggac 2760
gggcatgatg accaacatcc gcttcccgct ctacggcacc gcggccacgg ccgagccaac 2820
ccgcttcatc acgccgtcca ccttccccgg cctgaacctc ttctacagga ccctgtcggc 2880
tcccatcttc cgcgacgagc cgggcgcgaa catcatcatc cgctacagga cctccctcgt 2940
ggagggcgtc ggcttcatcc agccgaacaa cggcgagcag ctgtaccgcg tgaggggcac 3000
gctggacagc ctggaccagc tcccactgga gggcgagtcc agcctcaccg agtactcgca 3060
caggctgtgc cacgtcaggt tcgcccagag cctcaggaac gcggagcccc tggactacgc 3120
cagggtgccc atgttcagct ggacccacag gtcggctacc cccaccaaca ccatcgaccc 3180
agacgtgatc acgcagatcc cgctcgtcaa ggcccacacc ctgcagtcgg gcaccaccgt 3240
ggtcaagggc cccggcttca cgggcggcga catcctgagg aggacctccg gcggcccatt 3300
cgccttcagc aacgtcaacc tcgactggaa cctgtcccag cgctacaggg cgcgcatcag 3360
gtacgccagc accacgaacc tgcgcatgta tgtgaccatc gcgggcgaga ggatcttcgc 3420
cggccagttc aacaagacga tgaacaccgg cgacccgctc accttccagt ccttcagcta 3480
cgcgacgatc gacaccgcct tcacgttccc cacgaaggcc tccagcctga ccgtgggcgc 3540
cgacaccttc tccagcggca acgaggtcta cgtggaccgc ttcgagctga tcccggtgac 3600
ggcgaccttc gaggccgagt acgacctgga gaaggcccag aaggcggtca acgccctctt 3660
cacctccagc aaccagatcg gcctgaagac ggacgtgacc gactaccaca tcgacaaggt 3720
gtccaacctc gtcgagtgcc tgagcgacga gttctgcctc gacgagaaga gggagctgtc 3780
cgagaaggtc aagcacgcca agcgcctctg cgacgagagg aacctcctgc aggacccgaa 3840
cttcagggga atcaaccgcc agccggacag gggctggagg ggcagcaccg acatcaccat 3900
ccagggcggc gacgacgtgt tcaaggagaa ctacgtcacg ctcccgggca ccttcgacga 3960
gtgctacccc acgtacctgt accagaagat cgacgagtcc aagctcaagg cctacacccg 4020
ctacgagctg aggggataca tcgaggacag ccaggacctc gagatctacc tgatccgcta 4080
caacgcgaag cacgagacgg tgaacgtccc cggcacgggc tccctgtggc ccctctcggc 4140
tcagtcgccg atcggcaagt gcggcgagcc caacaggtgc gccacccacc tcgagtggaa 4200
cccggacctg gactgctcct gccgggacgg cgagaagtgc gctcaccact cccaccactt 4260
cagcctggac atcgacgtgg gctgcacgga cctcaacgag gacctgggcg tgtgggtcat 4320
cttcaaaatc aagacgcagg acggccacgc taggctgggc aacctcgagt tcctggagga 4380
gaagccgctg gtgggcgagg ctctggccag ggtcaagagg gcggagaaga agtggcgcga 4440
caagagggag aagctggagc tggagacgaa catcgtctac aaggaggcca agaagtccgt 4500
ggacgcgctc ttcgtcaaca gccagtacga caggctgcag gcggacacca acatcgccat 4560
catccacgcc gcggacaagc gcgtgcactc catcagggag gcctacctcc ccgagctgag 4620
cgtgatcccg ggcgtcaacg ctgccatctt cgaggagctg gagggccgca tcttcaccgc 4680
ctactccctg tacgacgcga ggaacgtcat caagaacggc gacttcaaca acggcctcag 4740
ctgctggaac gtgaagggcc acgtggacgt cgaggagcag aacaaccacc gctcggtgct 4800
ggtggtcccc gagtgggagg ctgaggtcag ccaggaggtg cgcgtctgcc cgggcagggg 4860
atacatcctc cgcgtgaccg cgtacaagga gggctacggc gagggctgcg tcacgatcca 4920
cgagatcgag gacaacaccg acgagctgaa gttctccaac tgcgtggagg aggagatcta 4980
cccgaacaac acggtcacct gcaacgacta cacggccacc caggaggagt acgagggcac 5040
gtacacgtcg aggaacaggg gctacgacgg cgcttacgag tccaacagct cggtgccggc 5100
cgactacgct agcgcgtacg aggagaaggc ctacacggac ggccgcaggg acaacacctg 5160
cgagtcgaac aggggctacg gcgactacac gccgctcccg gccggctacg tgaccaagga 5220
gctggagtac ttcccggaga cggacaaggt ctggatcgag atcggcgaga cggagggcac 5280
cttcatcgtg gactcagtcg agctgctgct catggaggag taggagctcg ccaacagtcg 5340
ttgaagctgc tgctgtatct gggttatcta gtgtctctgc ctttgcccaa ggatagtgct 5400
gtctttcaaa gtatttgtat cgtttgtgtc gtgagtcgtg actgagctgg tttcaaggac 5460
cagttgtgtt ctcgttaccc aaaactatcg tgcgaccgca tatggcttaa tcatgaataa 5520
atgttgtttg aatttaaact attcgctgaa tattgttgtt ttttgtcatg tcagttaatg 5580
ttactaaatt ggttgccttc taatttttgt ttactggtgt ttgtcgcacc ttatcttttt 5640
actgtatgtt tacttcaggt tctggcagtc tcatttttttg tgactagtta aaacttacag 5700
ctaaaaaaat gcagttttta attttaattt gaagtttgat tagagctatt gatacccgga 5760
ccatcaggtt aggttagttg tgcatagaat cataaatatt aatcatgttt tctatgaatt 5820
aagtcaaact tgaaagtctg gctgaatata gtttctatga atcatattga tatacatgtt 5880
tgattatttg ttttgctatt agctatttac tttggtgaat ctatataggc ttatgcagaa 5940
cctttttttt tgttctatat atccatatcc tagtactcag tagctctatg ttttctggag 6000

-continued

```
actagtggct tgctttttcg tatgtctaat tttttgcttg accattgcaa aacaaaaatt   6060
acctagtgta atctcttttt ataataatct tgtaatgcgt ctacctatag gtcaaagtag   6120
gttttgtttg gaacccttag agctaactgt tagctagttg ataaattatt agctgagtta   6180
agctagctaa tgaactagtt ttgatattag ctgaggatgt ttgaaaccta ataattattt   6240
tttattagct aactatacta aattttagta gagagattcc aaacaggagt taacatggga   6300
tcagattggc tatgcgtttg caatcccata ctaattagct aacggaccgc taattagcta   6360
acgatcgctt aattaagctt gcatgcctgc agtgcagcgt gacccggtcg tgcccctctc   6420
tagagataat gagcattgca tgtctaagtt ataaaaaatt accacatatt ttttttgtca   6480
cacttgtttg aagtgcagtt tatctatctt tatacatata tttaaacttt actctacgaa   6540
taatataatc tatagtacta caataaatatc agtgttttag agaatcatat aaatgaacag  6600
ttagacatgg tctaaaggac aattgagtat tttgacaaca ggactctaca gttttatctt   6660
tttagtgtgc atgtgttctc cttttttttt gcaaatagct tcacctatat aatacttcat   6720
ccattttatt agtacatcca tttagggttt agggttaatg gtttttatag actaattttt   6780
ttagtacatc tattttattc tattttagcc tctaaattaa gaaaactaaa actctatttt   6840
agttttttta tttaataatt tagatataaa atagaataaa ataaagtgac taaaaattaa   6900
acaaataccc tttaagaaat taaaaaaact aaggaaacat ttttcttgtt tcgagtagat   6960
aatgccagcc tgttaaacgc cgccgacgag tctaacggac accaaccagc gaaccagcag   7020
cgtcgcgtcg ggccaagcga agcagacggc acggcatctc tgtcgctgcc tctggacccc   7080
tctcgagagt tccgctccac cgttggactt gctccgctgt cggcatccag aaattgcgtg   7140
gcggagcggc agacgtgagc cggcacggca ggcggcctcc tcctcctctc acggcaccgg   7200
cagctacggg ggattccttt cccaccgctc cttcgctttc ccttcctcgc ccgccgtaat   7260
aaatagacac cccctccaca ccctctttcc ccaacctcgt gttgttcgga gcgcacacac   7320
acacaaccag atctccccca aatccacccg tcggcacctc cgcttcaagg tacgccgctc   7380
gtcctccccc ccccccccctc tctaccttct ctagatcggc gttccggtcc atagttaggg  7440
cccggtagtt ctacttctgt tcatgtttgt gttagatccg tgtttgtgtt agatccgtgc   7500
tgttagcgtt cgtacacgga tgcgacctgt acgtcagaca cgttctgatt gctaacttgc   7560
cagtgtttct ctttggggaa tcctgggatg gctctagccg ttccgcagac gggatcgatt   7620
tcatgatttt ttttgtttcg ttgcataggg tttggtttgc ccttttcctt tatttcaata   7680
tatgccgtgc acttgtttgt cgggtcatct tttcatgctt ttttttgtct tggttgtgat   7740
gatgtggtct ggttgggcgg tcgttctaga tcggagtaga attctgtttc aaactacctg   7800
gtggatttat taattttgga tctgtatgtg tgtgccatac atattcatag ttacgaattg   7860
aagatgatgg atggaaatat cgatctagga taggtataca tgttgatgcg ggttttactg   7920
atgcatatac agagatgctt tttgttcgct tggttgtgat gatgtggtgt ggttgggcgg   7980
tcgttcattt cgttctagat cggagtagaa tactgtttca aactacctgg tgtatttatt   8040
aattttggaa ctgtatgtgt gtgtcataca tcttcatagt tacgagttta agatggatgg   8100
aaatatcgat ctaggatagg tatacatgtt gatgtgggtt ttactgatgc atatacatga   8160
tggcatatgc agcatctatt catatgctct aaccttgagt acctatctat tataataaac   8220
aagtatgttt tataattatt ttgatcttga tatacttgga tgatggcata tccagcagct   8280
atatctggat ttttttagcc ctgccttcat acgctattta tttgcttggt actgtttctt   8340
ttgtcgttgc tcaccctgtt gtttggtgtt acttctgcag ggatctccga tcatgcaaaa   8400
```

```
actcattaac tcagtgcaaa actatgcctg gggcagcaaa acggcgttga ctgaacttta   8460
cggtatggaa aatccgtcca gccagccgat ggccgagctg tggatgggcg cacatccgaa   8520
aagcagttca cgagtgcaga atgccgccgg agatatcgtt tcactgcgtg atgtgattga   8580
gagtgataaa tcgactctgc tcggagaggc cgttgccaaa cgctttggcg aactgccttt   8640
cctgttcaaa gtattatgcg cagcacagcc actctccatt caggttcatc caaacaaaca   8700
caattctgaa atcggttttg ccaaagaaaa tgccgcaggt atcccgatgg atgccgccga   8760
gcgtaactat aaagatccta accacaagcc ggagctggtt tttgcgctga cgcctttcct   8820
tgcgatgaac gcgtttcgtg aattttccga gattgtctcc ctactccagc cggtcgcagg   8880
tgcacatccg gcgattgctc actttttaca acagcctgat gccgaacgtt taagcgaact   8940
gttcgccagc ctgttgaata tgcagggtga agaaaaatcc cgcgcgctgg cgattttaaa   9000
atcggccctc gatagccagc agggtgaacc gtggcaaacg attcgtttaa tttctgaatt   9060
ttacccggaa gacagcggtc tgttctcccc gctattgctg aatgtggtga aattgaaccc   9120
tggcgaagcg atgttcctgt tcgctgaaac accgcacgct tacctgcaag gcgtggcgct   9180
ggaagtgatg gcaaactccg ataacgtgct gcgtgcgggt ctgacgccta aatacattga   9240
tattccggaa ctggttgcca atgtgaaatt cgaagccaaa ccggctaacc agttgttgac   9300
ccagccggtg aaacaaggtg cagaactgga cttcccgatt ccagtggacg attttgcctt   9360
ctcgctgcac gaccttagtg ataaagaaac caccattagc cagcagagtg ccgccatttt   9420
gttctgcgtc gaaggcgatg caacgttgtg gaaaggttct cagcagttac agcttaaacc   9480
gggtgaatca gcgtttattg ccgccaacga atcaccggtg actgtcaaag gccacggccg   9540
tttagcgcgt gtttacaaca agctgtaaga gcttactgaa aaaattaaca tctcttgcta   9600
agctgggtca tgggtcgttt aagctgccga tgtgcctgcg tcgtctggtg ccctctctcc   9660
atatggaggt tgtcaaagta tctgctgttc gtgtcatgag tcgtgtcagt gttggtttaa   9720
taatggaccg gttgtgttgt gtgtgcgtac tacccagaac tatgacaaat catgaataag   9780
tttgatgttt gaaattaaag cctgtgctca ttatgttctg tctttcagtt gtctcctaat   9840
atttgcctcc aggtactggc tatctaccgt ttcttactta ggaggtgttt gaatgcacta   9900
aaactaatag ttagtggcta aaattagtta aaacatccaa acaccatagc taatagttga   9960
actattagct atttttggaa aattagttaa tagtgaggta gttatttgtt agctagctaa  10020
ttcaactaac aatttttagc caactaacaa ttagtttcag tgcattcaaa cacccccctta  10080
atgttaacgt ggttctatct accgtctcct aatatatggt tgattgttcg gtttgttgct  10140
atgctattgg gttctgattg ctgctagttc ttgctgaatc cagaagttct cgtagtatag  10200
ctcagattca tattatttat ttgagtgata agtgatccag gttattacta tgttagctag  10260
gttttttttta caaggataaa ttatctgtga tcataattct tatgaaagct ttatgtttcc  10320
tggaggcagt ggcatgcaat gcatgacagc aacttgatca caccagctga ggtagatacg  10380
gtaacaaggt tcttaaatct gttcaccaaa tcattggaga acacacatac acattcttgc  10440
cagtcttggt tagagaaatt tcatgacaaa atgccaaagc tgtcttgact cttcactttt  10500
ggccatgagt cgtgacttag tttggtttaa tggaccggtt ctcctagctt gttctactca  10560
aaactgttgt tgatgcgaat aagttgtgat ggttgatctc tggattttgt tttgctctca  10620
atagtggacg agattagata g                                          10641
```

<210> SEQ ID NO 15

<211> LENGTH: 10643
<212> TYPE: DNA
<213> ORGANISM: Artificial sequence
<220> FEATURE:
<223> OTHER INFORMATION: Synthetic polynucleotide

<400> SEQUENCE: 15
gaattcatta tgtggtctag gtaggttcta tatataagaa aacttgaaat gttctaaaaa 60
aaaattcaag cccatgcatg attgaagcaa acggtatagc aacggtgtta acctgatcta 120
gtgatctctt gcaatcctta acggccacct accgcaggta gcaaacggcg tccccctcct 180
cgatatctcc gcggcgacct ctggcttttt ccgcggaatt gcgcggtggg gacggattcc 240
acgagaccgc gacgcaaccg cctctcgccg ctgggcccca caccgctcgg tgccgtagcc 300
tcacgggact ctttctccct cctcccccgt tataaattgg cttcatcccc tccttgcctc 360
atccatccaa atcccagtcc ccaatcccat cccttcgtag gagaaattca tcgaagctaa 420
gcgaatcctc gcgatcctct caaggtactg cgagttttcg atccccctct cgacccctcg 480
tatgtttgtg tttgtcgtag cgtttgatta ggtatgcttt ccctgtttgt gttcgtcgta 540
gcgtttgatt aggtatgctt tccctgttcg tgttcatcgt agtgtttgat taggtcgtgt 600
gaggcgatgg cctgctcgcg tccttcgatc tgtagtcgat ttgcgggtcg tggtgtagat 660
ctgcgggctg tgatgaagtt atttggtgtg atctgctcgc ctgattctgc tggttggctc 720
gagtagatat gatggttgga ccggttggtt cgtttaccgc gctagggttg ggctgggatg 780
atgttgcatg cgccgttgcg cgtgatcccg cagcaggact tgcgtttgat tgccagatct 840
cgttacgatt atgtgatttg gtttggactt tttagatctg tagcttctgc ttatgtgcca 900
gatgcgccta ctgctcatat gcctgatgat aatcataaat ggctgtggaa ctaactagtt 960
gattgcggag tcatgtatca gctacaggtg tagggactag ctacaggtgt agggacttgc 1020
gtctaattgt ttggtccttt actcatgttg caattatgca atttagttta gattgtttgt 1080
tccactcatc taggctgtaa aagggacact gcttagattg ctgtttaatc tttttagtag 1140
attatattat attggtaact tattacccct attacatgcc atacgtgact tctgctcatg 1200
cctgatgata atcatagatc actgtggaat taattagttg attgttgaat catgtttcat 1260
gtacatacca cggcacaatt gcttagttcc ttaacaaatg caaattttac tgatccatgt 1320
atgatttgcg tggttctcta atgtgaaata ctatagctac ttgttagtaa gaatcaggtt 1380
cgtatgctta atgctgtatg tgccttctgc tcatgcctga tgataatcat atatcactgg 1440
aattaattag ttgatcgttt aatcatatat caagtacata ccatgccaca atttttagtc 1500
acttaaccca tgcagattga actggtccct gcatgttttg ctaaattgtt ctattctgat 1560
tagaccatat atcatgtatt ttttttggt aatggttctc ttattttaaa tgctatatag 1620
ttctggtact tgttagaaag atctgcttca tagtttagtt gcctatccct cgaattagga 1680
tgctgagcag ctgatcctat agctttgttt catgtatcaa ttcttttgtg ttcaacagtc 1740
agtttttgtt agattcattg taacttatgg tcgcttactc ttctggtcct caatgcttgc 1800
agggatccta aaccatggag atcaacaacc agaaccagtg cgtgccgtac aactgcctta 1860
acaaccccga gtccgagatc ctgaacgtgg ccatcttctc cagcgagcag gtcgcggaga 1920
tccacctcaa gatcacgcgc ctgatcctcg agaacttcct gccgggcggc tccttcgctt 1980
tcggcctgtt cgacctcatc tggggcatct tcaacgagga ccagtggagc gcgttcctca 2040
ggcaggtgga ggagctgatc aaccagcgca tcacggagtt cgccaggggc caggctatcc 2100
agcggctggt gggcttcggc aggtcctacg acgagtacat cctggccctc aaggagtggg 2160
agaacgaccc cgacaacccg gccagcaagg agcgcgtgag gacccgcttc aggaccaccg 2220
acgacgctct cctgacgggc gtccccctca tggctatccc gggcttcgag ctggccaccc 2280
tctcggtgta cgctcagtcg gccaacctgc acctcgccct cctgcgggac gctgtgttct 2340
tcggcgagag gtggggcctg acccagacga acatcaacga cctctactcc aggctgaaga 2400
acagcatccg cgactacacg aaccactgcg tgcgcttcta caacatcggc ctgggcaacc 2460
tcaacgtcat caggccggag tactaccgct tccagaggga gctgaccatc agcgtgctgg 2520
acctcgtcgc cctgttcccc aactacgaca tccgcacgta cccgatccca accaagtccc 2580
agctcacgag ggagatctac accgacccga tcatctcgcc gggcgcccag gccggctaca 2640
ccctgcagga cgtcctgagg gagccccacc tgatggactt cctgaacagg ctcatcatct 2700
acaccggcga gtacaggggc atcaggcact gggcgggcca cgaggtggag tccagcagga 2760
cgggcatgat gaccaacatc cgcttcccgc tctacggcac cgcggccacg gccgagccaa 2820
cccgcttcat cacgccgtcc accttccccg gcctgaacct cttctacagg accctgtcgg 2880
ctcccatctt ccgcgacgag ccgggcgcga acatcatcat ccgctacagg acctccctcg 2940
tggagggcgt cggcttcatc cagccgaaca acggcgagca gctgtaccgc gtgaggggca 3000
cgctggacag cctggaccag ctcccactgg agggcgagtc cagcctcacc gagtactcgc 3060
acaggctgtg ccacgtcagg ttcgcccaga gcctcaggaa cgcggagccc ctggactacg 3120
ccagggtgcc catgttcagc tggacccaca ggtcggctac ccccaccaac accatcgacc 3180
cagacgtgat cacgcagatc ccgctcgtca aggcccacac cctgcagtcg ggcaccaccg 3240
tggtcaaggg ccccggcttc acgggcggcg acatcctgag gaggacctcc ggcggcccat 3300
tcgccttcag caacgtcaac ctcgactgga acctgtccca gcgctacagg gcgcgcatca 3360
ggtacgccag caccacgaac ctgcgcatgt atgtgaccat cgcgggcgag aggatcttcg 3420
ccggccagtt caacaagacg atgaacaccg gcgacccgct caccttccag tccttcagct 3480
acgcgacgat cgacaccgcc ttcacgttcc ccacgaaggc ctccagcctg accgtgggcg 3540
ccgacacctt ctccagcggc aacgaggtct acgtggaccg cttcgagctg atcccggtga 3600
cggcgacctt cgaggccgag tacgacctgg agaaggccca gaaggcggtc aacgccctct 3660
tcacctccag caaccagatc ggcctgaaga cggacgtgac cgactaccac atcgacaagg 3720
tgtccaacct cgtcgagtgc ctgagcgacg agttctgcct cgacgagaag agggagctgt 3780
ccgagaaggt caagcacgcc aagcgcctct gcgacgagag gaacctcctg caggacccga 3840
acttcagggg aatcaaccgc cagccggaca ggggctggag gggcagcacc gacatcacca 3900
tccagggcgg cgacgacgtg ttcaaggaga actacgtcac gctcccgggc accttcgacg 3960
agtgctaccc cacgtacctg taccagaaga tcgacgagtc caagctcaag gcctacaccc 4020
gctacgagct gaggggatac atcgaggaca gccaggacct cgagatctac ctgatccgct 4080
acaacgcgaa gcacgagacg gtgaacgtcc ccggcacggg ctccctgtgg cccctctcgg 4140
ctcagtcgcc gatcggcaag tgcggcgagc ccaacaggtg cgccacccac ctcgagtgga 4200
acccggacct ggactgctcc tgccgggacg gcgagaagtg cgctcaccac tcccaccact 4260
tcagcctgga catcgacgtg ggctgcacgg acctcaacga ggacctgggc gtgtgggtca 4320
tcttcaaaat caagacgcag gacggccacg ctaggctggg caacctcgag ttcctggagg 4380
agaagccgct ggtgggcgag gctctggcca gggtcaagag ggcggagaag aagtggcgcg 4440
acaagaggga gaagctggag ctggagacga acatcgtcta caaggaggcc aagaagtccg 4500

```
tggacgcgct cttcgtcaac agccagtacg acaggctgca ggcggacacc aacatcgcca   4560
tcatccacgc cgcggacaag cgcgtgcact ccatcaggga ggcctacctc cccgagctga   4620
gcgtgatccc gggcgtcaac gctgccatct tcgaggagct ggagggccgc atcttcaccg   4680
cctactccct gtacgacgcg aggaacgtca tcaagaacgg cgacttcaac aacggcctca   4740
gctgctggaa cgtgaagggc cacgtggacg tcgaggagca gaacaaccac cgctcggtgc   4800
tggtggtccc cgagtgggag gctgaggtca gccaggaggt gcgcgtctgc ccgggcaggg   4860
gatacatcct ccgcgtgacc gcgtacaagg agggctacgg cgagggctgc gtcacgatcc   4920
acgagatcga ggacaacacc gacgagctga agttctccaa ctgcgtggag gaggagatct   4980
acccgaacaa cacggtcacc tgcaacgact acacggccac ccaggaggag tacgagggca   5040
cgtacacgtc gaggaacagg ggctacgacg gcgcttacga gtccaacagc tcggtgccgg   5100
ccgactacgc tagcgcgtac gaggagaagg cctacacgga cggccgcagg gacaacacct   5160
gcgagtcgaa caggggctac ggcgactaca cgccgctccc ggccggctac gtgaccaagg   5220
agctggagta cttcccggag acggacaagg tctggatcga gatcggcgag acggagggca   5280
ccttcatcgt ggactcagtc gagctgctgc tcatggagga gtaggagctc gccaacagtc   5340
gttgaagctg ctgctgtatc tgggttatct agtgtctctg cctttgccca aggatagtgc   5400
tgtctttcaa agtatttgta tcgtttgtgt cgtgagtcgt gactgagctg gtttcaagga   5460
ccagttgtgt tctcgttacc caaaactatc gtgcgaccgc atatggctta atcatgaata   5520
aatgttgttt gaatttaaac tattcgctga atattgttgt tttttgtcat gtcagttaat   5580
gttactaaat tggttgcctt ctaatttttg tttactggtg tttgtcgcac cttatctttt   5640
tactgtatgt ttacttcagg ttctggcagt ctcatttttt gtgactagtt aaaacttaca   5700
gctaaaaaaa tgcagttttt aattttaatt tgaagtttga ttagagctat tgatacccgg   5760
accatcaggt taggttagtt gtgcatagaa tcataaatat taatcatgtt ttctatgaat   5820
taagtcaaac ttgaaagtct ggctgaatat agtttctatg aatcatattg atatacatgt   5880
ttgattattt gttttgctat tagctattta ctttggtgaa tctatatagg cttatgcaga   5940
accttttttt ttgttctata tatccatatc ctagtactca gtagctctat gttttctgga   6000
gactagtggc ttgctttttc gtatgtctaa ttttttgctt gaccattgca aaacaaaaat   6060
tacctagtgt aatctctttt tataataatc ttgtaatgcg tctacctata ggtcaaagta   6120
ggttttgttt ggaaccctta gagctaactg ttagctagtt gataaattat tagctgagtt   6180
aagctagcta atgaactagt tttgatatta gctgaggatg tttgaaacct aataattatt   6240
ttttattagc taactatact aaattttagt agagagattc caaacaggag ttaacatggg   6300
atcagattgg ctatgcgttt gcaatcccat actaattagc taacggaccg ctaattagct   6360
aacgatcgct taattaagct tgcatgcctg cagtgcagcg tgacccggtc gtgcccctct   6420
ctagagataa tgagcattgc atgtctaagt tataaaaaat taccacatat ttttttgtc    6480
acacttgttt gaagtgcagt ttatctatct ttatacatat atttaaactt tactctacga   6540
ataatataat ctatagtact acaataatat cagtgtttta gagaatcata taaatgaaca   6600
gttagacatg gtctaaagga caattgagta ttttgacaac aggactctac agttttatct   6660
ttttagtgtg catgtgttct cctttttttt tgcaaatagc ttcacctata taatacttca   6720
tccattttat tagtacatcc atttagggtt tagggttaat ggtttttata gactaatttt   6780
tttagtacat ctattttatt ctattttagc ctctaaatta agaaaactaa aactctattt   6840
tagttttttt atttaataat ttagatataa aatagaataa aataaagtga ctaaaaatta   6900
```

-continued

```
aacaaatacc ctttaagaaa ttaaaaaaac taaggaaaca tttttcttgt ttcgagtaga   6960
taatgccagc ctgttaaacg ccgccgacga gtctaacgga caccaaccag cgaaccagca   7020
gcgtcgcgtc gggccaagcg aagcagacgg cacggcatct ctgtcgctgc ctctggaccc   7080
ctctcgagag ttccgctcca ccgttggact tgctccgctg tcggcatcca gaaattgcgt   7140
ggcggagcgg cagacgtgag ccggcacggc aggcggcctc ctcctcctct cacggcaccg   7200
gcagctacgg gggattcctt tcccaccgct ccttcgcttt cccttcctcg cccgccgtaa   7260
taaatagaca cccccctcca caccctcttt ccccaacctc gtgttgttcg gagcgcacac   7320
acacacaacc agatctcccc caaatccacc cgtcggcacc tccgcttcaa ggtacgccgc   7380
tcgtcctccc cccccccccc tctctacctt ctctagatcg gcgttccggt ccatagttag   7440
ggcccggtag ttctacttct gttcatgttt gtgttagatc cgtgtttgtg ttagatccgt   7500
gctgttagcg ttcgtacacg gatgcgacct gtacgtcaga cacgttctga ttgctaactt   7560
gccagtgttt ctctttgggg aatcctggga tggctctagc cgttccgcag acgggatcga   7620
tttcatgatt ttttttgttt cgttgcatag ggtttggttt gccctttcc tttatttcaa    7680
tatatgccgt gcacttgttt gtcgggtcat cttttcatgc ttttttttgt cttggttgtg   7740
atgatgtggt ctggttgggc ggtcgttcta gatcggagta gaattctgtt tcaaactacc   7800
tggtggattt attaattttg gatctgtatg tgtgtgccat acatattcat agttacgaat   7860
tgaagatgat ggatggaaat atcgatctag gataggtata catgttgatg cgggttttac   7920
tgatgcatat acagagatgc tttttgttcg cttggttgtg atgatgtggt gtggttgggc   7980
ggtcgttcat ttcgttctag atcggagtag aatactgttt caaactacct ggtgtattta   8040
ttaattttgg aactgtatgt gtgtgtcata catcttcata gttacgagtt taagatggat   8100
ggaaatatcg atctaggata ggtatacatg ttgatgtggg ttttactgat gcatatacat   8160
gatggcatat gcagcatcta ttcatatgct ctaaccttga gtacctatct attataataa   8220
acaagtatgt tttataatta ttttgatctt gatatacttg gatgatggca tatccagcag   8280
ctatatctgg atttttttag ccctgccttc atacgctatt tatttgcttg gtactgtttc   8340
ttttgtcgtt gctcaccctg ttgtttggtg ttacttctgc agggatctcc gatcatgcaa   8400
aaactcatta actcagtgca aaactatgcc tggggcagca aaacggcgtt gactgaactt   8460
tacggtatgg aaaatccgtc cagccagccg atggccgagc tgtggatggg cgcacatccg   8520
aaaagcagtt cacgagtgca gaatgccgcc ggagatatcg tttcactgcg tgatgtgatt   8580
gagagtgata aatcgactct gctcggagag gccgttgcca aacgctttgg cgaactgcct   8640
ttcctgttca aagtattatg cgcagcacag ccactctcca ttcaggttca tccaaacaaa   8700
cacaattctg aaatcggttt tgccaaagaa aatgccgcag gtatcccgat ggatgccgcc   8760
gagcgtaact ataaagatcc taaccacaag ccggagctgg tttttgcgct gacgcctttc   8820
cttgcgatga acgcgtttcg tgaattttcc gagattgtct ccctactcca gccggtcgca   8880
ggtgcacatc cggcgattgc tcactttta caacagcctg atgccgaacg tttaagcgaa    8940
ctgttcgcca gcctgttgaa tatgcagggt gaagaaaaat cccgcgcgct ggcgatttta   9000
aaatcggccc tcgatagcca gcagggtgaa ccgtggcaaa cgattcgttt aatttctgaa   9060
ttttacccgg aagacagcgg tctgttctcc ccgctattgc tgaatgtggt gaaattgaac   9120
cctggcgaag cgatgttcct gttcgctgaa acaccgcacg cttacctgca aggcgtggcg   9180
ctggaagtga tggcaaactc cgataacgtg ctgcgtgcgg gtctgacgcc taaatacatt   9240
```

gatattccgg aactggttgc caatgtgaaa ttcgaagcca aaccggctaa ccagttgttg 9300
acccagccgg tgaaacaagg tgcagaactg gacttcccga ttccagtgga cgattttgcc 9360
ttctcgctgc acgaccttag tgataaagaa accaccatta gccagcagag tgccgccatt 9420
ttgttctgcg tcgaaggcga tgcaacgttg tggaaaggtt ctcagcagtt acagcttaaa 9480
ccgggtgaat cagcgtttat tgccgccaac gaatcaccgg tgactgtcaa aggccacggc 9540
cgtttagcgc gtgtttacaa caagctgtaa gagcttactg aaaaaattaa catctcttgc 9600
taagctgggt catgggtcgt ttaagctgcc gatgtgcctg cgtcgtctgg tgccctctct 9660
ccatatggag gttgtcaaag tatctgctgt tcgtgtcatg agtcgtgtca gtgttggttt 9720
aataatggac cggttgtgtt gtgtgtgcgt actacccaga actatgacaa atcatgaata 9780
agtttgatgt ttgaaattaa agcctgtgct cattatgttc tgtctttcag ttgtctccta 9840
atatttgcct ccaggtactg gctatctacc gtttcttact taggaggtgt ttgaatgcac 9900
taaaactaat agttagtggc taaaattagt taaaacatcc aaacaccata gctaatagtt 9960
gaactattag ctatttttgg aaaattagtt aatagtgagg tagttatttg ttagctagct 10020
aattcaacta acaattttta gccaactaac aattagtttc agtgcattca aacacccccct 10080 taatgttaac gtggttctat ctaccgtctc ctaatatatg gttgattgtt cggtttgttg 10140
ctatgctatt gggttctgat tgctgctagt tcttgctgaa tccagaagtt ctcgtagtat 10200
agctcagatt catattattt atttgagtga taagtgatcc aggttattac tatgttagct 10260
aggttttttt tacaaggata aattatctgt gatcataatt cttatgaaag ctttatgttt 10320
cctggaggca gtggcatgca atgcatgaca gcaacttgat cacaccagct gaggtagata 10380
cggtaacaag gttcttaaat ctgttcacca aatcattgga gaacacacat acacattctt 10440
gccagtcttg gttagagaaa tttcatgaca aaatgccaaa gctgtcttga ctcttcactt 10500
ttggccatga gtcgtgactt agtttggttt aatggaccgg ttctcctagc ttgttctact 10560
caaaactgtt gttgatgcga ataagttgtg atggttgatc tctggatttt gttttgctct 10620
caatagtgga cgagattaga tag 10643

<210> SEQ ID NO 16
<211> LENGTH: 10643
<212> TYPE: DNA
<213> ORGANISM: Artificial sequence
<220> FEATURE:
<223> OTHER INFORMATION: Synthetic polynucleotide

<400> SEQUENCE: 16
gaattcatta tgtggtctag gtaggttcta tatataagaa aacttgaaat gttctaaaaa 60
aaaattcaag cccatgcatg attgaagcaa acggtatagc aacggtgtta acctgatcta 120
gtgatctctt gcaatcctta acggccacct accgcaggta gcaaacggcg tccccctcct 180
cgatatctcc gcggcgacct ctggcttttt ccgcggaatt gcgcggtggg gacggattcc 240
acgagaccgc gacgcaaccg cctctcgccg ctgggcccca caccgctcgg tgccgtagcc 300
tcacgggact ctttctccct cctcccccgt tataaattgg cttcatcccc tccttgcctc 360
atccatccaa atcccagtcc ccaatcccat cccttcgtag gagaaattca tcgaagctaa 420
gcgaatcctc gcgatcctct caaggtactg cgagttttcg atccccctct cgacccctcg 480
tatgtttgtg tttgtcgtag cgtttgatta ggtatgcttt ccctgtttgt gttcgtcgta 540
gcgtttgatt aggtatgctt tccctgttcg tgttcatcgt agtgtttgat taggtcgtgt 600
gaggcgatgg cctgctcgcg tccttcgatc tgtagtcgat ttgcgggtcg tggtgtagat 660

```
ctgcgggctg tgatgaagtt atttggtgtg atctgctcgc ctgattctgc tggttggctc    720
gagtagatat gatggttgga ccggttggtt cgtttaccgc gctagggttg ggctgggatg    780
atgttgcatg cgccgttgcg cgtgatcccg cagcaggact tgcgtttgat tgccagatct    840
cgttacgatt atgtgatttg gtttggactt tttagatctg tagcttctgc ttatgtgcca    900
gatgcgccta ctgctcatat gcctgatgat aatcataaat ggctgtggaa ctaactagtt    960
gattgcggag tcatgtatca gctacaggtg tagggactag ctacaggtgt agggacttgc   1020
gtctaattgt ttggtccttt actcatgttg caattatgca atttagttta gattgtttgt   1080
tccactcatc taggctgtaa aagggacact gcttagattg ctgtttaatc tttttagtag   1140
attatattat attggtaact tattacccct attacatgcc atacgtgact tctgctcatg   1200
cctgatgata atcatagatc actgtggaat taattagttg attgttgaat catgtttcat   1260
gtacatacca cggcacaatt gcttagttcc ttaacaaatg caaattttac tgatccatgt   1320
atgatttgcg tggttctcta atgtgaaata ctatagctac ttgttagtaa gaatcaggtt   1380
cgtatgctta atgctgtatg tgccttctgc tcatgcctga tgataatcat atatcactgg   1440
aattaattag ttgatcgttt aatcatatat caagtacata ccatgccaca atttttagtc   1500
acttaaccca tgcagattga actggtccct gcatgttttg ctaaattgtt ctattctgat   1560
tagaccatat atcatgtatt ttttttggt aatggttctc ttattttaaa tgctatatag   1620
ttctggtact tgttagaaag atctgcttca tagtttagtt gcctatccct cgaattagga   1680
tgctgagcag ctgatcctat agctttgttt catgtatcaa ttcttttgtg ttcaacagtc   1740
agtttttgtt agattcattg taacttatgg tcgcttactc ttctggtcct caatgcttgc   1800
agggatccta aaccatggag atcaacaacc agaaccagtg cgtgccgtac aactgcctta   1860
acaaccccga gtccgagatc ctgaacgtgg ccatcttctc cagcgagcag gtcgcggaga   1920
tccacctcaa gatcacgcgc ctgatcctcg agaacttcct gccgggcggc tccttcgctt   1980
tcggcctgtt cgacctcatc tggggcatct tcaacgagga ccagtggagc gcgttcctca   2040
ggcaggtgga ggagctgatc aaccagcgca tcacggagtt cgccaggggc caggctatcc   2100
agcggctggt gggcttcggc aggtcctacg acgagtacat cctggccctc aaggagtggg   2160
agaacgaccc cgacaacccg gccagcaagg agcgcgtgag gacccgcttc aggaccaccg   2220
acgacgctct cctgacgggc gtccccctca tggctatccc gggcttcgag ctggccaccc   2280
tctcggtgta cgctcagtcg gccaacctgc acctcgccct cctgcgggac gctgtgttct   2340
tcggcgagag gtggggcctg acccagacga acatcaacga cctctactcc aggctgaaga   2400
acagcatccg cgactacacg aaccactgcg tgcgcttcta caacatcggc ctgggcaacc   2460
tcaacgtcat caggccggag tactaccgct tccagaggga gctgaccatc agcgtgctgg   2520
acctcgtcgc cctgttcccc aactacgaca tccgcacgta cccgatccca accaagtccc   2580
agctcacgag ggagatctac accgacccga tcatctcgcc gggcgcccag gccggctaca   2640
ccctgcagga cgtcctgagg gagccccacc tgatggactt cctgaacagg ctcatcatct   2700
acaccggcga gtacaggggc atcaggcact gggcgggcca cgaggtggag tccagcagga   2760
cgggcatgat gaccaacatc cgcttcccgc tctacggcac cgcggccacg gccgagccaa   2820
cccgcttcat cacgccgtcc accttccccg gcctgaacct cttctacagg accctgtcgg   2880
ctcccatctt ccgcgacgag ccgggcgcga acatcatcat ccgctacagg acctccctcg   2940
tggagggcgt cggcttcatc cagccgaaca acggcgagca gctgtaccgc gtgaggggca   3000
```

cgctggacag cctggaccag ctcccactgg agggcgagtc cagcctcacc gagtactcgc 3060
acaggctgtg ccacgtcagg ttcgcccaga gcctcaggaa cgcggagccc ctggactacg 3120
ccagggtgcc catgttcagc tggacccaca ggtcggctac cccccaccaac accatcgacc 3180
cagacgtgat cacgcagatc ccgctcgtca aggcccacac cctgcagtcg ggcaccaccg 3240
tggtcaaggg ccccggcttc acgggcggcg acatcctgag gaggacctcc ggcggcccat 3300
tcgccttcag caacgtcaac ctcgactgga acctgtccca gcgctacagg gcgcgcatca 3360
ggtacgccag caccacgaac ctgcgcatgt atgtgaccat cgcgggcgag aggatcttcg 3420
ccggccagtt caacaagacg atgaacaccg gcgacccgct caccttccag tccttcagct 3480
acgcgacgat cgacaccgcc ttcacgttcc ccacgaaggc ctccagcctg accgtgggcg 3540
ccgacacctt ctccagcggc aacgaggtct acgtggaccg cttcgagctg atcccggtga 3600
cggcgacctt cgaggccgag tacgacctgg agaaggccca gaaggcggtc aacgccctct 3660
tcacctccag caaccagatc ggcctgaaga cggacgtgac cgactaccac atcgacaagg 3720
tgtccaacct cgtcgagtgc ctgagcgacg agttctgcct cgacgagaag agggagctgt 3780
ccgagaaggt caagcacgcc aagcgcctct gcgacgagag gaacctcctg caggacccga 3840
acttcagggg aatcaaccgc cagccggaca ggggctggag gggcagcacc gacatcacca 3900
tccagggcgg cgacgacgtg ttcaaggaga actacgtcac gctcccgggc accttcgacg 3960
agtgctaccc cacgtacctg taccagaaga tcgacgagtc caagctcaag gcctacaccc 4020
gctacgagct gaggggatac atcgaggaca gccaggacct cgagatctac ctgatccgct 4080
acaacgcgaa gcacgagacg gtgaacgtcc ccggcacggg ctccctgtgg cccctctcgg 4140
ctcagtcgcc gatcggcaag tgcggcgagc ccaacaggtg cgccacccac ctcgagtgga 4200
acccggacct ggactgctcc tgccgggacg gcgagaagtg cgctcaccac tcccaccact 4260
tcagcctgga catcgacgtg ggctgcacgg acctcaacga ggacctgggc gtgtgggtca 4320
tcttcaaaat caagacgcag gacggccacg ctaggctggg caacctcgag ttcctggagg 4380
agaagccgct ggtgggcgag gctctggcca gggtcaagag ggcggagaag aagtggcgcg 4440
acaagaggga gaagctggag ctggagacga acatcgtcta caaggaggcc aagaagtccg 4500
tggacgcgct cttcgtcaac agccagtacg acaggctgca ggcggacacc aacatcgcca 4560
tcatccacgc cgcggacaag cgcgtgcact ccatcaggga ggcctacctc cccgagctga 4620
gcgtgatccc gggcgtcaac gctgccatct tcgaggagct ggagggccgc atcttcaccg 4680
cctactccct gtacgacgcg aggaacgtca tcaagaacgg cgacttcaac aacggcctca 4740
gctgctggaa cgtgaagggc cacgtggacg tcgaggagca gaacaaccac cgctcggtgc 4800
tggtggtccc cgagtgggag gctgaggtca gccaggaggt gcgcgtctgc ccgggcaggg 4860
gatacatcct ccgcgtgacc gcgtacaagg agggctacgg cgagggctgc gtcacgatcc 4920
acgagatcga ggacaacacc gacgagctga agttctccaa ctgcgtggag gaggagatct 4980
acccgaacaa cacggtcacc tgcaacgact acacggccac ccaggaggag tacgagggca 5040
cgtacacgtc gaggaacagg ggctacgacg gcgcttacga gtccaacagc tcggtgccgg 5100
ccgactacgc tagcgcgtac gaggagaagg cctacacgga cggccgcagg gacaacacct 5160
gcgagtcgaa caggggctac ggcgactaca cgccgctccc ggccggctac gtgaccaagg 5220
agctggagta cttcccggag acggacaagg tctggatcga gatcggcgag acggagggca 5280
ccttcatcgt ggactcagtc gagctgctgc tcatggagga gtaggagctc gccaacagtc 5340
gttgaagctg ctgctgtatc tgggttatct agtgtctctg cctttgccca aggatagtgc 5400
tgtctttcaa agtatttgta tcgtttgtgt cgtgagtcgt gactgagctg gtttcaagga 5460
ccagttgtgt tctcgttacc caaaactatc gtgcgaccgc atatggctta atcatgaata 5520
aatgttgttt gaatttaaac tattcgctga atattgttgt tttttgtcat gtcagttaat 5580
gttactaaat tggttgcctt ctaatttttg tttactggtg tttgtcgcac cttatctttt 5640
tactgtatgt ttacttcagg ttctggcagt ctcatttttt gtgactagtt aaaacttaca 5700
gctaaaaaaa tgcagttttt aattttaatt tgaagtttga ttagagctat tgatacccgg 5760
accatcaggt taggttagtt gtgcatagaa tcataaatat taatcatgtt ttctatgaat 5820
taagtcaaac ttgaaagtct ggctgaatat agtttctatg aatcatattg atatacatgt 5880
ttgattattt gttttgctat tagctattta ctttggtgaa tctatatagg cttatgcaga 5940
accttttttt ttgttctata tatccatatc ctagtactca gtagctctat gttttctgga 6000
gactagtggc ttgcttttc gtatgtctaa tttttgctt gaccattgca aaacaaaaat 6060
tacctagtgt aatctctttt tataataatc ttgtaatgcg tctacctata ggtcaaagta 6120
ggttttgttt ggaaccctta gagctaactg ttagctagtt gataaattat tagctgagtt 6180
aagctagcta atgaactagt tttgatatta gctgaggatg tttgaaacct aataattatt 6240
ttttattagc taactatact aaattttagt agagagattc caaacaggag ttaacatggg 6300
atcagattgg ctatgcgttt gcaatcccat actaattagc taacggaccg ctaattagct 6360
aacgatcgct taattaagct tgcatgcctg cagtgcagcg tgacccggtc gtgcccctct 6420
ctagagataa tgagcattgc atgtctaagt tataaaaaat taccacatat tttttttgtc 6480
acacttgttt gaagtgcagt ttatctatct ttatacatat atttaaactt tactctacga 6540
ataatataat ctatagtact acaataatat cagtgtttta gagaatcata taaatgaaca 6600
gttagacatg gtctaaagga caattgagta ttttgacaac aggactctac agttttatct 6660
ttttagtgtg catgtgttct cctttttttt tgcaaatagc ttcacctata taatacttca 6720
tccattttat tagtacatcc atttagggtt tagggttaat ggtttttata gactaatttt 6780
tttagtacat ctattttatt ctattttagc ctctaaatta agaaaactaa aactctattt 6840 tagtttttt atttaataat ttagatataa aatagaataa aataaagtga ctaaaaatta 6900
aacaaatacc ctttaagaaa ttaaaaaaac taaggaaaca tttttcttgt ttcgagtaga 6960
taatgccagc ctgttaaacg ccgccgacga gtctaacgga caccaaccag cgaaccagca 7020
gcgtcgcgtc gggccaagcg aagcagacgg cacggcatct ctgtcgctgc ctctggaccc 7080
ctctcgagag ttccgctcca ccgttggact tgctccgctg tcggcatcca gaaattgcgt 7140
ggcggagcgg cagacgtgag ccggcacggc aggcggcctc ctcctcctct cacggcaccg 7200
gcagctacgg gggattcctt tcccaccgct ccttcgcttt cccttcctcg cccgccgtaa 7260
taaatagaca ccccctccac accctctttc cccaacctcg tgttgttcgg agcgcacaca 7320
cacacaacca gatctccccc aaatccaccc gtcggcacct ccgcttcaag gtacgccgct 7380
cgtcctcccc cccccccccc tctctacctt ctctagatcg gcgttccggt ccatagttag 7440
ggcccggtag ttctacttct gttcatgttt gtgttagatc cgtgtttgtg ttagatccgt 7500
gctgttagcg ttcgtacacg gatgcgacct gtacgtcaga cacgttctga ttgctaactt 7560
gccagtgttt ctctttgggg aatcctggga tggctctagc cgttccgcag acgggatcga 7620
tttcatgatt ttttttgttt cgttgcatag ggtttggttt gccctttcc tttatttcaa 7680 tatatgccgt gcacttgttt gtcgggtcat cttttcatgc ttttttttgt cttggttgtg 7740

-continued

```
atgatgtggt ctggttgggc ggtcgttcta gatcggagta gaattctgtt tcaaactacc   7800
tggtggattt attaattttg gatctgtatg tgtgtgccat acatattcat agttacgaat   7860
tgaagatgat ggatggaaat atcgatctag gataggtata catgttgatg cgggttttac   7920
tgatgcatat acagagatgc tttttgttcg cttggttgtg atgatgtggt gtggttgggc   7980
ggtcgttcat ttcgttctag atcggagtag aatactgttt caaactacct ggtgtattta   8040
ttaattttgg aactgtatgt gtgtgtcata catcttcata gttacgagtt taagatggat   8100
ggaaatatcg atctaggata ggtatacatg ttgatgtggg ttttactgat gcatatacat   8160
gatggcatat gcagcatcta ttcatatgct ctaaccttga gtacctatct attataataa   8220
acaagtatgt tttataatta ttttgatctt gatatacttg gatgatggca tatccagcag   8280
ctatatctgg atttttttag ccctgccttc atacgctatt tatttgcttg gtactgtttc   8340
ttttgtcgtt gctcaccctg ttgtttggtg ttacttctgc agggatctcc gatcatgcaa   8400
aaactcatta actcagtgca aaactatgcc tggggcagca aaacggcgtt gactgaactt   8460
tacggtatgg aaaatccgtc cagccagccg atggccgagc tgtggatggg cgcacatccg   8520
aaaagcagtt cacgagtgca gaatgccgcc ggagatatcg tttcactgcg tgatgtgatt   8580
gagagtgata aatcgactct gctcggagag gccgttgcca aacgctttgg cgaactgcct   8640
ttcctgttca aagtattatg cgcagcacag ccactctcca ttcaggttca tccaaacaaa   8700
cacaattctg aaatcggttt tgccaaagaa aatgccgcag gtatcccgat ggatgccgcc   8760
gagcgtaact ataaagatcc taaccacaag ccggagctgg tttttgcgct gacgcctttc   8820
cttgcgatga acgcgtttcg tgaattttcc gagattgtct ccctactcca gccggtcgca   8880
ggtgcacatc cggcgattgc tcacttttta caacagcctg atgccgaacg tttaagcgaa   8940
ctgttcgcca gcctgttgaa tatgcagggt gaagaaaaat cccgcgcgct ggcgatttta   9000
aaatcggccc tcgatagcca gcagggtgaa ccgtggcaaa cgattcgttt aatttctgaa   9060
ttttacccgg aagacagcgg tctgttctcc ccgctattgc tgaatgtggt gaaattgaac   9120
cctggcgaag cgatgttcct gttcgctgaa acaccgcacg cttacctgca aggcgtggcg   9180
ctggaagtga tggcaaactc cgataacgtg ctgcgtgcgg gtctgacgcc taaatacatt   9240
gatattccgg aactggttgc caatgtgaaa ttcgaagcca aaccggctaa ccagttgttg   9300
acccagccgg tgaaacaagg tgcagaactg gacttcccga ttccagtgga cgattttgcc   9360
ttctcgctgc acgaccttag tgataaagaa accaccatta gccagcagag tgccgccatt   9420
ttgttctgcg tcgaaggcga tgcaacgttg tggaaaggtt ctcagcagtt acagcttaaa   9480
ccgggtgaat cagcgtttat tgccgccaac gaatcaccgg tgactgtcaa aggccacggc   9540
cgtttagcgc gtgtttacaa caagctgtaa gagcttactg aaaaaattaa catctcttgc   9600
taagctgggt catgggtcgt ttaagctgcc gatgtgcctg cgtcgtctgg tgccctctct   9660
ccatatggag gttgtcaaag tatctgctgt tcgtgtcatg agtcgtgtca gtgttggttt   9720
aataatggac cggttgtgtt gtgtgtgcgt actacccaga actatgacaa atcatgaata   9780
agtttgatgt ttgaaattaa agcctgtgct cattatgttc tgtctttcag ttgtctccta   9840
atatttgcct ccaggtactg gctatctacc gtttcttact taggaggtgt ttgaatgcac   9900
taaaactaat agttagtggc taaaattagt taaaacatcc aaacaccata gctaatagtt   9960
gaactattag ctatttttgg aaaattagtt aatagtgagg tagttatttg ttagctagct  10020
aattcaacta acaattttta gccaactaac aattagtttc agtgcattca aacacccccct 10080
taatgttaac gtggttctat ctaccgtctc ctaatatatg gttgattgtt cggtttgttg  10140
```

```
ctatgctatt gggttctgat tgctgctagt tcttgctgaa tccagaagtt ctcgtagtat  10200

agctcagatt catattattt atttgagtga taagtgatcc aggttattac tatgttagct  10260

aggttttttt tacaaggata aattatctgt gatcataatt cttatgaaag ctttatgttt  10320

cctggaggca gtggcatgca atgcatgaca gcaacttgat cacaccagct gaggtagata  10380

cggtaacaag gttcttaaat ctgttcacca aatcattgga gaacacacat acacattctt  10440

gccagtcttg gttagagaaa tttcatgaca aaatgccaaa gctgtcttga ctcttcactt  10500

ttggccatga gtcgtgactt agtttggttt aatggaccgg ttctcctagc ttgttctact  10560

caaaactgtt gttgatgcga ataagttgtg atggttgatc tctggatttt gttttgctct  10620

caatagtgga cgagattaga tag                                          10643
```

<210> SEQ ID NO 17
<211> LENGTH: 10641
<212> TYPE: DNA
<213> ORGANISM: Artificial sequence
<220> FEATURE:
<223> OTHER INFORMATION: Synthetic polynucleotide

<400> SEQUENCE: 17

```
gaattcatta tgtggtctag gtaggttcta tatataagaa aacttgaaat gttctaaaaa     60

aaaattcaag cccatgcatg attgaagcaa acggtatagc aacggtgtta acctgatcta    120

gtgatctctt gcaatcctta acggccacct accgcaggta gcaaacggcg tccccctcct    180

cgatatctcc gcggcgacct ctggcttttt ccgcggaatt gcgcggtggg gacggattcc    240

acgagaccgc gacgcaaccg cctctcgccg ctgggcccca caccgctcgg tgccgtagcc    300

tcacgggact ctttctccct cctccccgtt ataaattggc ttcatcccct ccttgcctca    360

tccatccaaa tcccagtccc caatcccatc ccttcgtagg agaaattcat cgaagctaag    420

cgaatcctcg cgatcctctc aaggtactgc gagttttcga tccccctctc gacccctcgt    480

atgtttgtgt ttgtcgtagc gtttgattag gtatgctttc cctgtttgtg ttcgtcgtag    540

cgtttgatta ggtatgcttt ccctgttcgt gttcatcgta gtgtttgatt aggtcgtgtg    600

aggcgatggc ctgctcgcgt ccttcgatct gtagtcgatt tgcgggtcgt ggtgtagatc    660

tgcgggctgt gatgaagtta tttggtgtga tctgctcgcc tgattctgct ggttggctcg    720

agtagatatg atggttggac cggttggttc gtttaccgcg ctagggttgg gctgggatga    780

tgttgcatgc gccgttgcgc gtgatcccgc agcaggactt gcgtttgatt gccagatctc    840

gttacgatta tgtgatttgg tttggacttt ttagatctgt agcttctgct tatgtgccag    900

atgcgcctac tgctcatatg cctgatgata atcataaatg gctgtggaac taactagttg    960

attgcggagt catgtatcag ctacaggtgt agggactagc tacaggtgta gggacttgcg   1020

tctaattgtt tggtccttta ctcatgttgc aattatgcaa tttagtttag attgtttgtt   1080

ccactcatct aggctgtaaa agggacactg cttagattgc tgtttaatct ttttagtaga   1140

ttatattata ttggtaactt attaccccta ttacatgcca tacgtgactt ctgctcatgc   1200

ctgatgataa tcatagatca ctgtggaatt aattagttga ttgttgaatc atgtttcatg   1260

tacataccac ggcacaattg cttagttcct taacaaatgc aaattttact gatccatgta   1320

tgatttgcgt ggttctctaa tgtgaaatac tatagctact tgttagtaag aatcaggttc   1380

gtatgcttaa tgctgtatgt gccttctgct catgcctgat gataatcata tatcactgga   1440

attaattagt tgatcgttta atcatatatc aagtacatac catgccacaa tttttagtca   1500
```

-continued

```
cttaacccat gcagattgaa ctggtccctg catgttttgc taaattgttc tattctgatt   1560
agaccatata tcatgtattt ttttttggta atggttctct tattttaaat gctatatagt   1620
tctggtactt gttagaaaga tctgcttcat agtttagttg cctatccctc gaattaggat   1680
gctgagcagc tgatcctata gctttgtttc atgtatcaat tcttttgtgt tcaacagtca   1740
gtttttgtta gattcattgt aacttatggt cgcttactct tctggtcctc aatgcttgca   1800
gggatcctaa accatggaga tcaacaacca gaaccagtgc gtgccgtaca actgccttaa   1860
caaccccgag tccgagatcc tgaacgtggc catcttctcc agcgagcagg tcgcggagat   1920
ccacctcaag atcacgcgcc tgatcctcga gaacttcctg ccgggcggct ccttcgcttt   1980
cggcctgttc gacctcatct ggggcatctt caacgaggac cagtggagcg cgttcctcag   2040
gcaggtggag gagctgatca accagcgcat cacggagttc gccaggggcc aggctatcca   2100
gcggctggtg ggcttcggca ggtcctacga cgagtacatc ctggccctca aggagtggga   2160
gaacgacccc gacaacccgg ccagcaagga gcgcgtgagg acccgcttca ggaccaccga   2220
cgacgctctc ctgacgggcg tcccccctcat ggctatcccg ggcttcgagc tggccaccct   2280
ctcggtgtac gctcagtcgg ccaacctgca cctcgccctc ctgcgggacg ctgtgttctt   2340
cggcgagagg tggggcctga cccagacgaa catcaacgac ctctactcca ggctgaagaa   2400
cagcatccgc gactacacga accactgcgt gcgcttctac aacatcggcc tgggcaacct   2460
caacgtcatc aggccggagt actaccgctt ccagagggag ctgaccatca gcgtgctgga   2520
cctcgtcgcc ctgttcccca actacgacat ccgcacgtac ccgatcccaa ccaagtccca   2580
gctcacgagg gagatctaca ccgacccgat catctcgccg ggcgcccagg ccggctacac   2640
cctgcaggac gtcctgaggg agccccacct gatggacttc ctgaacaggc tcatcatcta   2700
caccggcgag tacaggggca tcaggcactg ggcgggccac gaggtggagt ccagcaggac   2760
gggcatgatg accaacatcc gcttcccgct ctacggcacc gcggccacgg ccgagccaac   2820
ccgcttcatc acgccgtcca ccttccccgg cctgaacctc ttctacagga ccctgtcggc   2880
tcccatcttc cgcgacgagc cgggcgcgaa catcatcatc cgctacagga cctccctcgt   2940
ggagggcgtc ggcttcatcc agccgaacaa cggcgagcag ctgtaccgcg tgaggggcac   3000
gctggacagc ctggaccagc tcccactgga gggcgagtcc agcctcaccg agtactcgca   3060
caggctgtgc cacgtcaggt tcgcccagag cctcaggaac gcggagcccc tggactacgc   3120
cagggtgccc atgttcagct ggacccacag gtcggctacc cccaccaaca ccatcgaccc   3180
agacgtgatc acgcagatcc cgctcgtcaa ggcccacacc ctgcagtcgg gcaccaccgt   3240
ggtcaagggc cccggcttca cgggcggcga catcctgagg aggacctccg gcggcccatt   3300
cgccttcagc aacgtcaacc tcgactggaa cctgtcccag cgctacaggg cgcgcatcag   3360
gtacgccagc accacgaacc tgcgcatgta tgtgaccatc gcgggcgaga ggatcttcgc   3420
cggccagttc aacaagacga tgaacaccgg cgacccgctc accttccagt ccttcagcta   3480
cgcgacgatc gacaccgcct tcacgttccc cacgaaggcc tccagcctga ccgtgggcgc   3540
cgacaccttc tccagcggca acgaggtcta cgtggaccgc ttcgagctga tcccggtgac   3600
ggcgaccttc gaggccgagt acgacctgga gaaggcccag aaggcggtca acgccctctt   3660
cacctccagc aaccagatcg gcctgaagac ggacgtgacc gactaccaca tcgacaaggt   3720
gtccaacctc gtcgagtgcc tgagcgacga gttctgcctc gacgagaaga gggagctgtc   3780
cgagaaggtc aagcacgcca agcgcctctg cgacgagagg aacctcctgc aggacccgaa   3840
cttcagggga atcaaccgcc agccggacag gggctggagg ggcagcaccg acatcaccat   3900
```

ccagggcggc gacgacgtgt tcaaggagaa ctacgtcacg ctcccgggca ccttcgacga 3960
gtgctacccc acgtacctgt accagaagat cgacgagtcc aagctcaagg cctacacccg 4020
ctacgagctg aggggataca tcgaggacag ccaggacctc gagatctacc tgatccgcta 4080
caacgcgaag cacgagacgg tgaacgtccc cggcacgggc tccctgtggc ccctctcggc 4140
tcagtcgccg atcggcaagt gcggcgagcc caacaggtgc gccacccacc tcgagtggaa 4200
cccggacctg gactgctcct gccgggacgg cgagaagtgc gctcaccact cccaccactt 4260
cagcctggac atcgacgtgg gctgcacgga cctcaacgag gacctgggcg tgtgggtcat 4320
cttcaaaatc aagacgcagg acggccacgc taggctgggc aacctcgagt tcctggagga 4380
gaagccgctg gtgggcgagg ctctggccag ggtcaagagg gcggagaaga agtggcgcga 4440
caagagggag aagctggagc tggagacgaa catcgtctac aaggaggcca agaagtccgt 4500
ggacgcgctc ttcgtcaaca gccagtacga caggctgcag gcggacacca acatcgccat 4560
catccacgcc gcggacaagc gcgtgcactc catcagggag gcctacctcc ccgagctgag 4620
cgtgatcccg ggcgtcaacg ctgccatctt cgaggagctg gagggccgca tcttcaccgc 4680
ctactccctg tacgacgcga ggaacgtcat caagaacggc gacttcaaca acggcctcag 4740
ctgctggaac gtgaagggcc acgtggacgt cgaggagcag aacaaccacc gctcggtgct 4800
ggtggtcccc gagtgggagg ctgaggtcag ccaggaggtg cgcgtctgcc cgggcagggg 4860
atacatcctc cgcgtgaccg cgtacaagga gggctacggc gagggctgcg tcacgatcca 4920
cgagatcgag gacaacaccg acgagctgaa gttctccaac tgcgtggagg aggagatcta 4980
cccgaacaac acggtcacct gcaacgacta cacggccacc caggaggagt acgagggcac 5040
gtacacgtcg aggaacaggg gctacgacgg cgcttacgag tccaacagct cggtgccggc 5100
cgactacgct agcgcgtacg aggagaaggc ctacacggac ggccgcaggg acaacacctg 5160
cgagtcgaac aggggctacg gcgactacac gccgctcccg gccggctacg tgaccaagga 5220
gctggagtac ttcccggaga cggacaaggt ctggatcgag atcggcgaga cggagggcac 5280
cttcatcgtg gactcagtcg agctgctgct catggaggag taggagctcg ccaacagtcg 5340
ttgaagctgc tgctgtatct gggttatcta gtgtctctgc ctttgcccaa ggatagtgct 5400
gtctttcaaa gtatttgtat cgtttgtgtc gtgagtcgtg actgagctgg tttcaaggac 5460
cagttgtgtt ctcgttaccc aaaactatcg tgcgaccgca tatggcttaa tcatgaataa 5520
atgttgtttg aatttaaact attcgctgaa tattgttgtt ttttgtcatg tcagttaatg 5580
ttactaaatt ggttgccttc taatttttgt ttactggtgt ttgtcgcacc ttatcttttt 5640
actgtatgtt tacttcaggt tctggcagtc tcatttttg tgactagtta aaacttacag 5700
ctaaaaaaat gcagttttta attttaattt gaagtttgat tagagctatt gatacccgga 5760
ccatcaggtt aggttagttg tgcatagaat cataaatatt aatcatgttt tctatgaatt 5820
aagtcaaact tgaaagtctg gctgaatata gtttctatga atcatattga tatacatgtt 5880
tgattatttg ttttgctatt agctatttac tttggtgaat ctatataggc ttatgcagaa 5940
ccttttttt tgttctatat atccatatcc tagtactcag tagctctatg ttttctggag 6000
actagtggct tgctttttcg tatgtctaat tttttgcttg accattgcaa aacaaaaatt 6060
acctagtgta atctcttttt ataataatct tgtaatgcgt ctacctatag gtcaaagtag 6120
gttttgtttg gaacccttag agctaactgt tagctagttg ataaattatt agctgagtta 6180
agctagctaa tgaactagtt ttgatattag ctgaggatgt ttgaaaccta ataattattt 6240

-continued

```
tttattagct aactatacta aattttagta gagagattcc aaacaggagt taacatggga   6300
tcagattggc tatgcgtttg caatcccata ctaattagct aacggaccgc taattagcta   6360
acgatcgctt aattaagctt gcatgcctgc agtgcagcgt gacccggtcg tgcccctctc   6420
tagagataat gagcattgca tgtctaagtt ataaaaaatt accacatatt ttttttgtca   6480
cacttgtttg aagtgcagtt tatctatctt tatacatata tttaaacttt actctacgaa   6540
taatataatc tatagtacta caataaatatc agtgttttag agaatcatat aaatgaacag   6600
ttagacatgg tctaaaggac aattgagtat tttgacaaca ggactctaca gttttatctt   6660
tttagtgtgc atgtgttctc cttttttttt gcaaatagct tcacctatat aatacttcat   6720
ccattttatt agtacatcca tttagggttt agggttaatg gtttttatag actaattttt   6780
ttagtacatc tattttattc tattttagcc tctaaattaa gaaaactaaa actctatttt   6840
agttttttta tttaataatt tagatataaa atagaataaa ataaagtgac taaaaattaa   6900
acaaataccc tttaagaaat taaaaaaact aaggaaacat ttttcttgtt tcgagtagat   6960
aatgccagcc tgttaaacgc cgccgacgag tctaacggac accaaccagc gaaccagcag   7020
cgtcgcgtcg ggccaagcga agcagacggc acggcatctc tgtcgctgcc tctggacccc   7080
tctcgagagt tccgctccac cgttggactt gctccgctgt cggcatccag aaattgcgtg   7140
gcggagcggc agacgtgagc cggcacggca ggcggcctcc tcctcctctc acggcaccgg   7200
cagctacggg ggattccttt cccaccgctc cttcgctttc ccttcctcgc ccgccgtaat   7260
aaatagacac ccccctccac accctctttc cccaacctcg tgttgttcgg agcgcacaca   7320
cacacaacca gatctccccc aaatccaccc gtcggcacct ccgcttcaag gtacgccgct   7380
cgtcctcccc cccccccct ctctaccttc tctagatcgg cgttccggtc catagttagg   7440
gcccggtagt tctacttctg ttcatgtttg tgttagatcc gtgtttgtgt tagatccgtg   7500
ctgttagcgt tcgtacacgg atgcgacctg tacgtcagac acgttctgat tgctaacttg   7560
ccagtgtttc tctttgggga atcctgggat ggctctagcc gttccgcaga cgggatcgat   7620
ttcatgattt tttttgtttc gttgcatagg gtttggtttg cccttttcct ttatttcaat   7680
atatgccgtg cacttgtttg tcgggtcatc ttttcatgct tttttttgtc ttggttgtga   7740
tgatgtggtc tggttgggcg gtcgttctag atcggagtag aattctgttt caaactacct   7800
ggtggattta ttaattttgg atctgtatgt gtgtgccata catattcata gttacgaatt   7860
gaagatgatg gatggaaata tcgatctagg ataggtatac atgttgatgc gggttttact   7920
gatgcatata cagagatgct tttgttcgc ttggttgtga tgatgtggtg tggttgggcg   7980
gtcgttcatt cgttctagat cggagtagaa tactgtttca aactacctgg tgtatttatt   8040
aattttggaa ctgtatgtgt gtgtcataca tcttcatagt tacgagttta agatggatgg   8100
aaatatcgat ctaggatagg tatacatgtt gatgtgggtt ttactgatgc atatacatga   8160
tggcatatgc agcatctatt catatgctct aaccttgagt acctatctat tataataaac   8220
aagtatgttt tataattatt ttgatcttga tatacttgga tgatggcata tccagcagct   8280
atatctggat ttttttagcc ctgccttcat acgctattta tttgcttggt actgtttctt   8340
ttgtcgttgc tcaccctgtt gtttggtgtt acttctgcag ggatctccga tcatgcaaaa   8400
actcattaac tcagtgcaaa actatgcctg gggcagcaaa acggcgttga ctgaacttta   8460
cggtatggaa aatccgtcca gccagccgat ggccgagctg tggatgggcg cacatccgaa   8520
aagcagttca cgagtgcaga atgccgccgg agatatcgtt tcactgcgtg atgtgattga   8580
gagtgataaa tcgactctgc tcggagaggc cgttgccaaa cgctttggcg aactgccttt   8640
```

```
cctgttcaaa gtattatgcg cagcacagcc actctccatt caggttcatc caaacaaaca   8700
caattctgaa atcggttttg ccaaagaaaa tgccgcaggt atcccgatgg atgccgccga   8760
gcgtaactat aaagatccta accacaagcc ggagctggtt tttgcgctga cgcctttcct   8820
tgcgatgaac gcgtttcgtg aattttccga gattgtctcc ctactccagc cggtcgcagg   8880
tgcacatccg gcgattgctc actttttaca acagcctgat gccgaacgtt taagcgaact   8940
gttcgccagc ctgttgaata tgcagggtga agaaaaatcc cgcgcgctgg cgattttaaa   9000
atcggccctc gatagccagc agggtgaacc gtggcaaacg attcgtttaa tttctgaatt   9060
ttacccggaa gacagcggtc tgttctcccc gctattgctg aatgtggtga aattgaaccc   9120
tggcgaagcg atgttcctgt tcgctgaaac accgcacgct tacctgcaag gcgtggcgct   9180
ggaagtgatg gcaaactccg ataacgtgct gcgtgcgggt ctgacgccta aatacattga   9240
tattccggaa ctggttgcca atgtgaaatt cgaagccaaa ccggctaacc agttgttgac   9300
ccagccggtg aaacaaggtg cagaactgga cttcccgatt ccagtggacg attttgcctt   9360
ctcgctgcac gaccttagtg ataaagaaac caccattagc cagcagagtg ccgccatttt   9420
gttctgcgtc gaaggcgatg caacgttgtg gaaaggttct cagcagttac agcttaaacc   9480
gggtgaatca gcgtttattg ccgccaacga atcaccggtg actgtcaaag gccacggccg   9540
tttagcgcgt gtttacaaca agctgtaaga gcttactgaa aaaattaaca tctcttgcta   9600
agctgggtca tgggtcgttt aagctgccga tgtgcctgcg tcgtctggtg ccctctctcc   9660
atatggaggt tgtcaaagta tctgctgttc gtgtcatgag tcgtgtcagt gttggtttaa   9720
taatggaccg gttgtgttgt gtgtgcgtac tacccagaac tatgacaaat catgaataag   9780
tttgatgttt gaaattaaag cctgtgctca ttatgttctg tctttcagtt gtctcctaat   9840
atttgcctcc aggtactggc tatctaccgt ttcttactta ggaggtgttt gaatgcacta   9900
aaactaatag ttagtggcta aaattagtta aaacatccaa acaccatagc taatagttga   9960
actattagct atttttggaa aattagttaa tagtgaggta gttatttgtt agctagctaa  10020
ttcaactaac aatttttagc caactaacaa ttagtttcag tgcattcaaa cacccccctta  10080
atgttaacgt ggttctatct accgtctcct aatatatggt tgattgttcg gtttgttgct  10140
atgctattgg gttctgattg ctgctagttc ttgctgaatc cagaagttct cgtagtatag  10200
ctcagattca tattatttat ttgagtgata agtgatccag gttattacta tgttagctag  10260
gttttttta caaggataaa ttatctgtga tcataattct tatgaaagct ttatgtttcc  10320
tggaggcagt ggcatgcaat gcatgacagc aacttgatca caccagctga ggtagatacg  10380
gtaacaaggt tcttaaatct gttcaccaaa tcattggaga acacacatac acattcttgc  10440
cagtcttggt tagagaaatt tcatgacaaa atgccaaagc tgtcttgact cttcactttt  10500
ggccatgagt cgtgacttag tttggtttaa tggaccggtt ctcctagctt gttctactca  10560
aaactgttgt tgatgcgaat aagttgtgat ggttgatctc tggattttgt tttgctctca  10620
atagtggacg agattagata g                                             10641
```

<210> SEQ ID NO 18
<211> LENGTH: 10641
<212> TYPE: DNA
<213> ORGANISM: Artificial sequence
<220> FEATURE:
<223> OTHER INFORMATION: Synthetic polynucleotide

<400> SEQUENCE: 18

```
gaattcatta tgtggtctag gtaggttcta tatataagaa aacttgaaat gttctaaaaa     60
aaaattcaag cccatgcatg attgaagcaa acggtatagc aacggtgtta acctgatcta    120
gtgatctctt gcaatcctta acggccacct accgcaggta gcaaacggcg tccccctcct    180
cgatatctcc gcggcgacct ctggcttttt ccgcggaatt gcgcggtggg gacggattcc    240
acgagaccgc gacgcaaccg cctctcgccg ctgggcccca caccgctcgg tgccgtagcc    300
tcacgggact ctttctccct cctccccgtt ataaattggc ttcatcccct ccttgcctca    360
tccatccaaa tcccagtccc caatcccatc ccttcgtagg agaaattcat cgaagctaag    420
cgaatcctcg cgatcctctc aaggtactgc gagttttcga tccccctctc gacccctcgt    480
atgtttgtgt ttgtcgtagc gtttgattag gtatgctttc cctgtttgtg ttcgtcgtag    540
cgtttgatta ggtatgcttt ccctgttcgt gttcatcgta gtgtttgatt aggtcgtgtg    600
aggcgatggc ctgctcgcgt ccttcgatct gtagtcgatt tgcgggtcgt ggtgtagatc    660
tgcgggctgt gatgaagtta tttggtgtga tctgctcgcc tgattctgct ggttggctcg    720
agtagatatg atggttggac cggttggttc gtttaccgcg ctagggttgg gctgggatga    780
tgttgcatgc gccgttgcgc gtgatcccgc agcaggactt gcgtttgatt gccagatctc    840
gttacgatta tgtgatttgg tttggacttt ttagatctgt agcttctgct tatgtgccag    900
atgcgcctac tgctcatatg cctgatgata atcataaatg gctgtggaac taactagttg    960
attgcggagt catgtatcag ctacaggtgt agggactagc tacaggtgta gggacttgcg   1020
tctaattgtt tggtccttta ctcatgttgc aattatgcaa tttagtttag attgtttgtt   1080
ccactcatct aggctgtaaa agggacactg cttagattgc tgtttaatct ttttagtaga   1140
ttatattata ttggtaactt attacccta ttacatgcca tacgtgactt ctgctcatgc    1200
ctgatgataa tcatagatca ctgtggaatt aattagttga ttgttgaatc atgtttcatg   1260
tacataccac ggcacaattg cttagttcct taacaaatgc aaattttact gatccatgta   1320
tgatttgcgt ggttctctaa tgtgaaatac tatagctact tgttagtaag aatcaggttc   1380
gtatgcttaa tgctgtatgt gccttctgct catgcctgat gataatcata tatcactgga   1440
attaattagt tgatcgttta atcatatatc aagtacatac catgccacaa tttttagtca   1500
cttaacccat gcagattgaa ctggtccctg catgttttgc taaattgttc tattctgatt   1560
agaccatata tcatgtattt ttttttggta atggttctct tattttaaat gctatatagt   1620
tctggtactt gttagaaaga tctgcttcat agtttagttg cctatccctc gaattaggat   1680
gctgagcagc tgatcctata gctttgtttc atgtatcaat tcttttgtgt tcaacagtca   1740
gtttttgtta gattcattgt aacttatggt cgcttactct tctggtcctc aatgcttgca   1800
gggatcctaa accatggaga tcaacaacca gaaccagtgc gtgccgtaca actgccttaa   1860
caaccccgag tccgagatcc tgaacgtggc catcttctcc agcgagcagg tcgcggagat   1920
ccacctcaag atcacgcgcc tgatcctcga gaacttcctg ccgggcggct ccttcgcttt   1980
cggcctgttc gacctcatct ggggcatctt caacgaggac cagtggagcg cgttcctcag   2040
gcaggtggag gagctgatca accagcgcat cacggagttc gccaggggcc aggctatcca   2100
gcggctggtg ggcttcggca ggtcctacga cgagtacatc ctggccctca aggagtggga   2160
gaacgacccc gacaacccgg ccagcaagga gcgcgtgagg acccgcttca ggaccaccga   2220
cgacgctctc ctgacgggcg tcccccctcat ggctatcccg ggcttcgagc tggccaccct   2280
ctcggtgtac gctcagtcgg ccaacctgca cctcgccctc ctgcgggacg ctgtgttctt   2340
cggcgagagg tggggcctga cccagacgaa catcaacgac ctctactcca ggctgaagaa   2400
```

```
cagcatccgc gactacacga accactgcgt gcgcttctac aacatcggcc tgggcaacct   2460
caacgtcatc aggccggagt actaccgctt ccagagggag ctgaccatca gcgtgctgga   2520
cctcgtcgcc ctgttcccca actacgacat ccgcacgtac ccgatcccaa ccaagtccca   2580
gctcacgagg gagatctaca ccgacccgat catctcgccg ggcgcccagg ccggctacac   2640
cctgcaggac gtcctgaggg agccccacct gatggacttc ctgaacaggc tcatcatcta   2700
caccggcgag tacaggggca tcaggcactg ggcgggccac gaggtggagt ccagcaggac   2760
gggcatgatg accaacatcc gcttcccgct ctacggcacc gcggccacgg ccgagccaac   2820
ccgcttcatc acgccgtcca ccttccccgg cctgaacctc ttctacagga ccctgtcggc   2880
tcccatcttc cgcgacgagc cgggcgcgaa catcatcatc cgctacagga cctccctcgt   2940
ggagggcgtc ggcttcatcc agccgaacaa cggcgagcag ctgtaccgcg tgaggggcac   3000
gctggacagc ctggaccagc tcccactgga gggcgagtcc agcctcaccg agtactcgca   3060
caggctgtgc cacgtcaggt tcgcccagag cctcaggaac gcggagcccc tggactacgc   3120
cagggtgccc atgttcagct ggacccacag gtcggctacc cccaccaaca ccatcgaccc   3180
agacgtgatc acgcagatcc cgctcgtcaa ggcccacacc ctgcagtcgg gcaccaccgt   3240
ggtcaagggc cccggcttca cgggcggcga catcctgagg aggacctccg gcggcccatt   3300
cgccttcagc aacgtcaacc tcgactggaa cctgtcccag cgctacaggg cgcgcatcag   3360
gtacgccagc accacgaacc tgcgcatgta tgtgaccatc gcgggcgaga ggatcttcgc   3420
cggccagttc aacaagacga tgaacaccgg cgacccgctc accttccagt ccttcagcta   3480
cgcgacgatc gacaccgcct tcacgttccc cacgaaggcc tccagcctga ccgtgggcgc   3540
cgacaccttc tccagcggca acgaggtcta cgtggaccgc ttcgagctga tcccggtgac   3600
ggcgaccttc gaggccgagt acgacctgga gaaggcccag aaggcggtca acgccctctt   3660
cacctccagc aaccagatcg gcctgaagac ggacgtgacc gactaccaca tcgacaaggt   3720
gtccaacctc gtcgagtgcc tgagcgacga gttctgcctc gacgagaaga gggagctgtc   3780
cgagaaggtc aagcacgcca agcgcctctg cgacgagagg aacctcctgc aggacccgaa   3840
cttcagggga atcaaccgcc agccggacag gggctggagg ggcagcaccg acatcaccat   3900
ccagggcggc gacgacgtgt tcaaggagaa ctacgtcacg ctcccgggca ccttcgacga   3960
gtgctacccc acgtacctgt accagaagat cgacgagtcc aagctcaagg cctacacccg   4020
ctacgagctg aggggataca tcgaggacag ccaggacctc gagatctacc tgatccgcta   4080
caacgcgaag cacgagacgg tgaacgtccc cggcacgggc tccctgtggc ccctctcggc   4140
tcagtcgccg atcggcaagt gcggcgagcc caacaggtgc gccacccacc tcgagtggaa   4200
cccggacctg gactgctcct gccgggacgg cgagaagtgc gctcaccact cccaccactt   4260
cagcctggac atcgacgtgg gctgcacgga cctcaacgag gacctgggcg tgtgggtcat   4320
cttcaaaatc aagacgcagg acggccacgc taggctgggc aacctcgagt tcctggagga   4380
gaagccgctg gtgggcgagg ctctggccag ggtcaagagg gcggagaaga agtggcgcga   4440
caagagggag aagctggagc tggagacgaa catcgtctac aaggaggcca agaagtccgt   4500
ggacgcgctc ttcgtcaaca gccagtacga caggctgcag gcggacacca acatcgccat   4560
catccacgcc gcggacaagc gcgtgcactc catcagggag gcctacctcc ccgagctgag   4620
cgtgatcccg ggcgtcaacg ctgccatctt cgaggagctg gagggccgca tcttcaccgc   4680
ctactccctg tacgacgcga ggaacgtcat caagaacggc gacttcaaca acggcctcag   4740
```

-continued

```
ctgctggaac gtgaagggcc acgtggacgt cgaggagcag aacaaccacc gctcggtgct   4800
ggtggtcccc gagtgggagg ctgaggtcag ccaggaggtg cgcgtctgcc cgggcagggg   4860
atacatcctc cgcgtgaccg cgtacaagga gggctacggc gagggctgcg tcacgatcca   4920
cgagatcgag gacaacaccg acgagctgaa gttctccaac tgcgtggagg aggagatcta   4980
cccgaacaac acggtcacct gcaacgacta cacggccacc caggaggagt acgagggcac   5040
gtacacgtcg aggaacaggg gctacgacgg cgcttacgag tccaacagct cggtgccggc   5100
cgactacgct agcgcgtacg aggagaaggc ctacacggac ggccgcaggg acaacacctg   5160
cgagtcgaac aggggctacg gcgactacac gccgctcccg gccggctacg tgaccaagga   5220
gctggagtac ttcccggaga cggacaaggt ctggatcgag atcggcgaga cggagggcac   5280
cttcatcgtg gactcagtcg agctgctgct catggaggag taggagctcg ccaacagtcg   5340
ttgaagctgc tgctgtatct gggttatcta gtgtctctgc ctttgcccaa ggatagtgct   5400
gtctttcaaa gtatttgtat cgtttgtgtc gtgagtcgtg actgagctgg tttcaaggac   5460
cagttgtgtt ctcgttaccc aaaactatcg tgcgaccgca tatggcttaa tcatgaataa   5520
atgttgtttg aatttaaact attcgctgaa tattgttgtt ttttgtcatg tcagttaatg   5580
ttactaaatt ggttgccttc taatttttgt ttactggtgt ttgtcgcacc ttatcttttt   5640
actgtatgtt tacttcaggt tctggcagtc tcatttttttg tgactagtta aaacttacag   5700
ctaaaaaaat gcagttttta attttaattt gaagtttgat tagagctatt gatacccgga   5760
ccatcaggtt aggttagttg tgcatagaat cataaatatt aatcatgttt tctatgaatt   5820
aagtcaaact tgaaagtctg gctgaatata gtttctatga atcatattga tatacatgtt   5880
tgattatttg ttttgctatt agctatttac tttggtgaat ctatataggc ttatgcagaa   5940
cctttttttt tgttctatat atccatatcc tagtactcag tagctctatg ttttctggag   6000
actagtggct tgctttttcg tatgtctaat tttttgcttg accattgcaa aacaaaaatt   6060
acctagtgta atctcttttt ataataatct tgtaatgcgt ctacctatag gtcaaagtag   6120
gttttgtttg gaacccttag agctaactgt tagctagttg ataaattatt agctgagtta   6180
agctagctaa tgaactagtt ttgatattag ctgaggatgt ttgaaaccta ataattattt   6240
tttattagct aactatacta aattttagta gagagattcc aaacaggagt taacatggga   6300
tcagattggc tatgcgtttg caatcccata ctaattagct aacggaccgc taattagcta   6360
acgatcgctt aattaagctt gcatgcctgc agtgcagcgt gacccggtcg tgcccctctc   6420
tagagataat gagcattgca tgtctaagtt ataaaaaatt accacatatt ttttttgtca   6480
cacttgtttg aagtgcagtt tatctatctt tatacatata tttaaacttt actctacgaa   6540
taatataatc tatagtacta caataaatatc agtgttttag agaatcatat aaatgaacag   6600
ttagacatgg tctaaaggac aattgagtat tttgacaaca ggactctaca gttttatctt   6660
tttagtgtgc atgtgttctc cttttttttt gcaaatagct tcacctatat aatacttcat   6720
ccattttatt agtacatcca tttagggttt agggttaatg gtttttatag actaattttt   6780
ttagtacatc tattttattc tattttagcc tctaaattaa gaaaactaaa actctatttt   6840
agttttttta tttaataatt tagatataaa atagaataaa ataaagtgac taaaaattaa   6900
acaaataccc tttaagaaat taaaaaaact aaggaaacat ttttcttgtt tcgagtagat   6960
aatgccagcc tgttaaacgc cgccgacgag tctaacggac accaaccagc gaaccagcag   7020
cgtcgcgtcg ggccaagcga agcagacggc acggcatctc tgtcgctgcc tctggacccc   7080
tctcgagagt tccgctccac cgttggactt gctccgctgt cggcatccag aaattgcgtg   7140
```

gcggagcggc agacgtgagc cggcacggca ggcggcctcc tcctcctctc acggcaccgg 7200
cagctacggg ggattccttt cccaccgctc cttcgctttc ccttcctcgc ccgccgtaat 7260
aaatagacac cccctccaca ccctctttcc ccaacctcgt gttgttcgga gcgcacacac 7320
acacaaccag atctccccca aatccacccg tcggcacctc cgcttcaagg tacgccgctc 7380
gtcctccccc cccccccct ctctaccttc tctagatcgg cgttccggtc catagttagg 7440
gcccggtagt tctacttctg ttcatgtttg tgttagatcc gtgtttgtgt tagatccgtg 7500
ctgttagcgt tcgtacacgg atgcgacctg tacgtcagac acgttctgat tgctaacttg 7560
ccagtgtttc tctttgggga atcctgggat ggctctagcc gttccgcaga cgggatcgat 7620
ttcatgattt tttttgtttc gttgcatagg gtttggtttg cccttttcct ttatttcaat 7680
atatgccgtg cacttgtttg tcgggtcatc ttttcatgct ttttttgtc ttggttgtga 7740
tgatgtggtc tggttgggcg gtcgttctag atcggagtag aattctgttt caaactacct 7800
ggtggattta ttaattttgg atctgtatgt gtgtgccata catattcata gttacgaatt 7860
gaagatgatg gatggaaata tcgatctagg ataggtatac atgttgatgc gggttttact 7920
gatgcatata cagagatgct ttttgttcgc ttggttgtga tgatgtggtg tggttgggcg 7980
gtcgttcatt cgttctagat cggagtagaa tactgtttca aactacctgg tgtatttatt 8040
aattttggaa ctgtatgtgt gtgtcataca tcttcatagt tacgagttta agatggatgg 8100
aaatatcgat ctaggatagg tatacatgtt gatgtgggtt ttactgatgc atatacatga 8160
tggcatatgc agcatctatt catatgctct aaccttgagt acctatctat tataataaac 8220
aagtatgttt tataattatt ttgatcttga tatacttgga tgatggcata tccagcagct 8280
atatctggat ttttttagcc ctgccttcat acgctattta tttgcttggt actgtttctt 8340
ttgtcgttgc tcaccctgtt gtttggtgtt acttctgcag ggatctccga tcatgcaaaa 8400
actcattaac tcagtgcaaa actatgcctg gggcagcaaa acggcgttga ctgaacttta 8460
cggtatggaa aatccgtcca gccagccgat ggccgagctg tggatgggcg cacatccgaa 8520
aagcagttca cgagtgcaga atgccgccgg agatatcgtt tcactgcgtg atgtgattga 8580
gagtgataaa tcgactctgc tcggagaggc cgttgccaaa cgctttggcg aactgccttt 8640
cctgttcaaa gtattatgcg cagcacagcc actctccatt caggttcatc caaacaaaca 8700
caattctgaa atcggttttg ccaaagaaaa tgccgcaggt atcccgatgg atgccgccga 8760
gcgtaactat aaagatccta accacaagcc ggagctggtt tttgcgctga cgcctttcct 8820
tgcgatgaac gcgtttcgtg aattttccga gattgtctcc ctactccagc cggtcgcagg 8880
tgcacatccg gcgattgctc actttttaca acagcctgat gccgaacgtt taagcgaact 8940
gttcgccagc ctgttgaata tgcagggtga agaaaaatcc cgcgcgctgg cgattttaaa 9000
atcggccctc gatagccagc agggtgaacc gtggcaaacg attcgtttaa tttctgaatt 9060
ttacccggaa gacagcggtc tgttctcccc gctattgctg aatgtggtga aattgaaccc 9120
tggcgaagcg atgttcctgt tcgctgaaac accgcacgct tacctgcaag gcgtggcgct 9180
ggaagtgatg gcaaactccg ataacgtgct gcgtgcgggt ctgacgccta aatacattga 9240
tattccggaa ctggttgcca atgtgaaatt cgaagccaaa ccggctaacc agttgttgac 9300
ccagccggtg aaacaaggtg cagaactgga cttcccgatt ccagtggacg attttgcctt 9360
ctcgctgcac gaccttagtg ataaagaaac caccattagc cagcagagtg ccgccatttt 9420
gttctgcgtc gaaggcgatg caacgttgtg gaaaggttct cagcagttac agcttaaacc 9480
gggtgaatca gcgtttattg ccgccaacga atcaccggtg actgtcaaag gccacggccg 9540
tttagcgcgt gtttacaaca agctgtaaga gcttactgaa aaaattaaca tctcttgcta 9600
agctgggtca tgggtcgttt aagctgccga tgtgcctgcg tcgtctggtg ccctctctcc 9660
atatggaggt tgtcaaagta tctgctgttc gtgtcatgag tcgtgtcagt gttggtttaa 9720
taatggaccg gttgtgttgt gtgtgcgtac tacccagaac tatgacaaat catgaataag 9780
tttgatgttt gaaattaaag cctgtgctca ttatgttctg tctttcagtt gtctcctaat 9840
atttgcctcc aggtactggc tatctaccgt ttcttactta ggaggtgttt gaatgcacta 9900
aaactaatag ttagtggcta aaattagtta aaacatccaa acaccatagc taatagttga 9960
actattagct atttttggaa aattagttaa tagtgaggta gttatttgtt agctagctaa 10020
ttcaactaac aatttttagc caactaacaa ttagtttcag tgcattcaaa cacccccta 10080 atgttaacgt ggttctatct accgtctcct aatatatggt tgattgttcg gtttgttgct 10140
atgctattgg gttctgattg ctgctagttc ttgctgaatc cagaagttct cgtagtatag 10200
ctcagattca tattatttat ttgagtgata agtgatccag gttattacta tgttagctag 10260
gtttttttta caaggataaa ttatctgtga tcataattct tatgaaagct ttatgtttcc 10320
tggaggcagt ggcatgcaat gcatgacagc aacttgatca caccagctga ggtagatacg 10380
gtaacaaggt tcttaaatct gttcaccaaa tcattggaga acacacatac acattcttgc 10440
cagtcttggt tagagaaatt tcatgacaaa atgccaaagc tgtcttgact cttcactttt 10500
ggccatgagt cgtgacttag tttggtttaa tggaccggtt ctcctagctt gttctactca 10560
aaactgttgt tgatgcgaat aagttgtgat ggttgatctc tggattttgt tttgctctca 10620
atagtggacg agattagata g 10641

<210> SEQ ID NO 19
<211> LENGTH: 10643
<212> TYPE: DNA
<213> ORGANISM: Artificial sequence
<220> FEATURE:
<223> OTHER INFORMATION: Synthetic polynucleotide

<400> SEQUENCE: 19
gaattcatta tgtggtctag gtaggttcta tatataagaa aacttgaaat gttctaaaaa 60
aaaattcaag cccatgcatg attgaagcaa acggtatagc aacggtgtta acctgatcta 120
gtgatctctt gcaatcctta acggccacct accgcaggta gcaaacggcg tccccctcct 180
cgatatctcc gcggcgacct ctggcttttt ccgcggaatt gcgcggtggg gacggattcc 240
acgagaccgc gacgcaaccg cctctcgccg ctgggcccca caccgctcgg tgccgtagcc 300
tcacgggact ctttctccct cctcccccgt tataaattgg cttcatcccc tccttgcctc 360
atccatccaa atcccagtcc ccaatcccat cccttcgtag gagaaattca tcgaagctaa 420
gcgaatcctc gcgatcctct caaggtactg cgagttttcg atccccctct cgacccctcg 480
tatgtttgtg tttgtcgtag cgtttgatta ggtatgcttt ccctgtttgt gttcgtcgta 540
gcgtttgatt aggtatgctt tccctgttcg tgttcatcgt agtgtttgat taggtcgtgt 600
gaggcgatgg cctgctcgcg tccttcgatc tgtagtcgat ttgcgggtcg tggtgtagat 660
ctgcgggctg tgatgaagtt atttggtgtg atctgctcgc ctgattctgc tggttggctc 720
gagtagatat gatggttgga ccggttggtt cgtttaccgc gctagggttg ggctgggatg 780
atgttgcatg cgccgttgcg cgtgatcccg cagcaggact tgcgtttgat tgccagatct 840
cgttacgatt atgtgatttg gtttggactt tttagatctg tagcttctgc ttatgtgcca 900
gatgcgccta ctgctcatat gcctgatgat aatcataaat ggctgtggaa ctaactagtt 960
gattgcggag tcatgtatca gctacaggtg tagggactag ctacaggtgt agggacttgc 1020
gtctaattgt ttggtccttt actcatgttg caattatgca atttagttta gattgtttgt 1080
tccactcatc taggctgtaa aagggacact gcttagattg ctgtttaatc tttttagtag 1140
attatattat attggtaact tattacccct attacatgcc atacgtgact tctgctcatg 1200
cctgatgata atcatagatc actgtggaat taattagttg attgttgaat catgtttcat 1260
gtacatacca cggcacaatt gcttagttcc ttaacaaatg caaattttac tgatccatgt 1320
atgatttgcg tggttctcta atgtgaaata ctatagctac ttgttagtaa gaatcaggtt 1380
cgtatgctta atgctgtatg tgccttctgc tcatgcctga tgataatcat atatcactgg 1440
aattaattag ttgatcgttt aatcatatat caagtacata ccatgccaca atttttagtc 1500
acttaaccca tgcagattga actggtccct gcatgttttg ctaaattgtt ctattctgat 1560
tagaccatat atcatgtatt tttttttggt aatggttctc ttattttaaa tgctatatag 1620
ttctggtact tgttagaaag atctgcttca tagtttagtt gcctatccct cgaattagga 1680
tgctgagcag ctgatcctat agctttgttt catgtatcaa ttcttttgtg ttcaacagtc 1740
agtttttgtt agattcattg taacttatgg tcgcttactc ttctggtcct caatgcttgc 1800
agggatccta aaccatggag atcaacaacc agaaccagtg cgtgccgtac aactgcctta 1860
acaaccccga gtccgagatc ctgaacgtgg ccatcttctc cagcgagcag gtcgcggaga 1920
tccacctcaa gatcacgcgc ctgatcctcg agaacttcct gccgggcggc tccttcgctt 1980
tcggcctgtt cgacctcatc tggggcatct tcaacgagga ccagtggagc gcgttcctca 2040
ggcaggtgga ggagctgatc aaccagcgca tcacggagtt cgccaggggc caggctatcc 2100
agcggctggt gggcttcggc aggtcctacg acgagtacat cctggccctc aaggagtggg 2160
agaacgaccc cgacaacccg gccagcaagg agcgcgtgag gacccgcttc aggaccaccg 2220
acgacgctct cctgacgggc gtccccctca tggctatccc gggcttcgag ctggccaccc 2280
tctcggtgta cgctcagtcg gccaacctgc acctcgccct cctgcgggac gctgtgttct 2340
tcggcgagag gtggggcctg acccagacga acatcaacga cctctactcc aggctgaaga 2400
acagcatccg cgactacacg aaccactgcg tgcgcttcta caacatcggc ctgggcaacc 2460
tcaacgtcat caggccggag tactaccgct tccagaggga gctgaccatc agcgtgctgg 2520
acctcgtcgc cctgttcccc aactacgaca tccgcacgta cccgatccca accaagtccc 2580
agctcacgag ggagatctac accgacccga tcatctcgcc gggcgcccag gccggctaca 2640
ccctgcagga cgtcctgagg gagccccacc tgatggactt cctgaacagg ctcatcatct 2700
acaccggcga gtacaggggc atcaggcact gggcgggcca cgaggtggag tccagcagga 2760
cgggcatgat gaccaacatc cgcttcccgc tctacggcac cgcggccacg gccgagccaa 2820
cccgcttcat cacgccgtcc accttccccg gcctgaacct cttctacagg accctgtcgg 2880
ctcccatctt ccgcgacgag ccgggcgcga acatcatcat ccgctacagg acctccctcg 2940
tggagggcgt cggcttcatc cagccgaaca acggcgagca gctgtaccgc gtgaggggca 3000
cgctggacag cctggaccag ctcccactgg agggcgagtc cagcctcacc gagtactcgc 3060
acaggctgtg ccacgtcagg ttcgcccaga gcctcaggaa cgcggagccc ctggactacg 3120
ccagggtgcc catgttcagc tggacccaca ggtcggctac ccccaccaac accatcgacc 3180
cagacgtgat cacgcagatc ccgctcgtca aggcccacac cctgcagtcg ggcaccaccg 3240

-continued

```
tggtcaaggg ccccggcttc acgggcggcg acatcctgag gaggacctcc ggcggcccat   3300
tcgccttcag caacgtcaac ctcgactgga acctgtccca gcgctacagg gcgcgcatca   3360
ggtacgccag caccacgaac ctgcgcatgt atgtgaccat cgcgggcgag aggatcttcg   3420
ccggccagtt caacaagacg atgaacaccg gcgacccgct caccttccag tccttcagct   3480
acgcgacgat cgacaccgcc ttcacgttcc ccacgaaggc ctccagcctg accgtgggcg   3540
ccgacacctt ctccagcggc aacgaggtct acgtggaccg cttcgagctg atcccggtga   3600
cggcgacctt cgaggccgag tacgacctgg agaaggccca gaaggcggtc aacgccctct   3660
tcacctccag caaccagatc ggcctgaaga cggacgtgac cgactaccac atcgacaagg   3720
tgtccaacct cgtcgagtgc ctgagcgacg agttctgcct cgacgagaag agggagctgt   3780
ccgagaaggt caagcacgcc aagcgcctct gcgacgagag gaacctcctg caggacccga   3840
acttcagggg aatcaaccgc cagccggaca ggggctggag gggcagcacc gacatcacca   3900
tccagggcgg cgacgacgtg ttcaaggaga actacgtcac gctcccgggc accttcgacg   3960
agtgctaccc cacgtacctg taccagaaga tcgacgagtc caagctcaag gcctacaccc   4020
gctacgagct gaggggatac atcgaggaca gccaggacct cgagatctac ctgatccgct   4080
acaacgcgaa gcacgagacg gtgaacgtcc ccggcacggg ctccctgtgg cccctctcgg   4140
ctcagtcgcc gatcggcaag tgcggcgagc ccaacaggtg cgccacccac ctcgagtgga   4200
acccggacct ggactgctcc tgccgggacg gcgagaagtg cgctcaccac tcccaccact   4260
tcagcctgga catcgacgtg ggctgcacgg acctcaacga ggacctgggc gtgtgggtca   4320
tcttcaaaat caagacgcag gacggccacg ctaggctggg caacctcgag ttcctggagg   4380
agaagccgct ggtgggcgag gctctggcca gggtcaagag ggcggagaag aagtggcgcg   4440
acaagaggga gaagctggag ctggagacga acatcgtcta caaggaggcc aagaagtccg   4500
tggacgcgct cttcgtcaac agccagtacg acaggctgca ggcggacacc aacatcgcca   4560
tcatccacgc cgcggacaag cgcgtgcact ccatcaggga ggcctacctc cccgagctga   4620
gcgtgatccc gggcgtcaac gctgccatct tcgaggagct ggagggccgc atcttcaccg   4680
cctactccct gtacgacgcg aggaacgtca tcaagaacgg cgacttcaac aacggcctca   4740
gctgctggaa cgtgaagggc cacgtggacg tcgaggagca gaacaaccac cgctcggtgc   4800
tggtggtccc cgagtgggag gctgaggtca gccaggaggt gcgcgtctgc ccgggcaggg   4860
gatacatcct ccgcgtgacc gcgtacaagg agggctacgg cgagggctgc gtcacgatcc   4920
acgagatcga ggacaacacc gacgagctga agttctccaa ctgcgtggag gaggagatct   4980
acccgaacaa cacggtcacc tgcaacgact acacggccac ccaggaggag tacgagggca   5040
cgtacacgtc gaggaacagg ggctacgacg gcgcttacga gtccaacagc tcggtgccgg   5100
ccgactacgc tagcgcgtac gaggagaagg cctacacgga cggccgcagg gacaacacct   5160
gcgagtcgaa caggggctac ggcgactaca cgccgctccc ggccggctac gtgaccaagg   5220
agctggagta cttcccggag acggacaagg tctggatcga gatcggcgag acggagggca   5280
ccttcatcgt ggactcagtc gagctgctgc tcatggagga gtaggagctc gccaacagtc   5340
gttgaagctg ctgctgtatc tgggttatct agtgtctctg cctttgccca aggatagtgc   5400
tgtctttcaa agtatttgta tcgtttgtgt cgtgagtcgt gactgagctg gtttcaagga   5460
ccagttgtgt tctcgttacc caaaactatc gtgcgaccgc atatggctta atcatgaata   5520
aatgttgttt gaatttaaac tattcgctga atattgttgt tttttgtcat gtcagttaat   5580
gttactaaat tggttgcctt ctaatttttg tttactggtg tttgtcgcac cttatctttt   5640
```

```
tactgtatgt ttacttcagg ttctggcagt ctcatttttt gtgactagtt aaaacttaca   5700
gctaaaaaaa tgcagttttt aattttaatt tgaagtttga ttagagctat tgatacccgg   5760
accatcaggt taggttagtt gtgcatagaa tcataaatat taatcatgtt ttctatgaat   5820
taagtcaaac ttgaaagtct ggctgaatat agtttctatg aatcatattg atatacatgt   5880
ttgattattt gttttgctat tagctattta ctttggtgaa tctatatagg cttatgcaga   5940
accttttttt ttgttctata tatccatatc ctagtactca gtagctctat gttttctgga   6000
gactagtggc ttgctttttc gtatgtctaa tttttttgctt gaccattgca aaacaaaaat   6060
tacctagtgt aatctctttt tataataatc ttgtaatgcg tctacctata ggtcaaagta   6120
ggttttgttt ggaaccctta gagctaactg ttagctagtt gataaattat tagctgagtt   6180
aagctagcta atgaactagt tttgatatta gctgaggatg tttgaaacct aataattatt   6240
ttttattagc taactatact aaattttagt agagagattc caaacaggag ttaacatggg   6300
atcagattgg ctatgcgttt gcaatcccat actaattagc taacggaccg ctaattagct   6360
aacgatcgct taattaagct tgcatgcctg cagtgcagcg tgacccggtc gtgcccctct   6420
ctagagataa tgagcattgc atgtctaagt tataaaaaat taccacatat ttttttgtc   6480
acacttgttt gaagtgcagt ttatctatct ttatacatat atttaaactt tactctacga   6540
ataatataat ctatagtact acaataatat cagtgtttta gagaatcata taaatgaaca   6600
gttagacatg gtctaaagga caattgagta ttttgacaac aggactctac agttttatct   6660
ttttagtgtg catgtgttct cctttttttt tgcaaatagc ttcacctata taatacttca   6720
tccattttat tagtacatcc atttagggtt tagggttaat ggtttttata gactaatttt   6780
tttagtacat ctattttatt ctattttagc ctctaaatta agaaaactaa aactctattt   6840
tagttttttt atttaataat ttagatataa aatagaataa aataaagtga ctaaaaatta   6900
aacaaatacc ctttaagaaa ttaaaaaaac taaggaaaca tttttcttgt ttcgagtaga   6960
taatgccagc ctgttaaacg ccgccgacga gtctaacgga caccaaccag cgaaccagca   7020
gcgtcgcgtc gggccaagcg aagcagacgg cacggcatct ctgtcgctgc ctctggaccc   7080
ctctcgagag ttccgctcca ccgttggact tgctccgctg tcggcatcca gaaattgcgt   7140
ggcggagcgg cagacgtgag ccggcacggc aggcggcctc ctcctcctct cacggcaccg   7200
gcagctacgg gggattcctt tcccaccgct ccttcgcttt cccttcctcg cccgccgtaa   7260
taaatagaca cccccctcca caccctcttt ccccaacctc gtgttgttcg gagcgcacac   7320
acacacaacc agatctcccc caaatccacc cgtcggcacc tccgcttcaa ggtacgccgc   7380
tcgtcctccc cccccccccc ctctctacct tctctagatc ggcgttccgg tccatagtta   7440
gggcccggta gttctacttc tgttcatgtt tgtgttagat ccgtgtttgt gttagatccg   7500
tgctgttagc gttcgtacac ggatgcgacc tgtacgtcag acacgttctg attgctaact   7560
tgccagtgtt tctctttggg gaatcctggg atggctctag ccgttccgca gacgggatcg   7620
atttcatgat tttttttgtt tcgttgcata gggtttggtt tgcccttttc ctttatttca   7680
atatatgccg tgcacttgtt tgtcgggtca tcttttcatg cttttttttg tcttggttgt   7740
gatgatgtgg tctggttggg cggtcgttct agatcggagt agaattctgt ttcaaactac   7800
ctggtggatt tattaatttt ggatctgtat gtgtgtgcca tacatattca tagttacgaa   7860
ttgaagatga tggatggaaa tatcgatcta ggataggtat acatgttgat gcgggtttta   7920
ctgatgcata tacagagatg ctttttgttc gcttggttgt gatgatgtgg tgtggttggg   7980
```

-continued

```
cggtcgttca ttcgttctag atcggagtag aatactgttt caaactacct ggtgtattta   8040
ttaattttgg aactgtatgt gtgtgtcata catcttcata gttacgagtt taagatggat   8100
ggaaatatcg atctaggata ggtatacatg ttgatgtggg ttttactgat gcatatacat   8160
gatggcatat gcagcatcta ttcatatgct ctaaccttga gtacctatct attataataa   8220
acaagtatgt tttataatta ttttgatctt gatatacttg gatgatggca tatccagcag   8280
ctatatctgg atttttttag ccctgccttc atacgctatt tatttgcttg gtactgtttc   8340
ttttgtcgtt gctcaccctg ttgtttggtg ttacttctgc agggatctcc gatcatgcaa   8400
aaactcatta actcagtgca aaactatgcc tggggcagca aaacggcgtt gactgaactt   8460
tacggtatgg aaaatccgtc cagccagccg atggccgagc tgtggatggg cgcacatccg   8520
aaaagcagtt cacgagtgca gaatgccgcc ggagatatcg tttcactgcg tgatgtgatt   8580
gagagtgata aatcgactct gctcggagag gccgttgcca aacgctttgg cgaactgcct   8640
ttcctgttca aagtattatg cgcagcacag ccactctcca ttcaggttca tccaaacaaa   8700
cacaattctg aaatcggttt tgccaaagaa aatgccgcag gtatcccgat ggatgccgcc   8760
gagcgtaact ataaagatcc taaccacaag ccggagctgg tttttgcgct gacgcctttc   8820
cttgcgatga acgcgtttcg tgaattttcc gagattgtct ccctactcca gccggtcgca   8880
ggtgcacatc cggcgattgc tcacttttta caacagcctg atgccgaacg tttaagcgaa   8940
ctgttcgcca gcctgttgaa tatgcagggt gaagaaaaat cccgcgcgct ggcgatttta   9000
aaatcggccc tcgatagcca gcagggtgaa ccgtggcaaa cgattcgttt aatttctgaa   9060
ttttacccgg aagacagcgg tctgttctcc ccgctattgc tgaatgtggt gaaattgaac   9120
cctggcgaag cgatgttcct gttcgctgaa acaccgcacg cttacctgca aggcgtggcg   9180
ctggaagtga tggcaaactc cgataacgtg ctgcgtgcgg gtctgacgcc taaatacatt   9240
gatattccgg aactggttgc caatgtgaaa ttcgaagcca aaccggctaa ccagttgttg   9300
acccagccgg tgaaacaagg tgcagaactg gacttcccga ttccagtgga cgattttgcc   9360
ttctcgctgc acgaccttag tgataaagaa accaccatta gccagcagag tgccgccatt   9420
ttgttctgcg tcgaaggcga tgcaacgttg tggaaaggtt ctcagcagtt acagcttaaa   9480
ccgggtgaat cagcgtttat tgccgccaac gaatcaccgg tgactgtcaa aggccacggc   9540
cgtttagcgc gtgtttacaa caagctgtaa gagcttactg aaaaaattaa catctcttgc   9600
taagctgggt catgggtcgt ttaagctgcc gatgtgcctg cgtcgtctgg tgccctctct   9660
ccatatggag gttgtcaaag tatctgctgt tcgtgtcatg agtcgtgtca gtgttggttt   9720
aataatggac cggttgtgtt gtgtgtgcgt actacccaga actatgacaa atcatgaata   9780
agtttgatgt ttgaaattaa agcctgtgct cattatgttc tgtctttcag ttgtctccta   9840
atatttgcct ccaggtactg gctatctacc gtttcttact taggaggtgt ttgaatgcac   9900
taaaactaat agttagtggc taaaattagt taaaacatcc aaacaccata gctaatagtt   9960
gaactattag ctatttttgg aaaattagtt aatagtgagg tagttatttg ttagctagct  10020
aattcaacta acaattttta gccaactaac aattagtttc agtgcattca aacacccccct 10080
taatgttaac gtggttctat ctaccgtctc ctaatatatg gttgattgtt cggtttgttg  10140
ctatgctatt gggttctgat tgctgctagt tcttgctgaa tccagaagtt ctcgtagtat  10200
agctcagatt catattattt atttgagtga taagtgatcc aggttattac tatgttagct  10260
aggttttttt tacaaggata aattatctgt gatcataatt cttatgaaag ctttatgttt  10320
cctggaggca gtggcatgca atgcatgaca gcaacttgat cacaccagct gaggtagata  10380
```

cggtaacaag gttcttaaat ctgttcacca aatcattgga gaacacacat acacattctt 10440
gccagtcttg gttagagaaa tttcatgaca aaatgccaaa gctgtcttga ctcttcactt 10500
ttggccatga gtcgtgactt agtttggttt aatggaccgg ttctcctagc ttgttctact 10560
caaaactgtt gttgatgcga ataagttgtg atggttgatc tctggatttt gttttgctct 10620
caatagtgga cgagattaga tag 10643

<210> SEQ ID NO 20
<211> LENGTH: 10642
<212> TYPE: DNA
<213> ORGANISM: Artificial sequence
<220> FEATURE:
<223> OTHER INFORMATION: Synthetic polynucleotide

<400> SEQUENCE: 20
gaattcatta tgtggtctag gtaggttcta tatataagaa aacttgaaat gttctaaaaa 60
aaaattcaag cccatgcatg attgaagcaa acggtatagc aacggtgtta acctgatcta 120
gtgatctctt gcaatcctta acggccacct accgcaggta gcaaacggcg tccccctcct 180
cgatatctcc gcggcgacct ctggcttttt ccgcggaatt gcgcggtggg gacggattcc 240
acgagaccgc gacgcaaccg cctctcgccg ctgggcccca caccgctcgg tgccgtagcc 300
tcacgggact ctttctccct cctccccgtt ataaattggc ttcatcccct ccttgcctca 360
tccatccaaa tcccagtccc caatcccatc ccttcgtagg agaaattcat cgaagctaag 420
cgaatcctcg cgatcctctc aaggtactgc gagttttcga tccccctctc gacccctcgt 480
atgtttgtgt ttgtcgtagc gtttgattag gtatgctttc cctgtttgtg ttcgtcgtag 540
cgtttgatta ggtatgcttt ccctgttcgt gttcatcgta gtgtttgatt aggtcgtgtg 600
aggcgatggc ctgctcgcgt ccttcgatct gtagtcgatt tgcgggtcgt ggtgtagatc 660
tgcgggctgt gatgaagtta tttggtgtga tctgctcgcc tgattctgct ggttggctcg 720
agtagatatg atggttggac cggttggttc gtttaccgcg ctagggttgg gctgggatga 780
tgttgcatgc gccgttgcgc gtgatcccgc agcaggactt gcgtttgatt gccagatctc 840
gttacgatta tgtgatttgg tttggacttt ttagatctgt agcttctgct tatgtgccag 900
atgcgcctac tgctcatatg cctgatgata atcataaatg gctgtggaac taactagttg 960
attgcggagt catgtatcag ctacaggtgt agggactagc tacaggtgta gggacttgcg 1020
tctaattgtt tggtccttta ctcatgttgc aattatgcaa tttagtttag attgtttgtt 1080
ccactcatct aggctgtaaa agggacactg cttagattgc tgtttaatct ttttagtaga 1140
ttatattata ttggtaactt attacccta ttacatgcca tacgtgactt ctgctcatgc 1200
ctgatgataa tcatagatca ctgtggaatt aattagttga ttgttgaatc atgtttcatg 1260
tacataccac ggcacaattg cttagttcct taacaaatgc aaattttact gatccatgta 1320
tgatttgcgt ggttctctaa tgtgaaatac tatagctact tgttagtaag aatcaggttc 1380
gtatgcttaa tgctgtatgt gccttctgct catgcctgat gataatcata tatcactgga 1440
attaattagt tgatcgttta atcatatatc aagtacatac catgccacaa tttttagtca 1500
cttaacccat gcagattgaa ctggtccctg catgttttgc taaattgttc tattctgatt 1560
agaccatata tcatgtattt ttttttggta atggttctct tattttaaat gctatatagt 1620
tctggtactt gttagaaaga tctgcttcat agtttagttg cctatccctc gaattaggat 1680
gctgagcagc tgatcctata gctttgtttc atgtatcaat tcttttgtgt tcaacagtca 1740

```
gtttttgtta gattcattgt aacttatggt cgcttactct tctggtcctc aatgcttgca   1800
gggatcctaa accatggaga tcaacaacca gaaccagtgc gtgccgtaca actgccttaa   1860
caaccccgag tccgagatcc tgaacgtggc catcttctcc agcgagcagg tcgcggagat   1920
ccacctcaag atcacgcgcc tgatcctcga gaacttcctg ccgggcggct ccttcgcttt   1980
cggcctgttc gacctcatct ggggcatctt caacgaggac cagtggagcg cgttcctcag   2040
gcaggtggag gagctgatca accagcgcat cacggagttc gccaggggcc aggctatcca   2100
gcggctggtg ggcttcggca ggtcctacga cgagtacatc ctggccctca aggagtggga   2160
gaacgacccc gacaacccgg ccagcaagga gcgcgtgagg acccgcttca ggaccaccga   2220
cgacgctctc ctgacgggcg tcccccctcat ggctatcccg ggcttcgagc tggccaccct   2280
ctcggtgtac gctcagtcgg ccaacctgca cctcgccctc ctgcgggacg ctgtgttctt   2340
cggcgagagg tggggcctga cccagacgaa catcaacgac ctctactcca ggctgaagaa   2400
cagcatccgc gactacacga accactgcgt gcgcttctac aacatcggcc tgggcaacct   2460
caacgtcatc aggccggagt actaccgctt ccagagggag ctgaccatca gcgtgctgga   2520
cctcgtcgcc ctgttcccca actacgacat ccgcacgtac ccgatcccaa ccaagtccca   2580
gctcacgagg gagatctaca ccgacccgat catctcgccg ggcgcccagg ccggctacac   2640
cctgcaggac gtcctgaggg agccccacct gatggacttc ctgaacaggc tcatcatcta   2700
caccggcgag tacaggggca tcaggcactg ggcgggccac gaggtggagt ccagcaggac   2760
gggcatgatg accaacatcc gcttcccgct ctacggcacc gcggccacgg ccgagccaac   2820
ccgcttcatc acgccgtcca ccttccccgg cctgaacctc ttctacagga ccctgtcggc   2880
tcccatcttc cgcgacgagc cgggcgcgaa catcatcatc cgctacagga cctccctcgt   2940
ggagggcgtc ggcttcatcc agccgaacaa cggcgagcag ctgtaccgcg tgaggggcac   3000
gctggacagc ctggaccagc tcccactgga gggcgagtcc agcctcaccg agtactcgca   3060
caggctgtgc cacgtcaggt tcgcccagag cctcaggaac gcggagcccc tggactacgc   3120
cagggtgccc atgttcagct ggacccacag gtcggctacc cccaccaaca ccatcgaccc   3180
agacgtgatc acgcagatcc cgctcgtcaa ggcccacacc ctgcagtcgg gcaccaccgt   3240
ggtcaagggc cccggcttca cgggcggcga catcctgagg aggacctccg gcggcccatt   3300
cgccttcagc aacgtcaacc tcgactggaa cctgtcccag cgctacaggg cgcgcatcag   3360
gtacgccagc accacgaacc tgcgcatgta tgtgaccatc gcgggcgaga ggatcttcgc   3420
cggccagttc aacaagacga tgaacaccgg cgacccgctc accttccagt ccttcagcta   3480
cgcgacgatc gacaccgcct tcacgttccc cacgaaggcc tccagcctga ccgtgggcgc   3540
cgacaccttc tccagcggca acgaggtcta cgtggaccgc ttcgagctga tcccggtgac   3600
ggcgaccttc gaggccgagt acgacctgga gaaggcccag aaggcggtca acgccctctt   3660
cacctccagc aaccagatcg gcctgaagac ggacgtgacc gactaccaca tcgacaaggt   3720
gtccaacctc gtcgagtgcc tgagcgacga gttctgcctc gacgagaaga gggagctgtc   3780
cgagaaggtc aagcacgcca agcgcctctg cgacgagagg aacctcctgc aggacccgaa   3840
cttcagggga atcaaccgcc agccggacag gggctggagg ggcagcaccg acatcaccat   3900
ccagggcggc gacgacgtgt tcaaggagaa ctacgtcacg ctcccgggca ccttcgacga   3960
gtgctacccc acgtacctgt accagaagat cgacgagtcc aagctcaagg cctacacccg   4020
ctacgagctg aggggataca tcgaggacag ccaggacctc gagatctacc tgatccgcta   4080
caacgcgaag cacgagacgg tgaacgtccc cggcacgggc tccctgtggc ccctctcggc   4140
```

```
tcagtcgccg atcggcaagt gcggcgagcc caacaggtgc gccacccacc tcgagtggaa   4200
cccggacctg gactgctcct gccgggacgg cgagaagtgc gctcaccact cccaccactt   4260
cagcctggac atcgacgtgg gctgcacgga cctcaacgag gacctgggcg tgtgggtcat   4320
cttcaaaatc aagacgcagg acggccacgc taggctgggc aacctcgagt tcctggagga   4380
gaagccgctg gtgggcgagg ctctggccag ggtcaagagg gcggagaaga agtggcgcga   4440
caagagggag aagctggagc tggagacgaa catcgtctac aaggaggcca agaagtccgt   4500
ggacgcgctc ttcgtcaaca gccagtacga caggctgcag gcggacacca acatcgccat   4560
catccacgcc gcggacaagc gcgtgcactc catcagggag gcctacctcc ccgagctgag   4620
cgtgatcccg ggcgtcaacg ctgccatctt cgaggagctg gagggccgca tcttcaccgc   4680
ctactccctg tacgacgcga ggaacgtcat caagaacggc gacttcaaca acggcctcag   4740
ctgctggaac gtgaagggcc acgtggacgt cgaggagcag aacaaccacc gctcggtgct   4800
ggtggtcccc gagtgggagg ctgaggtcag ccaggaggtg cgcgtctgcc cgggcagggg   4860
atacatcctc cgcgtgaccg cgtacaagga gggctacggc gagggctgcg tcacgatcca   4920
cgagatcgag gacaacaccg acgagctgaa gttctccaac tgcgtggagg aggagatcta   4980
cccgaacaac acggtcacct gcaacgacta cacggccacc caggaggagt acgagggcac   5040
gtacacgtcg aggaacaggg gctacgacgg cgcttacgag tccaacagct cggtgccggc   5100
cgactacgct agcgcgtacg aggagaaggc ctacacggac ggccgcaggg acaacacctg   5160
cgagtcgaac aggggctacg gcgactacac gccgctcccg gccggctacg tgaccaagga   5220
gctggagtac ttcccggaga cggacaaggt ctggatcgag atcggcgaga cggagggcac   5280
cttcatcgtg gactcagtcg agctgctgct catggaggag taggagctcg ccaacagtcg   5340
ttgaagctgc tgctgtatct gggttatcta gtgtctctgc ctttgcccaa ggatagtgct   5400
gtctttcaaa gtatttgtat cgtttgtgtc gtgagtcgtg actgagctgg tttcaaggac   5460
cagttgtgtt ctcgttaccc aaaactatcg tgcgaccgca tatggcttaa tcatgaataa   5520
atgttgtttg aatttaaact attcgctgaa tattgttgtt ttttgtcatg tcagttaatg   5580
ttactaaatt ggttgccttc taatttttgt ttactggtgt ttgtcgcacc ttatcttttt   5640
actgtatgtt tacttcaggt tctggcagtc tcatttttttg tgactagtta aaacttacag   5700
ctaaaaaaat gcagttttta attttaattt gaagtttgat tagagctatt gatacccgga   5760
ccatcaggtt aggttagttg tgcatagaat cataaatatt aatcatgttt tctatgaatt   5820
aagtcaaact tgaaagtctg gctgaatata gtttctatga atcatattga tatacatgtt   5880
tgattatttg ttttgctatt agctatttac tttggtgaat ctatataggc ttatgcagaa   5940
cctttttttt tgttctatat atccatatcc tagtactcag tagctctatg ttttctggag   6000
actagtggct tgctttttcg tatgtctaat tttttgcttg accattgcaa aacaaaaatt   6060
acctagtgta atctcttttt ataataatct tgtaatgcgt ctacctatag gtcaaagtag   6120
gttttgtttg gaacccttag agctaactgt tagctagttg ataaattatt agctgagtta   6180
agctagctaa tgaactagtt ttgatattag ctgaggatgt ttgaaaccta ataattattt   6240
tttattagct aactatacta aattttagta gagagattcc aaacaggagt taacatggga   6300
tcagattggc tatgcgtttg caatcccata ctaattagct aacggaccgc taattagcta   6360
acgatcgctt aattaagctt gcatgcctgc agtgcagcgt gacccggtcg tgcccctctc   6420
tagagataat gagcattgca tgtctaagtt ataaaaaatt accacatatt tttttgtca   6480
```

cacttgtttg aagtgcagtt tatctatctt tatacatata tttaaacttt actctacgaa 6540
taatataatc tatagtacta caataatatc agtgttttag agaatcatat aaatgaacag 6600
ttagacatgg tctaaaggac aattgagtat tttgacaaca ggactctaca gttttatctt 6660
tttagtgtgc atgtgttctc cttttttttt gcaaatagct tcacctatat aatacttcat 6720
ccattttatt agtacatcca tttagggttt agggttaatg gtttttatag actaattttt 6780
ttagtacatc tattttattc tattttagcc tctaaattaa gaaaactaaa actctatttt 6840
agttttttta tttaataatt tagatataaa atagaataaa ataaagtgac taaaaattaa 6900
acaaataccc tttaagaaat taaaaaaact aaggaaacat ttttcttgtt tcgagtagat 6960
aatgccagcc tgttaaacgc cgccgacgag tctaacggac accaaccagc gaaccagcag 7020
cgtcgcgtcg ggccaagcga agcagacggc acggcatctc tgtcgctgcc tctggacccc 7080
tctcgagagt tccgctccac cgttggactt gctccgctgt cggcatccag aaattgcgtg 7140
gcggagcggc agacgtgagc cggcacggca ggcggcctcc tcctcctctc acggcaccgg 7200
cagctacggg ggattccttt cccaccgctc cttcgctttc ccttcctcgc ccgccgtaat 7260
aaatagacac cccccctccac accctctttc cccaacctcg tgttgttcgg agcgcacaca 7320
cacacaacca gatctccccc aaatccaccc gtcggcacct ccgcttcaag gtacgccgct 7380
cgtcctcccc cccccccct ctctaccttc tctagatcgg cgttccggtc catagttagg 7440
gcccggtagt tctacttctg ttcatgtttg tgttagatcc gtgtttgtgt tagatccgtg 7500
ctgttagcgt tcgtacacgg atgcgacctg tacgtcagac acgttctgat tgctaacttg 7560
ccagtgtttc tctttgggga atcctgggat ggctctagcc gttccgcaga cgggatcgat 7620
ttcatgattt tttttgtttc gttgcatagg gtttggtttg ccctttttcct ttatttcaat 7680
atatgccgtg cacttgtttg tcgggtcatc ttttcatgct ttttttgtc ttggttgtga 7740
tgatgtggtc tggttgggcg gtcgttctag atcggagtag aattctgttt caaactacct 7800
ggtggattta ttaattttgg atctgtatgt gtgtgccata catattcata gttacgaatt 7860
gaagatgatg gatggaaata tcgatctagg ataggtatac atgttgatgc gggttttact 7920
gatgcatata cagagatgct tttgttcgc ttggttgtga tgatgtggtg tggttgggcg 7980
gtcgttcatt tcgttctaga tcggagtaga atactgtttc aaactacctg gtgtatttat 8040
taattttgga actgtatgtg tgtgtcatac atcttcatag ttacgagttt aagatggatg 8100
gaaatatcga tctaggatag gtatacatgt tgatgtgggt tttactgatg catatacatg 8160
atggcatatg cagcatctat tcatatgctc taaccttgag tacctatcta ttataataaa 8220
caagtatgtt ttataattat tttgatcttg atatacttgg atgatggcat atccagcagc 8280
tatatctgga tttttttagc cctgccttca tacgctattt atttgcttgg tactgtttct 8340
tttgtcgttg ctcaccctgt tgtttggtgt tacttctgca gggatctccg atcatgcaaa 8400
aactcattaa ctcagtgcaa aactatgcct ggggcagcaa aacggcgttg actgaacttt 8460
acggtatgga aaatccgtcc agccagccga tggccgagct gtggatgggc gcacatccga 8520
aaagcagttc acgagtgcag aatgccgccg gagatatcgt ttcactgcgt gatgtgattg 8580
agagtgataa atcgactctg ctcggagagg ccgttgccaa acgctttggc gaactgcctt 8640
tcctgttcaa agtattatgc gcagcacagc cactctccat tcaggttcat ccaaacaaac 8700
acaattctga aatcggtttt gccaaagaaa atgccgcagg tatcccgatg gatgccgccg 8760
agcgtaacta taaagatcct aaccacaagc cggagctggt tttgcgctg acgcctttcc 8820
ttgcgatgaa cgcgtttcgt gaattttccg agattgtctc cctactccag ccggtcgcag 8880
gtgcacatcc ggcgattgct cactttttac aacagcctga tgccgaacgt ttaagcgaac 8940
tgttcgccag cctgttgaat atgcagggtg aagaaaaatc ccgcgcgctg gcgattttaa 9000
aatcggccct cgatagccag cagggtgaac cgtggcaaac gattcgttta atttctgaat 9060
tttacccgga agacagcggt ctgttctccc cgctattgct gaatgtggtg aaattgaacc 9120
ctggcgaagc gatgttcctg ttcgctgaaa caccgcacgc ttacctgcaa ggcgtggcgc 9180
tggaagtgat ggcaaactcc gataacgtgc tgcgtgcggg tctgacgcct aaatacattg 9240
atattccgga actggttgcc aatgtgaaat tcgaagccaa accggctaac cagttgttga 9300
cccagccggt gaaacaaggt gcagaactgg acttcccgat tccagtggac gattttgcct 9360
tctcgctgca cgaccttagt gataaagaaa ccaccattag ccagcagagt gccgccattt 9420
tgttctgcgt cgaaggcgat gcaacgttgt ggaaaggttc tcagcagtta cagcttaaac 9480
cgggtgaatc agcgtttatt gccgccaacg aatcaccggt gactgtcaaa ggccacggcc 9540
gtttagcgcg tgtttacaac aagctgtaag agcttactga aaaaattaac atctcttgct 9600
aagctgggtc atgggtcgtt taagctgccg atgtgcctgc gtcgtctggt gccctctctc 9660
catatggagg ttgtcaaagt atctgctgtt cgtgtcatga gtcgtgtcag tgttggttta 9720
ataatggacc ggttgtgttg tgtgtgcgta ctacccagaa ctatgacaaa tcatgaataa 9780
gtttgatgtt tgaaattaaa gcctgtgctc attatgttct gtctttcagt tgtctcctaa 9840
tatttgcctc caggtactgg ctatctaccg tttcttactt aggaggtgtt tgaatgcact 9900
aaaactaata gttagtggct aaaattagtt aaaacatcca aacaccatag ctaatagttg 9960
aactattagc tatttttgga aaattagtta atagtgaggt agttatttgt tagctagcta 10020
attcaactaa caatttttag ccaactaaca attagtttca gtgcattcaa acaccccctt 10080
aatgttaacg tggttctatc taccgtctcc taatatatgg ttgattgttc ggtttgttgc 10140
tatgctattg ggttctgatt gctgctagtt cttgctgaat ccagaagttc tcgtagtata 10200
gctcagattc atattattta tttgagtgat aagtgatcca ggttattact atgttagcta 10260
ggtttttttt acaaggataa attatctgtg atcataattc ttatgaaagc tttatgtttc 10320
ctggaggcag tggcatgcaa tgcatgacag caacttgatc acaccagctg aggtagatac 10380
ggtaacaagg ttcttaaatc tgttcaccaa atcattggag aacacacata cacattcttg 10440
ccagtcttgg ttagagaaat ttcatgacaa aatgccaaag ctgtcttgac tcttcacttt 10500
tggccatgag tcgtgactta gtttggttta atggaccggt tctcctagct tgttctactc 10560
aaaactgttg ttgatgcgaa taagttgtga tggttgatct ctggattttg ttttgctctc 10620
aatagtggac gagattagat ag 10642

<210> SEQ ID NO 21
<211> LENGTH: 10642
<212> TYPE: DNA
<213> ORGANISM: Artificial sequence
<220> FEATURE:
<223> OTHER INFORMATION: Synthetic polynucleotide

<400> SEQUENCE: 21
gaattcatta tgtggtctag gtaggttcta tatataagaa aacttgaaat gttctaaaaa 60
aaaattcaag cccatgcatg attgaagcaa acggtatagc aacggtgtta acctgatcta 120
gtgatctctt gcaatcctta acggccacct accgcaggta gcaaacggcg tccccctcct 180
cgatatctcc gcggcgacct ctggcttttt ccgcggaatt gcgcggtggg gacggattcc 240

```
acgagaccgc gacgcaaccg cctctcgccg ctgggcccca caccgctcgg tgccgtagcc    300
tcacgggact ctttctccct cctccccgtt ataaattggc ttcatcccct ccttgcctca    360
tccatccaaa tcccagtccc caatcccatc ccttcgtagg agaaattcat cgaagctaag    420
cgaatcctcg cgatcctctc aaggtactgc gagttttcga tccccctctc gacccctcgt    480
atgtttgtgt ttgtcgtagc gtttgattag gtatgctttc cctgtttgtg ttcgtcgtag    540
cgtttgatta ggtatgcttt ccctgttcgt gttcatcgta gtgtttgatt aggtcgtgtg    600
aggcgatggc ctgctcgcgt ccttcgatct gtagtcgatt tgcgggtcgt ggtgtagatc    660
tgcgggctgt gatgaagtta tttggtgtga tctgctcgcc tgattctgct ggttggctcg    720
agtagatatg atggttggac cggttggttc gtttaccgcg ctagggttgg gctgggatga    780
tgttgcatgc gccgttgcgc gtgatcccgc agcaggactt gcgtttgatt gccagatctc    840
gttacgatta tgtgatttgg tttggacttt ttagatctgt agcttctgct tatgtgccag    900
atgcgcctac tgctcatatg cctgatgata atcataaatg gctgtggaac taactagttg    960
attgcggagt catgtatcag ctacaggtgt agggactagc tacaggtgta gggacttgcg   1020
tctaattgtt tggtccttta ctcatgttgc aattatgcaa tttagtttag attgtttgtt   1080
ccactcatct aggctgtaaa agggacactg cttagattgc tgtttaatct ttttagtaga   1140
ttatattata ttggtaactt attaccccta ttacatgcca tacgtgactt ctgctcatgc   1200
ctgatgataa tcatagatca ctgtggaatt aattagttga ttgttgaatc atgtttcatg   1260
tacataccac ggcacaattg cttagttcct taacaaatgc aaattttact gatccatgta   1320
tgatttgcgt ggttctctaa tgtgaaatac tatagctact tgttagtaag aatcaggttc   1380
gtatgcttaa tgctgtatgt gccttctgct catgcctgat gataatcata tatcactgga   1440
attaattagt tgatcgttta atcatatatc aagtacatac catgccacaa tttttagtca   1500
cttaacccat gcagattgaa ctggtccctg catgttttgc taaattgttc tattctgatt   1560
agaccatata tcatgtattt ttttttggta atggttctct tattttaaat gctatatagt   1620
tctggtactt gttagaaaga tctgcttcat agtttagttg cctatccctc gaattaggat   1680
gctgagcagc tgatcctata gctttgtttc atgtatcaat tcttttgtgt tcaacagtca   1740
gtttttgtta gattcattgt aacttatggt cgcttactct tctggtcctc aatgcttgca   1800
gggatcctaa accatggaga tcaacaacca gaaccagtgc gtgccgtaca actgccttaa   1860
caaccccgag tccgagatcc tgaacgtggc catcttctcc agcgagcagg tcgcggagat   1920
ccacctcaag atcacgcgcc tgatcctcga gaacttcctg ccgggcggct ccttcgcttt   1980
cggcctgttc gacctcatct ggggcatctt caacgaggac cagtggagcg cgttcctcag   2040
gcaggtggag gagctgatca accagcgcat cacggagttc gccaggggcc aggctatcca   2100
gcggctggtg ggcttcggca ggtcctacga cgagtacatc ctggccctca aggagtggga   2160
gaacgacccc gacaacccgg ccagcaagga gcgcgtgagg acccgcttca ggaccaccga   2220
cgacgctctc ctgacgggcg tccccctcat ggctatcccg ggcttcgagc tggccaccct   2280
ctcggtgtac gctcagtcgg ccaacctgca cctcgccctc ctgcgggacg ctgtgttctt   2340
cggcgagagg tggggcctga cccagacgaa catcaacgac ctctactcca ggctgaagaa   2400
cagcatccgc gactacacga accactgcgt gcgcttctac aacatcggcc tgggcaacct   2460
caacgtcatc aggccggagt actaccgctt ccagagggag ctgaccatca gcgtgctgga   2520
cctcgtcgcc ctgttcccca actacgacat ccgcacgtac ccgatcccaa ccaagtccca   2580
gctcacgagg gagatctaca ccgacccgat catctcgccg ggcgcccagg ccggctacac   2640
```

```
cctgcaggac gtcctgaggg agccccacct gatggacttc ctgaacaggc tcatcatcta   2700
caccggcgag tacaggggca tcaggcactg ggcgggccac gaggtggagt ccagcaggac   2760
gggcatgatg accaacatcc gcttcccgct ctacggcacc gcggccacgg ccgagccaac   2820
ccgcttcatc acgccgtcca ccttccccgg cctgaacctc ttctacagga ccctgtcggc   2880
tcccatcttc cgcgacgagc cgggcgcgaa catcatcatc cgctacagga cctccctcgt   2940
ggagggcgtc ggcttcatcc agccgaacaa cggcgagcag ctgtaccgcg tgaggggcac   3000
gctggacagc ctggaccagc tcccactgga gggcgagtcc agcctcaccg agtactcgca   3060
caggctgtgc cacgtcaggt tcgcccagag cctcaggaac gcggagcccc tggactacgc   3120
cagggtgccc atgttcagct ggacccacag gtcggctacc cccaccaaca ccatcgaccc   3180
agacgtgatc acgcagatcc cgctcgtcaa ggcccacacc ctgcagtcgg gcaccaccgt   3240
ggtcaagggc cccggcttca cgggcggcga catcctgagg aggacctccg gcggcccatt   3300
cgccttcagc aacgtcaacc tcgactggaa cctgtcccag cgctacaggg cgcgcatcag   3360
gtacgccagc accacgaacc tgcgcatgta tgtgaccatc gcgggcgaga ggatcttcgc   3420
cggccagttc aacaagacga tgaacaccgg cgacccgctc accttccagt ccttcagcta   3480
cgcgacgatc gacaccgcct tcacgttccc cacgaaggcc tccagcctga ccgtgggcgc   3540
cgacaccttc tccagcggca acgaggtcta cgtggaccgc ttcgagctga tcccggtgac   3600
ggcgaccttc gaggccgagt acgacctgga gaaggcccag aaggcggtca acgccctctt   3660
cacctccagc aaccagatcg gcctgaagac ggacgtgacc gactaccaca tcgacaaggt   3720
gtccaacctc gtcgagtgcc tgagcgacga gttctgcctc gacgagaaga gggagctgtc   3780
cgagaaggtc aagcacgcca agcgcctctg cgacgagagg aacctcctgc aggacccgaa   3840
cttcagggga atcaaccgcc agccggacag gggctggagg ggcagcaccg acatcaccat   3900
ccagggcggc gacgacgtgt tcaaggagaa ctacgtcacg ctcccgggca ccttcgacga   3960
gtgctacccc acgtacctgt accagaagat cgacgagtcc aagctcaagg cctacacccg   4020
ctacgagctg aggggataca tcgaggacag ccaggacctc gagatctacc tgatccgcta   4080
caacgcgaag cacgagacgg tgaacgtccc cggcacgggc tccctgtggc ccctctcggc   4140
tcagtcgccg atcggcaagt gcggcgagcc caacaggtgc gccacccacc tcgagtggaa   4200
cccggacctg gactgctcct gccgggacgg cgagaagtgc gctcaccact cccaccactt   4260
cagcctggac atcgacgtgg gctgcacgga cctcaacgag gacctgggcg tgtgggtcat   4320
cttcaaaatc aagacgcagg acggccacgc taggctgggc aacctcgagt tcctggagga   4380
gaagccgctg gtgggcgagg ctctggccag ggtcaagagg gcggagaaga agtggcgcga   4440
caagagggag aagctggagc tggagacgaa catcgtctac aaggaggcca agaagtccgt   4500
ggacgcgctc ttcgtcaaca gccagtacga caggctgcag gcggacacca acatcgccat   4560
catccacgcc gcggacaagc gcgtgcactc catcagggag gcctacctcc ccgagctgag   4620
cgtgatcccg ggcgtcaacg ctgccatctt cgaggagctg gagggccgca tcttcaccgc   4680
ctactccctg tacgacgcga ggaacgtcat caagaacggc gacttcaaca acggcctcag   4740
ctgctggaac gtgaagggcc acgtggacgt cgaggagcag aacaaccacc gctcggtgct   4800
ggtggtcccc gagtgggagg ctgaggtcag ccaggaggtg cgcgtctgcc cgggcagggg   4860
atacatcctc cgcgtgaccg cgtacaagga gggctacggc gagggctgcg tcacgatcca   4920
cgagatcgag gacaacaccg acgagctgaa gttctccaac tgcgtggagg aggagatcta   4980
```

```
cccgaacaac acggtcacct gcaacgacta cacggccacc caggaggagt acgagggcac   5040
gtacacgtcg aggaacaggg gctacgacgg cgcttacgag tccaacagct cggtgccggc   5100
cgactacgct agcgcgtacg aggagaaggc ctacacggac ggccgcaggg acaacacctg   5160
cgagtcgaac aggggctacg gcgactacac gccgctcccg gccggctacg tgaccaagga   5220
gctggagtac ttcccggaga cggacaaggt ctggatcgag atcggcgaga cggagggcac   5280
cttcatcgtg gactcagtcg agctgctgct catggaggag taggagctcg ccaacagtcg   5340
ttgaagctgc tgctgtatct gggttatcta gtgtctctgc ctttgcccaa ggatagtgct   5400
gtctttcaaa gtatttgtat cgtttgtgtc gtgagtcgtg actgagctgg tttcaaggac   5460
cagttgtgtt ctcgttaccc aaaactatcg tgcgaccgca tatggcttaa tcatgaataa   5520
atgttgtttg aatttaaact attcgctgaa tattgttgtt ttttgtcatg tcagttaatg   5580
ttactaaatt ggttgccttc taatttttgt ttactggtgt ttgtcgcacc ttatcttttt   5640
actgtatgtt tacttcaggt tctggcagtc tcatttttttg tgactagtta aaacttacag   5700
ctaaaaaaat gcagttttta attttaattt gaagtttgat tagagctatt gatacccgga   5760
ccatcaggtt aggttagttg tgcatagaat cataaatatt aatcatgttt tctatgaatt   5820
aagtcaaact tgaaagtctg gctgaatata gtttctatga atcatattga tatacatgtt   5880
tgattatttg ttttgctatt agctatttac tttggtgaat ctatataggc ttatgcagaa   5940
ccttttttttt tgttctatat atccatatcc tagtactcag tagctctatg ttttctggag   6000
actagtggct tgctttttcg tatgtctaat tttttgcttg accattgcaa aacaaaaatt   6060
acctagtgta atctcttttt ataataatct tgtaatgcgt ctacctatag gtcaaagtag   6120
gttttgtttg gaacccttag agctaactgt tagctagttg ataaattatt agctgagtta   6180
agctagctaa tgaactagtt ttgatattag ctgaggatgt ttgaaaccta ataattattt   6240
tttattagct aactatacta aattttagta gagagattcc aaacaggagt taacatggga   6300
tcagattggc tatgcgtttg caatcccata ctaattagct aacggaccgc taattagcta   6360
acgatcgctt aattaagctt gcatgcctgc agtgcagcgt gacccggtcg tgcccctctc   6420
tagagataat gagcattgca tgtctaagtt ataaaaaatt accacatatt ttttttgtca   6480
cacttgtttg aagtgcagtt tatctatctt tatacatata tttaaacttt actctacgaa   6540
taatataatc tatagtacta caataaatatc agtgttttag agaatcatat aaatgaacag   6600
ttagacatgg tctaaaggac aattgagtat tttgacaaca ggactctaca gttttatctt   6660
tttagtgtgc atgtgttctc cttttttttt gcaaatagct tcacctatat aatacttcat   6720
ccattttatt agtacatcca tttagggttt agggttaatg gtttttatag actaattttt   6780
ttagtacatc tattttattc tattttagcc tctaaattaa gaaaactaaa actctatttt   6840
agttttttta tttaataatt tagatataaa atagaataaa ataaagtgac taaaaattaa   6900
acaaataccc tttaagaaat taaaaaaact aaggaaacat ttttcttgtt tcgagtagat   6960
aatgccagcc tgttaaacgc cgccgacgag tctaacggac accaaccagc gaaccagcag   7020
cgtcgcgtcg ggccaagcga agcagacggc acggcatctc tgtcgctgcc tctggacccc   7080
tctcgagagt tccgctccac cgttggactt gctccgctgt cggcatccag aaattgcgtg   7140
gcggagcggc agacgtgagc cggcacggca ggcggcctcc tcctcctctc acggcaccgg   7200
cagctacggg ggattccttt cccaccgctc cttcgctttc ccttcctcgc ccgccgtaat   7260
aaatagacac cccctccaca ccctctttcc ccaacctcgt gttgttcgga gcgcacacac   7320
acacaaccag atctccccca aatccacccg tcggcacctc cgcttcaagg tacgccgctc   7380
```

```
gtcctccccc cccccccccct ctctaccttc tctagatcgg cgttccggtc catagttagg   7440
gcccggtagt tctacttctg ttcatgtttg tgttagatcc gtgtttgtgt tagatccgtg   7500
ctgttagcgt tcgtacacgg atgcgacctg tacgtcagac acgttctgat tgctaacttg   7560
ccagtgtttc tctttgggga atcctgggat ggctctagcc gttccgcaga cgggatcgat   7620
ttcatgattt tttttgtttc gttgcatagg gtttggtttg ccctttttcct ttatttcaat   7680
atatgccgtg cacttgtttg tcgggtcatc ttttcatgct tttttttgtc ttggttgtga   7740
tgatgtggtc tggttgggcg gtcgttctag atcggagtag aattctgttt caaactacct   7800
ggtggattta ttaattttgg atctgtatgt gtgtgccata catattcata gttacgaatt   7860
gaagatgatg gatggaaata tcgatctagg ataggtatac atgttgatgc gggttttact   7920
gatgcatata cagagatgct ttttgttcgc ttggttgtga tgatgtggtg tggttgggcg   7980
gtcgttcatt tcgttctaga tcggagtaga atactgtttc aaactacctg gtgtatttat   8040
taattttgga actgtatgtg tgtgtcatac atcttcatag ttacgagttt aagatggatg   8100
gaaatatcga tctaggatag gtatacatgt tgatgtgggt tttactgatg catatacatg   8160
atggcatatg cagcatctat tcatatgctc taaccttgag tacctatcta ttataataaa   8220
caagtatgtt ttataattat tttgatcttg atatacttgg atgatggcat atccagcagc   8280
tatatctgga ttttttttagc cctgccttca tacgctattt atttgcttgg tactgtttct   8340
tttgtcgttg ctcaccctgt tgtttggtgt tacttctgca gggatctccg atcatgcaaa   8400
aactcattaa ctcagtgcaa aactatgcct ggggcagcaa aacggcgttg actgaacttt   8460
acggtatgga aaatccgtcc agccagccga tggccgagct gtggatgggc gcacatccga   8520
aaagcagttc acgagtgcag aatgccgccg gagatatcgt ttcactgcgt gatgtgattg   8580
agagtgataa atcgactctg ctcggagagg ccgttgccaa acgctttggc gaactgcctt   8640
tcctgttcaa agtattatgc gcagcacagc cactctccat tcaggttcat ccaaacaaac   8700
acaattctga aatcggtttt gccaaagaaa atgccgcagg tatcccgatg gatgccgccg   8760
agcgtaacta taaagatcct aaccacaagc cggagctggt ttttgcgctg acgcctttcc   8820
ttgcgatgaa cgcgtttcgt gaattttccg agattgtctc cctactccag ccggtcgcag   8880
gtgcacatcc ggcgattgct cactttttac aacagcctga tgccgaacgt ttaagcgaac   8940
tgttcgccag cctgttgaat atgcagggtg aagaaaaatc ccgcgcgctg gcgattttaa   9000
aatcggccct cgatagccag cagggtgaac cgtggcaaac gattcgttta atttctgaat   9060
tttacccgga agacagcggt ctgttctccc cgctattgct gaatgtggtg aaattgaacc   9120
ctggcgaagc gatgttcctg ttcgctgaaa caccgcacgc ttacctgcaa ggcgtggcgc   9180
tggaagtgat ggcaaactcc gataacgtgc tgcgtgcggg tctgacgcct aaatacattg   9240
atattccgga actggttgcc aatgtgaaat tcgaagccaa accggctaac cagttgttga   9300
cccagccggt gaaacaaggt gcagaactgg acttcccgat tccagtggac gatttttgcct   9360
tctcgctgca cgaccttagt gataaagaaa ccaccattag ccagcagagt gccgccattt   9420
tgttctgcgt cgaaggcgat gcaacgttgt ggaaaggttc tcagcagtta cagcttaaac   9480
cgggtgaatc agcgtttatt gccgccaacg aatcaccggt gactgtcaaa ggccacggcc   9540
gtttagcgcg tgtttacaac aagctgtaag agcttactga aaaaattaac atctcttgct   9600
aagctgggtc atgggtcgtt taagctgccg atgtgcctgc gtcgtctggt gccctctctc   9660
catatggagg ttgtcaaagt atctgctgtt cgtgtcatga gtcgtgtcag tgttggttta   9720
```

ataatggacc ggttgtgttg tgtgtgcgta ctacccagaa ctatgacaaa tcatgaataa 9780
gtttgatgtt tgaaattaaa gcctgtgctc attatgttct gtctttcagt tgtctcctaa 9840
tatttgcctc caggtactgg ctatctaccg tttcttactt aggaggtgtt tgaatgcact 9900
aaaactaata gttagtggct aaaattagtt aaaacatcca aacaccatag ctaatagttg 9960
aactattagc tatttttgga aaattagtta atagtgaggt agttatttgt tagctagcta 10020
attcaactaa caatttttag ccaactaaca attagtttca gtgcattcaa acaccccctt 10080
aatgttaacg tggttctatc taccgtctcc taatatatgg ttgattgttc ggtttgttgc 10140
tatgctattg ggttctgatt gctgctagtt cttgctgaat ccagaagttc tcgtagtata 10200
gctcagattc atattattta tttgagtgat aagtgatcca ggttattact atgttagcta 10260
ggtttttttt acaaggataa attatctgtg atcataattc ttatgaaagc tttatgtttc 10320
ctggaggcag tggcatgcaa tgcatgacag caacttgatc acaccagctg aggtagatac 10380
ggtaacaagg ttcttaaatc tgttcaccaa atcattggag aacacacata cacattcttg 10440
ccagtcttgg ttagagaaat ttcatgacaa aatgccaaag ctgtcttgac tcttcacttt 10500
tggccatgag tcgtgactta gtttggttta atggaccggt tctcctagct tgttctactc 10560
aaaactgttg ttgatgcgaa taagttgtga tggttgatct ctggattttg ttttgctctc 10620
aatagtggac gagattagat ag 10642

<210> SEQ ID NO 22
<211> LENGTH: 10644
<212> TYPE: DNA
<213> ORGANISM: Artificial sequence
<220> FEATURE:
<223> OTHER INFORMATION: Synthetic polynucleotide

<400> SEQUENCE: 22
gaattcatta tgtggtctag gtaggttcta tatataagaa aacttgaaat gttctaaaaa 60
aaaattcaag cccatgcatg attgaagcaa acggtatagc aacggtgtta acctgatcta 120
gtgatctctt gcaatcctta acggccacct accgcaggta gcaaacggcg tccccctcct 180
cgatatctcc gcggcgacct ctggcttttt ccgcggaatt gcgcggtggg gacggattcc 240
acgagaccgc gacgcaaccg cctctcgccg ctgggcccca caccgctcgg tgccgtagcc 300
tcacgggact ctttctccct cctcccccgt tataaattgg cttcatcccc tccttgcctc 360
atccatccaa atcccagtcc ccaatcccat cccttcgtag gagaaattca tcgaagctaa 420
gcgaatcctc gcgatcctct caaggtactg cgagttttcg atccccctct cgacccctcg 480
tatgtttgtg tttgtcgtag cgtttgatta ggtatgcttt ccctgtttgt gttcgtcgta 540
gcgtttgatt aggtatgctt tccctgttcg tgttcatcgt agtgtttgat taggtcgtgt 600
gaggcgatgg cctgctcgcg tccttcgatc tgtagtcgat ttgcgggtcg tggtgtagat 660
ctgcgggctg tgatgaagtt atttggtgtg atctgctcgc ctgattctgc tggttggctc 720
gagtagatat gatggttgga ccggttggtt cgtttaccgc gctagggttg ggctgggatg 780
atgttgcatg cgccgttgcg cgtgatcccg cagcaggact tgcgtttgat tgccagatct 840
cgttacgatt atgtgatttg gtttggactt tttagatctg tagcttctgc ttatgtgcca 900
gatgcgccta ctgctcatat gcctgatgat aatcataaat ggctgtggaa ctaactagtt 960
gattgcggag tcatgtatca gctacaggtg tagggactag ctacaggtgt agggacttgc 1020
gtctaattgt ttggtccttt actcatgttg caattatgca atttagttta gattgtttgt 1080
tccactcatc taggctgtaa aagggacact gcttagattg ctgtttaatc tttttagtag 1140

```
attatattat attggtaact tattacccct attacatgcc atacgtgact tctgctcatg   1200
cctgatgata atcatagatc actgtggaat taattagttg attgttgaat catgtttcat   1260
gtacatacca cggcacaatt gcttagttcc ttaacaaatg caaattttac tgatccatgt   1320
atgatttgcg tggttctcta atgtgaaata ctatagctac ttgttagtaa gaatcaggtt   1380
cgtatgctta atgctgtatg tgccttctgc tcatgcctga tgataatcat atatcactgg   1440
aattaattag ttgatcgttt aatcatatat caagtacata ccatgccaca atttttagtc   1500
acttaaccca tgcagattga actggtccct gcatgttttg ctaaattgtt ctattctgat   1560
tagaccatat atcatgtatt ttttttggt aatggttctc ttattttaaa tgctatatag   1620
ttctggtact tgttagaaag atctgcttca tagtttagtt gcctatccct cgaattagga   1680
tgctgagcag ctgatcctat agctttgttt catgtatcaa ttcttttgtg ttcaacagtc   1740
agtttttgtt agattcattg taacttatgg tcgcttactc ttctggtcct caatgcttgc   1800
agggatccta aaccatggag atcaacaacc agaaccagtg cgtgccgtac aactgcctta   1860
acaaccccga gtccgagatc ctgaacgtgg ccatcttctc cagcgagcag gtcgcggaga   1920
tccacctcaa gatcacgcgc ctgatcctcg agaacttcct gccgggcggc tccttcgctt   1980
tcggcctgtt cgacctcatc tggggcatct tcaacgagga ccagtggagc gcgttcctca   2040
ggcaggtgga ggagctgatc aaccagcgca tcacggagtt cgccaggggc caggctatcc   2100
agcggctggt gggcttcggc aggtcctacg acgagtacat cctggccctc aaggagtggg   2160
agaacgaccc cgacaacccg gccagcaagg agcgcgtgag gacccgcttc aggaccaccg   2220
acgacgctct cctgacgggc gtccccctca tggctatccc gggcttcgag ctggccaccc   2280
tctcggtgta cgctcagtcg gccaacctgc acctcgccct cctgcgggac gctgtgttct   2340
tcggcgagag gtggggcctg acccagacga acatcaacga cctctactcc aggctgaaga   2400
acagcatccg cgactacacg aaccactgcg tgcgcttcta caacatcggc ctgggcaacc   2460
tcaacgtcat caggccggag tactaccgct tccagaggga gctgaccatc agcgtgctgg   2520
acctcgtcgc cctgttcccc aactacgaca tccgcacgta cccgatccca accaagtccc   2580
agctcacgag ggagatctac accgacccga tcatctcgcc gggcgcccag gccggctaca   2640
ccctgcagga cgtcctgagg gagccccacc tgatggactt cctgaacagg ctcatcatct   2700
acaccggcga gtacaggggc atcaggcact gggcgggcca cgaggtggag tccagcagga   2760
cgggcatgat gaccaacatc cgcttcccgc tctacggcac cgcggccacg gccgagccaa   2820
cccgcttcat cacgccgtcc accttccccg gcctgaacct cttctacagg accctgtcgg   2880
ctcccatctt ccgcgacgag ccgggcgcga acatcatcat ccgctacagg acctccctcg   2940
tggagggcgt cggcttcatc cagccgaaca acggcgagca gctgtaccgc gtgaggggca   3000
cgctggacag cctggaccag ctcccactgg agggcgagtc cagcctcacc gagtactcgc   3060
acaggctgtg ccacgtcagg ttcgcccaga gcctcaggaa cgcggagccc ctggactacg   3120
ccagggtgcc catgttcagc tggacccaca ggtcggctac ccccaccaac accatcgacc   3180
cagacgtgat cacgcagatc ccgctcgtca aggcccacac cctgcagtcg ggcaccaccg   3240
tggtcaaggg ccccggcttc acgggcggcg acatcctgag gaggacctcc ggcggcccat   3300
tcgccttcag caacgtcaac ctcgactgga acctgtccca gcgctacagg gcgcgcatca   3360
ggtacgccag caccacgaac ctgcgcatgt atgtgaccat cgcgggcgag aggatcttcg   3420
ccggccagtt caacaagacg atgaacaccg gcgacccgct caccttccag tccttcagct   3480
```

-continued acgcgacgat cgacaccgcc ttcacgttcc ccacgaaggc ctccagcctg accgtgggcg 3540
ccgacacctt ctccagcggc aacgaggtct acgtggaccg cttcgagctg atcccggtga 3600
cggcgacctt cgaggccgag tacgacctgg agaaggccca gaaggcggtc aacgccctct 3660
tcacctccag caaccagatc ggcctgaaga cggacgtgac cgactaccac atcgacaagg 3720
tgtccaacct cgtcgagtgc ctgagcgacg agttctgcct cgacgagaag agggagctgt 3780
ccgagaaggt caagcacgcc aagcgcctct gcgacgagag gaacctcctg caggacccga 3840
acttcagggg aatcaaccgc cagccggaca ggggctggag gggcagcacc gacatcacca 3900
tccagggcgg cgacgacgtg ttcaaggaga actacgtcac gctcccgggc accttcgacg 3960
agtgctaccc cacgtacctg taccagaaga tcgacgagtc caagctcaag gcctacaccc 4020
gctacgagct gaggggatac atcgaggaca gccaggacct cgagatctac ctgatccgct 4080
acaacgcgaa gcacgagacg gtgaacgtcc ccggcacggg ctccctgtgg cccctctcgg 4140
ctcagtcgcc gatcggcaag tgcggcgagc ccaacaggtg cgccacccac ctcgagtgga 4200
acccggacct ggactgctcc tgccgggacg gcgagaagtg cgctcaccac tcccaccact 4260
tcagcctgga catcgacgtg ggctgcacgg acctcaacga ggacctgggc gtgtgggtca 4320
tcttcaaaat caagacgcag gacggccacg ctaggctggg caacctcgag ttcctggagg 4380
agaagccgct ggtgggcgag gctctggcca gggtcaagag ggcggagaag aagtggcgcg 4440
acaagaggga gaagctggag ctggagacga acatcgtcta caaggaggcc aagaagtccg 4500
tggacgcgct cttcgtcaac agccagtacg acaggctgca ggcggacacc aacatcgcca 4560
tcatccacgc cgcggacaag cgcgtgcact ccatcaggga ggcctacctc cccgagctga 4620
gcgtgatccc gggcgtcaac gctgccatct tcgaggagct ggagggccgc atcttcaccg 4680
cctactccct gtacgacgcg aggaacgtca tcaagaacgg cgacttcaac aacggcctca 4740
gctgctggaa cgtgaagggc cacgtggacg tcgaggagca gaacaaccac cgctcggtgc 4800
tggtggtccc cgagtgggag gctgaggtca gccaggaggt gcgcgtctgc ccgggcaggg 4860
gatacatcct ccgcgtgacc gcgtacaagg agggctacgg cgagggctgc gtcacgatcc 4920
acgagatcga ggacaacacc gacgagctga agttctccaa ctgcgtggag gaggagatct 4980
acccgaacaa cacggtcacc tgcaacgact acacggccac ccaggaggag tacgagggca 5040
cgtacacgtc gaggaacagg ggctacgacg gcgcttacga gtccaacagc tcggtgccgg 5100
ccgactacgc tagcgcgtac gaggagaagg cctacacgga cggccgcagg gacaacacct 5160
gcgagtcgaa caggggctac ggcgactaca cgccgctccc ggccggctac gtgaccaagg 5220
agctggagta cttcccggag acggacaagg tctggatcga gatcggcgag acggagggca 5280
ccttcatcgt ggactcagtc gagctgctgc tcatggagga gtaggagctc gccaacagtc 5340
gttgaagctg ctgctgtatc tgggttatct agtgtctctg cctttgccca aggatagtgc 5400
tgtctttcaa agtatttgta tcgtttgtgt cgtgagtcgt gactgagctg gtttcaagga 5460
ccagttgtgt tctcgttacc caaaactatc gtgcgaccgc atatggctta atcatgaata 5520
aatgttgttt gaatttaaac tattcgctga atattgttgt tttttgtcat gtcagttaat 5580
gttactaaat tggttgcctt ctaatttttg tttactggtg tttgtcgcac cttatctttt 5640
tactgtatgt ttacttcagg ttctggcagt ctcatttttt gtgactagtt aaaacttaca 5700
gctaaaaaaa tgcagttttt aattttaatt tgaagtttga ttagagctat tgatacccgg 5760
accatcaggt taggttagtt gtgcatagaa tcataaatat taatcatgtt ttctatgaat 5820
taagtcaaac ttgaaagtct ggctgaatat agtttctatg aatcatattg atatacatgt 5880
ttgattattt gttttgctat tagctattta ctttggtgaa tctatatagg cttatgcaga 5940
accttttttt ttgttctata tatccatatc ctagtactca gtagctctat gttttctgga 6000
gactagtggc ttgcttttc gtatgtctaa ttttttgctt gaccattgca aaacaaaaat 6060
tacctagtgt aatctctttt tataataatc ttgtaatgcg tctacctata ggtcaaagta 6120
ggttttgttt ggaaccctta gagctaactg ttagctagtt gataaattat tagctgagtt 6180
aagctagcta atgaactagt tttgatatta gctgaggatg tttgaaacct aataattatt 6240
ttttattagc taactatact aaattttagt agagagattc caaacaggag ttaacatggg 6300
atcagattgg ctatgcgttt gcaatcccat actaattagc taacggaccg ctaattagct 6360
aacgatcgct taattaagct tgcatgcctg cagtgcagcg tgacccggtc gtgcccctct 6420
ctagagataa tgagcattgc atgtctaagt tataaaaaat taccacatat ttttttttgtc 6480
acacttgttt gaagtgcagt ttatctatct ttatacatat atttaaactt tactctacga 6540
ataatataat ctatagtact acaataatat cagtgtttta gagaatcata taaatgaaca 6600
gttagacatg gtctaaagga caattgagta ttttgacaac aggactctac agttttatct 6660
ttttagtgtg catgtgttct cctttttttt tgcaaatagc ttcacctata taatacttca 6720
tccattttat tagtacatcc atttagggtt tagggttaat ggtttttata gactaatttt 6780
tttagtacat ctattttatt ctattttagc ctctaaatta agaaaactaa aactctattt 6840
tagttttttt atttaataat ttagatataa aatagaataa aataaagtga ctaaaaatta 6900
aacaaatacc ctttaagaaa ttaaaaaaac taaggaaaca tttttcttgt ttcgagtaga 6960
taatgccagc ctgttaaacg ccgccgacga gtctaacgga caccaaccag cgaaccagca 7020
gcgtcgcgtc gggccaagcg aagcagacgg cacggcatct ctgtcgctgc ctctggaccc 7080
ctctcgagag ttccgctcca ccgttggact tgctccgctg tcggcatcca gaaattgcgt 7140
ggcggagcgg cagacgtgag ccggcacggc aggcggcctc ctcctcctct cacggcaccg 7200
gcagctacgg gggattcctt tcccaccgct ccttcgcttt cccttcctcg cccgccgtaa 7260
taaatagaca cccccctcca caccctcttt ccccaacctc gtgttgttcg gagcgcacac 7320
acacacaacc agatctcccc caaatccacc cgtcggcacc tccgcttcaa ggtacgccgc 7380
tcgtcctccc cccccccccc ctctctacct tctctagatc ggcgttccgg tccatagtta 7440
gggcccggta gttctacttc tgttcatgtt tgtgttagat ccgtgtttgt gttagatccg 7500
tgctgttagc gttcgtacac ggatgcgacc tgtacgtcag acacgttctg attgctaact 7560
tgccagtgtt tctctttggg gaatcctggg atggctctag ccgttccgca gacgggatcg 7620
atttcatgat tttttttgtt tcgttgcata gggtttggtt tgccctttc ctttatttca 7680
atatatgccg tgcacttgtt tgtcgggtca tcttttcatg cttttttttg tcttggttgt 7740
gatgatgtgg tctggttggg cggtcgttct agatcggagt agaattctgt ttcaaactac 7800
ctggtggatt tattaatttt ggatctgtat gtgtgtgcca tacatattca tagttacgaa 7860
ttgaagatga tggatggaaa tatcgatcta ggataggtat acatgttgat gcgggtttta 7920
ctgatgcata tacagagatg ctttttgttc gcttggttgt gatgatgtgg tgtggttggg 7980
cggtcgttca tttcgttcta gatcggagta gaatactgtt tcaaactacc tggtgtattt 8040
attaattttg gaactgtatg tgtgtgtcat acatcttcat agttacgagt ttaagatgga 8100
tggaaatatc gatctaggat aggtatacat gttgatgtgg gttttactga tgcatataca 8160
tgatggcata tgcagcatct attcatatgc tctaaccttg agtacctatc tattataata 8220
aacaagtatg ttttataatt attttgatct tgatatactt ggatgatggc atatccagca 8280
gctatatctg gattttttta gccctgcctt catacgctat ttatttgctt ggtactgttt 8340
cttttgtcgt tgctcaccct gttgtttggt gttacttctg cagggatctc cgatcatgca 8400
aaaactcatt aactcagtgc aaaactatgc ctggggcagc aaaacggcgt tgactgaact 8460
ttacggtatg gaaaatccgt ccagccagcc gatggccgag ctgtggatgg gcgcacatcc 8520
gaaaagcagt tcacgagtgc agaatgccgc cggagatatc gtttcactgc gtgatgtgat 8580
tgagagtgat aaatcgactc tgctcggaga ggccgttgcc aaacgctttg gcgaactgcc 8640
tttcctgttc aaagtattat gcgcagcaca gccactctcc attcaggttc atccaaacaa 8700
acacaattct gaaatcggtt ttgccaaaga aaatgccgca ggtatcccga tggatgccgc 8760
cgagcgtaac tataaagatc ctaaccacaa gccggagctg gtttttgcgc tgacgccttt 8820
ccttgcgatg aacgcgtttc gtgaattttc cgagattgtc tccctactcc agccggtcgc 8880
aggtgcacat ccggcgattg ctcacttttt acaacagcct gatgccgaac gtttaagcga 8940
actgttcgcc agcctgttga atatgcaggg tgaagaaaaa tcccgcgcgc tggcgatttt 9000
aaaatcggcc ctcgatagcc agcagggtga accgtggcaa acgattcgtt taatttctga 9060
atttacccg gaagacagcg gtctgttctc cccgctattg ctgaatgtgg tgaaattgaa 9120
ccctggcgaa gcgatgttcc tgttcgctga aacaccgcac gcttacctgc aaggcgtggc 9180
gctggaagtg atggcaaact ccgataacgt gctgcgtgcg ggtctgacgc ctaaatacat 9240
tgatattccg gaactggttg ccaatgtgaa attcgaagcc aaaccggcta accagttgtt 9300
gacccagccg gtgaaacaag gtgcagaact ggacttcccg attccagtgg acgattttgc 9360
cttctcgctg cacgacctta gtgataaaga aaccaccatt agccagcaga gtgccgccat 9420
tttgttctgc gtcgaaggcg atgcaacgtt gtggaaaggt tctcagcagt tacagcttaa 9480
accgggtgaa tcagcgttta ttgccgccaa cgaatcaccg gtgactgtca aaggccacgg 9540
ccgtttagcg cgtgtttaca acaagctgta agagcttact gaaaaaatta acatctcttg 9600
ctaagctggg tcatgggtcg tttaagctgc cgatgtgcct gcgtcgtctg gtgccctctc 9660
tccatatgga ggttgtcaaa gtatctgctg ttcgtgtcat gagtcgtgtc agtgttggtt 9720
taataatgga ccggttgtgt tgtgtgtgcg tactacccag aactatgaca aatcatgaat 9780
aagtttgatg tttgaaatta aagcctgtgc tcattatgtt ctgtctttca gttgtctcct 9840
aatatttgcc tccaggtact ggctatctac cgtttcttac ttaggaggtg tttgaatgca 9900
ctaaaactaa tagttagtgg ctaaaattag ttaaaacatc caaacaccat agctaatagt 9960
tgaactatta gctatttttg gaaaattagt taatagtgag gtagttattt gttagctagc 10020
taattcaact aacaattttt agccaactaa caattagttt cagtgcattc aaacaccccc 10080
ttaatgttaa cgtggttcta tctaccgtct cctaatatat ggttgattgt tcggtttgtt 10140
gctatgctat tgggttctga ttgctgctag ttcttgctga atccagaagt tctcgtagta 10200
tagctcagat tcatattatt tatttgagtg ataagtgatc caggttatta ctatgttagc 10260
taggtttttt ttacaaggat aaattatctg tgatcataat tcttatgaaa gctttatgtt 10320
tcctggaggc agtggcatgc aatgcatgac agcaacttga tcacaccagc tgaggtagat 10380
acggtaacaa ggttcttaaa tctgttcacc aaatcattgg agaacacaca tacacattct 10440
tgccagtctt ggttagagaa atttcatgac aaaatgccaa agctgtcttg actcttcact 10500
tttggccatg agtcgtgact tagtttggtt taatggaccg gttctcctag cttgttctac 10560
tcaaaactgt tgttgatgcg aataagttgt gatggttgat ctctggattt tgttttgctc 10620
tcaatagtgg acgagattag atag 10644

<210> SEQ ID NO 23
<211> LENGTH: 10643
<212> TYPE: DNA
<213> ORGANISM: Artificial sequence
<220> FEATURE:
<223> OTHER INFORMATION: Synthetic polynucleotide

<400> SEQUENCE: 23
gaattcatta tgtggtctag gtaggttcta tatataagaa aacttgaaat gttctaaaaa 60
aaaattcaag cccatgcatg attgaagcaa acggtatagc aacggtgtta acctgatcta 120
gtgatctctt gcaatcctta acggccacct accgcaggta gcaaacggcg tccccctcct 180
cgatatctcc gcggcgacct ctggcttttt ccgcggaatt gcgcggtggg gacggattcc 240
acgagaccgc gacgcaaccg cctctcgccg ctgggcccca caccgctcgg tgccgtagcc 300
tcacgggact ctttctccct cctccccgtt ataaattggc ttcatcccct ccttgcctca 360
tccatccaaa tcccagtccc caatcccatc ccttcgtagg agaaattcat cgaagctaag 420
cgaatcctcg cgatcctctc aaggtactgc gagttttcga tccccctctc gacccctcgt 480
atgtttgtgt ttgtcgtagc gtttgattag gtatgctttc cctgtttgtg ttcgtcgtag 540
cgtttgatta ggtatgcttt ccctgttcgt gttcatcgta gtgtttgatt aggtcgtgtg 600
aggcgatggc ctgctcgcgt ccttcgatct gtagtcgatt tgcgggtcgt ggtgtagatc 660
tgcgggctgt gatgaagtta tttggtgtga tctgctcgcc tgattctgct ggttggctcg 720
agtagatatg atggttggac cggttggttc gtttaccgcg ctagggttgg gctgggatga 780
tgttgcatgc gccgttgcgc gtgatcccgc agcaggactt gcgtttgatt gccagatctc 840
gttacgatta tgtgatttgg tttggacttt ttagatctgt agcttctgct tatgtgccag 900
atgcgcctac tgctcatatg cctgatgata atcataaatg gctgtggaac taactagttg 960
attgcggagt catgtatcag ctacaggtgt agggactagc tacaggtgta gggacttgcg 1020
tctaattgtt tggtccttta ctcatgttgc aattatgcaa tttagtttag attgtttgtt 1080
ccactcatct aggctgtaaa agggacactg cttagattgc tgtttaatct ttttagtaga 1140
ttatattata ttggtaactt attacccta ttacatgcca tacgtgactt ctgctcatgc 1200
ctgatgataa tcatagatca ctgtggaatt aattagttga ttgttgaatc atgtttcatg 1260
tacataccac ggcacaattg cttagttcct taacaaatgc aaattttact gatccatgta 1320
tgatttgcgt ggttctctaa tgtgaaatac tatagctact tgttagtaag aatcaggttc 1380
gtatgcttaa tgctgtatgt gccttctgct catgcctgat gataatcata tatcactgga 1440
attaattagt tgatcgttta atcatatatc aagtacatac catgccacaa tttttagtca 1500
cttaacccat gcagattgaa ctggtccctg catgttttgc taaattgttc tattctgatt 1560
agaccatata tcatgtattt ttttttggta atggttctct tattttaaat gctatatagt 1620
tctggtactt gttagaaaga tctgcttcat agtttagttg cctatccctc gaattaggat 1680
gctgagcagc tgatcctata gctttgtttc atgtatcaat tcttttgtgt tcaacagtca 1740
gtttttgtta gattcattgt aacttatggt cgcttactct tctggtcctc aatgcttgca 1800
gggatcctaa accatggaga tcaacaacca gaaccagtgc gtgccgtaca actgccttaa 1860
caaccccgag tccgagatcc tgaacgtggc catcttctcc agcgagcagg tcgcggagat 1920
ccacctcaag atcacgcgcc tgatcctcga gaacttcctg ccgggcggct ccttcgcttt 1980

```
cggcctgttc gacctcatct ggggcatctt caacgaggac cagtggagcg cgttcctcag   2040
gcaggtggag gagctgatca accagcgcat cacggagttc gccaggggcc aggctatcca   2100
gcggctggtg ggcttcggca ggtcctacga cgagtacatc ctggccctca aggagtggga   2160
gaacgacccc gacaacccgg ccagcaagga gcgcgtgagg acccgcttca ggaccaccga   2220
cgacgctctc ctgacgggcg tcccccctcat ggctatcccg ggcttcgagc tggccacccct   2280
ctcggtgtac gctcagtcgg ccaacctgca cctcgccctc ctgcgggacg ctgtgttctt   2340
cggcgagagg tggggcctga cccagacgaa catcaacgac ctctactcca ggctgaagaa   2400
cagcatccgc gactacacga accactgcgt gcgcttctac aacatcggcc tgggcaacct   2460
caacgtcatc aggccggagt actaccgctt ccagagggag ctgaccatca gcgtgctgga   2520
cctcgtcgcc ctgttcccca actacgacat ccgcacgtac ccgatcccaa ccaagtccca   2580
gctcacgagg gagatctaca ccgacccgat catctcgccg ggcgcccagg ccggctacac   2640
cctgcaggac gtcctgaggg agccccacct gatggacttc ctgaacaggc tcatcatcta   2700
caccggcgag tacaggggca tcaggcactg ggcgggccac gaggtggagt ccagcaggac   2760
gggcatgatg accaacatcc gcttcccgct ctacggcacc gcggccacgg ccgagccaac   2820
ccgcttcatc acgccgtcca ccttccccgg cctgaacctc ttctacagga ccctgtcggc   2880
tcccatcttc cgcgacgagc cgggcgcgaa catcatcatc cgctacagga cctccctcgt   2940
ggagggcgtc ggcttcatcc agccgaacaa cggcgagcag ctgtaccgcg tgaggggcac   3000
gctggacagc ctggaccagc tcccactgga gggcgagtcc agcctcaccg agtactcgca   3060
caggctgtgc cacgtcaggt tcgcccagag cctcaggaac gcggagcccc tggactacgc   3120
cagggtgccc atgttcagct ggacccacag gtcggctacc cccaccaaca ccatcgaccc   3180
agacgtgatc acgcagatcc cgctcgtcaa ggcccacacc ctgcagtcgg gcaccaccgt   3240
ggtcaagggc cccggcttca cgggcggcga catcctgagg aggacctccg gcggcccatt   3300
cgccttcagc aacgtcaacc tcgactggaa cctgtcccag cgctacaggg cgcgcatcag   3360
gtacgccagc accacgaacc tgcgcatgta tgtgaccatc gcgggcgaga ggatcttcgc   3420
cggccagttc aacaagacga tgaacaccgg cgacccgctc accttccagt ccttcagcta   3480
cgcgacgatc gacaccgcct tcacgttccc cacgaaggcc tccagcctga ccgtgggcgc   3540
cgacaccttc tccagcggca acgaggtcta cgtggaccgc ttcgagctga tcccggtgac   3600
ggcgaccttc gaggccgagt acgacctgga gaaggcccag aaggcggtca acgccctctt   3660
cacctccagc aaccagatcg gcctgaagac ggacgtgacc gactaccaca tcgacaaggt   3720
gtccaacctc gtcgagtgcc tgagcgacga gttctgcctc gacgagaaga gggagctgtc   3780
cgagaaggtc aagcacgcca agcgcctctg cgacgagagg aacctcctgc aggacccgaa   3840
cttcagggga atcaaccgcc agccggacag ggctggaggg ggcagcaccg acatcaccat   3900
ccagggcggc gacgacgtgt tcaaggagaa ctacgtcacg ctcccgggca ccttcgacga   3960
gtgctacccc acgtacctgt accagaagat cgacgagtcc aagctcaagg cctacacccg   4020
ctacgagctg aggggataca tcgaggacag ccaggacctc gagatctacc tgatccgcta   4080
caacgcgaag cacgagacgg tgaacgtccc cggcacgggc tccctgtggc ccctctcggc   4140
tcagtcgccg atcggcaagt gcggcgagcc caacaggtgc gccacccacc tcgagtggaa   4200
cccggacctg gactgctcct gccgggacgg cgagaagtgc gctcaccact cccaccactt   4260
cagcctggac atcgacgtgg gctgcacgga cctcaacgag gacctgggcg tgtgggtcat   4320
cttcaaaatc aagacgcagg acggccacgc taggctgggc aacctcgagt tcctggagga   4380
```

```
gaagccgctg gtgggcgagg ctctggccag ggtcaagagg gcggagaaga agtggcgcga   4440
caagagggag aagctggagc tggagacgaa catcgtctac aaggaggcca agaagtccgt   4500
ggacgcgctc ttcgtcaaca gccagtacga caggctgcag gcggacacca acatcgccat   4560
catccacgcc gcggacaagc gcgtgcactc catcagggag gcctacctcc ccgagctgag   4620
cgtgatcccg ggcgtcaacg ctgccatctt cgaggagctg gagggccgca tcttcaccgc   4680
ctactccctg tacgacgcga ggaacgtcat caagaacggc gacttcaaca acggcctcag   4740
ctgctggaac gtgaagggcc acgtggacgt cgaggagcag aacaaccacc gctcggtgct   4800
ggtggtcccc gagtgggagg ctgaggtcag ccaggaggtg cgcgtctgcc cgggcagggg   4860
atacatcctc cgcgtgaccg cgtacaagga gggctacggc gagggctgcg tcacgatcca   4920
cgagatcgag gacaacaccg acgagctgaa gttctccaac tgcgtggagg aggagatcta   4980
cccgaacaac acggtcacct gcaacgacta cacggccacc caggaggagt acgagggcac   5040
gtacacgtcg aggaacaggg gctacgacgg cgcttacgag tccaacagct cggtgccggc   5100
cgactacgct agcgcgtacg aggagaaggc ctacacggac ggccgcaggg acaacacctg   5160
cgagtcgaac aggggctacg gcgactacac gccgctcccg gccggctacg tgaccaagga   5220
gctggagtac ttcccggaga cggacaaggt ctggatcgag atcggcgaga cggagggcac   5280
cttcatcgtg gactcagtcg agctgctgct catggaggag taggagctcg ccaacagtcg   5340
ttgaagctgc tgctgtatct gggttatcta gtgtctctgc ctttgcccaa ggatagtgct   5400
gtctttcaaa gtatttgtat cgtttgtgtc gtgagtcgtg actgagctgg tttcaaggac   5460
cagttgtgtt ctcgttaccc aaaactatcg tgcgaccgca tatggcttaa tcatgaataa   5520
atgttgtttg aatttaaact attcgctgaa tattgttgtt ttttgtcatg tcagttaatg   5580
ttactaaatt ggttgccttc taatttttgt ttactggtgt ttgtcgcacc ttatcttttt   5640
actgtatgtt tacttcaggt tctggcagtc tcatttttttg tgactagtta aaacttacag   5700
ctaaaaaaat gcagttttta attttaattt gaagtttgat tagagctatt gatacccgga   5760
ccatcaggtt aggttagttg tgcatagaat cataaatatt aatcatgttt tctatgaatt   5820
aagtcaaact tgaaagtctg gctgaatata gtttctatga atcatattga tatacatgtt   5880
tgattatttg ttttgctatt agctatttac tttggtgaat ctatataggc ttatgcagaa   5940
cctttttttt tgttctatat atccatatcc tagtactcag tagctctatg ttttctggag   6000
actagtggct tgctttttcg tatgtctaat tttttgcttg accattgcaa aacaaaaatt   6060
acctagtgta atctcttttt ataataatct tgtaatgcgt ctacctatag gtcaaagtag   6120
gttttgtttg gaacccttag agctaactgt tagctagttg ataaattatt agctgagtta   6180
agctagctaa tgaactagtt ttgatattag ctgaggatgt ttgaaaccta ataattattt   6240
tttattagct aactatacta aattttagta gagagattcc aaacaggagt taacatggga   6300
tcagattggc tatgcgtttg caatcccata ctaattagct aacggaccgc taattagcta   6360
acgatcgctt aattaagctt gcatgcctgc agtgcagcgt gacccggtcg tgcccctctc   6420
tagagataat gagcattgca tgtctaagtt ataaaaaatt accacatatt tttttgtca   6480
cacttgtttg aagtgcagtt tatctatctt tatacatata tttaaacttt actctacgaa   6540
taatataatc tatagtacta caataaatatc agtgttttag agaatcatat aaatgaacag   6600
ttagacatgg tctaaaggac aattgagtat tttgacaaca ggactctaca gttttatctt   6660
tttagtgtgc atgtgttctc cttttttttt gcaaatagct tcacctatat aatacttcat   6720
```

```
ccattttatt agtacatcca tttagggttt agggttaatg gtttttatag actaattttt   6780
ttagtacatc tattttattc tattttagcc tctaaattaa gaaaactaaa actctatttt   6840
agttttttta tttaataatt tagatataaa atagaataaa ataaagtgac taaaaattaa   6900
acaaataccc tttaagaaat taaaaaaact aaggaaacat ttttcttgtt tcgagtagat   6960
aatgccagcc tgttaaacgc cgccgacgag tctaacggac accaaccagc gaaccagcag   7020
cgtcgcgtcg ggccaagcga agcagacggc acggcatctc tgtcgctgcc tctggacccc   7080
tctcgagagt tccgctccac cgttggactt gctccgctgt cggcatccag aaattgcgtg   7140
gcggagcggc agacgtgagc cggcacggca ggcggcctcc tcctcctctc acggcaccgg   7200
cagctacggg ggattccttt cccaccgctc cttcgctttc ccttcctcgc ccgccgtaat   7260
aaatagacac cccctccac accctctttc cccaacctcg tgttgttcgg agcgcacaca   7320
cacacaacca gatctccccc aaatccaccc gtcggcacct ccgcttcaag gtacgccgct   7380
cgtcctcccc cccccccccc tctctacctt ctctagatcg gcgttccggt ccatagttag   7440
ggcccggtag ttctacttct gttcatgttt gtgttagatc cgtgtttgtg ttagatccgt   7500
gctgttagcg ttcgtacacg gatgcgacct gtacgtcaga cacgttctga ttgctaactt   7560
gccagtgttt ctctttgggg aatcctggga tggctctagc cgttccgcag acgggatcga   7620
tttcatgatt ttttttgttt cgttgcatag ggtttggttt gccctttcc tttatttcaa   7680
tatatgccgt gcacttgttt gtcgggtcat cttttcatgc ttttttttgt cttggttgtg   7740
atgatgtggt ctggttgggc ggtcgttcta gatcggagta gaattctgtt tcaaactacc   7800
tggtggattt attaatttg gatctgtatg tgtgtgccat acatattcat agttacgaat   7860
tgaagatgat ggatggaaat atcgatctag gataggtata catgttgatg cgggttttac   7920
tgatgcatat acagagatgc tttttgttcg cttggttgtg atgatgtggt gtggttgggc   7980
ggtcgttcat ttcgttctag atcggagtag aatactgttt caaactacct ggtgtattta   8040
ttaattttgg aactgtatgt gtgtgtcata catcttcata gttacgagtt taagatggat   8100
ggaaatatcg atctaggata ggtatacatg ttgatgtggg ttttactgat gcatatacat   8160
gatggcatat gcagcatcta ttcatatgct ctaaccttga gtacctatct attataataa   8220
acaagtatgt tttataatta ttttgatctt gatatacttg gatgatggca tatccagcag   8280
ctatatctgg atttttttag ccctgccttc atacgctatt tatttgcttg gtactgtttc   8340
ttttgtcgtt gctcaccctg ttgtttggtg ttacttctgc agggatctcc gatcatgcaa   8400
aaactcatta actcagtgca aaactatgcc tggggcagca aaacggcgtt gactgaactt   8460
tacggtatgg aaaatccgtc cagccagccg atggccgagc tgtggatggg cgcacatccg   8520
aaaagcagtt cacgagtgca gaatgccgcc ggagatatcg tttcactgcg tgatgtgatt   8580
gagagtgata aatcgactct gctcggagag gccgttgcca aacgctttgg cgaactgcct   8640
ttcctgttca aagtattatg cgcagcacag ccactctcca ttcaggttca tccaaacaaa   8700
cacaattctg aaatcggttt tgccaaagaa aatgccgcag gtatcccgat ggatgccgcc   8760
gagcgtaact ataaagatcc taaccacaag ccggagctgg tttttgcgct gacgcctttc   8820
cttgcgatga acgcgtttcg tgaattttcc gagattgtct ccctactcca gccggtcgca   8880
ggtgcacatc cggcgattgc tcactttta caacagcctg atgccgaacg tttaagcgaa   8940
ctgttcgcca gcctgttgaa tatgcagggt gaagaaaaat cccgcgcgct ggcgatttta   9000
aaatcggccc tcgatagcca gcagggtgaa ccgtggcaaa cgattcgttt aatttctgaa   9060
ttttacccgg aagacagcgg tctgttctcc ccgctattgc tgaatgtggt gaaattgaac   9120
```

```
cctggcgaag cgatgttcct gttcgctgaa acaccgcacg cttacctgca aggcgtggcg   9180
ctggaagtga tggcaaactc cgataacgtg ctgcgtgcgg gtctgacgcc taaatacatt   9240
gatattccgg aactggttgc caatgtgaaa ttcgaagcca aaccggctaa ccagttgttg   9300
acccagccgg tgaaacaagg tgcagaactg gacttcccga ttccagtgga cgattttgcc   9360
ttctcgctgc acgaccttag tgataaagaa accaccatta gccagcagag tgccgccatt   9420
ttgttctgcg tcgaaggcga tgcaacgttg tggaaaggtt ctcagcagtt acagcttaaa   9480
ccgggtgaat cagcgtttat tgccgccaac gaatcaccgg tgactgtcaa aggccacggc   9540
cgtttagcgc gtgtttacaa caagctgtaa gagcttactg aaaaaattaa catctcttgc   9600
taagctgggt catgggtcgt ttaagctgcc gatgtgcctg cgtcgtctgg tgccctctct   9660
ccatatggag gttgtcaaag tatctgctgt tcgtgtcatg agtcgtgtca gtgttggttt   9720
aataatggac cggttgtgtt gtgtgtgcgt actacccaga actatgacaa atcatgaata   9780
agtttgatgt ttgaaattaa agcctgtgct cattatgttc tgtctttcag ttgtctccta   9840
atatttgcct ccaggtactg gctatctacc gtttcttact taggaggtgt ttgaatgcac   9900
taaaactaat agttagtggc taaaattagt taaaacatcc aaacaccata gctaatagtt   9960
gaactattag ctatttttgg aaaattagtt aatagtgagg tagttatttg ttagctagct  10020
aattcaacta acaattttta gccaactaac aattagtttc agtgcattca aacacccccct 10080
taatgttaac gtggttctat ctaccgtctc ctaatatatg gttgattgtt cggtttgttg  10140
ctatgctatt gggttctgat tgctgctagt tcttgctgaa tccagaagtt ctcgtagtat  10200
agctcagatt catattattt atttgagtga taagtgatcc aggttattac tatgttagct  10260
aggttttttt tacaaggata aattatctgt gatcataatt cttatgaaag ctttatgttt  10320
cctggaggca gtggcatgca atgcatgaca gcaacttgat cacaccagct gaggtagata  10380
cggtaacaag gttcttaaat ctgttcacca aatcattgga gaacacacat acacattctt  10440
gccagtcttg gttagagaaa tttcatgaca aaatgccaaa gctgtcttga ctcttcactt  10500
ttggccatga gtcgtgactt agtttggttt aatggaccgg ttctcctagc ttgttctact  10560
caaaactgtt gttgatgcga ataagttgtg atggttgatc tctggatttt gttttgctct  10620
caatagtgga cgagattaga tag                                          10643
```

```
<210> SEQ ID NO 24
<211> LENGTH: 10644
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<222> LOCATION: (324)..(324)
<223> OTHER INFORMATION: n is c or absent
<220> FEATURE:
<221> NAME/KEY: misc_feature
<222> LOCATION: (7271)..(7271)
<223> OTHER INFORMATION: n is c or absent
<220> FEATURE:
<221> NAME/KEY: misc_feature
<222> LOCATION: (7388)..(7388)
<223> OTHER INFORMATION: n is c or absent
<220> FEATURE:
<221> NAME/KEY: misc_feature
<222> LOCATION: (7991)..(7991)
<223> OTHER INFORMATION: n is t or absent

<400> SEQUENCE: 24
```

-continued

```
gaattcatta tgtggtctag gtaggttcta tatataagaa aacttgaaat gttctaaaaa     60
aaaattcaag cccatgcatg attgaagcaa acggtatagc aacggtgtta acctgatcta    120
gtgatctctt gcaatcctta acggccacct accgcaggta gcaaacggcg tccccctcct    180
cgatatctcc gcggcgacct ctggcttttt ccgcggaatt gcgcggtggg gacggattcc    240
acgagaccgc gacgcaaccg cctctcgccg ctgggcccca caccgctcgg tgccgtagcc    300
tcacgggact ctttctccct cctnccccgt tataaattgg cttcatcccc tccttgcctc    360
atccatccaa atcccagtcc ccaatcccat cccttcgtag gagaaattca tcgaagctaa    420
gcgaatcctc gcgatcctct caaggtactg cgagttttcg atccccctct cgacccctcg    480
tatgtttgtg tttgtcgtag cgtttgatta ggtatgcttt ccctgtttgt gttcgtcgta    540
gcgtttgatt aggtatgctt tccctgttcg tgttcatcgt agtgtttgat taggtcgtgt    600
gaggcgatgg cctgctcgcg tccttcgatc tgtagtcgat ttgcgggtcg tggtgtagat    660
ctgcgggctg tgatgaagtt atttggtgtg atctgctcgc ctgattctgc tggttggctc    720
gagtagatat gatggttgga ccggttggtt cgtttaccgc gctagggttg ggctgggatg    780
atgttgcatg cgccgttgcg cgtgatcccg cagcaggact tgcgtttgat tgccagatct    840
cgttacgatt atgtgatttg gtttggactt tttagatctg tagcttctgc ttatgtgcca    900
gatgcgccta ctgctcatat gcctgatgat aatcataaat ggctgtggaa ctaactagtt    960
gattgcggag tcatgtatca gctacaggtg tagggactag ctacaggtgt agggacttgc   1020
gtctaattgt ttggtccttt actcatgttg caattatgca atttagttta gattgtttgt   1080
tccactcatc taggctgtaa aagggacact gcttagattg ctgtttaatc tttttagtag   1140
attatattat attggtaact tattacccct attacatgcc atacgtgact tctgctcatg   1200
cctgatgata atcatagatc actgtggaat taattagttg attgttgaat catgtttcat   1260
gtacatacca cggcacaatt gcttagttcc ttaacaaatg caaattttac tgatccatgt   1320
atgatttgcg tggttctcta atgtgaaata ctatagctac ttgttagtaa gaatcaggtt   1380
cgtatgctta atgctgtatg tgccttctgc tcatgcctga tgataatcat atatcactgg   1440
aattaattag ttgatcgttt aatcatatat caagtacata ccatgccaca atttttagtc   1500
acttaaccca tgcagattga actggtccct gcatgttttg ctaaattgtt ctattctgat   1560
tagaccatat atcatgtatt tttttttggt aatggttctc ttattttaaa tgctatatag   1620
ttctggtact tgttagaaag atctgcttca tagtttagtt gcctatccct cgaattagga   1680
tgctgagcag ctgatcctat agctttgttt catgtatcaa ttcttttgtg ttcaacagtc   1740
agtttttgtt agattcattg taacttatgg tcgcttactc ttctggtcct caatgcttgc   1800
agggatccta aaccatggag atcaacaacc agaaccagtg cgtgccgtac aactgcctta   1860
acaaccccga gtccgagatc ctgaacgtgg ccatcttctc cagcgagcag gtcgcggaga   1920
tccacctcaa gatcacgcgc ctgatcctcg agaacttcct gccgggcggc tccttcgctt   1980
tcggcctgtt cgacctcatc tggggcatct tcaacgagga ccagtggagc gcgttcctca   2040
ggcaggtgga ggagctgatc aaccagcgca tcacggagtt cgccaggggc caggctatcc   2100
agcggctggt gggcttcggc aggtcctacg acgagtacat cctggccctc aaggagtggg   2160
agaacgaccc cgacaacccg gccagcaagg agcgcgtgag gacccgcttc aggaccaccg   2220
acgacgctct cctgacgggc gtccccctca tggctatccc gggcttcgag ctggccaccc   2280
tctcggtgta cgctcagtcg gccaacctgc acctcgccct cctgcgggac gctgtgttct   2340
tcggcgagag gtggggcctg acccagacga acatcaacga cctctactcc aggctgaaga   2400
```

```
acagcatccg cgactacacg aaccactgcg tgcgcttcta caacatcggc ctgggcaacc   2460
tcaacgtcat caggccggag tactaccgct tccagaggga gctgaccatc agcgtgctgg   2520
acctcgtcgc cctgttcccc aactacgaca tccgcacgta cccgatccca accaagtccc   2580
agctcacgag ggagatctac accgacccga tcatctcgcc gggcgcccag gccggctaca   2640
ccctgcagga cgtcctgagg gagccccacc tgatggactt cctgaacagg ctcatcatct   2700
acaccggcga gtacaggggc atcaggcact gggcgggcca cgaggtggag tccagcagga   2760
cgggcatgat gaccaacatc cgcttcccgc tctacggcac cgcggccacg gccgagccaa   2820
cccgcttcat cacgccgtcc accttccccg gcctgaacct cttctacagg accctgtcgg   2880
ctcccatctt ccgcgacgag ccgggcgcga acatcatcat ccgctacagg acctccctcg   2940
tggagggcgt cggcttcatc cagccgaaca acggcgagca gctgtaccgc gtgaggggca   3000
cgctggacag cctggaccag ctcccactgg agggcgagtc cagcctcacc gagtactcgc   3060
acaggctgtg ccacgtcagg ttcgcccaga gcctcaggaa cgcggagccc ctggactacg   3120
ccagggtgcc catgttcagc tggacccaca ggtcggctac ccccaccaac accatcgacc   3180
cagacgtgat cacgcagatc ccgctcgtca aggcccacac cctgcagtcg ggcaccaccg   3240
tggtcaaggg ccccggcttc acgggcggcg acatcctgag gaggacctcc ggcggcccat   3300
tcgccttcag caacgtcaac ctcgactgga acctgtccca gcgctacagg gcgcgcatca   3360
ggtacgccag caccacgaac ctgcgcatgt atgtgaccat cgcgggcgag aggatcttcg   3420
ccggccagtt caacaagacg atgaacaccg gcgacccgct caccttccag tccttcagct   3480
acgcgacgat cgacaccgcc ttcacgttcc ccacgaaggc ctccagcctg accgtgggcg   3540
ccgacacctt ctccagcggc aacgaggtct acgtggaccg cttcgagctg atcccggtga   3600
cggcgacctt cgaggccgag tacgacctgg agaaggccca gaaggcggtc aacgccctct   3660
tcacctccag caaccagatc ggcctgaaga cggacgtgac cgactaccac atcgacaagg   3720
tgtccaacct cgtcgagtgc ctgagcgacg agttctgcct cgacgagaag agggagctgt   3780
ccgagaaggt caagcacgcc aagcgcctct gcgacgagag gaacctcctg caggacccga   3840
acttcagggg aatcaaccgc cagccggaca ggggctggag gggcagcacc gacatcacca   3900
tccagggcgg cgacgacgtg ttcaaggaga actacgtcac gctcccgggc accttcgacg   3960
agtgctaccc cacgtacctg taccagaaga tcgacgagtc caagctcaag gcctacaccc   4020
gctacgagct gaggggatac atcgaggaca gccaggacct cgagatctac ctgatccgct   4080
acaacgcgaa gcacgagacg gtgaacgtcc ccggcacggg ctccctgtgg cccctctcgg   4140
ctcagtcgcc gatcggcaag tgcggcgagc ccaacaggtg cgccacccac ctcgagtgga   4200
acccggacct ggactgctcc tgccgggacg gcgagaagtg cgctcaccac tcccaccact   4260
tcagcctgga catcgacgtg ggctgcacgg acctcaacga ggacctgggc gtgtgggtca   4320
tcttcaaaat caagacgcag gacggccacg ctaggctggg caacctcgag ttcctggagg   4380
agaagccgct ggtgggcgag gctctggcca gggtcaagag ggcggagaag aagtggcgcg   4440
acaagaggga gaagctggag ctggagacga acatcgtcta caaggaggcc aagaagtccg   4500
tggacgcgct cttcgtcaac agccagtacg acaggctgca ggcggacacc aacatcgcca   4560
tcatccacgc cgcggacaag cgcgtgcact ccatcaggga ggcctacctc cccgagctga   4620
gcgtgatccc gggcgtcaac gctgccatct tcgaggagct ggagggccgc atcttcaccg   4680
cctactccct gtacgacgcg aggaacgtca tcaagaacgg cgacttcaac aacggcctca   4740
```

-continued gctgctggaa cgtgaagggc cacgtggacg tcgaggagca gaacaaccac cgctcggtgc 4800
tggtggtccc cgagtgggag gctgaggtca gccaggaggt gcgcgtctgc ccgggcaggg 4860
gatacatcct ccgcgtgacc gcgtacaagg agggctacgg cgagggctgc gtcacgatcc 4920
acgagatcga ggacaacacc gacgagctga agttctccaa ctgcgtggag gaggagatct 4980
acccgaacaa cacggtcacc tgcaacgact acacggccac ccaggaggag tacgagggca 5040
cgtacacgtc gaggaacagg ggctacgacg gcgcttacga gtccaacagc tcggtgccgg 5100
ccgactacgc tagcgcgtac gaggagaagg cctacacgga cggccgcagg gacaacacct 5160
gcgagtcgaa caggggctac ggcgactaca cgccgctccc ggccggctac gtgaccaagg 5220
agctggagta cttcccggag acggacaagg tctggatcga gatcggcgag acggagggca 5280
ccttcatcgt ggactcagtc gagctgctgc tcatggagga gtaggagctc gccaacagtc 5340
gttgaagctg ctgctgtatc tgggttatct agtgtctctg cctttgccca aggatagtgc 5400
tgtctttcaa agtatttgta tcgtttgtgt cgtgagtcgt gactgagctg gtttcaagga 5460
ccagttgtgt tctcgttacc caaaactatc gtgcgaccgc atatggctta atcatgaata 5520
aatgttgttt gaatttaaac tattcgctga atattgttgt tttttgtcat gtcagttaat 5580
gttactaaat tggttgcctt ctaatttttg tttactggtg tttgtcgcac cttatctttt 5640
tactgtatgt ttacttcagg ttctggcagt ctcatttttt gtgactagtt aaaacttaca 5700
gctaaaaaaa tgcagttttt aattttaatt tgaagtttga ttagagctat tgatacccgg 5760
accatcaggt taggttagtt gtgcatagaa tcataaatat taatcatgtt ttctatgaat 5820
taagtcaaac ttgaaagtct ggctgaatat agtttctatg aatcatattg atatacatgt 5880
ttgattattt gttttgctat tagctattta ctttggtgaa tctatatagg cttatgcaga 5940
accttttttt ttgttctata tatccatatc ctagtactca gtagctctat gttttctgga 6000
gactagtggc ttgcttttc gtatgtctaa ttttttgctt gaccattgca aaacaaaaat 6060
tacctagtgt aatctctttt tataataatc ttgtaatgcg tctacctata ggtcaaagta 6120
ggttttgttt ggaaccctta gagctaactg ttagctagtt gataaattat tagctgagtt 6180
aagctagcta atgaactagt tttgatatta gctgaggatg tttgaaacct aataattatt 6240
ttttattagc taactatact aaattttagt agagagattc caaacaggag ttaacatggg 6300
atcagattgg ctatgcgttt gcaatcccat actaattagc taacggaccg ctaattagct 6360
aacgatcgct taattaagct tgcatgcctg cagtgcagcg tgacccggtc gtgcccctct 6420
ctagagataa tgagcattgc atgtctaagt tataaaaaat taccacatat ttttttgtc 6480
acacttgttt gaagtgcagt ttatctatct ttatacatat atttaaactt tactctacga 6540
ataatataat ctatagtact acaataatat cagtgtttta gagaatcata taaatgaaca 6600
gttagacatg gtctaaagga caattgagta ttttgacaac aggactctac agttttatct 6660
ttttagtgtg catgtgttct cctttttttt tgcaaatagc ttcacctata taatacttca 6720
tccattttat tagtacatcc atttagggtt tagggttaat ggtttttata gactaatttt 6780
tttagtacat ctattttatt ctattttagc ctctaaatta agaaaactaa aactctattt 6840
tagtttttt atttaataat ttagatataa aatagaataa aataaagtga ctaaaaatta 6900
aacaaatacc ctttaagaaa ttaaaaaaac taaggaaaca tttttcttgt ttcgagtaga 6960
taatgccagc ctgttaaacg ccgccgacga gtctaacgga caccaaccag cgaaccagca 7020
gcgtcgcgtc gggccaagcg aagcagacgg cacggcatct ctgtcgctgc ctctggaccc 7080
ctctcgagag ttccgctcca ccgttggact tgctccgctg tcggcatcca gaaattgcgt 7140
ggcggagcgg cagacgtgag ccggcacggc aggcggcctc ctcctcctct cacggcaccg 7200
gcagctacgg gggattcctt tcccaccgct ccttcgcttt cccttcctcg cccgccgtaa 7260
taaatagaca ncccccctcca caccctcttt ccccaacctc gtgttgttcg gagcgcacac 7320
acacacaacc agatctcccc caaatccacc cgtcggcacc tccgcttcaa ggtacgccgc 7380
tcgtcctncc cccccccccc ctctctacct tctctagatc ggcgttccgg tccatagtta 7440
gggcccggta gttctacttc tgttcatgtt tgtgttagat ccgtgtttgt gttagatccg 7500
tgctgttagc gttcgtacac ggatgcgacc tgtacgtcag acacgttctg attgctaact 7560
tgccagtgtt tctctttggg gaatcctggg atggctctag ccgttccgca gacgggatcg 7620
atttcatgat ttttttgtt tcgttgcata gggtttggtt tgccctttc ctttatttca 7680
atatatgccg tgcacttgtt tgtcgggtca tcttttcatg cttttttttg tcttggttgt 7740
gatgatgtgg tctggttggg cggtcgttct agatcggagt agaattctgt ttcaaactac 7800
ctggtggatt tattaatttt ggatctgtat gtgtgtgcca tacatattca tagttacgaa 7860
ttgaagatga tggatggaaa tatcgatcta ggataggtat acatgttgat gcgggtttta 7920
ctgatgcata tacagagatg ctttttgttc gcttggttgt gatgatgtgg tgtggttggg 7980
cggtcgttca nttcgttcta gatcggagta gaatactgtt tcaaactacc tggtgtattt 8040
attaattttg gaactgtatg tgtgtgtcat acatcttcat agttacgagt ttaagatgga 8100
tggaaatatc gatctaggat aggtatacat gttgatgtgg gttttactga tgcatataca 8160
tgatggcata tgcagcatct attcatatgc tctaaccttg agtacctatc tattataata 8220
aacaagtatg ttttataatt attttgatct tgatatactt ggatgatggc atatccagca 8280
gctatatctg gatttttta gccctgcctt catacgctat ttatttgctt ggtactgttt 8340
cttttgtcgt tgctcaccct gttgtttggt gttacttctg cagggatctc cgatcatgca 8400
aaaactcatt aactcagtgc aaaactatgc ctggggcagc aaaacggcgt tgactgaact 8460
ttacggtatg gaaaatccgt ccagccagcc gatggccgag ctgtggatgg gcgcacatcc 8520
gaaaagcagt tcacgagtgc agaatgccgc cggagatatc gtttcactgc gtgatgtgat 8580
tgagagtgat aaatcgactc tgctcggaga ggccgttgcc aaacgctttg gcgaactgcc 8640
tttcctgttc aaagtattat gcgcagcaca gccactctcc attcaggttc atccaaacaa 8700
acacaattct gaaatcggtt ttgccaaaga aaatgccgca ggtatcccga tggatgccgc 8760
cgagcgtaac tataaagatc ctaaccacaa gccggagctg gtttttgcgc tgacgccttt 8820
ccttgcgatg aacgcgtttc gtgaattttc cgagattgtc tccctactcc agccggtcgc 8880
aggtgcacat ccggcgattg ctcacttttt acaacagcct gatgccgaac gtttaagcga 8940
actgttcgcc agcctgttga atatgcaggg tgaagaaaaa tcccgcgcgc tggcgatttt 9000
aaaatcggcc ctcgatagcc agcagggtga accgtggcaa acgattcgtt taatttctga 9060
attttacccg gaagacagcg gtctgttctc cccgctattg ctgaatgtgg tgaaattgaa 9120
ccctggcgaa gcgatgttcc tgttcgctga aacaccgcac gcttacctgc aaggcgtggc 9180
gctggaagtg atggcaaact ccgataacgt gctgcgtgcg ggtctgacgc ctaaatacat 9240
tgatattccg gaactggttg ccaatgtgaa attcgaagcc aaaccggcta accagttgtt 9300
gacccagccg gtgaaacaag gtgcagaact ggacttcccg attccagtgg acgattttgc 9360
cttctcgctg cacgacctta gtgataaaga aaccaccatt agccagcaga gtgccgccat 9420
tttgttctgc gtcgaaggcg atgcaacgtt gtggaaaggt tctcagcagt tacagcttaa 9480
accgggtgaa tcagcgttta ttgccgccaa cgaatcaccg gtgactgtca aaggccacgg 9540
ccgtttagcg cgtgtttaca acaagctgta agagcttact gaaaaaatta acatctcttg 9600
ctaagctggg tcatgggtcg tttaagctgc cgatgtgcct gcgtcgtctg gtgccctctc 9660
tccatatgga ggttgtcaaa gtatctgctg ttcgtgtcat gagtcgtgtc agtgttggtt 9720
taataatgga ccggttgtgt tgtgtgtgcg tactacccag aactatgaca aatcatgaat 9780
aagtttgatg tttgaaatta aagcctgtgc tcattatgtt ctgtctttca gttgtctcct 9840
aatatttgcc tccaggtact ggctatctac cgtttcttac ttaggaggtg tttgaatgca 9900
ctaaaactaa tagttagtgg ctaaaattag ttaaaacatc caaacaccat agctaatagt 9960
tgaactatta gctatttttg gaaaattagt taatagtgag gtagttattt gttagctagc 10020
taattcaact aacaattttt agccaactaa caattagttt cagtgcattc aaacaccccc 10080
ttaatgttaa cgtggttcta tctaccgtct cctaatatat ggttgattgt tcggtttgtt 10140
gctatgctat tgggttctga ttgctgctag ttcttgctga atccagaagt tctcgtagta 10200
tagctcagat tcatattatt tatttgagtg ataagtgatc caggttatta ctatgttagc 10260
taggtttttt ttacaaggat aaattatctg tgatcataat tcttatgaaa gctttatgtt 10320
tcctggaggc agtggcatgc aatgcatgac agcaacttga tcacaccagc tgaggtagat 10380
acggtaacaa ggttcttaaa tctgttcacc aaatcattgg agaacacaca tacacattct 10440
tgccagtctt ggttagagaa atttcatgac aaaatgccaa agctgtcttg actcttcact 10500
tttggccatg agtcgtgact tagtttggtt taatggaccg gttctcctag cttgttctac 10560
tcaaaactgt tgttgatgcg aataagttgt gatggttgat ctctggattt tgttttgctc 10620
tcaatagtgg acgagattag atag 10644

<210> SEQ ID NO 25
<211> LENGTH: 10642
<212> TYPE: DNA
<213> ORGANISM: Artificial sequence
<220> FEATURE:
<223> OTHER INFORMATION: Synthetic polynucleotide

<400> SEQUENCE: 25
gaattcatta tgtggtctag gtaggttcta tatataagaa aacttgaaat gttctaaaaa 60
aaaattcaag cccatgcatg attgaagcaa acggtatagc aacggtgtta acctgatcta 120
gtgatctctt gcaatcctta acggccacct accgcaggta gcaaacggcg tccccctcct 180
cgatatctcc gcggcgacct ctggcttttt ccgcggaatt gcgcggtggg gacggattcc 240
acgagaccgc gacgcaaccg cctctcgccg ctgggcccca caccgctcgg tgccgtagcc 300
tcacgggact ctttctccct cctcccccgt tataaattgg cttcatcccc tccttgcctc 360
atccatccaa atcccagtcc ccaatcccat cccttcgtag gagaaattca tcgaagctaa 420
gcgaatcctc gcgatcctct caaggtactg cgagttttcg atccccctct cgacccctcg 480
tatgtttgtg tttgtcgtag cgtttgatta ggtatgcttt ccctgtttgt gttcgtcgta 540
gcgtttgatt aggtatgctt tccctgttcg tgttcatcgt agtgtttgat taggtcgtgt 600
gaggcgatgg cctgctcgcg tccttcgatc tgtagtcgat ttgcgggtcg tggtgtagat 660
ctgcgggctg tgatgaagtt atttggtgtg atctgctcgc ctgattctgc gggttggctc 720
gagtagatat gatggttgga ccggttggtt cgtttaccgc gctagggttg ggctgggatg 780
atgttgcatg cgccgttgcg cgtgatcccg cagcaggact tgcgtttgat tgccagatct 840
cgttacgatt atgtgatttg gtttggactt tttagatctg tagcttctgc ttatgtgcca 900

```
gatgcgccta ctgctcatat gcctgatgat aatcataaat ggctgtggaa ctaactagtt    960
gattgcggag tcatgtatca gctacaggtg tagggactag ctacaggtgt agggacttgc   1020
gtctaattgt ttggtccttt actcatgttg caattatgca atttagttta gattgtttgt   1080
tccactcatc taggctgtaa aagggacact gcttagattg ctgtttaatc tttttagtag   1140
attatattat attggtaact tattacccct attacatgcc atacgtgact tctgctcatg   1200
cctgatgata atcatagatc actgtggaat taattagttg attgttgaat catgtttcat   1260
gtacatacca cggcacaatt gcttagttcc ttaacaaatg caaattttac tgatccatgt   1320
atgatttgcg tggttctcta atgtgaaata ctatagctac ttgttagtaa gaatcaggtt   1380
cgtatgctta atgctgtatg tgccttctgc tcatgcctga tgataatcat atatcactgg   1440
aattaattag ttgatcgttt aatcatatat caagtacata ccatgccaca atttttagtc   1500
acttaaccca tgcagattga actggtccct gcatgttttg ctaaattgtt ctattctgat   1560
tagaccatat atcatgtatt ttttttggt aatggttctc ttattttaaa tgctatatag   1620
ttctggtact tgttagaaag atctgcttca tagtttagtt gcctatccct cgaattagga   1680
tgctgagcag ctgatcctat agctttgttt catgtatcaa ttcttttgtg ttcaacagtc   1740
agtttttgtt agattcattg taacttatgg tcgcttactc ttctggtcct caatgcttgc   1800
agggatccta aaccatggag atcaacaacc agaaccagtg cgtgccgtac aactgcctta   1860
acaaccccga gtccgagatc ctgaacgtgg ccatcttctc cagcgagcag gtcgcggaga   1920
tccacctcaa gatcacgcgc ctgatcctcg agaacttcct gccgggcggc tccttcgctt   1980
tcggcctgtt cgacctcatc tggggcatct tcaacgagga ccagtggagc gcgttcctca   2040
ggcaggtgga ggagctgatc aaccagcgca tcacggagtt cgccaggggc caggctatcc   2100
agcggctggt gggcttcggc aggtcctacg acgagtacat cctggccctc aaggagtggg   2160
agaacgaccc cgacaacccg gccagcaagg agcgcgtgag gacccgcttc aggaccaccg   2220
acgacgctct cctgacgggc gtccccctca tggctatccc gggcttcgag ctggccaccc   2280
tctcggtgta cgctcagtcg gccaacctgc acctcgccct cctgcgggac gctgtgttct   2340
tcggcgagag gtggggcctg acccagacga acatcaacga cctctactcc aggctgaaga   2400
acagcatccg cgactacacg aaccactgcg tgcgcttcta caacatcggc ctgggcaacc   2460
tcaacgtcat caggccggag tactaccgct tccagaggga gctgaccatc agcgtgctgg   2520
acctcgtcgc cctgttcccc aactacgaca tccgcacgta cccgatccca accaagtccc   2580
agctcacgag ggagatctac accgacccga tcatctcgcc gggcgcccag gccggctaca   2640
ccctgcagga cgtcctgagg gagccccacc tgatggactt cctgaacagg ctcatcatct   2700
acaccggcga gtacaggggc atcaggcact gggcgggcca cgaggtggag tccagcagga   2760
cgggcatgat gaccaacatc cgcttcccgc tctacggcac cgcggccacg gccgagccaa   2820
cccgcttcat cacgccgtcc accttccccg gcctgaacct cttctacagg accctgtcgg   2880
ctcccatctt ccgcgacgag ccgggcgcga acatcatcat ccgctacagg acctccctcg   2940
tggagggcgt cggcttcatc cagccgaaca acggcgagca gctgtaccgc gtgaggggca   3000
cgctggacag cctggaccag ctcccactgg agggcgagtc cagcctcacc gagtactcgc   3060
acaggctgtg ccacgtcagg ttcgcccaga gcctcaggaa cgcggagccc ctggactacg   3120
ccagggtgcc catgttcagc tggacccaca ggtcggctac ccccaccaac accatcgacc   3180
cagacgtgat cacgcagatc ccgctcgtca aggcccacac cctgcagtcg ggcaccaccg   3240
```

tggtcaaggg ccccggcttc acgggcggcg acatcctgag gaggacctcc ggcggcccat 3300
tcgccttcag caacgtcaac ctcgactgga acctgtccca gcgctacagg gcgcgcatca 3360
ggtacgccag caccacgaac ctgcgcatgt atgtgaccat cgcgggcgag aggatcttcg 3420
ccggccagtt caacaagacg atgaacaccg gcgacccgct caccttccag tccttcagct 3480
acgcgacgat cgacaccgcc ttcacgttcc ccacgaaggc ctccagcctg accgtgggcg 3540
ccgacacctt ctccagcggc aacgaggtct acgtggaccg cttcgagctg atcccggtga 3600
cggcgacctt cgaggccgag tacgacctgg agaaggccca gaaggcggtc aacgccctct 3660
tcacctccag caaccagatc ggcctgaaga cggacgtgac cgactaccac atcgacaagg 3720
tgtccaacct cgtcgagtgc ctgagcgacg agttctgcct cgacgagaag agggagctgt 3780
ccgagaaggt caagcacgcc aagcgcctct gcgacgagag gaacctcctg caggacccga 3840
acttcagggg aatcaaccgc cagccggaca ggggctggag gggcagcacc gacatcacca 3900
tccagggcgg cgacgacgtg ttcaaggaga actacgtcac gctcccgggc accttcgacg 3960
agtgctaccc cacgtacctg taccagaaga tcgacgagtc caagctcaag gcctacaccc 4020
gctacgagct gaggggatac atcgaggaca gccaggacct cgagatctac ctgatccgct 4080
acaacgcgaa gcacgagacg gtgaacgtcc ccggcacggg ctccctgtgg cccctctcgg 4140
ctcagtcgcc gatcggcaag tgcggcgagc ccaacaggtg cgccacccac ctcgagtgga 4200
acccggacct ggactgctcc tgccgggacg gcgagaagtg cgctcaccac tcccaccact 4260
tcagcctgga catcgacgtg ggctgcacgg acctcaacga ggacctgggc gtgtgggtca 4320
tcttcaaaat caagacgcag gacggccacg ctaggctggg caacctcgag ttcctggagg 4380
agaagccgct ggtgggcgag gctctggcca gggtcaagag ggcggagaag aagtggcgcg 4440
acaagaggga gaagctggag ctggagacga acatcgtcta caaggaggcc aagaagtccg 4500
tggacgcgct cttcgtcaac agccagtacg acaggctgca ggcggacacc aacatcgcca 4560
tcatccacgc cgcggacaag cgcgtgcact ccatcaggga ggcctacctc cccgagctga 4620
gcgtgatccc gggcgtcaac gctgccatct tcgaggagct ggagggccgc atcttcaccg 4680
cctactccct gtacgacgcg aggaacgtca tcaagaacgg cgacttcaac aacggcctca 4740
gctgctggaa cgtgaagggc cacgtggacg tcgaggagca gaacaaccac cgctcggtgc 4800
tggtggtccc cgagtgggag gctgaggtca gccaggaggt gcgcgtctgc ccgggcaggg 4860
gatacatcct ccgcgtgacc gcgtacaagg agggctacgg cgagggctgc gtcacgatcc 4920
acgagatcga ggacaacacc gacgagctga agttctccaa ctgcgtggag gaggagatct 4980
acccgaacaa cacggtcacc tgcaacgact acacggccac ccaggaggag tacgagggca 5040
cgtacacgtc gaggaacagg ggctacgacg gcgcttacga gtccaacagc tcggtgccgg 5100
ccgactacgc tagcgcgtac gaggagaagg cctacacgga cggccgcagg gacaacacct 5160
gcgagtcgaa caggggctac ggcgactaca cgccgctccc ggccggctac gtgaccaagg 5220
agctggagta cttcccggag acggacaagg tctggatcga gatcggcgag acggagggca 5280
ccttcatcgt ggactcagtc gagctgctgc tcatggagga gtaggagctc gccaacagtc 5340
gttgaagctg ctgctgtatc tgggttatct agtgtctctg cctttgccca aggatagtgc 5400
tgtctttcaa agtatttgta tcgtttgtgt cgtgagtcgt gactgagctg gtttcaagga 5460
ccagttgtgt tctcgttacc caaaactatc gtgcgaccgc atatggctta atcatgaata 5520
aatgttgttt gaatttaaac tattcgctga atattgttgt tttttgtcat gtcagttaat 5580
gttactaaat tggttgcctt ctaatttttg tttactggtg tttgtcgcac cttatctttt 5640

```
tactgtatgt ttacttcagg ttctggcagt ctcatttttt gtgactagtt aaaacttaca   5700
gctaaaaaaa tgcagttttt aattttaatt tgaagtttga ttagagctat tgatacccgg   5760
accatcaggt taggttagtt gtgcatagaa tcataaatat taatcatgtt ttctatgaat   5820
taagtcaaac ttgaaagtct ggctgaatat agtttctatg aatcatattg atatacatgt   5880
ttgattattt gttttgctat tagctattta ctttggtgaa tctatatagg cttatgcaga   5940
accttttttt ttgttctata tatccatatc ctagtactca gtagctctat gttttctgga   6000
gactagtggc ttgctttttt cgtatgtcta attttttgct tgaccattgc aaaacaaaaa   6060
ttacctagtg taatctcttt ttataataat cttgtaatgc gtctacctat aggtcaaagt   6120
aggttttgtt tggaaccctt agagctaact gttagctagt tgataaatta ttagctgagt   6180
taagctagct aatgaactag ttttgatatt agctgaggat gtttgaaacc taataattat   6240
tttttattag ctaactatac taaattttag tagagagatt ccaaacagga gttaacatgg   6300
gatcagattg gctatgcgtt tgcaatccca tactaattag ctaacggacc gctaattagc   6360
taacgatcgc ttaattaagc ttgcatgcct gcagtgcagc gtgacccggt cgtgcccctc   6420
tctagagata atgagcattg catgtctaag ttataaaaaa ttaccacata tttttttgtc   6480
acacttgttt gaagtgcagt ttatctatct ttatacatat atttaaactt tactctacga   6540
ataatataat ctatagtact acaataatat cagtgtttta gagaatcata taaatgaaca   6600
gttagacatg gtctaaagga caattgagta ttttgacaac aggactctac agttttatct   6660
ttttagtgtg catgtgttct cctttttttt gcaaatagct tcacctatat aatacttcat   6720
ccattttatt agtacatcca tttagggttt agggttaatg gtttttatag actaattttt   6780
ttagtacatc tattttattc tattttagcc tctaaattaa gaaaactaaa actctatttt   6840
agttttttta tttaataatt tagatataaa atagaataaa ataaagtgac taaaaattaa   6900
acaaataccc tttaagaaat taaaaaaact aaggaaacat ttttcttgtt tcgagtagat   6960
aatgccagcc tgttaaacgc cgccgacgag tctaacggac accaaccagc gaaccagcag   7020
cgtcgcgtcg ggccaagcga agcagacggc acggcatctc tgtcgctgcc tctggacccc   7080
tctcgagagt tccgctccac cgttggactt gctccgctgt cggcatccag aaattgcgtg   7140
gcggagcggc agacgtgagc cggcacggca ggcggcctcc tcctcctctc acggcaccgg   7200
cagctacggg ggattccttt cccaccgctc cttcgctttc ccttcctcgc ccgccgtaat   7260
aaatagacac cccctccaca ccctctttcc ccaacctcgt gttgttcgga gcgcacacac   7320
acacaaccag atctccccca aatccacccg tcggcacctc cgcttcaagg tacgccgctc   7380
gtcctccccc cccccccct ctctaccttc tctagatcgg cgttccggtc catagttagg   7440
gcccggtagt tctacttctg ttcatgtttg tgttagatcc gtgtttgtgt tagatccgtg   7500
ctgttagcgt tcgtacacgg atgcgacctg tacgtcagac acgttctgat tgctaacttg   7560
ccagtgtttc tctttgggga atcctgggat ggctctagcc gttccgcaga cgggatcgat   7620
ttcatgattt tttttgtttc gttgcatagg gtttggtttg cccttttcct ttatttcaat   7680
atatgccgtg cacttgtttg tcgggtcatc ttttcatgct tttttttgtc ttggttgtga   7740
tgatgtggtc tggttgggcg gtcgttctag atcggagtag aattctgttt caaactacct   7800
ggtggattta ttaattttgg atctgtatgt gtgtgccata catattcata gttacgaatt   7860
gaagatgatg gatggaaata tcgatctagg ataggtatac atgttgatgc gggttttact   7920
gatgcatata cagagatgct tttgttcgc ttggttgtga tgatgtggtg tggttgggcg    7980
```

gtcgttcatt cgttctagat cggagtagaa tactgtttca aactacctgg tgtatttatt 8040
aattttggaa ctgtatgtgt gtgtcataca tcttcatagt tacgagttta agatggatgg 8100
aaatatcgat ctaggatagg tatacatgtt gatgtgggtt ttactgatgc atatacatga 8160
tggcatatgc agcatctatt catatgctct aaccttgagt acctatctat tataataaac 8220
aagtatgttt tataattatt ttgatcttga tatacttgga tgatggcata tccagcagct 8280
atatctggat ttttttagcc ctgccttcat acgctattta tttgcttggt actgtttctt 8340
ttgtcgttgc tcaccctgtt gtttggtgtt acttctgcag ggatctccga tcatgcaaaa 8400
aactcattaa ctcagtgcaa aactatgcct ggggcagcaa aacggcgttg actgaacttt 8460
acggtatgga aaatccgtcc agccagccga tggccgagct gtggatgggc gcacatccga 8520
aaagcagttc acgagtgcag aatgccgccg gagatatcgt ttcactgcgt gatgtgattg 8580
agagtgataa atcgactctg ctcggagagg ccgttgccaa acgctttggc gaactgcctt 8640
tcctgttcaa agtattatgc gcagcacagc cactctccat tcaggttcat ccaaacaaac 8700
acaattctga aatcggtttt gccaaagaaa atgccgcagg tatcccgatg gatgccgccg 8760
agcgtaacta taaagatcct aaccacaagc cggagctggt tttgcgctg acgcctttcc 8820
ttgcgatgaa cgcgtttcgt gaattttccg agattgtctc cctactccag ccggtcgcag 8880
gtgcacatcc ggcgattgct cactttttac aacagcctga tgccgaacgt ttaagcgaac 8940
tgttcgccag cctgttgaat atgcagggtg aagaaaaatc ccgcgcgctg gcgattttaa 9000
aatcggccct cgatagccag cagggtgaac cgtggcaaac gattcgttta atttctgaat 9060
tttacccgga agacagcggt ctgttctccc cgctattgct gaatgtggtg aaattgaacc 9120
ctggcgaagc gatgttcctg ttcgctgaaa caccgcacgc ttacctgcaa ggcgtggcgc 9180
tggaagtgat ggcaaactcc gataacgtgc tgcgtgcggg tctgacgcct aaatacattg 9240
atattccgga actggttgcc aatgtgaaat tcgaagccaa accggctaac cagttgttga 9300
cccagccggt gaaacaaggt gcagaactgg acttcccgat tccagtggac gattttgcct 9360
tctcgctgca cgaccttagt gataaagaaa ccaccattag ccagcagagt gccgccattt 9420
tgttctgcgt cgaaggcgat gcaacgttgt ggaaaggttc tcagcagtta cagcttaaac 9480
cgggtgaatc agcgtttatt gccgccaacg aatcaccggt gactgtcaaa ggccacggcc 9540
gtttagcgcg tgtttacaac aagctgtaag agcttactga aaaaattaac atctcttgct 9600
aagctgggtc atgggtcgtt taagctgccg atgtgcctgc gtcgtctggt gccctctctc 9660
catatggagg ttgtcaaagt atctgctgtt cgtgtcatga gtcgtgtcag tgttggttta 9720
ataatggacc ggttgtgttg tgtgtgcgta ctacccagaa ctatgacaaa tcatgaataa 9780
gtttgatgtt tgaaattaaa gcctgtgctc attatgttct gtctttcagt tgtctcctaa 9840
tatttgcctc caggtactgg ctatctaccg tttcttactt aggaggtgtt tgaatgcact 9900
aaaactaata gttagtggct aaaattagtt aaaacatcca aacaccatag ctaatagttg 9960
aactattagc tatttttgga aaattagtta atagtgaggt agttatttgt tagctagcta 10020
attcaactaa caatttttag ccaactaaca attagtttca gtgcattcaa acaccccctt 10080
aatgttaacg tggttctatc taccgtctcc taatatatgg ttgattgttc ggtttgttgc 10140
tatgctattg ggttctgatt gctgctagtt cttgctgaat ccagaagttc tcgtagtata 10200
gctcagattc atattattta tttgagtgat aagtgatcca ggttattact atgttagcta 10260
ggtttttttt acaaggataa attatctgtg atcataattc ttatgaaagc tttatgtttc 10320
ctggaggcag tggcatgcaa tgcatgacag caacttgatc acaccagctg aggtagatac 10380

```
ggtaacaagg ttcttaaatc tgttcaccaa atcattggag aacacacata cacattcttg  10440

ccagtcttgg ttagagaaat ttcatgacaa aatgccaaag ctgtcttgac tcttcacttt  10500

tggccatgag tcgtgactta gtttggttta atggaccggt tctcctagct tgttctactc  10560

aaaactgttg ttgatgcgaa taagttgtga tggttgatct ctggattttg ttttgctctc  10620

aatagtggac gagattagat ag                                           10642
```

```
<210> SEQ ID NO 26
<211> LENGTH: 10644
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<222> LOCATION: (6015)..(6015)
<223> OTHER INFORMATION: n is t or absent
<220> FEATURE:
<221> NAME/KEY: misc_feature
<222> LOCATION: (6471)..(6471)
<223> OTHER INFORMATION: n is t or absent
<220> FEATURE:
<221> NAME/KEY: misc_feature
<222> LOCATION: (6684)..(6684)
<223> OTHER INFORMATION: n is t or absent
<220> FEATURE:
<221> NAME/KEY: misc_feature
<222> LOCATION: (7388)..(7388)
<223> OTHER INFORMATION: n is c or absent
<220> FEATURE:
<221> NAME/KEY: misc_feature
<222> LOCATION: (8399)..(8399)
<223> OTHER INFORMATION: n is a or absent

<400> SEQUENCE: 26

gaattcatta tgtggtctag gtaggttcta tatataagaa aacttgaaat gttctaaaaa     60

aaaattcaag cccatgcatg attgaagcaa acggtatagc aacggtgtta acctgatcta    120

gtgatctctt gcaatcctta acggccacct accgcaggta gcaaacggcg tccccctcct    180

cgatatctcc gcggcgacct ctggcttttt ccgcggaatt gcgcggtggg gacggattcc    240

acgagaccgc gacgcaaccg cctctcgccg ctgggcccca caccgctcgg tgccgtagcc    300

tcacgggact ctttctccct cctcccccgt tataaattgg cttcatcccc tccttgcctc    360

atccatccaa atcccagtcc ccaatcccat cccttcgtag gagaaattca tcgaagctaa    420

gcgaatcctc gcgatcctct caaggtactg cgagttttcg atccccctct cgacccctcg    480

tatgtttgtg tttgtcgtag cgtttgatta ggtatgcttt ccctgtttgt gttcgtcgta    540

gcgtttgatt aggtatgctt tccctgttcg tgttcatcgt agtgtttgat taggtcgtgt    600

gaggcgatgg cctgctcgcg tccttcgatc tgtagtcgat ttgcgggtcg tggtgtagat    660

ctgcgggctg tgatgaagtt atttggtgtg atctgctcgc ctgattctgc gggttggctc    720

gagtagatat gatggttgga ccggttggtt cgtttaccgc gctagggttg ggctgggatg    780

atgttgcatg cgccgttgcg cgtgatcccg cagcaggact tgcgtttgat tgccagatct    840

cgttacgatt atgtgatttg gtttggactt tttagatctg tagcttctgc ttatgtgcca    900

gatgcgccta ctgctcatat gcctgatgat aatcataaat ggctgtggaa ctaactagtt    960

gattgcggag tcatgtatca gctacaggtg tagggactag ctacaggtgt agggacttgc   1020

gtctaattgt ttggtccttt actcatgttg caattatgca atttagttta gattgtttgt   1080

tccactcatc taggctgtaa aagggacact gcttagattg ctgtttaatc tttttagtag   1140
```

attatattat attggtaact tattacccct attacatgcc atacgtgact tctgctcatg 1200
cctgatgata atcatagatc actgtggaat taattagttg attgttgaat catgtttcat 1260
gtacatacca cggcacaatt gcttagttcc ttaacaaatg caaattttac tgatccatgt 1320
atgatttgcg tggttctcta atgtgaaata ctatagctac ttgttagtaa gaatcaggtt 1380
cgtatgctta atgctgtatg tgccttctgc tcatgcctga tgataatcat atatcactgg 1440
aattaattag ttgatcgttt aatcatatat caagtacata ccatgccaca atttttagtc 1500
acttaaccca tgcagattga actggtccct gcatgttttg ctaaattgtt ctattctgat 1560
tagaccatat atcatgtatt ttttttggt aatggttctc ttattttaaa tgctatatag 1620
ttctggtact tgttagaaag atctgcttca tagtttagtt gcctatccct cgaattagga 1680
tgctgagcag ctgatcctat agctttgttt catgtatcaa ttcttttgtg ttcaacagtc 1740
agtttttgtt agattcattg taacttatgg tcgcttactc ttctggtcct caatgcttgc 1800
agggatccta aaccatggag atcaacaacc agaaccagtg cgtgccgtac aactgcctta 1860
acaaccccga gtccgagatc ctgaacgtgg ccatcttctc cagcgagcag gtcgcggaga 1920
tccacctcaa gatcacgcgc ctgatcctcg agaacttcct gccgggcggc tccttcgctt 1980
tcggcctgtt cgacctcatc tggggcatct tcaacgagga ccagtggagc gcgttcctca 2040
ggcaggtgga ggagctgatc aaccagcgca tcacggagtt cgccaggggc caggctatcc 2100
agcggctggt gggcttcggc aggtcctacg acgagtacat cctggccctc aaggagtggg 2160
agaacgaccc cgacaacccg gccagcaagg agcgcgtgag gacccgcttc aggaccaccg 2220
acgacgctct cctgacgggc gtccccctca tggctatccc gggcttcgag ctggccaccc 2280
tctcggtgta cgctcagtcg gccaacctgc acctcgccct cctgcgggac gctgtgttct 2340
tcggcgagag gtggggcctg acccagacga acatcaacga cctctactcc aggctgaaga 2400
acagcatccg cgactacacg aaccactgcg tgcgcttcta caacatcggc ctgggcaacc 2460
tcaacgtcat caggccggag tactaccgct tccagaggga gctgaccatc agcgtgctgg 2520
acctcgtcgc cctgttcccc aactacgaca tccgcacgta cccgatccca accaagtccc 2580
agctcacgag ggagatctac accgacccga tcatctcgcc gggcgcccag gccggctaca 2640
ccctgcagga cgtcctgagg gagccccacc tgatggactt cctgaacagg ctcatcatct 2700
acaccggcga gtacaggggc atcaggcact gggcgggcca cgaggtggag tccagcagga 2760
cgggcatgat gaccaacatc cgcttcccgc tctacggcac cgcggccacg gccgagccaa 2820
cccgcttcat cacgccgtcc accttccccg gcctgaacct cttctacagg accctgtcgg 2880
ctcccatctt ccgcgacgag ccgggcgcga acatcatcat ccgctacagg acctccctcg 2940
tggagggcgt cggcttcatc cagccgaaca acggcgagca gctgtaccgc gtgaggggca 3000
cgctggacag cctggaccag ctcccactgg agggcgagtc cagcctcacc gagtactcgc 3060
acaggctgtg ccacgtcagg ttcgcccaga gcctcaggaa cgcggagccc ctggactacg 3120
ccagggtgcc catgttcagc tggacccaca ggtcggctac ccccaccaac accatcgacc 3180
cagacgtgat cacgcagatc ccgctcgtca aggcccacac cctgcagtcg ggcaccaccg 3240
tggtcaaggg ccccggcttc acgggcggcg acatcctgag gaggacctcc ggcggcccat 3300
tcgccttcag caacgtcaac ctcgactgga acctgtccca gcgctacagg gcgcgcatca 3360
ggtacgccag caccacgaac ctgcgcatgt atgtgaccat cgcgggcgag aggatcttcg 3420
ccggccagtt caacaagacg atgaacaccg gcgacccgct caccttccag tccttcagct 3480
acgcgacgat cgacaccgcc ttcacgttcc ccacgaaggc ctccagcctg accgtgggcg 3540
ccgacacctt ctccagcggc aacgaggtct acgtggaccg cttcgagctg atcccggtga 3600
cggcgacctt cgaggccgag tacgacctgg agaaggccca gaaggcggtc aacgccctct 3660
tcacctccag caaccagatc ggcctgaaga cggacgtgac cgactaccac atcgacaagg 3720
tgtccaacct cgtcgagtgc ctgagcgacg agttctgcct cgacgagaag agggagctgt 3780
ccgagaaggt caagcacgcc aagcgcctct gcgacgagag gaacctcctg caggacccga 3840
acttcagggg aatcaaccgc cagccggaca ggggctggag gggcagcacc gacatcacca 3900
tccagggcgg cgacgacgtg ttcaaggaga actacgtcac gctcccgggc accttcgacg 3960
agtgctaccc cacgtacctg taccagaaga tcgacgagtc caagctcaag gcctacaccc 4020
gctacgagct gaggggatac atcgaggaca gccaggacct cgagatctac ctgatccgct 4080
acaacgcgaa gcacgagacg gtgaacgtcc ccggcacggg ctccctgtgg cccctctcgg 4140
ctcagtcgcc gatcggcaag tgcggcgagc ccaacaggtg cgccacccac ctcgagtgga 4200
acccggacct ggactgctcc tgccgggacg gcgagaagtg cgctcaccac tcccaccact 4260
tcagcctgga catcgacgtg ggctgcacgg acctcaacga ggacctgggc gtgtgggtca 4320
tcttcaaaat caagacgcag gacggccacg ctaggctggg caacctcgag ttcctggagg 4380
agaagccgct ggtgggcgag gctctggcca gggtcaagag ggcggagaag aagtggcgcg 4440
acaagaggga gaagctggag ctggagacga acatcgtcta caaggaggcc aagaagtccg 4500
tggacgcgct cttcgtcaac agccagtacg acaggctgca ggcggacacc aacatcgcca 4560
tcatccacgc cgcggacaag cgcgtgcact ccatcaggga ggcctacctc cccgagctga 4620
gcgtgatccc gggcgtcaac gctgccatct tcgaggagct ggagggccgc atcttcaccg 4680
cctactccct gtacgacgcg aggaacgtca tcaagaacgg cgacttcaac aacggcctca 4740
gctgctggaa cgtgaagggc cacgtggacg tcgaggagca gaacaaccac cgctcggtgc 4800
tggtggtccc cgagtgggag gctgaggtca gccaggaggt gcgcgtctgc ccgggcaggg 4860
gatacatcct ccgcgtgacc gcgtacaagg agggctacgg cgagggctgc gtcacgatcc 4920
acgagatcga ggacaacacc gacgagctga agttctccaa ctgcgtggag gaggagatct 4980
acccgaacaa cacggtcacc tgcaacgact acacggccac ccaggaggag tacgagggca 5040
cgtacacgtc gaggaacagg ggctacgacg gcgcttacga gtccaacagc tcggtgccgg 5100
ccgactacgc tagcgcgtac gaggagaagg cctacacgga cggccgcagg gacaacacct 5160
gcgagtcgaa caggggctac ggcgactaca cgccgctccc ggccggctac gtgaccaagg 5220
agctggagta cttcccggag acggacaagg tctggatcga gatcggcgag acggagggca 5280
ccttcatcgt ggactcagtc gagctgctgc tcatggagga gtaggagctc gccaacagtc 5340
gttgaagctg ctgctgtatc tgggttatct agtgtctctg cctttgccca aggatagtgc 5400
tgtctttcaa agtatttgta tcgtttgtgt cgtgagtcgt gactgagctg gtttcaagga 5460
ccagttgtgt tctcgttacc caaaactatc gtgcgaccgc atatggctta atcatgaata 5520
aatgttgttt gaatttaaac tattcgctga atattgttgt tttttgtcat gtcagttaat 5580
gttactaaat tggttgcctt ctaatttttg tttactggtg tttgtcgcac cttatctttt 5640
tactgtatgt ttacttcagg ttctggcagt ctcatttttt gtgactagtt aaaacttaca 5700
gctaaaaaaa tgcagttttt aattttaatt tgaagtttga ttagagctat tgatacccgg 5760
accatcaggt taggttagtt gtgcatagaa tcataaatat taatcatgtt ttctatgaat 5820
taagtcaaac ttgaaagtct ggctgaatat agtttctatg aatcatattg atatacatgt 5880

```
ttgattattt gttttgctat tagctattta ctttggtgaa tctatatagg cttatgcaga   5940
accttttttt ttgttctata tatccatatc ctagtactca gtagctctat gttttctgga   6000
gactagtggc ttgcntttt cgtatgtcta attttttgct tgaccattgc aaaacaaaaa   6060
ttacctagtg taatctcttt ttataataat cttgtaatgc gtctacctat aggtcaaagt   6120
aggttttgtt tggaaccctt agagctaact gttagctagt tgataaatta ttagctgagt   6180
taagctagct aatgaactag ttttgatatt agctgaggat gtttgaaacc taataattat   6240
tttttattag ctaactatac taaattttag tagagagatt ccaaacagga gttaacatgg   6300
gatcagattg gctatgcgtt tgcaatccca tactaattag ctaacggacc gctaattagc   6360
taacgatcgc ttaattaagc ttgcatgcct gcagtgcagc gtgacccggt cgtgcccctc   6420
tctagagata atgagcattg catgtctaag ttataaaaaa ttaccacata nttttttgt   6480
cacacttgtt tgaagtgcag tttatctatc tttatacata tatttaaact ttactctacg   6540
aataatataa tctatagtac tacaataata tcagtgtttt agagaatcat ataaatgaac   6600
agttagacat ggtctaaagg acaattgagt attttgacaa caggactcta cagttttatc   6660
tttttagtgt gcatgtgttc tccntttttt ttgcaaatag cttcacctat ataatacttc   6720
atccatttta ttagtacatc catttagggt ttagggttaa tggtttttat agactaattt   6780
ttttagtaca tctattttat tctattttag cctctaaatt aagaaaacta aaactctatt   6840
ttagtttttt tatttaataa tttagatata aaatagaata aaataaagtg actaaaaatt   6900
aaacaaatac cctttaagaa attaaaaaaa ctaaggaaac atttttcttg tttcgagtag   6960
ataatgccag cctgttaaac gccgccgacg agtctaacgg acaccaacca gcgaaccagc   7020
agcgtcgcgt cgggccaagc gaagcagacg gcacggcatc tctgtcgctg cctctggacc   7080
cctctcgaga gttccgctcc accgttggac ttgctccgct gtcggcatcc agaaattgcg   7140
tggcggagcg gcagacgtga gccggcacgg caggcggcct cctcctcctc tcacggcacc   7200
ggcagctacg gggattcct ttcccaccgc tccttcgctt tcccttcctc gcccgccgta   7260
ataaatagac accccctcca caccctcttt ccccaacctc gtgttgttcg gagcgcacac   7320
acacacaacc agatctcccc caaatccacc cgtcggcacc tccgcttcaa ggtacgccgc   7380
tcgtcctncc cccccccccc ctctctacct tctctagatc ggcgttccgg tccatagtta   7440
gggcccggta gttctacttc tgttcatgtt tgtgttagat ccgtgtttgt gttagatccg   7500
tgctgttagc gttcgtacac ggatgcgacc tgtacgtcag acacgttctg attgctaact   7560
tgccagtgtt tctctttggg gaatcctggg atggctctag ccgttccgca gacgggatcg   7620
atttcatgat ttttttgtt tcgttgcata gggtttggtt tgcccttttc ctttatttca   7680
atatatgccg tgcacttgtt tgtcgggtca tcttttcatg cttttttttg tcttggttgt   7740
gatgatgtgg tctggttggg cggtcgttct agatcggagt agaattctgt ttcaaactac   7800
ctggtggatt tattaatttt ggatctgtat gtgtgtgcca tacatattca tagttacgaa   7860
ttgaagatga tggatggaaa tatcgatcta ggataggtat acatgttgat gcgggtttta   7920
ctgatgcata tacagagatg ctttttgttc gcttggttgt gatgatgtgg tgtggttggg   7980
cggtcgttca ttcgttctag atcggagtag aatactgttt caaactacct ggtgtattta   8040
ttaattttgg aactgtatgt gtgtgtcata catcttcata gttacgagtt taagatggat   8100
ggaaatatcg atctaggata ggtatacatg ttgatgtggg ttttactgat gcatatacat   8160
gatggcatat gcagcatcta ttcatatgct ctaaccttga gtacctatct attataataa   8220
acaagtatgt tttataatta ttttgatctt gatatacttg gatgatggca tatccagcag   8280
```

ctatatctgg atttttttag ccctgccttc atacgctatt tatttgcttg gtactgtttc 8340
ttttgtcgtt gctcaccctg ttgtttggtg ttacttctgc agggatctcc gatcatgcna 8400
aaaactcatt aactcagtgc aaaactatgc ctggggcagc aaaacggcgt tgactgaact 8460
ttacggtatg gaaaatccgt ccagccagcc gatggccgag ctgtggatgg gcgcacatcc 8520
gaaaagcagt tcacgagtgc agaatgccgc cggagatatc gtttcactgc gtgatgtgat 8580
tgagagtgat aaatcgactc tgctcggaga ggccgttgcc aaacgctttg gcgaactgcc 8640
tttcctgttc aaagtattat gcgcagcaca gccactctcc attcaggttc atccaaacaa 8700
acacaattct gaaatcggtt ttgccaaaga aaatgccgca ggtatcccga tggatgccgc 8760
cgagcgtaac tataaagatc ctaaccacaa gccggagctg gtttttgcgc tgacgccttt 8820
ccttgcgatg aacgcgtttc gtgaattttc cgagattgtc tccctactcc agccggtcgc 8880
aggtgcacat ccggcgattg ctcacttttt acaacagcct gatgccgaac gtttaagcga 8940
actgttcgcc agcctgttga atatgcaggg tgaagaaaaa tcccgcgcgc tggcgatttt 9000
aaaatcggcc ctcgatagcc agcagggtga accgtggcaa acgattcgtt taatttctga 9060
attttacccg gaagacagcg gtctgttctc cccgctattg ctgaatgtgg tgaaattgaa 9120
ccctggcgaa gcgatgttcc tgttcgctga aacaccgcac gcttacctgc aaggcgtggc 9180
gctggaagtg atggcaaact ccgataacgt gctgcgtgcg ggtctgacgc ctaaatacat 9240
tgatattccg gaactggttg ccaatgtgaa attcgaagcc aaaccggcta accagttgtt 9300
gacccagccg gtgaaacaag gtgcagaact ggacttcccg attccagtgg acgattttgc 9360
cttctcgctg cacgacctta gtgataaaga aaccaccatt agccagcaga gtgccgccat 9420
tttgttctgc gtcgaaggcg atgcaacgtt gtggaaaggt tctcagcagt tacagcttaa 9480
accgggtgaa tcagcgttta ttgccgccaa cgaatcaccg gtgactgtca aaggccacgg 9540
ccgtttagcg cgtgtttaca acaagctgta agagcttact gaaaaaatta acatctcttg 9600
ctaagctggg tcatgggtcg tttaagctgc cgatgtgcct gcgtcgtctg gtgccctctc 9660
tccatatgga ggttgtcaaa gtatctgctg ttcgtgtcat gagtcgtgtc agtgttggtt 9720
taataatgga ccggttgtgt tgtgtgtgcg tactacccag aactatgaca aatcatgaat 9780
aagtttgatg tttgaaatta aagcctgtgc tcattatgtt ctgtctttca gttgtctcct 9840
aatatttgcc tccaggtact ggctatctac cgtttcttac ttaggaggtg tttgaatgca 9900
ctaaaactaa tagttagtgg ctaaaattag ttaaaacatc caaacaccat agctaatagt 9960
tgaactatta gctatttttg gaaaattagt taatagtgag gtagttattt gttagctagc 10020
taattcaact aacaattttt agccaactaa caattagttt cagtgcattc aaacaccccc 10080
ttaatgttaa cgtggttcta tctaccgtct cctaatatat ggttgattgt tcggtttgtt 10140
gctatgctat tgggttctga ttgctgctag ttcttgctga atccagaagt tctcgtagta 10200
tagctcagat tcatattatt tatttgagtg ataagtgatc caggttatta ctatgttagc 10260
taggtttttt ttacaaggat aaattatctg tgatcataat tcttatgaaa gctttatgtt 10320
tcctggaggc agtggcatgc aatgcatgac agcaacttga tcacaccagc tgaggtagat 10380
acggtaacaa ggttcttaaa tctgttcacc aaatcattgg agaacacaca tacacattct 10440
tgccagtctt ggttagagaa atttcatgac aaaatgccaa agctgtcttg actcttcact 10500
tttggccatg agtcgtgact tagtttggtt taatggaccg gttctcctag cttgttctac 10560
tcaaaactgt tgttgatgcg aataagttgt gatggttgat ctctggattt tgttttgctc 10620
tcaatagtgg acgagattag atag 10644

<210> SEQ ID NO 27
<211> LENGTH: 10640
<212> TYPE: DNA
<213> ORGANISM: Artificial sequence
<220> FEATURE:
<223> OTHER INFORMATION: Synthetic polynucleotide

<400> SEQUENCE: 27
gaattcatta tgtggtctag gtaggttcta tatataagaa aacttgaaat gttctaaaaa 60
aaaattcaag cccatgcatg attgaagcaa acggtatagc aacggtgtta acctgatcta 120
gtgatctctt gcaatcctta acggccacct accgcaggta gcaaacggcg tccccctcct 180
cgatatctcc gcggcgacct ctggcttttt ccgcggaatt gcgcggtggg gacggattcc 240
acgagaccgc gacgcaaccg cctctcgccg ctgggcccca caccgctcgg tgccgtagcc 300
tcacgggact ctttctccct cctcccccgt tataaattgg cttcatcccc tccttgcctc 360
atccatccaa atcccagtcc ccaatcccat cccttcgtag gagaaattca tcgaagctaa 420
gcgaatcctc gcgatcctct caaggtactg cgagttttcg atccccctct cgacccctcg 480
tatgtttgtg tttgtcgtag cgtttgatta ggtatgcttt ccctgtttgt gttcgtcgta 540
gcgtttgatt aggtatgctt tccctgttcg tgttcatcgt agtgtttgat taggtcgtgt 600
gaggcgatgg cctgctcgcg tccttcgatc tgtagtcgat ttgcgggtcg tggtgtagat 660
ctgcgggctg tgatgaagtt atttggtgtg atctgctcgc ctgattctgc gggttggctc 720
gagtagatat gatggttgga ccggttggtt cgtttaccgc gctagggttg ggctgggatg 780
atgttgcatg cgccgttgcg cgtgatcccg cagcaggact tgcgtttgat tgccagatct 840
cgttacgatt atgtgatttg gtttggactt tttagatctg tagcttctgc ttatgtgcca 900
gatgcgccta ctgctcatat gcctgatgat aatcataaat ggctgtggaa ctaactagtt 960
gattgcggag tcatgtatca gctacaggtg tagggactag ctacaggtgt agggacttgc 1020
gtctaattgt ttggtccttt actcatgttg caattatgca atttagttta gattgtttgt 1080
tccactcatc taggctgtaa aagggacact gcttagattg ctgtttaatc tttttagtag 1140
attatattat attggtaact tattacccct attacatgcc atacgtgact tctgctcatg 1200
cctgatgata atcatagatc actgtggaat taattagttg attgttgaat catgtttcat 1260
gtacatacca cggcacaatt gcttagttcc ttaacaaatg caaattttac tgatccatgt 1320
atgatttgcg tggttctcta atgtgaaata ctatagctac ttgttagtaa gaatcaggtt 1380
cgtatgctta atgctgtatg tgccttctgc tcatgcctga tgataatcat atatcactgg 1440
aattaattag ttgatcgttt aatcatatat caagtacata ccatgccaca atttttagtc 1500
acttaaccca tgcagattga actggtccct gcatgttttg ctaaattgtt ctattctgat 1560
tagaccatat atcatgtatt ttttttggt aatggttctc ttattttaaa tgctatatag 1620
ttctggtact tgttagaaag atctgcttca tagtttagtt gcctatccct cgaattagga 1680
tgctgagcag ctgatcctat agctttgttt catgtatcaa ttcttttgtg ttcaacagtc 1740
agtttttgtt agattcattg taacttatgg tcgcttactc ttctggtcct caatgcttgc 1800
agggatccta aaccatggag atcaacaacc agaaccagtg cgtgccgtac aactgcctta 1860
acaaccccga gtccgagatc ctgaacgtgg ccatcttctc cagcgagcag gtcgcggaga 1920
tccacctcaa gatcacgcgc ctgatcctcg agaacttcct gccgggcggc tccttcgctt 1980
tcggcctgtt cgacctcatc tggggcatct tcaacgagga ccagtggagc gcgttcctca 2040

```
ggcaggtgga ggagctgatc aaccagcgca tcacggagtt cgccaggggc caggctatcc   2100
agcggctggt gggcttcggc aggtcctacg acgagtacat cctggccctc aaggagtggg   2160
agaacgaccc cgacaacccg gccagcaagg agcgcgtgag gacccgcttc aggaccaccg   2220
acgacgctct cctgacgggc gtccccctca tggctatccc gggcttcgag ctggccaccc   2280
tctcggtgta cgctcagtcg gccaacctgc acctcgccct cctgcgggac gctgtgttct   2340
tcggcgagag gtggggcctg acccagacga acatcaacga cctctactcc aggctgaaga   2400
acagcatccg cgactacacg aaccactgcg tgcgcttcta caacatcggc ctgggcaacc   2460
tcaacgtcat caggccggag tactaccgct tccagaggga gctgaccatc agcgtgctgg   2520
acctcgtcgc cctgttcccc aactacgaca tccgcacgta cccgatccca accaagtccc   2580
agctcacgag ggagatctac accgacccga tcatctcgcc gggcgcccag gccggctaca   2640
ccctgcagga cgtcctgagg gagccccacc tgatggactt cctgaacagg ctcatcatct   2700
acaccggcga gtacaggggc atcaggcact gggcgggcca cgaggtggag tccagcagga   2760
cgggcatgat gaccaacatc cgcttcccgc tctacggcac cgcggccacg gccgagccaa   2820
cccgcttcat cacgccgtcc accttccccg gcctgaacct cttctacagg accctgtcgg   2880
ctcccatctt ccgcgacgag ccgggcgcga acatcatcat ccgctacagg acctccctcg   2940
tggagggcgt cggcttcatc cagccgaaca acggcgagca gctgtaccgc gtgaggggca   3000
cgctggacag cctggaccag ctcccactgg agggcgagtc cagcctcacc gagtactcgc   3060
acaggctgtg ccacgtcagg ttcgcccaga gcctcaggaa cgcggagccc ctggactacg   3120
ccagggtgcc catgttcagc tggacccaca ggtcggctac ccccaccaac accatcgacc   3180
cagacgtgat cacgcagatc ccgctcgtca aggcccacac cctgcagtcg ggcaccaccg   3240
tggtcaaggg ccccggcttc acgggcggcg acatcctgag gaggacctcc ggcggcccat   3300
tcgccttcag caacgtcaac ctcgactgga acctgtccca gcgctacagg gcgcgcatca   3360
ggtacgccag caccacgaac ctgcgcatgt atgtgaccat cgcgggcgag aggatcttcg   3420
ccggccagtt caacaagacg atgaacaccg gcgacccgct caccttccag tccttcagct   3480
acgcgacgat cgacaccgcc ttcacgttcc ccacgaaggc ctccagcctg accgtgggcg   3540
ccgacacctt ctccagcggc aacgaggtct acgtggaccg cttcgagctg atcccggtga   3600
cggcgacctt cgaggccgag tacgacctgg agaaggccca gaaggcggtc aacgccctct   3660
tcacctccag caaccagatc ggcctgaaga cggacgtgac cgactaccac atcgacaagg   3720
tgtccaacct cgtcgagtgc ctgagcgacg agttctgcct cgacgagaag agggagctgt   3780
ccgagaaggt caagcacgcc aagcgcctct gcgacgagag gaacctcctg caggacccga   3840
acttcagggg aatcaaccgc cagccggaca ggggctggag ggcagcaccc gacatcacca   3900
tccagggcgg cgacgacgtg ttcaaggaga actacgtcac gctcccgggc accttcgacg   3960
agtgctaccc cacgtacctg taccagaaga tcgacgagtc caagctcaag gcctacaccc   4020
gctacgagct gaggggatac atcgaggaca gccaggacct cgagatctac ctgatccgct   4080
acaacgcgaa gcacgagacg gtgaacgtcc ccggcacggg ctccctgtgg cccctctcgg   4140
ctcagtcgcc gatcggcaag tgcggcgagc ccaacaggtg cgccacccac ctcgagtgga   4200
acccggacct ggactgctcc tgccgggacg gcgagaagtg cgctcaccac tcccaccact   4260
tcagcctgga catcgacgtg ggctgcacgg acctcaacga ggacctgggc gtgtgggtca   4320
tcttcaaaat caagacgcag gacggccacg ctaggctggg caacctcgag ttcctggagg   4380
```

agaagccgct ggtgggcgag gctctggcca gggtcaagag ggcggagaag aagtggcgcg 4440
acaagaggga gaagctggag ctggagacga acatcgtcta caaggaggcc aagaagtccg 4500
tggacgcgct cttcgtcaac agccagtacg acaggctgca ggcggacacc aacatcgcca 4560
tcatccacgc cgcggacaag cgcgtgcact ccatcaggga ggcctacctc cccgagctga 4620
gcgtgatccc gggcgtcaac gctgccatct tcgaggagct ggagggccgc atcttcaccg 4680
cctactccct gtacgacgcg aggaacgtca tcaagaacgg cgacttcaac aacggcctca 4740
gctgctggaa cgtgaagggc cacgtggacg tcgaggagca gaacaaccac cgctcggtgc 4800
tggtggtccc cgagtgggag gctgaggtca gccaggaggt gcgcgtctgc ccgggcaggg 4860
gatacatcct ccgcgtgacc gcgtacaagg agggctacgg cgagggctgc gtcacgatcc 4920
acgagatcga ggacaacacc gacgagctga agttctccaa ctgcgtggag gaggagatct 4980
acccgaacaa cacggtcacc tgcaacgact acacggccac ccaggaggag tacgagggca 5040
cgtacacgtc gaggaacagg ggctacgacg gcgcttacga gtccaacagc tcggtgccgg 5100
ccgactacgc tagcgcgtac gaggagaagg cctacacgga cggccgcagg gacaacacct 5160
gcgagtcgaa caggggctac ggcgactaca cgccgctccc ggccggctac gtgaccaagg 5220
agctggagta cttcccggag acggacaagg tctggatcga gatcggcgag acggagggca 5280
ccttcatcgt ggactcagtc gagctgctgc tcatggagga gtaggagctc gccaacagtc 5340
gttgaagctg ctgctgtatc tgggttatct agtgtctctg cctttgccca aggatagtgc 5400
tgtctttcaa agtatttgta tcgtttgtgt cgtgagtcgt gactgagctg gtttcaagga 5460
ccagttgtgt tctcgttacc caaaactatc gtgcgaccgc atatggctta atcatgaata 5520
aatgttgttt gaatttaaac tattcgctga atattgttgt tttttgtcat gtcagttaat 5580
gttactaaat tggttgcctt ctaatttttg tttactggtg tttgtcgcac cttatctttt 5640
tactgtatgt ttacttcagg ttctggcagt ctcatttttt gtgactagtt aaaacttaca 5700
gctaaaaaaa tgcagttttt aattttaatt tgaagtttga ttagagctat tgatacccgg 5760
accatcaggt taggttagtt gtgcatagaa tcataaatat taatcatgtt ttctatgaat 5820
taagtcaaac ttgaaagtct ggctgaatat agtttctatg aatcatattg atatacatgt 5880
ttgattattt gttttgctat tagctattta ctttggtgaa tctatatagg cttatgcaga 5940
accttttttt tgttctatat atccatatcc tagtactcag tagctctatg ttttctggag 6000
actagtggct tgcttttcgt atgtctaatt ttttgcttga ccattgcaaa acaaaaaatta 6060
cctagtgtaa tctcttttta taataatctt gtaatgcgtc tacctatagg tcaaagtagg 6120
ttttgtttgg aaccccttaga gctaactgtt agctagttga taaattatta gctgagttaa 6180
gctagctaat gaactagttt tgatattagc tgaggatgtt tgaaacctaa taattatttt 6240
ttattagcta actatactaa attttagtag agagattcca aacaggagtt aacatgggat 6300
cagattggct atgcgtttgc aatcccatac taattagcta acggaccgct aattagctaa 6360
cgatcgctta attaagcttg catgcctgca gtgcagcgtg acccggtcgt gcccctctct 6420
agagataatg agcattgcat gtctaagtta taaaaaatta ccacatattt tttttgtcac 6480
acttgtttga agtgcagttt atctatcttt atacatatat ttaaacttta ctctacgaat 6540
aatataatct atagtactac aataatatca gtgttttaga gaatcatata aatgaacagt 6600
tagacatggt ctaaaggaca attgagtatt ttgacaacag gactctacag ttttatcttt 6660
ttagtgtgca tgtgttctcc tttttttttg caaatagctt cacctatata atacttcatc 6720
cattttatta gtacatccat ttagggttta gggttaatgg tttttataga ctaatttttt 6780

```
tagtacatct attttattct attttagcct ctaaattaag aaaactaaaa ctctatttta   6840
gttttttat ttaataattt agatataaaa tagaataaaa taaagtgact aaaaattaaa   6900
caaataccct ttaagaaatt aaaaaaacta aggaaacatt tttcttgttt cgagtagata   6960
atgccagcct gttaaacgcc gccgacgagt ctaacggaca ccaaccagcg aaccagcagc   7020
gtcgcgtcgg gccaagcgaa gcagacggca cggcatctct gtcgctgcct ctggacccct   7080
ctcgagagtt ccgctccacc gttggacttg ctccgctgtc ggcatccaga aattgcgtgg   7140
cggagcggca gacgtgagcc ggcacggcag gcggcctcct cctcctctca cggcaccggc   7200
agctacgggg gattcctttc ccaccgctcc ttcgctttcc cttcctcgcc cgccgtaata   7260
aatagacacc ccctccacac cctctttccc caacctcgtg ttgttcggag cgcacacaca   7320
cacaaccaga tctcccccaa atccacccgt cggcacctcc gcttcaaggt acgccgctcg   7380
tcctcccccc cccccccctc tctaccttct ctagatcggc gttccggtcc atagttaggg   7440
cccggtagtt ctacttctgt tcatgtttgt gttagatccg tgtttgtgtt agatccgtgc   7500
tgttagcgtt cgtacacgga tgcgacctgt acgtcagaca cgttctgatt gctaacttgc   7560
cagtgtttct ctttgggaat cctgggatgg ctctagccgt tccgcagacg ggatcgattt   7620
catgattttt tttgtttcgt tgcatagggt ttggtttgcc cttttccttt atttcaatat   7680
atgccgtgca cttgtttgtc gggtcatctt ttcatgcttt tttttgtctt ggttgtgatg   7740
atgtggtctg gttgggcggt cgttctagat cggagtagaa ttctgtttca aactacctgg   7800
tggatttatt aattttggat ctgtatgtgt gtgccataca tattcatagt tacgaattga   7860
agatgatgga tggaaatatc gatctaggat aggtatacat gttgatgcgg gttttactga   7920
tgcatataca gagatgcttt ttgttcgctt ggttgtgatg atgtggtgtg gttgggcggt   7980
cgttcattcg ttctagatcg gagtagaata ctgtttcaaa ctacctggtg tatttattaa   8040
ttttggaact gtatgtgtgt gtcatacatc ttcatagtta cgagtttaag atggatggaa   8100
atatcgatct aggataggta tacatgttga tgtgggtttt actgatgcat atacatgatg   8160
gcatatgcag catctattca tatgctctaa ccttgagtac ctatctatta taataaacaa   8220
gtatgtttta taattatttt gatcttgata tacttggatg atggcatatc cagcagctat   8280
atctggattt ttttagccct gccttcatac gctatttatt tgcttggtac tgtttctttt   8340
gtcgttgctc accctgttgt ttggtgttac ttctgcaggg atctccgatc atgcaaaaac   8400
tcattaactc agtgcaaaac tatgcctggg gcagcaaaac ggcgttgact gaactttacg   8460
gtatggaaaa tccgtccagc cagccgatgg ccgagctgtg gatgggcgca catccgaaaa   8520
gcagttcacg agtgcagaat gccgccggag atatcgtttc actgcgtgat gtgattgaga   8580
gtgataaatc gactctgctc ggagaggccg ttgccaaacg ctttggcgaa ctgcctttcc   8640
tgttcaaagt attatgcgca gcacagccac tctccattca ggttcatcca aacaaacaca   8700
attctgaaat cggttttgcc aaagaaaatg ccgcaggtat cccgatggat gccgccgagc   8760
gtaactataa agatcctaac cacaagccgg agctggtttt tgcgctgacg cctttccttg   8820
cgatgaacgc gtttcgtgaa ttttccgaga ttgtctccct actccagccg gtcgcaggtg   8880
cacatccggc gattgctcac tttttacaac agcctgatgc cgaacgttta agcgaactgt   8940
tcgccagcct gttgaatatg cagggtgaag aaaaatcccg cgcgctggcg attttaaaat   9000
cggccctcga tagccagcag ggtgaaccgt ggcaaacgat tcgtttaatt tctgaatttt   9060
acccggaaga cagcggtctg ttctccccgc tattgctgaa tgtggtgaaa ttgaaccctg   9120
```

gcgaagcgat gttcctgttc gctgaaacac cgcacgctta cctgcaaggc gtggcgctgg 9180
aagtgatggc aaactccgat aacgtgctgc gtgcgggtct gacgcctaaa tacattgata 9240
ttccggaact ggttgccaat gtgaaattcg aagccaaacc ggctaaccag ttgttgaccc 9300
agccggtgaa acaaggtgca gaactggact tcccgattcc agtggacgat tttgccttct 9360
cgctgcacga ccttagtgat aaagaaacca ccattagcca gcagagtgcc gccattttgt 9420
tctgcgtcga aggcgatgca acgttgtgga aaggttctca gcagttacag cttaaaccgg 9480
gtgaatcagc gtttattgcc gccaacgaat caccggtgac tgtcaaaggc cacggccgtt 9540
tagcgcgtgt ttacaacaag ctgtaagagc ttactgaaaa aattaacatc tcttgctaag 9600
ctgggtcatg ggtcgtttaa gctgccgatg tgcctgcgtc gtctggtgcc ctctctccat 9660
atggaggttg tcaaagtatc tgctgttcgt gtcatgagtc gtgtcagtgt tggtttaata 9720
atggaccggt tgtgttgtgt gtgcgtacta cccagaacta tgacaaatca tgaataagtt 9780
tgatgtttga aattaaagcc tgtgctcatt atgttctgtc tttcagttgt ctcctaatat 9840
ttgcctccag gtactggcta tctaccgttt cttacttagg aggtgtttga atgcactaaa 9900
actaatagtt agtggctaaa attagttaaa acatccaaac accatagcta atagttgaac 9960
tattagctat ttttggaaaa ttagttaata gtgaggtagt tatttgttag ctagctaatt 10020
caactaacaa tttttagcca actaacaatt agttttcagt gcattcaaac accccttaa 10080 tgttaacgtg gttctatcta ccgtctccta atatatggtt gattgttcgg tttgttgcta 10140
tgctattggg ttctgattgc tgctagttct tgctgaatcc agaagttctc gtagtatagc 10200
tcagattcat attatttatt tgagtgataa gtgatccagg ttattactat gttagctagg 10260 tttttttac aaggataaat tatctgtgat cataattctt atgaaagctt tatgtttcct 10320
ggaggcagtg gcatgcaatg catgacagca acttgatcac accagctgag gtagatacgg 10380
taacaaggtt cttaaatctg ttcaccaaat cattggagaa cacacataca cattcttgcc 10440
agtcttggtt agagaaattt catgacaaaa tgccaaagct gtcttgactc ttcacttttg 10500
gccatgagtc gtgacttagt ttggtttaat ggaccggttc tcctagcttg ttctactcaa 10560
aactgttgtt gatgcgaata agttgtgatg gttgatctct ggattttgtt ttgctctcaa 10620
tagtggacga gattagatag 10640

<210> SEQ ID NO 28
<211> LENGTH: 10643
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<222> LOCATION: (5944)..(5944)
<223> OTHER INFORMATION: n is t or absent
<220> FEATURE:
<221> NAME/KEY: misc_feature
<222> LOCATION: (6015)..(6015)
<223> OTHER INFORMATION: n is t or absent
<220> FEATURE:
<221> NAME/KEY: misc_feature
<222> LOCATION: (7387)..(7387)
<223> OTHER INFORMATION: n is c or absent
<220> FEATURE:
<221> NAME/KEY: misc_feature
<222> LOCATION: (7577)..(7577)
<223> OTHER INFORMATION: n is g or absent
<220> FEATURE:
<221> NAME/KEY: misc_feature
<222> LOCATION: (10056)..(10056)
<223> OTHER INFORMATION: n is t or absent

<400> SEQUENCE: 28
gaattcatta tgtggtctag gtaggttcta tatataagaa aacttgaaat gttctaaaaa 60
aaaattcaag cccatgcatg attgaagcaa acggtatagc aacggtgtta acctgatcta 120
gtgatctctt gcaatcctta acggccacct accgcaggta gcaaacggcg tccccctcct 180
cgatatctcc gcggcgacct ctggcttttt ccgcggaatt gcgcggtggg gacggattcc 240
acgagaccgc gacgcaaccg cctctcgccg ctgggcccca caccgctcgg tgccgtagcc 300
tcacgggact ctttctccct cctcccccgt tataaattgg cttcatcccc tccttgcctc 360
atccatccaa atcccagtcc ccaatcccat cccttcgtag gagaaattca tcgaagctaa 420
gcgaatcctc gcgatcctct caaggtactg cgagttttcg atccccctct cgacccctcg 480
tatgtttgtg tttgtcgtag cgtttgatta ggtatgcttt ccctgtttgt gttcgtcgta 540
gcgtttgatt aggtatgctt tccctgttcg tgttcatcgt agtgtttgat taggtcgtgt 600
gaggcgatgg cctgctcgcg tccttcgatc tgtagtcgat ttgcgggtcg tggtgtagat 660
ctgcgggctg tgatgaagtt atttggtgtg atctgctcgc ctgattctgc gggttggctc 720
gagtagatat gatggttgga ccggttggtt cgtttaccgc gctagggttg ggctgggatg 780
atgttgcatg cgccgttgcg cgtgatcccg cagcaggact tgcgtttgat tgccagatct 840
cgttacgatt atgtgatttg gtttggactt tttagatctg tagcttctgc ttatgtgcca 900
gatgcgccta ctgctcatat gcctgatgat aatcataaat ggctgtggaa ctaactagtt 960
gattgcggag tcatgtatca gctacaggtg tagggactag ctacaggtgt agggacttgc 1020
gtctaattgt ttggtccttt actcatgttg caattatgca atttagttta gattgtttgt 1080
tccactcatc taggctgtaa aagggacact gcttagattg ctgtttaatc tttttagtag 1140
attatattat attggtaact tattacccct attacatgcc atacgtgact tctgctcatg 1200
cctgatgata atcatagatc actgtggaat taattagttg attgttgaat catgtttcat 1260
gtacatacca cggcacaatt gcttagttcc ttaacaaatg caaattttac tgatccatgt 1320
atgatttgcg tggttctcta atgtgaaata ctatagctac ttgttagtaa gaatcaggtt 1380
cgtatgctta atgctgtatg tgccttctgc tcatgcctga tgataatcat atatcactgg 1440
aattaattag ttgatcgttt aatcatatat caagtacata ccatgccaca atttttagtc 1500
acttaaccca tgcagattga actggtccct gcatgttttg ctaaattgtt ctattctgat 1560
tagaccatat atcatgtatt ttttttggt aatggttctc ttattttaaa tgctatatag 1620
ttctggtact tgttagaaag atctgcttca tagtttagtt gcctatccct cgaattagga 1680
tgctgagcag ctgatcctat agctttgttt catgtatcaa ttcttttgtg ttcaacagtc 1740
agtttttgtt agattcattg taacttatgg tcgcttactc ttctggtcct caatgcttgc 1800
agggatccta aaccatggag atcaacaacc agaaccagtg cgtgccgtac aactgcctta 1860
acaaccccga gtccgagatc ctgaacgtgg ccatcttctc cagcgagcag gtcgcggaga 1920
tccacctcaa gatcacgcgc ctgatcctcg agaacttcct gccgggcggc tccttcgctt 1980
tcggcctgtt cgacctcatc tggggcatct tcaacgagga ccagtggagc gcgttcctca 2040
ggcaggtgga ggagctgatc aaccagcgca tcacggagtt cgccaggggc caggctatcc 2100
agcggctggt gggcttcggc aggtcctacg acgagtacat cctggccctc aaggagtggg 2160
agaacgaccc cgacaacccg gccagcaagg agcgcgtgag gacccgcttc aggaccaccg 2220
acgacgctct cctgacgggc gtccccctca tggctatccc gggcttcgag ctggccaccc 2280
tctcggtgta cgctcagtcg gccaacctgc acctcgccct cctgcgggac gctgtgttct 2340
tcggcgagag gtggggcctg acccagacga acatcaacga cctctactcc aggctgaaga 2400
acagcatccg cgactacacg aaccactgcg tgcgcttcta caacatcggc ctgggcaacc 2460
tcaacgtcat caggccggag tactaccgct tccagaggga gctgaccatc agcgtgctgg 2520
acctcgtcgc cctgttcccc aactacgaca tccgcacgta cccgatccca accaagtccc 2580
agctcacgag ggagatctac accgacccga tcatctcgcc gggcgcccag gccggctaca 2640
ccctgcagga cgtcctgagg gagccccacc tgatggactt cctgaacagg ctcatcatct 2700
acaccggcga gtacaggggc atcaggcact gggcgggcca cgaggtggag tccagcagga 2760
cgggcatgat gaccaacatc cgcttcccgc tctacggcac cgcggccacg gccgagccaa 2820
cccgcttcat cacgccgtcc accttccccg gcctgaacct cttctacagg accctgtcgg 2880
ctcccatctt ccgcgacgag ccgggcgcga acatcatcat ccgctacagg acctccctcg 2940
tggagggcgt cggcttcatc cagccgaaca acggcgagca gctgtaccgc gtgaggggca 3000
cgctggacag cctggaccag ctcccactgg agggcgagtc cagcctcacc gagtactcgc 3060
acaggctgtg ccacgtcagg ttcgcccaga gcctcaggaa cgcggagccc ctggactacg 3120
ccagggtgcc catgttcagc tggacccaca ggtcggctac ccccaccaac accatcgacc 3180
cagacgtgat cacgcagatc ccgctcgtca aggcccacac cctgcagtcg ggcaccaccg 3240
tggtcaaggg ccccggcttc acgggcggcg acatcctgag gaggacctcc ggcggcccat 3300
tcgccttcag caacgtcaac ctcgactgga acctgtccca gcgctacagg gcgcgcatca 3360
ggtacgccag caccacgaac ctgcgcatgt atgtgaccat cgcgggcgag aggatcttcg 3420
ccggccagtt caacaagacg atgaacaccg gcgacccgct caccttccag tccttcagct 3480
acgcgacgat cgacaccgcc ttcacgttcc ccacgaaggc ctccagcctg accgtgggcg 3540
ccgacacctt ctccagcggc aacgaggtct acgtggaccg cttcgagctg atcccggtga 3600
cggcgacctt cgaggccgag tacgacctgg agaaggccca gaaggcggtc aacgccctct 3660
tcacctccag caaccagatc ggcctgaaga cggacgtgac cgactaccac atcgacaagg 3720
tgtccaacct cgtcgagtgc ctgagcgacg agttctgcct cgacgagaag agggagctgt 3780
ccgagaaggt caagcacgcc aagcgcctct gcgacgagag gaacctcctg caggacccga 3840
acttcagggg aatcaaccgc cagccggaca ggggctggag gggcagcacc gacatcacca 3900
tccagggcgg cgacgacgtg ttcaaggaga actacgtcac gctcccgggc accttcgacg 3960
agtgctaccc cacgtacctg taccagaaga tcgacgagtc caagctcaag gcctacaccc 4020
gctacgagct gaggggatac atcgaggaca gccaggacct cgagatctac ctgatccgct 4080
acaacgcgaa gcacgagacg gtgaacgtcc ccggcacggg ctccctgtgg cccctctcgg 4140
ctcagtcgcc gatcggcaag tgcggcgagc ccaacaggtg cgccacccac ctcgagtgga 4200
acccggacct ggactgctcc tgccgggacg gcgagaagtg cgctcaccac tcccaccact 4260
tcagcctgga catcgacgtg ggctgcacgg acctcaacga ggacctgggc gtgtgggtca 4320
tcttcaaaat caagacgcag gacggccacg ctaggctggg caacctcgag ttcctggagg 4380
agaagccgct ggtgggcgag gctctggcca gggtcaagag ggcggagaag aagtggcgcg 4440
acaagaggga gaagctggag ctggagacga acatcgtcta caaggaggcc aagaagtccg 4500
tggacgcgct cttcgtcaac agccagtacg acaggctgca ggcggacacc aacatcgcca 4560
tcatccacgc cgcggacaag cgcgtgcact ccatcaggga ggcctacctc cccgagctga 4620
gcgtgatccc gggcgtcaac gctgccatct tcgaggagct ggagggccgc atcttcaccg 4680

```
cctactccct gtacgacgcg aggaacgtca tcaagaacgg cgacttcaac aacggcctca   4740
gctgctggaa cgtgaagggc cacgtggacg tcgaggagca gaacaaccac cgctcggtgc   4800
tggtggtccc cgagtgggag gctgaggtca gccaggaggt gcgcgtctgc ccgggcaggg   4860
gatacatcct ccgcgtgacc gcgtacaagg agggctacgg cgagggctgc gtcacgatcc   4920
acgagatcga ggacaacacc gacgagctga agttctccaa ctgcgtggag gaggagatct   4980
acccgaacaa cacggtcacc tgcaacgact acacggccac ccaggaggag tacgagggca   5040
cgtacacgtc gaggaacagg ggctacgacg gcgcttacga gtccaacagc tcggtgccgg   5100
ccgactacgc tagcgcgtac gaggagaagg cctacacgga cggccgcagg gacaacacct   5160
gcgagtcgaa caggggctac ggcgactaca cgccgctccc ggccggctac gtgaccaagg   5220
agctggagta cttcccggag acggacaagg tctggatcga gatcggcgag acggagggca   5280
ccttcatcgt ggactcagtc gagctgctgc tcatggagga gtaggagctc gccaacagtc   5340
gttgaagctg ctgctgtatc tgggttatct agtgtctctg cctttgccca aggatagtgc   5400
tgtctttcaa agtatttgta tcgtttgtgt cgtgagtcgt gactgagctg gtttcaagga   5460
ccagttgtgt tctcgttacc caaaactatc gtgcgaccgc atatggctta atcatgaata   5520
aatgttgttt gaatttaaac tattcgctga atattgttgt tttttgtcat gtcagttaat   5580
gttactaaat tggttgcctt ctaatttttg tttactggtg tttgtcgcac cttatctttt   5640
tactgtatgt ttacttcagg ttctggcagt ctcatttttt gtgactagtt aaaacttaca   5700
gctaaaaaaa tgcagttttt aattttaatt tgaagtttga ttagagctat tgatacccgg   5760
accatcaggt taggttagtt gtgcatagaa tcataaatat taatcatgtt ttctatgaat   5820
taagtcaaac ttgaaagtct ggctgaatat agtttctatg aatcatattg atatacatgt   5880
ttgattattt gttttgctat tagctattta ctttggtgaa tctatatagg cttatgcaga   5940
accntttttt ttgttctata tatccatatc ctagtactca gtagctctat gttttctgga   6000
gactagtggc ttgcnttttc gtatgtctaa tttttttgctt gaccattgca aaacaaaaat   6060
tacctagtgt aatctctttt tataataatc ttgtaatgcg tctacctata ggtcaaagta   6120
ggttttgttt ggaaccctta gagctaactg ttagctagtt gataaattat tagctgagtt   6180
aagctagcta atgaactagt tttgatatta gctgaggatg tttgaaacct aataattatt   6240
ttttattagc taactatact aaattttagt agagagattc caaacaggag ttaacatggg   6300
atcagattgg ctatgcgttt gcaatcccat actaattagc taacggaccg ctaattagct   6360
aacgatcgct taattaagct tgcatgcctg cagtgcagcg tgacccggtc gtgcccctct   6420
ctagagataa tgagcattgc atgtctaagt tataaaaaat taccacatat ttttttttgtc   6480
acacttgttt gaagtgcagt ttatctatct ttatacatat atttaaactt tactctacga   6540
ataatataat ctatagtact acaataatat cagtgtttta gagaatcata taaatgaaca   6600
gttagacatg gtctaaagga caattgagta ttttgacaac aggactctac agttttatct   6660
ttttagtgtg catgtgttct ccttttttttt tgcaaatagc ttcacctata taatacttca   6720
tccattttat tagtacatcc atttagggtt tagggttaat ggtttttata gactaatttt   6780
tttagtacat ctattttatt ctattttagc ctctaaatta agaaaactaa aactctattt   6840
tagttttttt atttaataat ttagatataa aatagaataa aataaagtga ctaaaaatta   6900
aacaaatacc ctttaagaaa ttaaaaaaac taaggaaaca tttttcttgt ttcgagtaga   6960
taatgccagc ctgttaaacg ccgccgacga gtctaacgga caccaaccag cgaaccagca   7020
```

gcgtcgcgtc gggccaagcg aagcagacgg cacggcatct ctgtcgctgc ctctggaccc 7080
ctctcgagag ttccgctcca ccgttggact tgctccgctg tcggcatcca gaaattgcgt 7140
ggcggagcgg cagacgtgag ccggcacggc aggcggcctc ctcctcctct cacggcaccg 7200
gcagctacgg gggattcctt tcccaccgct ccttcgcttt cccttcctcg cccgccgtaa 7260
taaatagaca ccccctccac accctctttc cccaacctcg tgttgttcgg agcgcacaca 7320
cacacaacca gatctccccc aaatccaccc gtcggcacct ccgcttcaag gtacgccgct 7380
cgtcctnccc cccccccccc tctctacctt ctctagatcg gcgttccggt ccatagttag 7440
ggcccggtag ttctacttct gttcatgttt gtgttagatc cgtgtttgtg ttagatccgt 7500
gctgttagcg ttcgtacacg gatgcgacct gtacgtcaga cacgttctga ttgctaactt 7560
gccagtgttt ctctttnggg aatcctggga tggctctagc cgttccgcag acgggatcga 7620
tttcatgatt ttttttgttt cgttgcatag ggtttggttt gcccttttcc tttatttcaa 7680
tatatgccgt gcacttgttt gtcgggtcat cttttcatgc ttttttttgt cttggttgtg 7740
atgatgtggt ctggttgggc ggtcgttcta gatcggagta gaattctgtt tcaaactacc 7800
tggtggattt attaattttg gatctgtatg tgtgtgccat acatattcat agttacgaat 7860
tgaagatgat ggatggaaat atcgatctag gataggtata catgttgatg cgggttttac 7920
tgatgcatat acagagatgc tttttgttcg cttggttgtg atgatgtggt gtggttgggc 7980
ggtcgttcat tcgttctaga tcggagtaga atactgtttc aaactacctg gtgtatttat 8040
taattttgga actgtatgtg tgtgtcatac atcttcatag ttacgagttt aagatggatg 8100
gaaatatcga tctaggatag gtatacatgt tgatgtgggt tttactgatg catatacatg 8160
atggcatatg cagcatctat tcatatgctc taaccttgag tacctatcta ttataataaa 8220
caagtatgtt ttataattat tttgatcttg atatacttgg atgatggcat atccagcagc 8280
tatatctgga ttttttagc cctgccttca tacgctattt atttgcttgg tactgtttct 8340
tttgtcgttg ctcaccctgt tgtttggtgt tacttctgca gggatctccg atcatgcaaa 8400
aactcattaa ctcagtgcaa aactatgcct ggggcagcaa aacggcgttg actgaacttt 8460
acggtatgga aaatccgtcc agccagccga tggccgagct gtggatgggc gcacatccga 8520
aaagcagttc acgagtgcag aatgccgccg gagatatcgt ttcactgcgt gatgtgattg 8580
agagtgataa atcgactctg ctcggagagg ccgttgccaa acgctttggc gaactgcctt 8640
tcctgttcaa agtattatgc gcagcacagc cactctccat tcaggttcat ccaaacaaac 8700
acaattctga aatcggtttt gccaaagaaa atgccgcagg tatcccgatg gatgccgccg 8760
agcgtaacta taaagatcct aaccacaagc cggagctggt ttttgcgctg acgcctttcc 8820
ttgcgatgaa cgcgtttcgt gaattttccg agattgtctc cctactccag ccggtcgcag 8880
gtgcacatcc ggcgattgct cactttttac aacagcctga tgccgaacgt ttaagcgaac 8940
tgttcgccag cctgttgaat atgcagggtg aagaaaaatc ccgcgcgctg gcgattttaa 9000
aatcggccct cgatagccag cagggtgaac cgtggcaaac gattcgttta atttctgaat 9060
tttacccgga agacagcggt ctgttctccc cgctattgct gaatgtggtg aaattgaacc 9120
ctggcgaagc gatgttcctg ttcgctgaaa caccgcacgc ttacctgcaa ggcgtggcgc 9180
tggaagtgat ggcaaactcc gataacgtgc tgcgtgcggg tctgacgcct aaatacattg 9240
atattccgga actggttgcc aatgtgaaat tcgaagccaa accggctaac cagttgttga 9300
cccagccggt gaaacaaggt gcagaactgg acttcccgat tccagtggac gattttgcct 9360
tctcgctgca cgaccttagt gataaagaaa ccaccattag ccagcagagt gccgccattt 9420
tgttctgcgt cgaaggcgat gcaacgttgt ggaaaggttc tcagcagtta cagcttaaac 9480
cgggtgaatc agcgtttatt gccgccaacg aatcaccggt gactgtcaaa ggccacggcc 9540
gtttagcgcg tgtttacaac aagctgtaag agcttactga aaaaattaac atctcttgct 9600
aagctgggtc atgggtcgtt taagctgccg atgtgcctgc gtcgtctggt gccctctctc 9660
catatggagg ttgtcaaagt atctgctgtt cgtgtcatga gtcgtgtcag tgttggttta 9720
ataatggacc ggttgtgttg tgtgtgcgta ctacccagaa ctatgacaaa tcatgaataa 9780
gtttgatgtt tgaaattaaa gcctgtgctc attatgttct gtctttcagt tgtctcctaa 9840
tatttgcctc caggtactgg ctatctaccg tttcttactt aggaggtgtt tgaatgcact 9900
aaaactaata gttagtggct aaaattagtt aaaacatcca aacaccatag ctaatagttg 9960
aactattagc tatttttgga aaattagtta atagtgaggt agttatttgt tagctagcta 10020
attcaactaa caatttttag ccaactaaca attagntttc agtgcattca aacacccccct 10080 taatgttaac gtggttctat ctaccgtctc ctaatatatg gttgattgtt cggtttgttg 10140
ctatgctatt gggttctgat tgctgctagt tcttgctgaa tccagaagtt ctcgtagtat 10200
agctcagatt catattattt atttgagtga taagtgatcc aggttattac tatgttagct 10260
aggttttttt tacaaggata aattatctgt gatcataatt cttatgaaag ctttatgttt 10320
cctggaggca gtggcatgca atgcatgaca gcaacttgat cacaccagct gaggtagata 10380
cggtaacaag gttcttaaat ctgttcacca aatcattgga gaacacacat acacattctt 10440
gccagtcttg gttagagaaa tttcatgaca aaatgccaaa gctgtcttga ctcttcactt 10500
ttggccatga gtcgtgactt agtttggttt aatggaccgg ttctcctagc ttgttctact 10560
caaaactgtt gttgatgcga ataagttgtg atggttgatc tctggatttt gttttgctct 10620
caatagtgga cgagattaga tag 10643

<210> SEQ ID NO 29
<211> LENGTH: 10641
<212> TYPE: DNA
<213> ORGANISM: Artificial sequence
<220> FEATURE:
<223> OTHER INFORMATION: Synthetic polynucleotide

<400> SEQUENCE: 29
gaattcatta tgtggtctag gtaggttcta tatataagaa aacttgaaat gttctaaaaa 60
aaaattcaag cccatgcatg attgaagcaa acggtatagc aacggtgtta acctgatcta 120
gtgatctctt gcaatcctta acggccacct accgcaggta gcaaacggcg tccccctcct 180
cgatatctcc gcggcgacct ctggcttttt ccgcggaatt gcgcggtggg gacggattcc 240
acgagaccgc gacgcaaccg cctctcgccg ctgggcccca caccgctcgg tgccgtagcc 300
tcacgggact ctttctccct cctcccccgt tataaattgg cttcatcccc tccttgcctc 360
atccatccaa atcccagtcc ccaatcccat cccttcgtag gagaaattca tcgaagctaa 420
gcgaatcctc gcgatcctct caaggtactg cgagttttcg atccccctct cgacccctcg 480
tatgtttgtg tttgtcgtag cgtttgatta ggtatgcttt ccctgtttgt gttcgtcgta 540
gcgtttgatt aggtatgctt tccctgttcg tgttcatcgt agtgtttgat taggtcgtgt 600
gaggcgatgg cctgctcgcg tccttcgatc tgtagtcgat ttgcgggtcg tggtgtagat 660
ctgcgggctg tgatgaagtt atttggtgtg atctgctcgc ctgattctgc gggttggctc 720
gagtagatat gatggttgga ccggttggtt cgtttaccgc gctagggttg ggctgggatg 780

```
atgttgcatg cgccgttgcg cgtgatcccg cagcaggact tgcgtttgat tgccagatct    840
cgttacgatt atgtgatttg gtttggactt tttagatctg tagcttctgc ttatgtgcca    900
gatgcgccta ctgctcatat gcctgatgat aatcataaat ggctgtggaa ctaactagtt    960
gattgcggag tcatgtatca gctacaggtg tagggactag ctacaggtgt agggacttgc   1020
gtctaattgt ttggtccttt actcatgttg caattatgca atttagttta gattgtttgt   1080
tccactcatc taggctgtaa aagggacact gcttagattg ctgtttaatc tttttagtag   1140
attatattat attggtaact tattacccct attacatgcc atacgtgact tctgctcatg   1200
cctgatgata atcatagatc actgtggaat taattagttg attgttgaat catgtttcat   1260
gtacatacca cggcacaatt gcttagttcc ttaacaaatg caaattttac tgatccatgt   1320
atgatttgcg tggttctcta atgtgaaata ctatagctac ttgttagtaa gaatcaggtt   1380
cgtatgctta atgctgtatg tgccttctgc tcatgcctga tgataatcat atatcactgg   1440
aattaattag ttgatcgttt aatcatatat caagtacata ccatgccaca atttttagtc   1500
acttaaccca tgcagattga actggtccct gcatgttttg ctaaattgtt ctattctgat   1560
tagaccatat atcatgtatt tttttttggt aatggttctc ttattttaaa tgctatatag   1620
ttctggtact tgttagaaag atctgcttca tagtttagtt gcctatccct cgaattagga   1680
tgctgagcag ctgatcctat agctttgttt catgtatcaa ttcttttgtg ttcaacagtc   1740
agtttttgtt agattcattg taacttatgg tcgcttactc ttctggtcct caatgcttgc   1800
agggatccta aaccatggag atcaacaacc agaaccagtg cgtgccgtac aactgcctta   1860
acaaccccga gtccgagatc ctgaacgtgg ccatcttctc cagcgagcag gtcgcggaga   1920
tccacctcaa gatcacgcgc ctgatcctcg agaacttcct gccgggcggc tccttcgctt   1980
tcggcctgtt cgacctcatc tggggcatct tcaacgagga ccagtggagc gcgttcctca   2040
ggcaggtgga ggagctgatc aaccagcgca tcacggagtt cgccaggggc caggctatcc   2100
agcggctggt gggcttcggc aggtcctacg acgagtacat cctggccctc aaggagtggg   2160
agaacgaccc cgacaacccg gccagcaagg agcgcgtgag gacccgcttc aggaccaccg   2220
acgacgctct cctgacgggc gtccccctca tggctatccc gggcttcgag ctggccaccc   2280
tctcggtgta cgctcagtcg gccaacctgc acctcgccct cctgcgggac gctgtgttct   2340
tcggcgagag gtggggcctg acccagacga acatcaacga cctctactcc aggctgaaga   2400
acagcatccg cgactacacg aaccactgcg tgcgcttcta caacatcggc ctgggcaacc   2460
tcaacgtcat caggccggag tactaccgct tccagaggga gctgaccatc agcgtgctgg   2520
acctcgtcgc cctgttcccc aactacgaca tccgcacgta cccgatccca accaagtccc   2580
agctcacgag ggagatctac accgacccga tcatctcgcc gggcgcccag gccggctaca   2640
ccctgcagga cgtcctgagg gagccccacc tgatggactt cctgaacagg ctcatcatct   2700
acaccggcga gtacaggggc atcaggcact gggcgggcca cgaggtggag tccagcagga   2760
cgggcatgat gaccaacatc cgcttcccgc tctacggcac cgcggccacg gccgagccaa   2820
cccgcttcat cacgccgtcc accttccccg gcctgaacct cttctacagg accctgtcgg   2880
ctcccatctt ccgcgacgag ccgggcgcga acatcatcat ccgctacagg acctccctcg   2940
tggagggcgt cggcttcatc cagccgaaca acggcgagca gctgtaccgc gtgaggggca   3000
cgctggacag cctggaccag ctcccactgg agggcgagtc cagcctcacc gagtactcgc   3060
acaggctgtg ccacgtcagg ttcgcccaga gcctcaggaa cgcggagccc ctggactacg   3120
ccagggtgcc catgttcagc tggacccaca ggtcggctac ccccaccaac accatcgacc   3180
```

cagacgtgat cacgcagatc ccgctcgtca aggcccacac cctgcagtcg ggcaccaccg 3240
tggtcaaggg ccccggcttc acgggcggcg acatcctgag gaggacctcc ggcggcccat 3300
tcgccttcag caacgtcaac ctcgactgga acctgtccca gcgctacagg gcgcgcatca 3360
ggtacgccag caccacgaac ctgcgcatgt atgtgaccat cgcgggcgag aggatcttcg 3420
ccggccagtt caacaagacg atgaacaccg gcgacccgct caccttccag tccttcagct 3480
acgcgacgat cgacaccgcc ttcacgttcc ccacgaaggc ctccagcctg accgtgggcg 3540
ccgacacctt ctccagcggc aacgaggtct acgtggaccg cttcgagctg atcccggtga 3600
cggcgacctt cgaggccgag tacgacctgg agaaggccca gaaggcggtc aacgccctct 3660
tcacctccag caaccagatc ggcctgaaga cggacgtgac cgactaccac atcgacaagg 3720
tgtccaacct cgtcgagtgc ctgagcgacg agttctgcct cgacgagaag agggagctgt 3780
ccgagaaggt caagcacgcc aagcgcctct gcgacgagag gaacctcctg caggacccga 3840
acttcagggg aatcaaccgc cagccggaca ggggctggag gggcagcacc gacatcacca 3900
tccagggcgg cgacgacgtg ttcaaggaga actacgtcac gctcccgggc accttcgacg 3960
agtgctaccc cacgtacctg taccagaaga tcgacgagtc caagctcaag gcctacaccc 4020
gctacgagct gaggggatac atcgaggaca gccaggacct cgagatctac ctgatccgct 4080
acaacgcgaa gcacgagacg gtgaacgtcc ccggcacggg ctccctgtgg cccctctcgg 4140
ctcagtcgcc gatcggcaag tgcggcgagc ccaacaggtg cgccacccac ctcgagtgga 4200
acccggacct ggactgctcc tgccgggacg gcgagaagtg cgctcaccac tcccaccact 4260
tcagcctgga catcgacgtg ggctgcacgg acctcaacga ggacctgggc gtgtgggtca 4320
tcttcaaaat caagacgcag gacggccacg ctaggctggg caacctcgag ttcctggagg 4380
agaagccgct ggtgggcgag gctctggcca gggtcaagag ggcggagaag aagtggcgcg 4440
acaagaggga gaagctggag ctggagacga acatcgtcta caaggaggcc aagaagtccg 4500
tggacgcgct cttcgtcaac agccagtacg acaggctgca ggcggacacc aacatcgcca 4560
tcatccacgc cgcggacaag cgcgtgcact ccatcaggga ggcctacctc cccgagctga 4620
gcgtgatccc gggcgtcaac gctgccatct tcgaggagct ggagggccgc atcttcaccg 4680
cctactccct gtacgacgcg aggaacgtca tcaagaacgg cgacttcaac aacggcctca 4740
gctgctggaa cgtgaagggc cacgtggacg tcgaggagca gaacaaccac cgctcggtgc 4800
tggtggtccc cgagtgggag gctgaggtca gccaggaggt gcgcgtctgc ccgggcaggg 4860
gatacatcct ccgcgtgacc gcgtacaagg agggctacgg cgagggctgc gtcacgatcc 4920
acgagatcga ggacaacacc gacgagctga agttctccaa ctgcgtggag gaggagatct 4980
acccgaacaa cacggtcacc tgcaacgact acacggccac ccaggaggag tacgagggca 5040
cgtacacgtc gaggaacagg ggctacgacg gcgcttacga gtccaacagc tcggtgccgg 5100
ccgactacgc tagcgcgtac gaggagaagg cctacacgga cggccgcagg gacaacacct 5160
gcgagtcgaa caggggctac ggcgactaca cgccgctccc ggccggctac gtgaccaagg 5220
agctggagta cttcccggag acggacaagg tctggatcga gatcggcgag acggagggca 5280
ccttcatcgt ggactcagtc gagctgctgc tcatggagga gtaggagctc gccaacagtc 5340
gttgaagctg ctgctgtatc tgggttatct agtgtctctg cctttgccca aggatagtgc 5400
tgtctttcaa agtatttgta tcgtttgtgt cgtgagtcgt gactgagctg gtttcaagga 5460
ccagttgtgt tctcgttacc caaaactatc gtgcgaccgc atatggctta atcatgaata 5520
aatgttgttt gaatttaaac tattcgctga atattgttgt tttttgtcat gtcagttaat 5580
gttactaaat tggttgcctt ctaatttttg tttactggtg tttgtcgcac cttatctttt 5640
tactgtatgt ttacttcagg ttctggcagt ctcatttttt gtgactagtt aaaacttaca 5700
gctaaaaaaa tgcagttttt aattttaatt tgaagtttga ttagagctat tgatacccgg 5760
accatcaggt taggttagtt gtgcatagaa tcataaatat taatcatgtt ttctatgaat 5820
taagtcaaac ttgaaagtct ggctgaatat agtttctatg aatcatattg atatacatgt 5880
ttgattattt gttttgctat tagctattta ctttggtgaa tctatatagg cttatgcaga 5940
accttttttt ttgttctata tatccatatc ctagtactca gtagctctat gttttctgga 6000
gactagtggc ttgctttttc gtatgtctaa ttttttgctt gaccattgca aaacaaaaat 6060
tacctagtgt aatctctttt tataataatc ttgtaatgcg tctacctata ggtcaaagta 6120
ggttttgttt ggaaccctta gagctaactg ttagctagtt gataaattat tagctgagtt 6180
aagctagcta atgaactagt tttgatatta gctgaggatg tttgaaacct aataattatt 6240
ttttattagc taactatact aaattttagt agagagattc caaacaggag ttaacatggg 6300
atcagattgg ctatgcgttt gcaatcccat actaattagc taacggaccg ctaattagct 6360
aacgatcgct taattaagct tgcatgcctg cagtgcagcg tgacccggtc gtgcccctct 6420
ctagagataa tgagcattgc atgtctaagt tataaaaaat taccacatat ttttttgtc 6480 acacttgttt gaagtgcagt ttatctatct ttatacatat atttaaactt tactctacga 6540
ataatataat ctatagtact acaataatat cagtgtttta gagaatcata taaatgaaca 6600
gttagacatg gtctaaagga caattgagta ttttgacaac aggactctac agttttatct 6660
ttttagtgtg catgtgttct cctttttttt tgcaaatagc ttcacctata taatacttca 6720
tccattttat tagtacatcc atttagggtt tagggttaat ggtttttata gactaatttt 6780
tttagtacat ctattttatt ctattttagc ctctaaatta agaaaactaa aactctattt 6840 tagtttttt atttaataat ttagatataa aatagaataa aataaagtga ctaaaaatta 6900
aacaaatacc ctttaagaaa ttaaaaaaac taaggaaaca tttttcttgt ttcgagtaga 6960
taatgccagc ctgttaaacg ccgccgacga gtctaacgga caccaaccag cgaaccagca 7020
gcgtcgcgtc gggccaagcg aagcagacgg cacggcatct ctgtcgctgc ctctggaccc 7080
ctctcgagag ttccgctcca ccgttggact tgctccgctg tcggcatcca gaaattgcgt 7140
ggcggagcgg cagacgtgag ccggcacggc aggcggcctc ctcctcctct cacggcaccg 7200
gcagctacgg gggattcctt tcccaccgct ccttcgcttt cccttcctcg cccgccgtaa 7260
taaatagaca ccccctccac accctctttc cccaacctcg tgttgttcgg agcgcacaca 7320
cacacaacca gatctccccc aaatccaccc gtcggcacct ccgcttcaag gtacgccgct 7380
cgtcctcccc cccccccct ctctaccttc tctagatcgg cgttccggtc catagttagg 7440
gcccggtagt tctacttctg ttcatgtttg tgttagatcc gtgtttgtgt tagatccgtg 7500
ctgttagcgt tcgtacacgg atgcgacctg tacgtcagac acgttctgat tgctaacttg 7560
ccagtgtttc tctttgggga atcctgggat ggctctagcc gttccgcaga cgggatcgat 7620
ttcatgattt tttttgtttc gttgcatagg gtttggtttg cccttttcct ttatttcaat 7680
atatgccgtg cacttgtttg tcgggtcatc ttttcatgct tttttttgtc ttggttgtga 7740
tgatgtggtc tggttgggcg gtcgttctag atcggagtag aattctgttt caaactacct 7800
ggtggattta ttaattttgg atctgtatgt gtgtgccata catattcata gttacgaatt 7860
gaagatgatg gatggaaata tcgatctagg ataggtatac atgttgatgc gggttttact 7920

```
gatgcatata cagagatgct ttttgttcgc ttggttgtga tgatgtggtg tggttgggcg   7980
gtcgttcatt cgttctagat cggagtagaa tactgtttca aactacctgg tgtatttatt   8040
aattttggaa ctgtatgtgt gtgtcataca tcttcatagt tacgagttta agatggatgg   8100
aaatatcgat ctaggatagg tatacatgtt gatgtgggtt ttactgatgc atatacatga   8160
tggcatatgc agcatctatt catatgctct aaccttgagt acctatctat tataataaac   8220
aagtatgttt tataattatt ttgatcttga tatacttgga tgatggcata tccagcagct   8280
atatctggat ttttttagcc ctgccttcat acgctattta tttgcttggt actgtttctt   8340
ttgtcgttgc tcaccctgtt gtttggtgtt acttctgcag ggatctccga tcatgcaaaa   8400
actcattaac tcagtgcaaa actatgcctg gggcagcaaa acggcgttga ctgaacttta   8460
cggtatggaa aatccgtcca gccagccgat ggccgagctg tggatgggcg cacatccgaa   8520
aagcagttca cgagtgcaga atgccgccgg agatatcgtt tcactgcgtg atgtgattga   8580
gagtgataaa tcgactctgc tcggagaggc cgttgccaaa cgctttggcg aactgccttt   8640
cctgttcaaa gtattgtgcg cagcacagcc actctccatt caggttcatc caaacaaaca   8700
caattctgaa atcggttttg ccaaagaaaa tgccgcaggt atcccgatgg atgccgccga   8760
gcgtaactat aaagatccta accacaagcc ggagctggtt tttgcgctga cgcctttcct   8820
tgcgatgaac gcgtttcgtg aattttccga gattgtctcc ctactccagc cggtcgcagg   8880
tgcacatccg gcgattgctc actttttaca acagcctgat gccgaacgtt taagcgaact   8940
gttcgccagc ctgttgaata tgcagggtga agaaaaatcc cgcgcgctgg cgattttaaa   9000
atcggccctc gatagccagc agggtgaacc gtggcaaacg attcgtttaa tttctgaatt   9060
ttacccggaa gacagcggtc tgttctcccc gctattgctg aatgtggtga aattgaaccc   9120
tggcgaagcg atgttcctgt tcgctgaaac accgcacgct tacctgcaag gcgtggcgct   9180
ggaagtgatg gcaaactccg ataacgtgct gcgtgcgggt ctgacgccta aatacattga   9240
tattccggaa ctggttgcca atgtgaaatt cgaagccaaa ccggctaacc agttgttgac   9300
ccagccggtg aaacaaggtg cagaactgga cttcccgatt ccagtggacg attttgcctt   9360
ctcgctgcac gaccttagtg ataaagaaac caccattagc cagcagagtg ccgccatttt   9420
gttctgcgtc gaaggcgatg caacgttgtg gaaaggttct cagcagttac agcttaaacc   9480
gggtgaatca gcgtttattg ccgccaacga atcaccggtg actgtcaaag gccacggccg   9540
tttagcgcgt gtttacaaca agctgtaaga gcttactgaa aaaattaaca tctcttgcta   9600
agctgggtca tgggtcgttt aagctgccga tgtgcctgcg tcgtctggtg ccctctctcc   9660
atatggaggt tgtcaaagta tctgctgttc gtgtcatgag tcgtgtcagt gttggtttaa   9720
taatggaccg gttgtgttgt gtgtgcgtac tacccagaac tatgacaaat catgaataag   9780
tttgatgttt gaaattaaag cctgtgctca ttatgttctg tctttcagtt gtctcctaat   9840
atttgcctcc aggtactggc tatctaccgt ttcttactta ggaggtgttt gaatgcacta   9900
aaactaatag ttagtggcta aaattagtta aaacatccaa acaccatagc taatagttga   9960
actattagct atttttggaa aattagttaa tagtgaggta gttatttgtt agctagctaa  10020
ttcaactaac aatttttagc caactaacaa ttagtttcag tgcattcaaa caccccctta  10080
atgttaacgt ggttctatct accgtctcct aatatatggt tgattgttcg gtttgttgct  10140
atgctattgg gttctgattg ctgctagttc ttgctgaatc cagaagttct cgtagtatag  10200
ctcagattca tattatttat ttgagtgata agtgatccag gttattacta tgttagctag  10260
```

```
gttttttttta caaggataaa ttatctgtga tcataattct tatgaaagct ttatgtttcc  10320

tggaggcagt ggcatgcaat gcatgacagc aacttgatca caccagctga ggtagatacg  10380

gtaacaaggt tcttaaatct gttcaccaaa tcattggaga acacacatac acattcttgc  10440

cagtcttggt tagagaaatt tcatgacaaa atgccaaagc tgtcttgact cttcactttt  10500

ggccatgagt cgtgacttag tttggtttaa tggaccggtt ctcctagctt gttctactca  10560

aaactgttgt tgatgcgaat aagttgtgat ggttgatctc tggattttgt tttgctctca  10620

atagtggacg agattagata g                                            10641
```

<210> SEQ ID NO 30
<211> LENGTH: 10639
<212> TYPE: DNA
<213> ORGANISM: Artificial sequence
<220> FEATURE:
<223> OTHER INFORMATION: Synthetic polynucleotide

<400> SEQUENCE: 30

```
gaattcatta tgtggtctag gtaggttcta tatataagaa aacttgaaat gttctaaaaa     60

aaaattcaag cccatgcatg attgaagcaa acggtatagc aacggtgtta acctgatcta    120

gtgatctctt gcaatcctta acggccacct accgcaggta gcaaacggcg tccccctcct    180

cgatatctcc gcggcgacct ctggcttttt ccgcggaatt gcgcggtggg gacggattcc    240

acgagaccgc gacgcaaccg cctctcgccg ctgggcccca caccgctcgg tgccgtagcc    300

tcacgggact ctttctccct cctcccccgt tataaattgg cttcatccct ccttgcctca    360

tccatccaaa tcccagtccc caatcccatc ccttcgtagg agaaattcat cgaagctaag    420

cgaatcctcg cgatcctctc aaggtactgc gagttttcga tccccctctc gacccctcgt    480

atgtttgtgt ttgtcgtagc gtttgattag gtatgctttc cctgtttgtg ttcgtcgtag    540

cgtttgatta ggtatgcttt ccctgttcgt gttcatcgta gtgtttgatt aggtcgtgtg    600

aggcgatggc ctgctcgcgt ccttcgatct gtagtcgatt tgcgggtcgt ggtgtagatc    660

tgcgggctgt gatgaagtta tttggtgtga tctgctcgcc tgattctgcg ggttggctcg    720

agtagatatg atggttggac cggttggttc gtttaccgcg ctagggttgg gctgggatga    780

tgttgcatgc gccgttgcgc gtgatcccgc agcaggactt gcgtttgatt gccagatctc    840

gttacgatta tgtgatttgg tttggacttt ttagatctgt agcttctgct tatgtgccag    900

atgcgcctac tgctcatatg cctgatgata atcataaatg gctgtggaac taactagttg    960

attgcggagt catgtatcag ctacaggtgt agggactagc tacaggtgta gggacttgcg   1020

tctaattgtt tggtccttta ctcatgttgc aattatgcaa tttagtttag attgtttgtt   1080

ccactcatct aggctgtaaa agggacactg cttagattgc tgtttaatct ttttagtaga   1140

ttatattata ttggtaactt attacccccta ttacatgcca tacgtgactt ctgctcatgc  1200

ctgatgataa tcatagatca ctgtggaatt aattagttga ttgttgaatc atgtttcatg   1260

tacataccac ggcacaattg cttagttcct taacaaatgc aaattttact gatccatgta   1320

tgatttgcgt ggttctctaa tgtgaaatac tatagctact tgttagtaag aatcaggttc   1380

gtatgcttaa tgctgtatgt gccttctgct catgcctgat gataatcata tatcactgga   1440

attaattagt tgatcgttta atcatatatc aagtacatac catgccacaa tttttagtca   1500

cttaacccat gcagattgaa ctggtccctg catgttttgc taaattgttc tattctgatt   1560

agaccatata tcatgtattt tttttttggt aatggttctc ttattttaaa tgctatatag   1620

ttctggtact tgttagaaag atctgcttca tagtttagtt gcctatccct cgaattagga   1680
```

```
tgctgagcag ctgatcctat agctttgttt catgtatcaa ttcttttgtg ttcaacagtc   1740
agtttttgtt agattcattg taacttatgg tcgcttactc ttctggtcct caatgcttgc   1800
agggatccta aaccatggag atcaacaacc agaaccagtg cgtgccgtac aactgcctta   1860
acaaccccga gtccgagatc ctgaacgtgg ccatcttctc cagcgagcag gtcgcggaga   1920
tccacctcaa gatcacgcgc ctgatcctcg agaacttcct gccgggcggc tccttcgctt   1980
tcggcctgtt cgacctcatc tggggcatct tcaacgagga ccagtggagc gcgttcctca   2040
ggcaggtgga ggagctgatc aaccagcgca tcacggagtt cgccaggggc caggctatcc   2100
agcggctggt gggcttcggc aggtcctacg acgagtacat cctggccctc aaggagtggg   2160
agaacgaccc cgacaacccg gccagcaagg agcgcgtgag gacccgcttc aggaccaccg   2220
acgacgctct cctgacgggc gtccccctca tggctatccc gggcttcgag ctggccaccc   2280
tctcggtgta cgctcagtcg gccaacctgc acctcgccct cctgcgggac gctgtgttct   2340
tcggcgagag gtggggcctg acccagacga acatcaacga cctctactcc aggctgaaga   2400
acagcatccg cgactacacg aaccactgcg tgcgcttcta caacatcggc ctgggcaacc   2460
tcaacgtcat caggccggag tactaccgct tccagaggga gctgaccatc agcgtgctgg   2520
acctcgtcgc cctgttcccc aactacgaca tccgcacgta cccgatccca accaagtccc   2580
agctcacgag ggagatctac accgacccga tcatctcgcc gggcgcccag gccggctaca   2640
ccctgcagga cgtcctgagg gagccccacc tgatggactt cctgaacagg ctcatcatct   2700
acaccggcga gtacaggggc atcaggcact gggcgggcca cgaggtggag tccagcagga   2760
cgggcatgat gaccaacatc cgcttcccgc tctacggcac cgcggccacg gccgagccaa   2820
cccgcttcat cacgccgtcc accttccccg gcctgaacct cttctacagg accctgtcgg   2880
ctcccatctt ccgcgacgag ccgggcgcga acatcatcat ccgctacagg acctccctcg   2940
tggagggcgt cggcttcatc cagccgaaca acggcgagca gctgtaccgc gtgaggggca   3000
cgctggacag cctggaccag ctcccactgg agggcgagtc cagcctcacc gagtactcgc   3060
acaggctgtg ccacgtcagg ttcgcccaga gcctcaggaa cgcggagccc ctggactacg   3120
ccagggtgcc catgttcagc tggacccaca ggtcggctac cccccaccaac accatcgacc   3180
cagacgtgat cacgcagatc ccgctcgtca aggcccacac cctgcagtcg ggcaccaccg   3240
tggtcaaggg ccccggcttc acgggcggcg acatcctgag gaggacctcc ggcggcccat   3300
tcgccttcag caacgtcaac ctcgactgga acctgtccca gcgctacagg gcgcgcatca   3360
ggtacgccag caccacgaac ctgcgcatgt atgtgaccat cgcgggcgag aggatcttcg   3420
ccggccagtt caacaagacg atgaacaccg gcgacccgct caccttccag tccttcagct   3480
acgcgacgat cgacaccgcc ttcacgttcc ccacgaaggc ctccagcctg accgtgggcg   3540
ccgacacctt ctccagcggc aacgaggtct acgtggaccg cttcgagctg atcccggtga   3600
cggcgacctt cgaggccgag tacgacctgg agaaggccca gaaggcggtc aacgccctct   3660
tcacctccag caaccagatc ggcctgaaga cggacgtgac cgactaccac atcgacaagg   3720
tgtccaacct cgtcgagtgc ctgagcgacg agttctgcct cgacgagaag agggagctgt   3780
ccgagaaggt caagcacgcc aagcgcctct gcgacgagag gaacctcctg caggacccga   3840
acttcagggg aatcaaccgc cagccggaca ggggctggag gggcagcacc gacatcacca   3900
tccagggcgg cgacgacgtg ttcaaggaga actacgtcac gctcccgggc accttcgacg   3960
agtgctaccc cacgtacctg taccagaaga tcgacgagtc caagctcaag gcctacaccc   4020
```

gctacgagct gaggggatac atcgaggaca gccaggacct cgagatctac ctgatccgct 4080
acaacgcgaa gcacgagacg gtgaacgtcc ccggcacggg ctccctgtgg cccctctcgg 4140
ctcagtcgcc gatcggcaag tgcggcgagc ccaacaggtg cgccacccac ctcgagtgga 4200
acccggacct ggactgctcc tgccgggacg gcgagaagtg cgctcaccac tcccaccact 4260
tcagcctgga catcgacgtg ggctgcacgg acctcaacga ggacctgggc gtgtgggtca 4320
tcttcaaaat caagacgcag gacggccacg ctaggctggg caacctcgag ttcctggagg 4380
agaagccgct ggtgggcgag gctctggcca gggtcaagag ggcggagaag aagtggcgcg 4440
acaagaggga gaagctggag ctggagacga acatcgtcta caaggaggcc aagaagtccg 4500
tggacgcgct cttcgtcaac agccagtacg acaggctgca ggcggacacc aacatcgcca 4560
tcatccacgc cgcggacaag cgcgtgcact ccatcaggga ggcctacctc cccgagctga 4620
gcgtgatccc gggcgtcaac gctgccatct tcgaggagct ggagggccgc atcttcaccg 4680
cctactccct gtacgacgcg aggaacgtca tcaagaacgg cgacttcaac aacggcctca 4740
gctgctggaa cgtgaagggc cacgtggacg tcgaggagca gaacaaccac cgctcggtgc 4800
tggtggtccc cgagtgggag gctgaggtca gccaggaggt gcgcgtctgc ccgggcaggg 4860
gatacatcct ccgcgtgacc gcgtacaagg agggctacgg cgagggctgc gtcacgatcc 4920
acgagatcga ggacaacacc gacgagctga agttctccaa ctgcgtggag gaggagatct 4980
acccgaacaa cacggtcacc tgcaacgact acacggccac ccaggaggag tacgagggca 5040
cgtacacgtc gaggaacagg ggctacgacg gcgcttacga gtccaacagc tcggtgccgg 5100
ccgactacgc tagcgcgtac gaggagaagg cctacacgga cggccgcagg gacaacacct 5160
gcgagtcgaa caggggctac ggcgactaca cgccgctccc ggccggctac gtgaccaagg 5220
agctggagta cttcccggag acggacaagg tctggatcga gatcggcgag acggagggca 5280
ccttcatcgt ggactcagtc gagctgctgc tcatggagga gtaggagctc gccaacagtc 5340
gttgaagctg ctgctgtatc tgggttatct agtgtctctg cctttgccca aggatagtgc 5400
tgtctttcaa agtatttgta tcgtttgtgt cgtgagtcgt gactgagctg gtttcaagga 5460
ccagttgtgt tctcgttacc caaaactatc gtgcgaccgc atatggctta atcatgaata 5520
aatgttgttt gaatttaaac tattcgctga atattgttgt tttttgtcat gtcagttaat 5580
gttactaaat tggttgcctt ctaatttttg tttactggtg tttgtcgcac cttatctttt 5640
tactgtatgt ttacttcagg ttctggcagt ctcatttttt gtgactagtt aaaacttaca 5700
gctaaaaaaa tgcagttttt aattttaatt tgaagtttga ttagagctat tgatacccgg 5760
accatcaggt taggttagtt gtgcatagaa tcataaatat taatcatgtt ttctatgaat 5820
taagtcaaac ttgaaagtct ggctgaatat agtttctatg aatcatattg atatacatgt 5880
ttgattattt gttttgctat tagctattta ctttggtgaa tctatatagg cttatgcaga 5940
accttttttt ttgttctata tatccatatc ctagtactca gtagctctat gttttctgga 6000
gactagtggc ttgctttttc gtatgtctaa ttttttgctt gaccattgca aaacaaaaat 6060
tacctagtgt aatctctttt tataataatc ttgtaatgcg tctacctata ggtcaaagta 6120
ggttttgttt ggaaccctta gagctaactg ttagctagtt gataaattat tagctgagtt 6180
aagctagcta atgaactagt tttgatatta gctgaggatg tttgaaacct aataattatt 6240
ttttattagc taactatact aaattttagt agagagattc caaacaggag ttaacatggg 6300
atcagattgg ctatgcgttt gcaatcccat actaattagc taacggaccg ctaattagct 6360
aacgatcgct taattaagct tgcatgcctg cagtgcagcg tgacccggtc gtgcccctct 6420

```
ctagagataa tgagcattgc atgtctaagt tataaaaaat taccacatat tttttttgtc   6480
acacttgttt gaagtgcagt ttatctatct ttatacatat atttaaactt tactctacga   6540
ataatataat ctatagtact acaataatat cagtgtttta gagaatcata taaatgaaca   6600
gttagacatg gtctaaagga caattgagta ttttgacaac aggactctac agttttatct   6660
ttttagtgtg catgtgttct cctttttttt tgcaaatagc ttcacctata taatacttca   6720
tccattttat tagtacatcc atttagggtt tagggttaat ggtttttata gactaatttt   6780
tttagtacat ctattttatt ctattttagc ctctaaatta agaaaactaa aactctattt   6840
tagttttttt atttaataat ttagatataa aatagaataa aataaagtga ctaaaaatta   6900
aacaaatacc ctttaagaaa ttaaaaaaac taaggaaaca tttttcttgt ttcgagtaga   6960
taatgccagc ctgttaaacg ccgccgacga gtctaacgga caccaaccag cgaaccagca   7020
gcgtcgcgtc gggccaagcg aagcagacgg cacggcatct ctgtcgctgc ctctggaccc   7080
ctctcgagag ttccgctcca ccgttggact tgctccgctg tcggcatcca gaaattgcgt   7140
ggcggagcgg cagacgtgag ccggcacggc aggcggcctc ctcctcctct cacggcaccg   7200
gcagctacgg gggattcctt tcccaccgct ccttcgcttt cccttcctcg cccgccgtaa   7260
taaatagaca ccccctccac accctctttc cccaacctcg tgttgttcgg agcgcacaca   7320
cacacaacca gatctccccc aaatccaccc gtcggcacct ccgcttcaag gtacgccgct   7380
cgtcctcccc cccccccccc tctctacctt ctctagatcg gcgttccggt ccatagttag   7440
ggcccggtag ttctacttct gttcatgttt gtgttagatc cgtgtttgtg ttagatccgt   7500
gctgttagcg ttcgtacacg gatgcgacct gtacgtcaga cacgttctga ttgctaactt   7560
gccagtgttt ctctttgggg aatcctggga tggctctagc cgttccgcag acgggatcga   7620
tttcatgatt ttttttgttt cgttgcatag ggtttggttt gccctttttcc tttatttcaa   7680
tatatgccgt gcacttgttt gtcgggtcat cttttcatgc ttttttttgtc ttggttgtga   7740
tgatgtggtc tggttgggcg gtcgttctag atcggagtag aattctgttt caaactacct   7800
ggtggattta ttaattttgg atctgtatgt gtgtgccata catattcata gttacgaatt   7860
gaagatgatg gatggaaata tcgatctagg ataggtatac atgttgatgc gggttttact   7920
gatgcatata cagagatgct tttgttcgc ttggttgtga tgatgtggtg tggttgggcg    7980
gtcgttcatt cgttctagat cggagtagaa tactgtttca aactacctgg tgtatttatt   8040
aattttggaa ctgtatgtgt gtgtcataca tcttcatagt tacgagttta agatggatgg   8100
aaatatcgat ctaggatagg tatacatgtt gatgtgggtt ttactgatgc atatacatga   8160
tggcatatgc agcatctatt catatgctct aaccttgagt acctatctat tataataaac   8220
aagtatgttt tataattatt ttgatcttga tatacttgga tgatggcata tccagcagct   8280
atatctggat ttttttagcc ctgccttcat acgctattta tttgcttggt actgtttctt   8340
ttgtcgttgc tcaccctgtt gtttggtgtt acttctgcag ggatctccga tcatgcaaaa   8400
actcattaac tcagtgcaaa actatgcctg gggcagcaaa acggcgttga ctgaacttta   8460
cggtatggaa aatccgtcca gccagccgat ggccgagctg tggatgggcg cacatccgaa   8520
aagcagttca cgagtgcaga atgccgccgg agatatcgtt tcactgcgtg atgtgattga   8580
gagtgataaa tcgactctgc tcggagaggc cgttgccaaa cgctttggcg aactgccttt   8640
cctgttcaaa gtattgtgcg cagcacagcc actctccatt caggttcatc caaacaaaca   8700
caattctgaa atcggttttg ccaaagaaaa tgccgcaggt atcccgatgg atgccgccga   8760
```

```
gcgtaactat aaagatccta accacaagcc ggagctggtt tttgcgctga cgcctttcct   8820

tgcgatgaac gcgtttcgtg aattttccga gattgtctcc ctactccagc ggtcgcaggt   8880

gcacatccgg cgattgctca ctttttacaa cagcctgatg ccgaacgttt aagcgaactg   8940

ttcgccagcc tgttgaatat gcagggtgaa gaaaaatccc gcgcgctggc gattttaaaa   9000

tcggccctcg atagccagca gggtgaaccg tggcaaacga ttcgtttaat ttctgaattt   9060

taccggaaga cagcggtctg ttctccccgc tattgctgaa tgtggtgaaa ttgaaccctg   9120

gcgaagcgat gttcctgttc gctgaaacac cgcacgctta cctgcaaggc gtggcgctgg   9180

aagtgatggc aaactccgat aacgtgctgc gtgcgggtct gacgcctaaa tacattgata   9240

ttccggaact ggttgccaat gtgaaattcg aagccaaacc ggctaaccag ttgttgaccc   9300

agccggtgaa acaaggtgca gaactggact tcccgattcc agtggacgat tttgccttct   9360

cgctgcacga ccttagtgat aaagaaacca ccattagcca gcagagtgcc gccattttgt   9420

tctgcgtcga aggcgatgca acgttgtgga aaggttctca gcagttacag cttaaaccgg   9480

gtgaatcagc gtttattgcc gccaacgaat caccggtgac tgtcaaaggc cacggccgtt   9540

tagcgcgtgt ttacaacaag ctgtaagagc ttactgaaaa aattaacatc tcttgctaag   9600

ctgggtcatg ggtcgtttaa gctgccgatg tgcctgcgtc gtctggtgcc ctctctccat   9660

atggaggttg tcaaagtatc tgctgttcgt gtcatgagtc gtgtcagtgt tggtttaata   9720

atggaccggt tgtgttgtgt gtgcgtacta cccagaacta tgacaaatca tgaataagtt   9780

tgatgtttga aattaaagcc tgtgctcatt atgttctgtc tttcagttgt ctcctaatat   9840

ttgcctccag gtactggcta tctaccgttt cttacttagg aggtgtttga atgcactaaa   9900

actaatagtt agtggctaaa attagttaaa acatccaaac accatagcta atagttgaac   9960

tattagctat ttttggaaaa ttagttaata gtgaggtagt tatttgttag ctagctaatt  10020

caactaacaa tttttagcca actaacaatt agtttcagtg cattcaaaca ccccccttaat  10080

gttaacgtgg ttctatctac cgtctcctaa tatatggttg attgttcggt ttgttgctat  10140

gctattgggt tctgattgct gctagttctt gctgaatcca gaagttctcg tagtatagct  10200

cagattcata ttatttattt gagtgataag tgatccaggt tattactatg ttagctaggt  10260

ttttttttaca aggataaatt atctgtgatc ataattctta tgaaagcttt atgtttcctg  10320

gaggcagtgg catgcaatgc atgacagcaa cttgatcaca ccagctgagg tagatacggt  10380

aacaaggttc ttaaatctgt tcaccaaatc attggagaac acacatacac attcttgcca  10440

gtcttggtta gagaaatttc atgacaaaat gccaaagctg tcttgactct tcacttttgg  10500

ccatgagtcg tgacttagtt tggtttaatg gaccggttct cctagcttgt tctactcaaa  10560

actgttgttg atgcgaataa gttgtgatgg ttgatctctg gattttgttt tgctctcaat  10620

agtggacgag attagatag                                                10639
```

<210> SEQ ID NO 31
<211> LENGTH: 10643
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<222> LOCATION: (347)..(347)
<223> OTHER INFORMATION: n is c or absent
<220> FEATURE:
<221> NAME/KEY: misc_feature
<222> LOCATION: (1579)..(1579)
<223> OTHER INFORMATION: n is t or absent
<220> FEATURE:
<221> NAME/KEY: misc_feature
<222> LOCATION: (7388)..(7388)
<223> OTHER INFORMATION: n is c or absent
<220> FEATURE:
<221> NAME/KEY: misc_feature
<222> LOCATION: (7722)..(7722)
<223> OTHER INFORMATION: n is t or absent
<220> FEATURE:
<221> NAME/KEY: misc_feature
<222> LOCATION: (8872)..(8872)
<223> OTHER INFORMATION: n is c or absent
<220> FEATURE:
<221> NAME/KEY: misc_feature
<222> LOCATION: (9066)..(9066)
<223> OTHER INFORMATION: n is c or absent

<400> SEQUENCE: 31
gaattcatta tgtggtctag gtaggttcta tatataagaa aacttgaaat gttctaaaaa 60
aaaattcaag cccatgcatg attgaagcaa acggtatagc aacggtgtta acctgatcta 120
gtgatctctt gcaatcctta acggccacct accgcaggta gcaaacggcg tccccctcct 180
cgatatctcc gcggcgacct ctggcttttt ccgcggaatt gcgcggtggg gacggattcc 240
acgagaccgc gacgcaaccg cctctcgccg ctgggcccca caccgctcgg tgccgtagcc 300
tcacgggact ctttctccct cctcccccgt tataaattgg cttcatnccc tccttgcctc 360
atccatccaa atcccagtcc ccaatcccat cccttcgtag gagaaattca tcgaagctaa 420
gcgaatcctc gcgatcctct caaggtactg cgagttttcg atccccctct cgacccctcg 480
tatgtttgtg tttgtcgtag cgtttgatta ggtatgcttt ccctgtttgt gttcgtcgta 540
gcgtttgatt aggtatgctt tccctgttcg tgttcatcgt agtgtttgat taggtcgtgt 600
gaggcgatgg cctgctcgcg tccttcgatc tgtagtcgat ttgcgggtcg tggtgtagat 660
ctgcgggctg tgatgaagtt atttggtgtg atctgctcgc ctgattctgc gggttggctc 720
gagtagatat gatggttgga ccggttggtt cgtttaccgc gctagggttg ggctgggatg 780
atgttgcatg cgccgttgcg cgtgatcccg cagcaggact tgcgtttgat tgccagatct 840
cgttacgatt atgtgatttg gtttggactt tttagatctg tagcttctgc ttatgtgcca 900
gatgcgccta ctgctcatat gcctgatgat aatcataaat ggctgtggaa ctaactagtt 960
gattgcggag tcatgtatca gctacaggtg tagggactag ctacaggtgt agggacttgc 1020
gtctaattgt ttggtccttt actcatgttg caattatgca atttagttta gattgtttgt 1080
tccactcatc taggctgtaa aagggacact gcttagattg ctgtttaatc tttttagtag 1140
attatattat attggtaact tattacccct attacatgcc atacgtgact tctgctcatg 1200
cctgatgata atcatagatc actgtggaat taattagttg attgttgaat catgtttcat 1260
gtacatacca cggcacaatt gcttagttcc ttaacaaatg caaattttac tgatccatgt 1320
atgatttgcg tggttctcta atgtgaaata ctatagctac ttgttagtaa gaatcaggtt 1380
cgtatgctta atgctgtatg tgccttctgc tcatgcctga tgataatcat atatcactgg 1440
aattaattag ttgatcgttt aatcatatat caagtacata ccatgccaca atttttagtc 1500
acttaaccca tgcagattga actggtccct gcatgttttg ctaaattgtt ctattctgat 1560
tagaccatat atcatgtant ttttttttgg taatggttct cttattttaa atgctatata 1620
gttctggtac ttgttagaaa gatctgcttc atagtttagt tgcctatccc tcgaattagg 1680
atgctgagca gctgatccta tagctttgtt tcatgtatca attcttttgt gttcaacagt 1740
cagtttttgt tagattcatt gtaacttatg gtcgcttact cttctggtcc tcaatgcttg 1800

```
cagggatcct aaaccatgga gatcaacaac cagaaccagt gcgtgccgta caactgcctt   1860
aacaaccccg agtccgagat cctgaacgtg gccatcttct ccagcgagca ggtcgcggag   1920
atccacctca agatcacgcg cctgatcctc gagaacttcc tgccgggcgg ctccttcgct   1980
ttcggcctgt tcgacctcat ctggggcatc ttcaacgagg accagtggag cgcgttcctc   2040
aggcaggtgg aggagctgat caaccagcgc atcacggagt tcgccagggg ccaggctatc   2100
cagcggctgg tgggcttcgg caggtcctac gacgagtaca tcctggccct caaggagtgg   2160
gagaacgacc ccgacaaccc ggccagcaag gagcgcgtga ggacccgctt caggaccacc   2220
gacgacgctc tcctgacggg cgtcccccctc atggctatcc cgggcttcga gctggccacc   2280
ctctcggtgt acgctcagtc ggccaacctg cacctcgccc tcctgcggga cgctgtgttc   2340
ttcggcgaga ggtggggcct gacccagacg aacatcaacg acctctactc caggctgaag   2400
aacagcatcc gcgactacac gaaccactgc gtgcgcttct acaacatcgg cctgggcaac   2460
ctcaacgtca tcaggccgga gtactaccgc ttccagaggg agctgaccat cagcgtgctg   2520
gacctcgtcg ccctgttccc caactacgac atccgcacgt acccgatccc aaccaagtcc   2580
cagctcacga gggagatcta caccgacccg atcatctcgc cgggcgccca ggccggctac   2640
accctgcagg acgtcctgag ggagccccac ctgatggact tcctgaacag gctcatcatc   2700
tacaccggcg agtacagggg catcaggcac tgggcgggcc acgaggtgga gtccagcagg   2760
acgggcatga tgaccaacat ccgcttcccg ctctacggca ccgcggccac ggccgagcca   2820
acccgcttca tcacgccgtc caccttcccc ggcctgaacc tcttctacag gaccctgtcg   2880
gctcccatct tccgcgacga gccgggcgcg aacatcatca tccgctacag gacctccctc   2940
gtggagggcg tcggcttcat ccagccgaac aacggcgagc agctgtaccg cgtgaggggc   3000
acgctggaca gcctggacca gctcccactg gagggcgagt ccagcctcac cgagtactcg   3060
cacaggctgt gccacgtcag gttcgcccag agcctcagga acgcggagcc cctggactac   3120
gccagggtgc ccatgttcag ctggacccac aggtcggcta cccccaccaa caccatcgac   3180
ccagacgtga tcacgcagat cccgctcgtc aaggcccaca ccctgcagtc gggcaccacc   3240
gtggtcaagg gccccggctt cacgggcggc gacatcctga ggaggacctc cggcggccca   3300
ttcgccttca gcaacgtcaa cctcgactgg aacctgtccc agcgctacag ggcgcgcatc   3360
aggtacgcca gcaccacgaa cctgcgcatg tatgtgacca tcgcgggcga gaggatcttc   3420
gccggccagt tcaacaagac gatgaacacc ggcgacccgc tcaccttcca gtccttcagc   3480
tacgcgacga tcgacaccgc cttcacgttc cccacgaagg cctccagcct gaccgtgggc   3540
gccgacacct tctccagcgg caacgaggtc tacgtggacc gcttcgagct gatcccggtg   3600
acggcgacct tcgaggccga gtacgacctg gagaaggccc agaaggcggt caacgccctc   3660
ttcacctcca gcaaccagat cggcctgaag acggacgtga ccgactacca catcgacaag   3720
gtgtccaacc tcgtcgagtg cctgagcgac gagttctgcc tcgacgagaa gagggagctg   3780
tccgagaagg tcaagcacgc caagcgcctc tgcgacgaga ggaacctcct gcaggacccg   3840
aacttcaggg gaatcaaccg ccagccggac aggggctgga ggggcagcac cgacatcacc   3900
atccagggcg gcgacgacgt gttcaaggag aactacgtca cgctcccggg caccttcgac   3960
gagtgctacc ccacgtacct gtaccagaag atcgacgagt ccaagctcaa ggcctacacc   4020
cgctacgagc tgaggggata catcgaggac agccaggacc tcgagatcta cctgatccgc   4080
tacaacgcga agcacgagac ggtgaacgtc cccggcacgg gctccctgtg gcccctctcg   4140
gctcagtcgc cgatcggcaa gtgcggcgag cccaacaggt gcgccaccca cctcgagtgg   4200
```

```
aacccggacc tggactgctc ctgccgggac ggcgagaagt gcgctcacca ctcccaccac   4260
ttcagcctgg acatcgacgt gggctgcacg gacctcaacg aggacctggg cgtgtgggtc   4320
atcttcaaaa tcaagacgca ggacggccac gctaggctgg gcaacctcga gttcctggag   4380
gagaagccgc tggtgggcga ggctctggcc agggtcaaga gggcggagaa gaagtggcgc   4440
gacaagaggg agaagctgga gctggagacg aacatcgtct acaaggaggc caagaagtcc   4500
gtggacgcgc tcttcgtcaa cagccagtac gacaggctgc aggcggacac caacatcgcc   4560
atcatccacg ccgcggacaa gcgcgtgcac tccatcaggg aggcctacct ccccgagctg   4620
agcgtgatcc cgggcgtcaa cgctgccatc ttcgaggagc tggagggccg catcttcacc   4680
gcctactccc tgtacgacgc gaggaacgtc atcaagaacg gcgacttcaa caacggcctc   4740
agctgctgga acgtgaaggg ccacgtggac gtcgaggagc agaacaacca ccgctcggtg   4800
ctggtggtcc ccgagtggga ggctgaggtc agccaggagg tgcgcgtctg cccgggcagg   4860
ggatacatcc tccgcgtgac cgcgtacaag gagggctacg gcgagggctg cgtcacgatc   4920
cacgagatcg aggacaacac cgacgagctg aagttctcca actgcgtgga ggaggagatc   4980
tacccgaaca acacggtcac ctgcaacgac tacacggcca cccaggagga gtacgagggc   5040
acgtacacgt cgaggaacag gggctacgac ggcgcttacg agtccaacag ctcggtgccg   5100
gccgactacg ctagcgcgta cgaggagaag gcctacacgg acggccgcag ggacaacacc   5160
tgcgagtcga acaggggcta cggcgactac acgccgctcc cggccggcta cgtgaccaag   5220
gagctggagt acttcccgga gacggacaag gtctggatcg agatcggcga gacggagggc   5280
accttcatcg tggactcagt cgagctgctg ctcatggagg agtaggagct cgccaacagt   5340
cgttgaagct gctgctgtat ctgggttatc tagtgtctct gcctttgccc aaggatagtg   5400
ctgtctttca aagtatttgt atcgtttgtg tcgtgagtcg tgactgagct ggtttcaagg   5460
accagttgtg ttctcgttac ccaaaactat cgtgcgaccg catatggctt aatcatgaat   5520
aaatgttgtt tgaatttaaa ctattcgctg aatattgttg tttttgtca tgtcagttaa   5580
tgttactaaa ttggttgcct tctaattttt gtttactggt gtttgtcgca ccttatcttt   5640
ttactgtatg tttacttcag gttctggcag tctcattttt tgtgactagt taaaacttac   5700
agctaaaaaa atgcagtttt taattttaat ttgaagtttg attagagcta ttgatacccg   5760
gaccatcagg ttaggttagt tgtgcataga atcataaata ttaatcatgt tttctatgaa   5820
ttaagtcaaa cttgaaagtc tggctgaata tagtttctat gaatcatatt gatatacatg   5880
tttgattatt tgttttgcta ttagctattt actttggtga atctatatag gcttatgcag   5940
aacctttttt tttgttctat atatccatat cctagtactc agtagctcta tgttttctgg   6000
agactagtgg cttgcttttt cgtatgtcta attttttgct tgaccattgc aaaacaaaaa   6060
ttacctagtg taatctcttt ttataataat cttgtaatgc gtctacctat aggtcaaagt   6120
aggttttgtt tggaaccctt agagctaact gttagctagt tgataaatta ttagctgagt   6180
taagctagct aatgaactag ttttgatatt agctgaggat gtttgaaacc taataattat   6240
tttttattag ctaactatac taaattttag tagagagatt ccaaacagga gttaacatgg   6300
gatcagattg gctatgcgtt tgcaatccca tactaattag ctaacggacc gctaattagc   6360
taacgatcgc ttaattaagc ttgcatgcct gcagtgcagc gtgacccggt cgtgcccctc   6420
tctagagata atgagcattg catgtctaag ttataaaaaa ttaccacata ttttttttgt   6480
cacacttgtt tgaagtgcag tttatctatc tttatacata tatttaaact ttactctacg   6540
```

```
aataatataa tctatagtac tacaataata tcagtgtttt agagaatcat ataaatgaac   6600
agttagacat ggtctaaagg acaattgagt attttgacaa caggactcta cagttttatc   6660
tttttagtgt gcatgtgttc tccttttttt ttgcaaatag cttcacctat ataatacttc   6720
atccatttta ttagtacatc catttagggt ttagggttaa tggtttttat agactaattt   6780
ttttagtaca tctattttat tctattttag cctctaaatt aagaaaacta aaactctatt   6840
ttagtttttt tatttaataa tttagatata aaatagaata aaataaagtg actaaaaatt   6900
aaacaaatac cctttaagaa attaaaaaaa ctaaggaaac atttttcttg tttcgagtag   6960
ataatgccag cctgttaaac gccgccgacg agtctaacgg acaccaacca gcgaaccagc   7020
agcgtcgcgt cgggccaagc gaagcagacg gcacggcatc tctgtcgctg cctctggacc   7080
cctctcgaga gttccgctcc accgttggac ttgctccgct gtcggcatcc agaaattgcg   7140
tggcggagcg gcagacgtga gccggcacgg caggcggcct cctcctcctc tcacggcacc   7200
ggcagctacg gggattcct ttcccaccgc tccttcgctt tcccttcctc gcccgccgta   7260
ataaatagac accccctcca caccctcttt ccccaacctc gtgttgttcg gagcgcacac   7320
acacacaacc agatctcccc caaatccacc cgtcggcacc tccgcttcaa ggtacgccgc   7380
tcgtcctncc cccccccccc ctctctacct tctctagatc ggcgttccgg tccatagtta   7440
gggcccggta gttctacttc tgttcatgtt tgtgttagat ccgtgtttgt gttagatccg   7500
tgctgttagc gttcgtacac ggatgcgacc tgtacgtcag acacgttctg attgctaact   7560
tgccagtgtt tctctttggg gaatcctggg atggctctag ccgttccgca gacgggatcg   7620
atttcatgat ttttttgtt tcgttgcata gggtttggtt tgccctttc ctttatttca   7680
atatatgccg tgcacttgtt tgtcgggtca tcttttcatg cnttttttttg tcttggttgt   7740
gatgatgtgg tctggttggg cggtcgttct agatcggagt agaattctgt ttcaaactac   7800
ctggtggatt tattaatttt ggatctgtat gtgtgtgcca tacatattca tagttacgaa   7860
ttgaagatga tggatggaaa tatcgatcta ggataggtat acatgttgat gcgggtttta   7920
ctgatgcata tacagagatg ctttttgttc gcttggttgt gatgatgtgg tgtggttggg   7980
cggtcgttca ttcgttctag atcggagtag aatactgttt caaactacct ggtgtattta   8040
ttaattttgg aactgtatgt gtgtgtcata catcttcata gttacgagtt taagatggat   8100
ggaaatatcg atctaggata ggtatacatg ttgatgtggg ttttactgat gcatatacat   8160
gatggcatat gcagcatcta ttcatatgct ctaaccttga gtacctatct attataataa   8220
acaagtatgt tttataatta ttttgatctt gatatacttg gatgatggca tatccagcag   8280
ctatatctgg attttttag ccctgccttc atacgctatt tatttgcttg gtactgtttc   8340
ttttgtcgtt gctcaccctg ttgtttggtg ttacttctgc agggatctcc gatcatgcaa   8400
aaactcatta actcagtgca aaactatgcc tggggcagca aaacggcgtt gactgaactt   8460
tacggtatgg aaaatccgtc cagccagccg atggccgagc tgtggatggg cgcacatccg   8520
aaaagcagtt cacgagtgca gaatgccgcc ggagatatcg tttcactgcg tgatgtgatt   8580
gagagtgata aatcgactct gctcggagag gccgttgcca aacgctttgg cgaactgcct   8640
ttcctgttca aagtattgtg cgcagcacag ccactctcca ttcaggttca tccaaacaaa   8700
cacaattctg aaatcggttt tgccaaagaa aatgccgcag gtatcccgat ggatgccgcc   8760
gagcgtaact ataaagatcc taaccacaag ccggagctgg tttttgcgct gacgcctttc   8820
cttgcgatga acgcgtttcg tgaattttcc gagattgtct ccctactcca gncggtcgca   8880
ggtgcacatc cggcgattgc tcacttttta caacagcctg atgccgaacg tttaagcgaa   8940
```

ctgttcgcca gcctgttgaa tatgcagggt gaagaaaaat cccgcgcgct ggcgatttta 9000
aaatcggccc tcgatagcca gcagggtgaa ccgtggcaaa cgattcgttt aatttctgaa 9060
ttttanccgg aagacagcgg tctgttctcc ccgctattgc tgaatgtggt gaaattgaac 9120
cctggcgaag cgatgttcct gttcgctgaa acaccgcacg cttacctgca aggcgtggcg 9180
ctggaagtga tggcaaactc cgataacgtg ctgcgtgcgg gtctgacgcc taaatacatt 9240
gatattccgg aactggttgc caatgtgaaa ttcgaagcca aaccggctaa ccagttgttg 9300
acccagccgg tgaaacaagg tgcagaactg gacttcccga ttccagtgga cgattttgcc 9360
ttctcgctgc acgaccttag tgataaagaa accaccatta gccagcagag tgccgccatt 9420
ttgttctgcg tcgaaggcga tgcaacgttg tggaaaggtt ctcagcagtt acagcttaaa 9480
ccgggtgaat cagcgtttat tgccgccaac gaatcaccgg tgactgtcaa aggccacggc 9540
cgtttagcgc gtgtttacaa caagctgtaa gagcttactg aaaaaattaa catctcttgc 9600
taagctgggt catgggtcgt ttaagctgcc gatgtgcctg cgtcgtctgg tgccctctct 9660
ccatatggag gttgtcaaag tatctgctgt tcgtgtcatg agtcgtgtca gtgttggttt 9720
aataatggac cggttgtgtt gtgtgtgcgt actacccaga actatgacaa atcatgaata 9780
agtttgatgt ttgaaattaa agcctgtgct cattatgttc tgtctttcag ttgtctccta 9840
atatttgcct ccaggtactg gctatctacc gtttcttact taggaggtgt ttgaatgcac 9900
taaaactaat agttagtggc taaaattagt taaaacatcc aaacaccata gctaatagtt 9960
gaactattag ctatttttgg aaaattagtt aatagtgagg tagttatttg ttagctagct 10020
aattcaacta acaattttta gccaactaac aattagtttc agtgcattca aacacccccct 10080 taatgttaac gtggttctat ctaccgtctc ctaatatatg gttgattgtt cggtttgttg 10140
ctatgctatt gggttctgat tgctgctagt tcttgctgaa tccagaagtt ctcgtagtat 10200
agctcagatt catattattt atttgagtga taagtgatcc aggttattac tatgttagct 10260
aggttttttt tacaaggata aattatctgt gatcataatt cttatgaaag ctttatgttt 10320
cctggaggca gtggcatgca atgcatgaca gcaacttgat cacaccagct gaggtagata 10380
cggtaacaag gttcttaaat ctgttcacca aatcattgga gaacacacat acacattctt 10440
gccagtcttg gttagagaaa tttcatgaca aaatgccaaa gctgtcttga ctcttcactt 10500
ttggccatga gtcgtgactt agtttggttt aatggaccgg ttctcctagc ttgttctact 10560
caaaactgtt gttgatgcga ataagttgtg atggttgatc tctggatttt gttttgctct 10620
caatagtgga cgagattaga tag 10643

<210> SEQ ID NO 32
<211> LENGTH: 18
<212> TYPE: DNA
<213> ORGANISM: Artificial sequence
<220> FEATURE:
<223> OTHER INFORMATION: Synthetic polynucleotide

<400> SEQUENCE: 32
ctccctcctc ccccgtta 18

<210> SEQ ID NO 33
<211> LENGTH: 17
<212> TYPE: DNA
<213> ORGANISM: Artificial sequence
<220> FEATURE:
<223> OTHER INFORMATION: Synthetic polynucleotide

<400> SEQUENCE: 33
ctccctcctc cccgtta 17

<210> SEQ ID NO 34
<211> LENGTH: 17
<212> TYPE: DNA
<213> ORGANISM: Artificial sequence
<220> FEATURE:
<223> OTHER INFORMATION: Synthetic polynucleotide

<400> SEQUENCE: 34
tgattctgcg ggttggc 17

<210> SEQ ID NO 35
<211> LENGTH: 17
<212> TYPE: DNA
<213> ORGANISM: Artificial sequence
<220> FEATURE:
<223> OTHER INFORMATION: Synthetic polynucleotide

<400> SEQUENCE: 35
tgattctgct ggttggc 17

<210> SEQ ID NO 36
<211> LENGTH: 31
<212> TYPE: DNA
<213> ORGANISM: Artificial sequence
<220> FEATURE:
<223> OTHER INFORMATION: Synthetic polynucleotide

<400> SEQUENCE: 36
taataaatag acaccccctc cacaccctct t 31

<210> SEQ ID NO 37
<211> LENGTH: 32
<212> TYPE: DNA
<213> ORGANISM: Artificial sequence
<220> FEATURE:
<223> OTHER INFORMATION: Synthetic polynucleotide

<400> SEQUENCE: 37
taataaatag acacccccct ccacaccctc tt 32

<210> SEQ ID NO 38
<211> LENGTH: 23
<212> TYPE: DNA
<213> ORGANISM: Artificial sequence
<220> FEATURE:
<223> OTHER INFORMATION: Synthetic polynucleotide

<400> SEQUENCE: 38
ctcgtcctcc cccccccccc ctc 23

<210> SEQ ID NO 39
<211> LENGTH: 24
<212> TYPE: DNA
<213> ORGANISM: Artificial sequence
<220> FEATURE:
<223> OTHER INFORMATION: Synthetic polynucleotide

<400> SEQUENCE: 39
ctcgtcctcc cccccccccc cctc 24

<210> SEQ ID NO 40
<211> LENGTH: 19

<212> TYPE: DNA
<213> ORGANISM: Artificial sequence
<220> FEATURE:
<223> OTHER INFORMATION: Synthetic polynucleotide

<400> SEQUENCE: 40
cggtcgttca ttcgttcta 19

<210> SEQ ID NO 41
<211> LENGTH: 20
<212> TYPE: DNA
<213> ORGANISM: Artificial sequence
<220> FEATURE:
<223> OTHER INFORMATION: Synthetic polynucleotide

<400> SEQUENCE: 41
cggtcgttca tttcgttcta 20

<210> SEQ ID NO 42
<211> LENGTH: 29
<212> TYPE: DNA
<213> ORGANISM: Artificial sequence
<220> FEATURE:
<223> OTHER INFORMATION: Synthetic polynucleotide

<400> SEQUENCE: 42
agactagtgg cttgcttttt cgtatgtct 29

<210> SEQ ID NO 43
<211> LENGTH: 30
<212> TYPE: DNA
<213> ORGANISM: Artificial sequence
<220> FEATURE:
<223> OTHER INFORMATION: Synthetic polynucleotide

<400> SEQUENCE: 43
agactagtgg cttgcttttt tcgtatgtct 30

<210> SEQ ID NO 44
<211> LENGTH: 30
<212> TYPE: DNA
<213> ORGANISM: Artificial sequence
<220> FEATURE:
<223> OTHER INFORMATION: Synthetic polynucleotide

<400> SEQUENCE: 44
aaaaaattac cacatatttt ttttgtcaca 30

<210> SEQ ID NO 45
<211> LENGTH: 29
<212> TYPE: DNA
<213> ORGANISM: Artificial sequence
<220> FEATURE:
<223> OTHER INFORMATION: Synthetic polynucleotide

<400> SEQUENCE: 45
aaaaaattac cacatatttt tttgtcaca 29

<210> SEQ ID NO 46
<211> LENGTH: 33
<212> TYPE: DNA
<213> ORGANISM: Artificial sequence
<220> FEATURE:
<223> OTHER INFORMATION: Synthetic polynucleotide

<400> SEQUENCE: 46
tagtgtgcat gtgttctcct tttttttgc aaa 33

<210> SEQ ID NO 47
<211> LENGTH: 32
<212> TYPE: DNA
<213> ORGANISM: Artificial sequence
<220> FEATURE:
<223> OTHER INFORMATION: Synthetic polynucleotide

<400> SEQUENCE: 47
tagtgtgcat gtgttctcct ttttttgca aa 32

<210> SEQ ID NO 48
<211> LENGTH: 32
<212> TYPE: DNA
<213> ORGANISM: Artificial sequence
<220> FEATURE:
<223> OTHER INFORMATION: Synthetic polynucleotide

<400> SEQUENCE: 48
gtacgccgct cgtcctcccc ccccccccct ct 32

<210> SEQ ID NO 49
<211> LENGTH: 33
<212> TYPE: DNA
<213> ORGANISM: Artificial sequence
<220> FEATURE:
<223> OTHER INFORMATION: Synthetic polynucleotide

<400> SEQUENCE: 49
gtacgccgct cgtcctcccc cccccccccc tct 33

<210> SEQ ID NO 50
<211> LENGTH: 34
<212> TYPE: DNA
<213> ORGANISM: Artificial sequence
<220> FEATURE:
<223> OTHER INFORMATION: Synthetic polynucleotide

<400> SEQUENCE: 50
gatctccgat catgcaaaaa ctcattaact cagt 34

<210> SEQ ID NO 51
<211> LENGTH: 35
<212> TYPE: DNA
<213> ORGANISM: Artificial sequence
<220> FEATURE:
<223> OTHER INFORMATION: Synthetic polynucleotide

<400> SEQUENCE: 51
gatctccgat catgcaaaaa actcattaac tcagt 35

<210> SEQ ID NO 52
<211> LENGTH: 23
<212> TYPE: DNA
<213> ORGANISM: Artificial sequence
<220> FEATURE:
<223> OTHER INFORMATION: Synthetic polynucleotide

<400> SEQUENCE: 52
cttatgcaga acctttttt ttg 23

<210> SEQ ID NO 53
<211> LENGTH: 22
<212> TYPE: DNA
<213> ORGANISM: Artificial sequence
<220> FEATURE:
<223> OTHER INFORMATION: Synthetic polynucleotide

<400> SEQUENCE: 53
cttatgcaga acctttttt tg 22

<210> SEQ ID NO 54
<211> LENGTH: 31
<212> TYPE: DNA
<213> ORGANISM: Artificial sequence
<220> FEATURE:
<223> OTHER INFORMATION: Synthetic polynucleotide

<400> SEQUENCE: 54
ggagactagt ggcttgcttt ttcgtatgtc t 31

<210> SEQ ID NO 55
<211> LENGTH: 30
<212> TYPE: DNA
<213> ORGANISM: Artificial sequence
<220> FEATURE:
<223> OTHER INFORMATION: Synthetic polynucleotide

<400> SEQUENCE: 55
ggagactagt ggcttgcttt tcgtatgtct 30

<210> SEQ ID NO 56
<211> LENGTH: 30
<212> TYPE: DNA
<213> ORGANISM: Artificial sequence
<220> FEATURE:
<223> OTHER INFORMATION: Synthetic polynucleotide

<400> SEQUENCE: 56
acgccgctcg tcctcccccc cccccccctct 30

<210> SEQ ID NO 57
<211> LENGTH: 31
<212> TYPE: DNA
<213> ORGANISM: Artificial sequence
<220> FEATURE:
<223> OTHER INFORMATION: Synthetic polynucleotide

<400> SEQUENCE: 57
acgccgctcg tcctcccccc ccccccccctc t 31

<210> SEQ ID NO 58
<211> LENGTH: 31
<212> TYPE: DNA
<213> ORGANISM: Artificial sequence
<220> FEATURE:
<223> OTHER INFORMATION: Synthetic polynucleotide

<400> SEQUENCE: 58
gccagtgttt ctctttgggg aatcctggga t 31

<210> SEQ ID NO 59
<211> LENGTH: 30
<212> TYPE: DNA
<213> ORGANISM: Artificial sequence
<220> FEATURE:
<223> OTHER INFORMATION: Synthetic polynucleotide

<400> SEQUENCE: 59
gccagtgttt ctctttggga atcctgggat 30

<210> SEQ ID NO 60
<211> LENGTH: 30
<212> TYPE: DNA
<213> ORGANISM: Artificial sequence
<220> FEATURE:
<223> OTHER INFORMATION: Synthetic polynucleotide

<400> SEQUENCE: 60
actaacaatt agtttcagtg cattcaaaca 30

<210> SEQ ID NO 61
<211> LENGTH: 31
<212> TYPE: DNA
<213> ORGANISM: Artificial sequence
<220> FEATURE:
<223> OTHER INFORMATION: Synthetic polynucleotide

<400> SEQUENCE: 61
actaacaatt agttttcagt gcattcaaac a 31

<210> SEQ ID NO 62
<211> LENGTH: 33
<212> TYPE: DNA
<213> ORGANISM: Artificial sequence
<220> FEATURE:
<223> OTHER INFORMATION: Synthetic polynucleotide

<400> SEQUENCE: 62
ttataaattg gcttcatccc ctccttgcct cat 33

<210> SEQ ID NO 63
<211> LENGTH: 32
<212> TYPE: DNA
<213> ORGANISM: Artificial sequence
<220> FEATURE:
<223> OTHER INFORMATION: Synthetic polynucleotide

<400> SEQUENCE: 63
ttataaattg gcttcatccc tccttgcctc at 32

<210> SEQ ID NO 64
<211> LENGTH: 24
<212> TYPE: DNA
<213> ORGANISM: Artificial sequence
<220> FEATURE:
<223> OTHER INFORMATION: Synthetic polynucleotide

<400> SEQUENCE: 64
catatatcat gtattttttt ttgg 24

<210> SEQ ID NO 65
<211> LENGTH: 25
<212> TYPE: DNA
<213> ORGANISM: Artificial sequence
<220> FEATURE:
<223> OTHER INFORMATION: Synthetic polynucleotide

<400> SEQUENCE: 65
catatatcat gtattttttt tttgg 25

<210> SEQ ID NO 66
<211> LENGTH: 29
<212> TYPE: DNA
<213> ORGANISM: Artificial sequence
<220> FEATURE:
<223> OTHER INFORMATION: Synthetic polynucleotide

<400> SEQUENCE: 66
tacgccgctc gtcctccccc cccccccct 29

<210> SEQ ID NO 67
<211> LENGTH: 30
<212> TYPE: DNA
<213> ORGANISM: Artificial sequence
<220> FEATURE:
<223> OTHER INFORMATION: Synthetic polynucleotide

<400> SEQUENCE: 67
tacgccgctc gtcctccccc ccccccccct 30

<210> SEQ ID NO 68
<211> LENGTH: 36
<212> TYPE: DNA
<213> ORGANISM: Artificial sequence
<220> FEATURE:
<223> OTHER INFORMATION: Synthetic polynucleotide

<400> SEQUENCE: 68
catcttttca tgcttttttt tgtcttggtt gtgatg 36

<210> SEQ ID NO 69
<211> LENGTH: 35
<212> TYPE: DNA
<213> ORGANISM: Artificial sequence
<220> FEATURE:
<223> OTHER INFORMATION: Synthetic polynucleotide

<400> SEQUENCE: 69
catcttttca tgcttttttt gtcttggttg tgatg 35

<210> SEQ ID NO 70
<211> LENGTH: 31
<212> TYPE: DNA
<213> ORGANISM: Artificial sequence
<220> FEATURE:
<223> OTHER INFORMATION: Synthetic polynucleotide

<400> SEQUENCE: 70
cctgttcaaa gtattatgcg cagcacagcc a 31

<210> SEQ ID NO 71
<211> LENGTH: 31
<212> TYPE: DNA
<213> ORGANISM: Artificial sequence
<220> FEATURE:
<223> OTHER INFORMATION: Synthetic polynucleotide

<400> SEQUENCE: 71
cctgttcaaa gtattgtgcg cagcacagcc a 31

<210> SEQ ID NO 72
<211> LENGTH: 31
<212> TYPE: DNA
<213> ORGANISM: Artificial sequence
<220> FEATURE:
<223> OTHER INFORMATION: Synthetic polynucleotide

<400> SEQUENCE: 72
gtctccctac tccagccggt cgcaggtgca c 31

<210> SEQ ID NO 73

```
<211> LENGTH: 30
<212> TYPE: DNA
<213> ORGANISM: Artificial sequence
<220> FEATURE:
<223> OTHER INFORMATION: Synthetic polynucleotide

<400> SEQUENCE: 73

gtctccctac tccagcggtc gcaggtgcac                                    30


<210> SEQ ID NO 74
<211> LENGTH: 30
<212> TYPE: DNA
<213> ORGANISM: Artificial sequence
<220> FEATURE:
<223> OTHER INFORMATION: Synthetic polynucleotide

<400> SEQUENCE: 74

aatttctgaa ttttacccgg aagacagcgg                                    30


<210> SEQ ID NO 75
<211> LENGTH: 29
<212> TYPE: DNA
<213> ORGANISM: Artificial sequence
<220> FEATURE:
<223> OTHER INFORMATION: Synthetic polynucleotide

<400> SEQUENCE: 75

aatttctgaa ttttaccgga agacagcgg                                     29
```

NUCLEIC ACID MOLECULES FOR CONFERRING INSECTICIDAL PROPERTIES IN PLANTS

RELATED APPLICATION INFORMATION

This application is a 371 of International Application No. PCT/US2022/027372, filed May 3, 2022, which claims priority to U.S. Application No. 63/183,672, filed May 4, 2021, the contents of which are incorporated herein by reference herein.

STATEMENT REGARDING ELECTRONIC SUBMISSION OF A SEQUENCE LISTING

A Sequence Listing in ASCII text format, submitted under 37 C.F.R. § 1.821, entitled "82347_ST25.txt", 395,000 bytes in size, generated on Nov. 3, 2023 and filed via EFS-Web is provided in lieu of a paper copy. This Sequence Listing is hereby incorporated by reference into the specification for its disclosures.

CROSS-REFERENCE TO RELATED APPLICATIONS

This application claims priority to U.S. Provisional Application No. 63/183,672, filed on May 4, 2021, the entire contents of which are incorporated by reference herein.

FIELD OF THE INVENTION

The present invention generally relates to nucleic acid sequences which confer expression of insecticidal proteins when introduced into a cell or plant, as well as related compositions and methods.

SEQUENCE LISTING

This application is accompanied by a sequence listing in ASCII text format entitled "82347-PCT_ST25.txt," created Apr. 14, 2022, which is approximately 395 kilobytes in size. This sequence listing is incorporated herein by reference in its entirety. This sequence listing is submitted herewith via EFS-Web, and is in compliance with 37 C.F.R. § 1.824(a) (2)-(6) and (b).

BACKGROUND

Plant pests are a major factor in the loss of the world's important agricultural crops, including maize. Plant pests are mainly controlled by intensive applications of chemical pesticides. Good pest control can thus be reached, but these chemicals can sometimes also affect beneficial organisms. Another problem resulting from the wide use of chemical pesticides is the appearance of resistant insect varieties. This has been partially alleviated by various resistance management practices, but there is an increasing need for alternative pest control strategies. One such alternative includes the expression of foreign genes encoding insecticidal proteins in transgenic plants. This approach has provided an efficient means of protection against selected insect pests, and transgenic plants expressing insecticidal toxins have been commercialized, allowing farmers to reduce applications of chemical insecticides.

*Bacillus thuringiensis* (Bt) Cry proteins (also called delta-endotoxins) are proteins that form a crystalline matrix in *Bacillus* that are known to possess insecticidal activity when ingested by certain insects. Genes coding for Cry proteins have been isolated and their expression in crop plants have been shown to provide another tool for the control of economically important insect pests.

Although the usage of transgenic plants expressing Cry proteins is another tool in the insect control toolbox, it is still susceptible to resistance breakdown. Insect pests that now have resistance against the Cry proteins expressed in certain transgenic plants are known. For example, fall armyworm (*Spodoptera frugiperda*) has documented field-evolved resistance to Cry1F, Cry1A.105 and Cry2Ab2 in certain countries. As a result, there is a need for additional insecticidal proteins to address the resistance issues.

Creating new insecticidal protein expression cassettes for use in transgenic plants is a challenging endeavor as the expression cassette must express enough protein(s) within the transgenic plant to have the desired activity (e.g., insecticidal activity) without causing negative effects on the plant itself (e.g., reduced yield, sterility, stunting, etc.).

Provided herein are nucleic acid sequences and related compositions and methods of use to address the aforementioned needs.

SUMMARY

In some aspects, the disclosure provides a nucleic acid molecule that expresses one or more insecticidal proteins. As described herein, an expression cassette was created (SEQ ID NO: 1) which encodes an eCry1Gb.1Ig protein (SEQ ID NO: 4). This expression cassette, when transformed into plants, confers insecticidal activity against Lepidoptera species, e.g., *Spodoptera frugiperda* (fall armyworm).

Accordingly, in some aspects, the disclosure provides a nucleic acid molecule comprising a nucleic acid sequence that is at least 90% identical to SEQ ID NO: 1 (e.g., at least 90% identical to SEQ ID NO: 1, at least 91% identical to SEQ ID NO: 1, at least 92% identical to SEQ ID NO: 1, at least 93% identical to SEQ ID NO: 1, at least 94% identical to SEQ ID NO: 1, at least 95% identical to SEQ ID NO: 1, at least 96% identical to SEQ ID NO: 1, at least 97% identical to SEQ ID NO: 1, at least 98% identical to SEQ ID NO: 1, at least 99% identical to SEQ ID NO: 1, or at least 99.5% identical to SEQ ID NO: 1), or the complement thereof. In some embodiments, the nucleic acid molecule encodes the same protein(s) that are encoded by SEQ ID NO: 1. In some embodiments, the nucleic acid sequence comprises any one of SEQ ID NOs: 1 or 8 to 31 or any one or more of the variants in Table 3. In some embodiments, the nucleic acid molecule encodes protein(s) that is/are insecticidal against one or more Lepidopteran pests, e.g., insecticidal against at least *Spodoptera frugiperda* (fall armyworm). In some embodiments, the nucleic acid molecule encodes protein(s) that is/are insecticidal against at least two (e.g., 2, 3, or 4) of *Spodoptera frugiperda* (fall armyworm), *Mythimna separata* (oriental armyworm), *Spodoptera litura* (common cutworm/oriental leafworm), and *Ostrinia furnacalis* (Asian corn borer). In some embodiments, the nucleic acid molecule is isolated.

In some embodiments, the disclosure provides a nucleic acid molecule comprising a nucleic acid sequence that is at least 95% identical to SEQ ID NO: 1 (e.g., at least 95% identical to SEQ ID NO: 1, at least 96% identical to SEQ ID NO: 1, at least 97% identical to SEQ ID NO: 1, at least 98% identical to SEQ ID NO: 1, at least 99% identical to SEQ ID NO: 1, or at least 99.5% identical to SEQ ID NO: 1), or the complement thereof, wherein the nucleic acid sequence encodes a polypeptide comprising the sequence of SEQ ID NO: 4 or encodes polypeptides comprising the sequences of SEQ ID NO: 4 and 6. In some embodiments, the nucleic acid sequence comprises SEQ ID NO: 3 or SEQ ID NO: 3 and 5 or a variant thereof of any of the foregoing comprising one or more silent mutations. In some embodiments, the nucleic acid sequence comprises any one of SEQ ID NOs: 1 or 8 to 31 or any one or more of the variants in Table 3 or a variant thereof of any of the foregoing comprising one or more silent mutations or other mutations that do not substantially affect the function of SEQ ID NO: 1.

In some aspects, the disclosure provides a recombinant nucleic acid vector comprising the nucleic acid molecule of any of the above-mentioned embodiments or any other embodiment described herein (e.g., comprising any one of SEQ ID NOs: 1 or 8 to 31 or any one or more of the variants in Table 3). In some embodiments, the vector is a binary vector. In some embodiments, the vector is a plasmid. In some embodiments, the vector is present in a host cell.

In some aspects, the disclosure provides a transgenic host cell comprising the nucleic acid molecule of any of the above-mentioned embodiments or any other embodiment described herein (e.g., comprising any one of SEQ ID NOs: 1 or 8 to 31 or any one or more of the variants in Table 3). In some embodiments, the cell is a plant cell, a yeast cell, a bacterial cell or an insect cell. In some embodiments, the cell is a bacterial cell or a plant cell. In some embodiments, the cell is a bacterial cell and the bacterial cell is an *Escherichia coli. Bacillus thuringiensis. Bacillus subtilis. Bacillus megaterium. Bacillus cereus. Agrobacterium* ssp. or a *Pseudomonas* ssp. cell. In some embodiments, the cell is a plant cell and the plant cell is a maize, sorghum, wheat, sunflower, tomato, crucifers, oat, turf grass, pasture grass, peppers, potato, cotton, rice, soybean, sugarcane, sugar beet, tobacco, barley, or oilseed rape cell. In some embodiments, the plant cell is a maize cell. In some embodiments, the plant cell is present in a plant. In some embodiments, the plant cell is isolated. In some embodiments, the plant cell is capable of regenerating a plant. In some embodiments, the plant cell is incapable of regenerating a whole plant.

In some aspects, the disclosure provides a transgenic plant comprising the nucleic acid molecule of any of the above-mentioned embodiments or any other embodiment described herein (e.g., comprising any one of SEQ ID NOs: 1 or 8 to 31 or any one or more of the variants in Table 3). In some embodiments, the plant is a monocot plant. In some embodiments, the plant is a dicot plant. In some embodiments, the plant is selected from the group consisting of maize, sorghum, wheat, sunflower, tomato, crucifers, oat, turf grass, pasture grass, peppers, potato, cotton, rice, soybean, sugarcane, sugar beet, tobacco, barley, and oilseed rape. In some embodiments, the plant is a maize plant. In some embodiments, the plant is a whole plant. In some embodiments, the plant is a transgenic whole maize plant comprising a nucleic acid molecule comprising any one of SEQ ID NOs: 1 or 8 to 31 or any one or more of the variants in Table 3. In some embodiments, the plant is insecticidal against at least *Spodoptera frugiperda* (fall armyworm). In some embodiments, the plant is insecticidal against at least two (e.g., 2, 3, or 4) of *Spodoptera frugiperda* (fall armyworm), *Mythimna separata* (oriental armyworm), *Spodoptera litura* (common cutworm/oriental leafworm), and *Ostrinia furnacalis* (Asian corn borer). In some embodiments, the plant has enhanced insecticidal properties, e.g., against at least *Spodoptera frugiperda* (fall armyworm), relative to a control plant, e.g., that does not comprise the nucleic acid molecule. In some aspects, the disclosure provides a progeny of any generation of the plant, wherein the progeny comprises the nucleic acid molecule. In some aspects, the disclosure provides a propagule of the plant, wherein the propagule comprises the nucleic acid molecule. In some aspects, the disclosure provides a plant part of the plant, wherein the plant part comprises the nucleic acid molecule. In some embodiments, the plant part is an embryo, pollen, ovule, seed, leaf, flower, branch, fruit, kernel, ear, cob, husk, stalk, root, root tip, anther, tuber, or rhizome. In some embodiments, the plant part is a seed.

In some aspects, the disclosure provides a method of producing a transgenic plant with enhanced insecticidal properties, comprising introducing the nucleic acid molecule of any of the above-mentioned embodiments or any other embodiment described herein (e.g., comprising any one of SEQ ID NOs: 1 or 8 to 31 or any one or more of the variants in Table 3) into a plant thereby producing a transgenic plant, wherein the nucleic acid molecule expresses effective insect-controlling amounts of protein. In some embodiments, the effective insect-controlling amounts of protein are effective for controlling at least *Spodoptera frugiperda* (fall armyworm). In some embodiments, the effective insect-controlling amounts of protein are effective for controlling at least two (e.g., 2, 3, or 4) of *Spodoptera frugiperda* (fall armyworm), *Mythimna separata* (oriental armyworm), *Spodoptera litura* (common cutworm/oriental leafworm), and *Ostrinia furnacalis* (Asian corn borer).

In some aspects, the disclosure provides a method of producing a transgenic plant with enhanced insecticidal properties, comprising the steps of: (a) providing the nucleic acid molecule of any of the above-mentioned embodiments or any other embodiment described herein (e.g., comprising any one of SEQ ID NOs: 1 or 8 to 31 or any one or more of the variants in Table 3); (b) introducing into a plant, tissue culture, or a plant cell the nucleic acid molecule of step (a) to obtain a transformed plant, transformed tissue culture, or a transformed cell having enhanced insecticidal properties; and (c) growing the transformed plant or regenerating a transformed plant from the transformed tissue culture or transformed plant cell, so a transgenic plant with enhanced insecticidal properties is produced. In some embodiments, the enhanced insecticidal properties are enhanced insecticidal properties against at least *Spodoptera frugiperda* (fall armyworm). In some embodiments, the enhanced insecticidal properties are enhanced insecticidal properties against at least two (e.g., 2, 3, or 4) of *Spodoptera frugiperda* (fall armyworm), *Mythimna separata* (oriental armyworm), *Spodoptera litura* (common cutworm/oriental leafworm), and *Ostrinia furnacalis* (Asian corn borer). In some embodiments, the transgenic plant is a transgenic maize plant.

In some aspects, the disclosure provides a method of producing transgenic seed, comprising the steps of: (a) obtaining a fertile transgenic plant of any of the above-mentioned embodiments or any other embodiment described herein (e.g., comprising any one of SEQ ID NOs: 1 or 8 to 31 or any one or more of the variants in Table 3); and (b) growing the plant under appropriate conditions to produce the transgenic seed. In some embodiments, the transgenic seed is transgenic maize seed.

In some aspects, the disclosure provides a method of producing progeny of any generation of a fertile transgenic plant with enhanced insecticidal properties, comprising the steps of: (a) obtaining a fertile transgenic plant with enhanced insecticidal properties comprising the nucleic acid molecule of any of the above-mentioned embodiments or any other embodiment described herein (e.g., comprising any one of SEQ ID NOs: 1 or 8 to 31 or any one or more of the variants in Table 3); (b) collecting transgenic seed from the transgenic plant; (c) planting the collected transgenic seed; and (d) growing the progeny transgenic plants from the seed, wherein the progeny has enhanced insecticidal properties relative to a non-transformed plant. In some embodiments, the progeny plant are maize plants.

In some aspects, the disclosure provides a method for producing a transgenic plant with enhanced insecticidal properties, comprising the steps of sexually crossing a first parent plant with a second parent plant, wherein the first or second parent plant is the plant of any of the above-mentioned embodiments or any other embodiment described herein (e.g., comprising any one of SEQ ID NOs: 1 or 8 to 31 or any one or more of the variants in Table 3), to produce a first generation progeny plant that comprises the nucleic acid molecule. In some embodiments, the enhanced insecticidal properties are enhanced insecticidal properties against at least *Spodoptera frugiperda* (fall armyworm). In some embodiments, the enhanced insecticidal properties are enhanced insecticidal properties against at least two (e.g., 2, 3, or 4) of *Spodoptera frugiperda* (fall armyworm), *Mythimna separata* (oriental armyworm), *Spodoptera litura* (common cutworm/oriental leafworm), and *Ostrinia furnacalis* (Asian corn borer). In some embodiments, the first generation progeny plant is a maize plant.

In some aspects, the disclosure provides a method for producing a transgenic plant with enhanced insecticidal properties, comprising the steps of: (a) sexually crossing a first parent plant with a second parent plant, wherein the first or second parent plant is the plant of any of the above-mentioned embodiments or any other embodiment described herein (e.g., comprising any one of SEQ ID NOs: 1 or 8 to 31 or any one or more of the variants in Table 3); and (b) selecting a first generation progeny plant with enhanced insecticidal properties, wherein the selected progeny plant comprises the nucleic acid molecule. In some embodiments, the enhanced insecticidal properties are enhanced insecticidal properties against at least *Spodoptera frugiperda* (fall armyworm). In some embodiments, the enhanced insecticidal properties are enhanced insecticidal properties against at least two (e.g., 2, 3, or 4) of *Spodoptera frugiperda* (fall armyworm), *Mythimna separata* (oriental armyworm), *Spodoptera litura* (common cutworm/oriental leafworm), and *Ostrinia furnacalis* (Asian corn borer). In some embodiments, the first generation progeny plant is a maize plant. In some embodiments, the method further comprises the steps of: (a) selfing the first generation progeny plant, thereby producing a plurality of second generation progeny plants; and (b) selecting from the second generation progeny plants a plant with enhanced insecticidal properties, wherein the selected second generation progeny plants comprise the nucleic acid molecule.

In some aspects, the disclosure provides a method of controlling a lepidopteran pest comprising feeding the pest a plant or plant part comprising the nucleic acid molecule of any of the above-mentioned embodiments or any other embodiment described herein (e.g., comprising any one of SEQ ID NOs: 1 or 8 to 31 or any one or more of the variants in Table 3). In some embodiments, the lepidopteran pest is *Spodoptera frugiperda* (fall armyworm). In some embodiments, the lepidopteran pest is at least two (e.g., 2, 3, or 4) of *Spodoptera frugiperda* (fall armyworm), *Mythimna separata* (oriental armyworm), *Spodoptera litura* (common cutworm/oriental leafworm), and *Ostrinia furnacalis* (Asian corn borer). In some embodiments, the plant or plant part is a maize plant or maize plant part.

In some aspects, the disclosure provides a method of producing a commodity plant product, the method comprising using the plant of any of the above-mentioned embodiments or any other embodiment described herein (e.g., comprising any one of SEQ ID NOs: 1 or 8 to 31 or any one or more of the variants in Table 3) to produce said commodity plant product therefrom. In some embodiments, the plant is a maize plant. In some embodiments, the commodity plant product is a grain, starch, seed oil, syrup, flour, meal, starch, cereal, or protein.

In some aspects, the disclosure provides a method of detecting the presence of a nucleic acid molecule in a sample, the method comprising: (a) contacting the sample with a pair of primers that, when used in a nucleic-acid amplification reaction with DNA comprising the nucleic acid molecule of any of the above-mentioned embodiments or any other embodiment described herein (e.g., comprising SEQ ID NO: any one of SEQ ID NOs: 1 or 8 to 31 or any one or more of the variants in Table 3), produces an amplicon that is diagnostic for the nucleic acid molecule; (b) performing a nucleic acid amplification reaction, thereby producing the amplicon; and (c) detecting the amplicon. In some embodiments, the pair of primers is a first primer and a second primer wherein the first primer comprises at least 10 contiguous nucleotides that are complementary to any one of SEQ ID NOs: 1 or 8 to 31 or any one or more of the variants in Table 3 and the second primer comprises at least 10 contiguous nucleotides that are complementary to the reverse complement of any one of SEQ ID NOs: 1 or 8 to 31 or any one or more of the variants in Table 3. In some embodiments, the first and second primer are between 10-30 nucleotides in length. In some embodiments, the sample is a sample obtained from a maize plant part or cell.

In some aspects, the disclosure provides a method of detecting the presence of a nucleic acid molecule in a sample, the method comprising: (a) contacting the sample with a probe that hybridizes under high stringency conditions with DNA comprising the nucleic acid molecule of any of the above-mentioned embodiments or any other embodiment described herein (e.g., comprising any one of SEQ ID NOs: 1 or 8 to 31 or any one or more of the variants in Table 3) and does not hybridize under high stringency conditions with DNA of a control maize plant not comprising the nucleic acid molecule; (b) subjecting the sample and probe to high stringency hybridization conditions; and (c) detecting hybridization of the probe to the nucleic acid molecule. In some embodiments, the probe comprises at least 10 contiguous nucleotides that are complementary to any one of SEQ ID NOs: 1 or 8 to 31 or any one or more of the variants in Table 3 or the reverse complement thereof. In some embodiments, the probe is between 10-50 nucleotides in length. In some embodiments, the sample is a sample obtained from a maize plant part or cell.

In some aspects, the disclosure provides a pair of polynucleotide primers comprising a first polynucleotide primer and a second polynucleotide primer which function together in the presence of the nucleic acid molecule of any of the above-mentioned embodiments or any other embodiment described herein (e.g., comprising any one of SEQ ID NOs: 1 or 8 to 31 or any one or more of the variants in Table 3) in a sample to produce an amplicon diagnostic for the presence of the nucleic acid molecule in a sample. In some embodiments, the sample is a sample obtained from a maize plant part or cell. In some embodiments, the first polynucleotide primer comprises at least 10 contiguous nucleotides that are complementary to any one of SEQ ID NOs: 1 or 8 to 31 or any one or more of the variants in Table 3 and the second polynucleotide primer comprises at least 10 contiguous nucleotides that are complementary to the reverse complement of any one of SEQ ID NOs: 1 or 8 to 31 or any one or more of the variants in Table 3. In some embodiments, the first and second primer are between 10-30 nucleotides in length.

In some aspects, the disclosure provides a kit for detecting the nucleic acid molecule of any of the above-mentioned embodiments or any other embodiment described herein (e.g., comprising any one of SEQ ID NOs: 1 or 8 to 31 or any one or more of the variants in Table 3), the kit comprising at least one nucleic acid molecule of sufficient length of contiguous nucleotides to function as a primer or probe in a nucleic acid detection method, and which upon amplification of or hybridization to a target nucleic acid sequence in a sample followed by detection of the amplicon or hybridization to the target sequence, are diagnostic for the presence of the nucleic acid molecule. In some embodiments, the at least one nucleic acid molecule comprises at least 10 contiguous nucleotides that are complementary to any one of SEQ ID NOs: 1 or 8 to 31 or any one or more of the variants in Table 3. In some embodiments, the at least one nucleic acid molecule comprises a pair of primers, wherein the first polynucleotide primer comprises at least 10 contiguous nucleotides that are complementary to any one of SEQ ID NOs: 1 or 8 to 31 or any one or more of the variants in Table 3 and the second polynucleotide primer comprises at least 10 contiguous nucleotides that are complementary to the reverse complement of any one of SEQ ID NOs: 1 or 8 to 31 or any one or more of the variants in Table 3. In some embodiments, the first and second primer are between 10-30 nucleotides in length. In some embodiments, the at least one nucleic acid molecule comprises a probe that comprises at least 10 contiguous nucleotides that are complementary to any one of SEQ ID NOs: 1 or 8 to 31 or any one or more of the variants in Table 3 or the reverse complement thereof. In some embodiments, the probe is between 10-50 nucleotides in length.

In some aspects, the disclosure provides a method, comprising introducing a modification into a nucleic acid molecule, transgenic host cell, or transgenic plant of any one of the above-mentioned embodiments, thereby producing a modified nucleic acid molecule, transgenic host cell, or a modified transgenic plant. In some embodiments, the modification is a deletion, an insertion, a substitution, a duplication, or inversion or a combination thereof. In some embodiments, the modification comprises deletion of a portion or all of a selectable marker coding sequence present in the nucleic acid molecule (e.g., PMI). In some embodiments, the modification is introduced using a nuclease or homologous recombination, or a combination thereof. In some embodiments, the nuclease is a CRISPR-Cas nuclease. In some embodiments, the method further comprises producing a plant from the modified transgenic host cell and selfing or crossing the plant with another plant, thereby producing a modified transgenic progeny plant. In some embodiments, the method further comprises selfing or crossing the modified transgenic plant with another plant, thereby producing a modified transgenic progeny plant. In some embodiments, the method further comprises selfing or outcrossing the modified transgenic progeny plant for at least one additional generation.

BRIEF DESCRIPTION OF THE DRAWINGS

FIG. 1 is a diagram of binary vector 24795, whose nucleic acid sequence is SEQ ID NO:2.

BRIEF DESCRIPTION OF THE SEQUENCES IN THE SEQUENCE LISTING

SEQ ID NO: 1 is the nucleic acid sequence of the expression cassette encoding an eCry1Gb.1Ig protein (SEQ ID NO: 4) as well as PMI (SEQ ID NO: 6) as a selectable marker.

SEQ ID NO: 2 is the nucleic acid sequence of the binary vector 24795, which includes the expression cassette of SEQ ID NO: 1.

SEQ ID NO: 3 is the nucleic acid sequence of a coding sequence encoding eCry1Gb.1Ig.

SEQ ID NO: 4 is the amino acid sequence of eCry1Gb.1Ig.

SEQ ID NO: 5 is the nucleic acid sequence of a coding sequence encoding PMI.

SEQ ID NO: 6 is the amino acid sequence of PMI.

SEQ ID NO: 7 is the nucleic acid sequence of a coding sequence encoding PMI which has a silent mutation at one nucleotide position relative to SEQ ID NO: 5.

SEQ ID NO: 8 is the nucleic acid sequence of the expression cassette encoding an eCry1Gb.1Ig protein (SEQ ID NO: 4) as well as PMI (SEQ ID NO: 6) as a selectable marker and containing the silent mutation in SEQ ID NO: 7.

SEQ ID NO: 9 is the nucleic acid sequence of the expression cassette encoding an eCry1Gb.1Ig protein (SEQ ID NO: 4) as well as PMI (SEQ ID NO: 6) as a selectable marker and containing an additional mutation relative to SEQ ID NO: 1.

SEQ ID NO: 10 is the nucleic acid sequence of the expression cassette encoding an eCry1Gb.1Ig protein (SEQ ID NO: 4) as well as PMI (SEQ ID NO: 6) as a selectable marker and containing additional mutations relative to SEQ ID NO: 1.

SEQ ID NO: 11 is the nucleic acid sequence of the expression cassette encoding an eCry1Gb.1Ig protein (SEQ ID NO: 4) as well as PMI (SEQ ID NO: 6) as a selectable marker and containing additional mutations relative to SEQ ID NO: 1.

SEQ ID NO: 12 is the nucleic acid sequence of the expression cassette encoding an eCry1Gb.1Ig protein (SEQ ID NO: 4) as well as PMI (SEQ ID NO: 6) as a selectable marker and containing additional mutations relative to SEQ ID NO: 1.

SEQ ID NO: 13 is the nucleic acid sequence of the expression cassette encoding an eCry1Gb.1Ig protein (SEQ ID NO: 4) as well as PMI (SEQ ID NO: 6) as a selectable marker and containing additional mutations relative to SEQ ID NO: 1.

SEQ ID NO: 14 is the nucleic acid sequence of the expression cassette encoding an eCry1Gb.1Ig protein (SEQ ID NO: 4) as well as PMI (SEQ ID NO: 6) as a selectable marker and containing additional mutations relative to SEQ ID NO: 1.

SEQ ID NO: 15 is the nucleic acid sequence of the expression cassette encoding an eCry1Gb.1Ig protein (SEQ ID NO: 4) as well as PMI (SEQ ID NO: 6) as a selectable marker and containing additional mutations relative to SEQ ID NO: 1.

SEQ ID NO: 16 is the nucleic acid sequence of the expression cassette encoding an eCry1Gb.1Ig protein (SEQ ID NO: 4) as well as PMI (SEQ ID NO: 6) as a selectable marker and containing additional mutations relative to SEQ ID NO: 1.

SEQ ID NO: 17 is the nucleic acid sequence of the expression cassette encoding an eCry1Gb.1Ig protein (SEQ ID NO: 4) as well as PMI (SEQ ID NO: 6) as a selectable marker and containing additional mutations relative to SEQ ID NO: 1.

SEQ ID NO: 18 is the nucleic acid sequence of the expression cassette encoding an eCry1Gb.1Ig protein (SEQ ID NO: 4) as well as PMI (SEQ ID NO: 6) as a selectable marker and containing additional mutations relative to SEQ ID NO: 1.

SEQ ID NO: 19 is the nucleic acid sequence of the expression cassette encoding an eCry1Gb.1Ig protein (SEQ ID NO: 4) as well as PMI (SEQ ID NO: 6) as a selectable marker and containing additional mutations relative to SEQ ID NO: 1.

SEQ ID NO: 20 is the nucleic acid sequence of the expression cassette encoding an eCry1Gb.1Ig protein (SEQ ID NO: 4) as well as PMI (SEQ ID NO: 6) as a selectable marker and containing additional mutations relative to SEQ ID NO: 1.

SEQ ID NO: 21 is the nucleic acid sequence of the expression cassette encoding an eCry1Gb.1Ig protein (SEQ ID NO: 4) as well as PMI (SEQ ID NO: 6) as a selectable marker and containing additional mutations relative to SEQ ID NO: 1.

SEQ ID NO: 22 is the nucleic acid sequence of the expression cassette encoding an eCry1Gb.1Ig protein (SEQ ID NO: 4) as well as PMI (SEQ ID NO: 6) as a selectable marker and containing additional mutations relative to SEQ ID NO: 1.

SEQ ID NO: 23 is the nucleic acid sequence of the expression cassette encoding an eCry1Gb.1Ig protein (SEQ ID NO: 4) as well as PMI (SEQ ID NO: 6) as a selectable marker and containing additional mutations relative to SEQ ID NO: 1.

SEQ ID NO: 24 is the nucleic acid sequence of the expression cassette encoding an eCry1Gb.1Ig protein (SEQ ID NO: 4) as well as PMI (SEQ ID NO: 6) as a selectable marker and containing additional mutations relative to SEQ ID NO: 1.

SEQ ID NO: 25 is the nucleic acid sequence of the expression cassette encoding an eCry1Gb.1Ig protein (SEQ ID NO: 4) as well as PMI (SEQ ID NO: 6) as a selectable marker and containing additional mutations relative to SEQ ID NO: 1.

SEQ ID NO: 26 is the nucleic acid sequence of the expression cassette encoding an eCry1Gb.1Ig protein (SEQ ID NO: 4) as well as PMI (SEQ ID NO: 6) as a selectable marker and containing additional mutations relative to SEQ ID NO: 1.

SEQ ID NO: 27 is the nucleic acid sequence of the expression cassette encoding an eCry1Gb.1Ig protein (SEQ ID NO: 4) as well as PMI (SEQ ID NO: 6) as a selectable marker and containing additional mutations relative to SEQ ID NO: 1.

SEQ ID NO: 28 is the nucleic acid sequence of the expression cassette encoding an eCry1Gb.1Ig protein (SEQ ID NO: 4) as well as PMI (SEQ ID NO: 6) as a selectable marker and containing additional mutations relative to SEQ ID NO: 1.

SEQ ID NO: 29 is the nucleic acid sequence of the expression cassette encoding an eCry1Gb.1Ig protein (SEQ ID NO: 4) as well as PMI (SEQ ID NO: 6) as a selectable marker and containing an additional mutation relative to SEQ ID NO: 1.

SEQ ID NO: 30 is the nucleic acid sequence of the expression cassette encoding an eCry1Gb.1Ig protein (SEQ ID NO: 4) as well as PMI (SEQ ID NO: 6) as a selectable marker and containing additional mutations relative to SEQ ID NO: 1.

SEQ ID NO: 31 is the nucleic acid sequence of the expression cassette encoding an eCry1Gb.1Ig protein (SEQ ID NO: 4) as well as PMI (SEQ ID NO: 6) as a selectable marker and containing additional mutations relative to SEQ ID NO: 1.

SEQ ID NOs: 32-75 are in Table 3.

DETAILED DESCRIPTION

This description is not intended to be a detailed catalog of all the different ways in which the invention may be implemented, or all the features that may be added to the instant invention. For example, features illustrated with respect to one embodiment may be incorporated into other embodiments, and features illustrated with respect to a particular embodiment may be deleted from that embodiment. Thus, the disclosure contemplates that in some embodiments, any feature or combination of features set forth herein can be excluded or omitted. In addition, numerous variations and additions to the various embodiments suggested herein will be apparent to those skilled in the art in light of the instant disclosure, which do not depart from the instant disclosure. Hence, the following descriptions are intended to illustrate some particular embodiments of the disclosure, and not to exhaustively specify all permutations, combinations and variations thereof.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

All publications, patent applications, patents and other references cited herein are incorporated by reference in their entireties for the teachings relevant to the sentence and/or paragraph in which the reference is presented.

Nucleotide sequences provided herein are presented in the 5' to 3' direction, from left to right and are presented using the standard code for representing nucleotide bases as set forth in 37 CFR §§ 1.821-1.825 and the World Intellectual Property Organization (WIPO) Standard ST.25, for example: adenine (A), cytosine (C), thymine (T), and guanine (G).

Amino acids are likewise indicated using the WIPO Standard ST.25, for example: alanine (Ala; A), arginine (Arg; R), asparagine (Asn; N), aspartic acid (Asp; D), cysteine (Cys; C), glutamine (Gln; Q), glutamic acid (Glu; E), glycine (Gly; G), histidine (His; H), isoleucine (Ile; 1), leucine (Leu; L), lysine (Lys; K), methionine (Met; M), phenylalanine (Phe; F), proline (Pro; P), serine (Ser; S), threonine (Thr; T), tryptophan (Trp; W), tyrosine (Tyr; Y), and valine (Val; V).

Unless the context indicates otherwise, it is specifically intended that the various features of the disclosure described herein can be used in any combination. Moreover, the present disclosure also contemplates that in some embodiments, any feature or combination of features set forth herein can be excluded or omitted. To illustrate, if the specification states that a composition comprises components A, B and C, it is specifically intended that any of A, B or C, or a combination thereof, can be omitted and disclaimed singularly or in any combination.

Definitions

For clarity, certain terms used in the specification are defined and presented as follows:

As used herein and in the appended claims, the singular forms "a," "an," and "the" include plural reference unless the context clearly dictates otherwise. Thus, for example, reference to "a plant" is a reference to one or more plants and includes equivalents thereof known to those skilled in the art, and so forth.

As used herein, the word "or" also encompasses "and/or" unless the context clearly indicates otherwise.

The term "about" is used herein to mean approximately, roughly, around, or in the region of. When the term "about" is used in conjunction with a numerical range, it modifies that range by extending the boundaries above and below the numerical values set forth. In general, the term "about" is used herein to modify a numerical value above and below the stated value by a variance of 20 percent, preferably 10 percent up or down (higher or lower). With regard to a temperature the term "about" means ±1° C., preferably ±0.5° C. Where the term "about" is used in the context of this disclosure (e.g., in combinations with temperature or molecular weight values) the exact value (i.e., without "about") is preferred.

As used herein, phrases such as "between about X and Y", "between about X and about Y", "from X to Y" and "from about X to about Y" (and similar phrases) should be interpreted to include X and Y, unless the context indicates otherwise.

The terms "comprises", "comprising", "includes", "including", "having" and their conjugates mean "including but not limited to". The term "consisting of means "including and limited to". The term "consisting essentially of" means that the composition, method or structure may include additional ingredients, steps and/or parts, but only if the additional ingredients, steps and/or parts do not materially alter the basic and novel characteristics of the claimed composition, method or structure.

Units, prefixes and symbols may be denoted in their SI accepted form. Unless otherwise indicated, nucleic acids are written left to right in 5' to 3' orientation; amino acid sequences are written left to right in N-terminus to C-terminus orientation, respectively. Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Activity" of the insecticidal proteins of the disclosure means that the insecticidal proteins function as orally active pest (e.g. insect) control agents, have a toxic effect (e.g., inhibiting the ability of the insect pest to survive, grow, and/or reproduce), and/or are able to disrupt or deter pest feeding, which may or may not cause death of the insect. When an insecticidal protein of the disclosure is delivered to the pest, the result is typically death of the pest, or the pest does not feed upon the source that makes the insecticidal protein available to the pest.

The term "chimeric polynucleotide" or "chimeric protein" (or similar terms) as used herein refers to a molecule comprising two or more polynucleotides or proteins, or fragments thereof, of different origin assembled into a single molecule. The term "chimeric construct", "chimeric gene", "chimeric polynucleotide" or "chimeric nucleic acid" refers to any construct or molecule that contains, without limitation, (1) polynucleotides (e.g., DNA), including regulatory and coding polynucleotides that are not found together in nature (i.e., at least one of the polynucleotides in the construct is heterologous with respect to at least one of its other polynucleotides), or (2) polynucleotides encoding parts of proteins not naturally adjoined, or (3) parts of promoters that are not naturally adjoined. Further, a chimeric construct, chimeric gene, chimeric polynucleotide or chimeric nucleic acid may comprise regulatory polynucleotides and coding polynucleotides that are derived from different sources, or comprise regulatory polynucleotides and coding polynucleotides derived from the same source, but arranged in a manner different from that found in nature. In some embodiments of the disclosure, the chimeric construct, chimeric gene, chimeric polynucleotide or chimeric nucleic acid comprises an expression cassette comprising a polynucleotide of the disclosure under the control of regulatory polynucleotides, particularly under the control of regulatory polynucleotides functional in plants or bacteria. The word "chimeric" and "hybrid," with respect to a polynucleotide or protein, are used interchangeably herein.

In the context of the present disclosure, a "chimeric" protein is a protein created by fusing all or a portion of at least two different proteins. A chimeric protein may also be further modified to include additions, substitutions and/or deletions of one or more amino acids. In some embodiments of the present disclosure, the chimeric protein is a chimeric Cry protein comprising all or a portion of two different Cry proteins fused together in a single polypeptide. In some embodiments, the chimeric Cry protein further comprises additional modifications such as additions, substitutions, and/or deletions of one or more amino acids. A "chimeric insecticidal protein" is a chimeric protein that has insecticidal activity.

As used herein, a "codon optimized" sequence means a nucleotide sequence wherein the codons are chosen to reflect the particular codon bias that a host cell or organism may have. This is typically done in such a way so as to preserve the amino acid sequence of the polypeptide encoded by the nucleotide sequence to be optimized. In certain embodiments, the DNA sequence of the recombinant DNA construct includes sequence that has been codon optimized for the cell (e.g., an animal, plant, or fungal cell) in which the construct is to be expressed. For example, a construct to be expressed in a plant cell can have all or parts of its sequence (e.g., the first gene suppression element or the gene expression element) codon optimized for expression in a plant. See, for example, U.S. Pat. No. 6,121,014, which is incorporated herein by reference. In some embodiments, the polynucleotides of the disclosure are codon-optimized for expression in a plant cell (e.g., a dicot cell or a monocot cell) or bacterial cell.

To "control" insects means to inhibit, through a toxic effect, the ability of insect pests to survive, grow, feed, and/or reproduce, and/or to limit insect-related damage or loss in crop plants and/or to protect the yield potential of a crop when grown in the presence of insect pests. To "control" insects may or may not mean killing the insects, although in some embodiments of the disclosure, "control" of the insect means killing the insects.

A "control plant" or "control" as used herein may be a non-transgenic plant of the parental line used to generate a transgenic plant herein. A control plant may in some cases be a transgenic plant line that includes an empty vector or marker gene but does not contain the recombinant polynucleotide of the present disclosure that is expressed in the transgenic plant being evaluated. In general, a control plant is a plant of the same line or variety as the transgenic plant being tested, lacking the specific trait-conferring, recombinant DNA that characterizes the transgenic plant. Such a progenitor plant that lacks that specific trait-conferring recombinant DNA can be a natural, wild-type plant, an elite, non-transgenic plant, or a transgenic plant without the specific trait-conferring, recombinant DNA that characterizes the transgenic plant. The progenitor plant lacking the specific, trait-conferring recombinant DNA can be a sibling of a transgenic plant having the specific, trait-conferring recombinant DNA. Such a progenitor sibling plant may include other recombinant DNA.

In the context of the disclosure, "corresponding to" or "corresponds to" means that when the amino acid sequences of a reference sequence are aligned with a second amino acid sequence (e.g. variant or homologous sequences), different from the reference sequence, the amino acids that "correspond to" certain enumerated positions in the second amino acid sequence are those that align with these positions in the reference amino acid sequence but that are not necessarily in the exact numerical positions relative to the particular reference amino acid sequence of the disclosure.

As used herein, the term "Cry protein" means an insecticidal protein of a *Bacillus thuringiensis* crystal delta-endotoxin type. The term "Cry protein" can refer to the protoxin form or any insecticidally active fragment or toxin thereof including partially processed and the mature toxin form (e.g., without the N-terminal peptidyl fragment and/or the C-terminal protoxin tail).

To "deliver" or "delivering" a composition or toxin means that the composition or toxin comes in contact with an insect, resulting in a toxic effect and control of the insect. The composition or toxin can be delivered in many recognized ways, e.g., orally by ingestion by the insect via transgenic plant expression.

The term "domain" refers to a set of amino acids conserved at specific positions along an alignment of sequences of evolutionarily related proteins. While amino acids at other positions can vary between homologues, amino acids that are highly conserved at specific positions indicate amino acids that are likely essential in the structure, stability or function of a protein. Identified by their high degree of conservation in aligned sequences of a family of protein homologues, they can be used as identifiers to determine if any polypeptide in question belongs to a previously identified polypeptide group.

An "engineered" protein of the disclosure refers to a protein that has a sequence that is different at at least one amino acid position compared to at least one corresponding parent protein. An engineered protein can be a mutant protein that contains, e.g., one or more modifications such as deletions, additions, and/or substitutions of one or more amino acid positions relative to a parent protein. An engineered protein can be a chimeric protein and contain, e.g., one or more swapped or shuffled domains or fragments from at least two parent proteins.

"Effective insect-controlling amount" means that concentration of toxin or toxins that inhibits, through a toxic effect, the ability of insects to survive, grow, feed and/or reproduce, or to limit insect-related damage or loss in crop plants. "Effective insect-controlling amount" may or may not mean killing the insects, although it preferably means killing the insects. "Insecticidal" is defined as a toxic biological activity capable of controlling insects, preferably by killing them. A transgenic plant with "enhanced insecticidal properties" is a plant that is expresses a protein or proteins at effective insect-controlling amounts, so that, in some embodiments, the plant is insecticidal to an increased range of insect species, relative to a plant of the same kind which is not transformed. This increased range of insect species includes insect plant pests, such as lepidopteran insect pests, e.g., *Spodoptera frugiperda* (fall armyworm).

The term "event" refers to the original transformant and/or progeny of the transformant that include the heterologous DNA. The term "event" also refers to progeny produced by a sexual outcross between the transformant and another maize line. Even after repeated backcrossing to a recurrent parent, the inserted DNA and the flanking DNA from the transformed parent is present in the progeny of the cross at the same chromosomal location. The term "event" also refers to DNA from the original transformant comprising the inserted DNA and flanking genomic sequence immediately adjacent to the inserted DNA that would be expected to be transferred to a progeny as the result of a sexual cross of one parental line that includes the inserted DNA (e.g., the original transformant and progeny resulting from selfing) and a parental line that does not contain the inserted DNA. Typically, transformation of plant tissue produces multiple events, each of which represent insertion of a DNA construct into a different location in the genome of a plant cell.

"Expression cassette" as used herein means a nucleic acid sequence capable of directing expression of a particular nucleotide sequence(s) in an appropriate host cell, comprising one or more transgene, each transgene comprising a promoter operably linked to a nucleotide sequence of interest which is operably linked to termination signals. Each transgene also typically comprises sequences required for proper translation of the nucleotide sequence. The expression cassette comprising the nucleotide sequence(s) of interest may have at least one of its components heterologous with respect to at least one of its other components. The expression cassette may also be one that is naturally occurring but has been obtained in a recombinant form useful for heterologous expression. Typically, however, the expression cassette is heterologous with respect to the host, i.e., the particular nucleic acid sequence of the expression cassette does not occur naturally in the host cell and must have been introduced into the host cell or an ancestor of the host cell by a transformation event. The expression of the nucleotide sequence in the expression cassette may be under the control of a constitutive promoter or of an inducible promoter that initiates transcription only when the host cell is exposed to some particular external stimulus. In the case of a multicellular organism, such as a plant, the promoter can also be specific to a particular tissue, or organ, or stage of development.

An expression cassette comprising a nucleotide sequence(s) of interest may be chimeric, meaning that at least one of its components is heterologous with respect to at least one of its other components. An expression cassette may also be one that comprises a native promoter driving its native gene; however, it has been obtained in a recombinant form useful for heterologous expression. Such usage of an expression cassette makes it so it is not naturally occurring in the cell into which it has been introduced.

An expression cassette also can optionally include one or more transcriptional and/or translational termination regions that is/are functional in plants. A variety of transcriptional terminators are available for use in expression cassettes and are responsible for the termination of transcription beyond the heterologous nucleotide sequence of interest and correct mRNA polyadenylation. The termination region may be native to the transcriptional initiation region, may be native to the operably linked nucleotide sequence of interest, may be native to the plant host, or may be derived from another source (i.e., foreign or heterologous to the promoter, the nucleotide sequence of interest, the plant host, or any combination thereof).

A "gene" comprises a coding nucleic acid sequence and typically also comprises other, primarily regulatory, nucleic acids responsible for the control of the expression, that is to say the transcription and translation, of the coding portion. A gene may also comprise other 5' and 3' untranslated sequences and termination sequences. Further elements that may be present are, for example, introns. The regulatory nucleic acid sequence of the gene may not normally be operatively linked to the associated nucleic acid sequence as found in nature and thus would be a chimeric gene.

The term "germplasm" refers to genetic material of or from an individual (e.g., a plant), a group of individuals (e.g., a plant line, variety or family), or a clone derived from a line, variety, species, or culture. The germplasm can be part of an organism or cell or can be separate from the organism or cell. In general, germplasm provides genetic material with a specific molecular makeup that provides a physical foundation for some or all of the hereditary qualities of an organism or cell culture. As used herein, germplasm includes cells, seed or tissues from which new plants may be grown, or plant parts, such as leaves, stems, pollen, or cells, which can be cultured into a whole plant.

The term "heterologous" when used in reference to a gene or a polynucleotide or a polypeptide refers to a gene or a polynucleotide or a polypeptide that is or contains a part thereof not in its natural environment (i.e., has been altered by the hand of man). For example, a heterologous gene may include a polynucleotide from one species introduced into another species. A heterologous gene may also include a polynucleotide native to an organism that has been altered in some way (e.g., mutated, added in multiple copies, linked to a non-native promoter or enhancer polynucleotide, etc.). Heterologous genes further may comprise plant gene polynucleotides that comprise cDNA forms of a plant gene; the cDNAs may be expressed in either a sense (to produce mRNA) or anti-sense orientation (to produce an anti-sense RNA transcript that is complementary to the mRNA transcript). In one aspect of the disclosure, heterologous genes are distinguished from endogenous plant genes in that the heterologous gene polynucleotides are typically joined to polynucleotides comprising regulatory elements such as promoters that are not found naturally associated with the gene for the protein encoded by the heterologous gene or with plant gene polynucleotides in the chromosome, or are associated with portions of the chromosome not found in nature (e.g., genes expressed in loci where the gene is not normally expressed). Further, a "heterologous" polynucleotide refers to a polynucleotide not naturally associated with a host cell into which it is introduced, including non-naturally occurring multiple copies of a naturally occurring polynucleotide.

The terms "increase", "increasing", "increased", "enhance", "enhanced", "enhancing", and "enhancement" and similar terms, as used herein, describe an elevation in control of a plant pest, e.g., by contacting pest with a plant of the disclosure (such as, for example, by transgenic expression or by topical application methods). The increase in control can be in reference to the level of control of the plant pest in the absence of a nucleic acid molecule of the disclosure (e.g., a plant that does not comprise the nucleic acid molecule). Thus in embodiments, the terms "increase", "increasing", "increased", "enhance", "enhanced", "enhancing", and "enhancement" and similar terms can indicate an elevation of at least about 5%, 10%, 15%, 20%, 25%, 30%, 35%, 40%, 45%, 50%, 55%, 60%, 65%, 70%, 75%, 80%, 85%, 90%, 95%, 100%, 125%, 150%, 200%, 300%, 400%, 500% or more as compared to a suitable control (e.g., a plant, plant part, plant cell that does not comprise the nucleic acid molecule).

The term "identity" or "identical" in the context of two nucleic acid or amino acid sequences, refers to the percentage of identical nucleotides or amino acids in a linear polynucleotide or amino acid sequence of a reference ("query") sequence (or its complementary strand) as compared to a test ("subject") sequence when the two sequences are globally aligned. Unless otherwise stated, sequence identity as used herein refers to the value obtained using the Needleman and Wunsch algorithm ((1970) J. Mol. Biol. 48:443-453) implemented in the EMBOSS Needle alignment tool using default matrix files EBLOSUM62 for protein with default parameters (Gap Open=10, Gap Extend=0.5, End Gap Penalty=False, End Gap Open=10, End Gap Extend=0.5) or DNA full for nucleic acids with default parameters (Gap Open=10, Gap Extend=0.5, End Gap Penalty=False, End Gap Open=10, End Gap Extend=0.5); or any equivalent program thereof. EMBOSS Needle is available, e.g., from EMBL-EBI such as at the following website: ebi.ac.uk/Tools/psa/emboss_needle/ and as described in the following publication: "The EMBL-EBI search and sequence analysis tools APIs in 2019." Madeira et al. Nucleic Acids Research, June 2019, 47(W1):W636-W641. The term "equivalent program" as used herein refers to any sequence comparison program that, for any two sequences in question, generates an alignment having identical nucleotide or amino acid residue matches and an identical percent sequence identity when compared to the corresponding alignment generated by EMBOSS Needle. In some embodiments, substantially identical nucleic acid or amino acid sequences may perform substantially the same function.

In some embodiments, the polynucleotides or polypeptides of the disclosure are "isolated". The term "isolated" polynucleotide or polypeptide is a polynucleotide or polypeptide that no longer exists in its natural environment. An isolated polynucleotide or polypeptide of the disclosure may exist in a purified form or may exist in a recombinant host such as in a transgenic bacteria or a transgenic plant. Therefore, in some embodiments, an "isolated" nucleic acid molecule encompasses a nucleic acid molecule when the nucleic acid molecule is comprised within a transgenic plant genome.

The term "isolated", when used in the context of the nucleic acid molecules or polynucleotides of the present disclosure, refers to a polynucleotide that is identified within and isolated/separated from its chromosomal polynucleotide context within the respective source organism. An isolated nucleic acid or polynucleotide is not a nucleic acid as it occurs in its natural context, if it indeed has a naturally occurring counterpart. In contrast, non-isolated nucleic acids are nucleic acids such as DNA and RNA, which are found in the state they exist in nature. For example, a given polynucleotide (e.g., a gene) is found on the host cell chromosome in proximity to neighboring genes. The isolated nucleic acid molecule may be present in single-stranded or double-stranded form. Alternatively, it may contain both the sense and antisense strands (i.e., the nucleic acid molecule may be double-stranded). In some embodiments, the nucleic acid molecules of the present disclosure are isolated.

As used herein, the term "maize" includes *Zea mays* and all plant varieties that can be bred with *Zea mays*, including wild maize species. The term "maize" and "corn" are used interchangeably herein.

The term "motif" or "consensus sequence" or "signature" refers to a short conserved region in the sequence of evolutionarily related proteins. Motifs are frequently highly conserved parts of domains, but may also include only part of the domain, or be located outside of conserved domain (if all of the amino acids of the motif fall outside of a defined domain).

A "native" or "wild type" nucleic acid, polynucleotide, nucleotide sequence, polypeptide or amino acid sequence refers to a naturally occurring or endogenous nucleic acid, polynucleotide, nucleotide sequence, polypeptide or amino acid sequence.

A "nucleic acid molecule" or "nucleic acid" or "polynucleotide" (which are used interchangeably herein) is a segment of single-stranded, double-stranded or partially double-stranded DNA or RNA, or a hybrid thereof, that can be isolated or synthesized from any source. In the context of the present disclosure, the nucleic acid molecule is typically a segment of DNA. In some embodiments, the nucleic acid molecules of the disclosure are isolated nucleic acid molecules. In some embodiments, the nucleic acid molecules of the disclosure are comprised within a vector, a plant, a plant cell or a bacterial cell. The terms also include reference to a deoxyribopolynucleotide, ribopolynucleotide or analogs thereof that have the essential nature of a natural ribonucleotide in that they hybridize, under stringent hybridization conditions, to substantially the same nucleotide sequence as naturally occurring nucleotides and/or allow translation into the same amino acid(s) as the naturally occurring nucleotide(s). A nucleic acid molecule can be full-length or a subsequence of a native or heterologous structural or regulatory gene. Unless otherwise indicated, the term includes reference to the specified sequence as well as the complementary sequence thereof.

Thus, DNAs or RNAs with backbones modified for stability or for other reasons are "polynucleotides" as that term is intended herein. Moreover, DNAs or RNAs comprising unusual bases, such as inosine or modified bases, such as tritylated bases, to name just two examples, are polynucleotides as the term is used herein. It will be appreciated that a great variety of modifications have been made to DNA and RNA that serve many useful purposes known to those of skill in the art. The term polynucleotide as it is employed herein embraces such chemically, enzymatically or metabolically modified forms of polynucleotides, as well as the chemical forms of DNA and RNA characteristic of viruses and cells, including inter alia, simple and complex cells.

"Operably linked" refers to the association of polynucleotides on a single nucleic acid molecule so that the function of one affects the function of the other. For example, a promoter is operably linked with a coding polynucleotide when it is capable of affecting the expression of that coding polynucleotide (i.e., that the coding polynucleotide is under the transcriptional control of the promoter). Coding polynucleotide in sense or antisense orientation can be operably linked to regulatory polynucleotides.

The term "plant" includes reference to whole plants, plant organs, plant tissues (e.g., leaves, stems, roots, etc.), seeds and plant cells and progeny of same. Plant cell, as used herein includes, without limitation, seeds, suspension cultures, embryos, meristematic regions, callus tissue, leaves, roots, shoots, gametophytes, sporophytes, pollen and microspores. The class of plants, which can be used in the methods of the disclosure, is generally as broad as the class of higher plants amenable to transformation techniques, including both monocotyledonous and dicotyledonous plants including species from the genera: *Cucurbita, Rosa, Vitis, Juglans*, Fragaria, Lotus, *Medicago, Onobrychis, Trifolium, Trigonella, Vigna, Citrus, Linum, Geranium, Manihot, Daucus, Arabidopsis, Brassica, Raphanus, Sinapis, Atropa, Capsicum, Datura, Hyoscyamus, Lycopersicon, Nicotiana, Solanum, Petunia, Digitalis, Majorana, Ciahorium, Helianthus, Lactuca, Bromus, Asparagus, Antirrhinum, Heterocallis, Nemesis, Pelargonium, Panieum, Pennisetum, Ranunculus, Senecio, Salpiglossis, Cucumis, Browaalia, Glycine, Pisum, Phaseolus, Lolium, Oryza, Avena, Hordeum, Secale, Allium* and *Triticum*. A particularly preferred plant is maize.

A "plant cell" is a structural and physiological unit of a plant, comprising a protoplast and a cell wall. The plant cell may be in the form of an isolated single cell or a cultured cell, or as a part of a higher organized unit such as, for example, plant tissue, a plant organ, or a whole plant.

"Plant cell culture" means cultures of plant units such as, for example, protoplasts, cell culture cells, cells in plant tissues, pollen, pollen tubes, ovules, embryo sacs, zygotes and embryos at various stages of development.

"Plant material" refers to leaves, stems, roots, flowers or flower parts, fruits, pollen, egg cells, zygotes, seeds, cuttings, cell or tissue cultures, or any other part or product of a plant.

A "plant organ" is a distinct and visibly structured and differentiated part of a plant such as a root, stem, leaf, flower bud, or embryo.

As used herein, "plant material," "plant part" or "plant tissue" means plant cells, plant protoplasts, plant cell tissue cultures from which plants can be regenerated, plant calli, plant clumps, and plant cells that are intact in plants or parts of plants such as embryos, pollen, ovules, seeds, leaves, flowers, branches, fruit, kernels, ears, cobs, husks, stalks, roots, root tips, anthers, tubers, rhizomes and the like. Any tissue of a plant in planta or in culture is included in the term "plant tissue."

As used herein "plant sample" or "biological sample" refers to either intact or non-intact (e.g. milled seed or plant tissue, chopped plant tissue, lyophilized tissue) plant tissue. It may also be an extract comprising intact or non-intact seed or plant tissue. The biological sample or extract may be selected from the group consisting of corn flour, corn meal, corn syrup, corn oil, corn starch, and cereals manufactured in whole or in part to contain corn by-products.

A "polynucleotide of interest" or "nucleic acid of interest" refers to any polynucleotide which, when transferred to an organism, e.g., a plant, confers upon the organism a desired characteristic such as insect resistance, disease resistance, herbicide tolerance, antibiotic resistance, improved nutritional value, improved performance in an industrial process, production of a commercially valuable enzyme or metabolite, an altered reproductive capability, and the like.

A "portion" or a "fragment" of a polypeptide of the disclosure will be understood to mean an amino acid sequence or nucleic acid sequence of reduced length relative to a reference amino acid sequence or nucleic acid sequence of the disclosure. Such a portion or a fragment according to the disclosure may be, where appropriate, included in a larger polypeptide or nucleic acid of which it is a constituent (e.g., a tagged or fusion protein or an expression cassette). In embodiments, the "portion" or "fragment" substantially retains the activity, such as insecticidal activity (e.g., at least 40%, 50%, 60%, 70%, 80%, 85%, 90%, 95% or even 100% of the activity) of the full-length protein or nucleic acid, or has even greater activity, e.g., insecticidal activity, than the full-length protein).

As used herein, "propagule" refers to any material that is used for propagating a plant, preferably a transgenic plant. A propagule may be a seed, cutting, or plurality of cells from a transgenic plant, which can be used to produce a crop of transgenic plants.

The terms "protein," "peptide," and "polypeptide" are used interchangeably herein.

The term "promoter," as used herein, refers to a polynucleotide, usually upstream (5') of the translation start site of a coding sequence, which controls the expression of the coding sequence by providing the recognition for RNA polymerase and other factors required for proper transcription. For example, a promoter may contain a region containing basal promoter elements recognized by RNA polymerase, a region containing the 5' untranslated region (UTR) of a coding sequence, and optionally an intron.

A "pollen-free promoter" is a promoter that drives low or no detectable gene expression in the pollen of the target plant species. Quantification of mRNA transcripts of a protein of interest in pollen could be measured by various methods including qRT-PCR/RNA-Seq; the protein can be measured by commonly used ELISA and Western blot methodology. A promoter is considered pollen-free in this disclosure if the promoter drives expression of a protein of the disclosure at <10 ng/mg TSP (total soluble protein) in pollen.

As used herein, the term "recombinant" refers to a form of nucleic acid (e.g., DNA or RNA), protein, cell, tissue, organism and the like that would not normally be found in nature and as such was created by human intervention. As used herein, a "recombinant nucleic acid molecule" is a nucleic acid molecule comprising a combination of polynucleotides that would not naturally occur together and is the result of human intervention, e.g., a nucleic acid molecule that is comprised of a combination of at least two polynucleotides heterologous to each other, or a nucleic acid molecule that is artificially synthesized, for example, a polynucleotide synthesized using an assembled nucleotide sequence, and comprises a polynucleotide that deviates from the polynucleotide that would normally exist in nature, or a nucleic acid molecule that comprises a transgene artificially incorporated into a host cell's genomic DNA and the associated flanking DNA of the host cell's genome. Another example of a recombinant nucleic acid molecule is a DNA molecule resulting from the insertion of a transgene into a plant's genomic DNA, which may ultimately result in the expression of a recombinant RNA or protein molecule in that organism. As used herein, a "recombinant plant" is a plant that would not normally exist in nature, is the result of human intervention, and contains a transgene or heterologous nucleic acid molecule which may be incorporated into its genome. As a result of such genomic alteration, the recombinant plant is distinctly different from the related wild-type plant. A "recombinant" bacteria is a bacteria not found in nature that comprises a heterologous nucleic acid molecule. Such a bacteria may be created by transforming the bacteria with the nucleic acid molecule or by the conjugation-like transfer of a plasmid from one bacteria strain to another, whereby the plasmid comprises the nucleic acid molecule.

The terms "reduce," "reduced," "reducing," "reduction," "diminish," and "suppress" (and grammatical variations thereof) and similar terms, as used herein, refer to a decrease in the survival, growth and/or reproduction of a plant pest, e.g., by contacting a pest with a plant of the disclosure. This decrease in survival, growth and/or reproduction can be in reference to the level observed in the absence of a nucleic acid molecule of the disclosure (e.g., a plant that does not comprise the nucleic acid molecule). Thus, in embodiments, the terms "reduce," "reduced," "reducing," "reduction," "diminish," and "suppress" (and grammatical variations thereof) and similar terms mean a decrease of at least about 5%, 10%, 15%, 20%, 25%, 30%, 35%, 40%, 45%, 50%, 55%, 60%, 65%, 70%, 75%, 80%, 85%, 90%, 95% or more as compared with a plant that is not contacted with a nucleic acid molecule of the disclosure (e.g., a plant that does not comprise the nucleic acid molecule). In representative embodiments, the reduction results in no or essentially no (i.e., an insignificant amount, e.g., less than about 10%, less than about 5% or even less than about 1%) detectable survival, growth and/or reproduction of the plant pest.

"Regulatory elements" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences include enhancers, promoters, translational enhancer sequences, introns, terminators, and polyadenylation signal sequences. They include natural and synthetic sequences as well as sequences which may be a combination of synthetic and natural sequences. Regulatory sequences may determine expression level, the spatial and temporal pattern of expression and, for a subset of promoters, expression under inductive conditions (regulation by external factors such as light, temperature, chemicals and hormones).

As used herein, "selectable marker" means a nucleotide sequence that when expressed imparts a distinct phenotype to the plant, plant part and/or plant cell expressing the marker and thus allows such transformed plants, plant parts and/or plant cells to be distinguished from those that do not have the marker. Such a nucleotide sequence may encode either a selectable or screenable marker, depending on whether the marker confers a trait that can be selected for by chemical means, such as by using a selective agent (e.g., an antibiotic, herbicide, or the like), or on whether the marker is simply a trait that one can identify through observation or testing, such as by screening (e.g., the R-locus trait).

The terms "stringent conditions" or "stringent hybridization conditions" include reference to conditions under which a nucleic acid will selectively hybridize to a target sequence to a detectably greater degree than other sequences (e.g., at least 2-fold over a non-target sequence), and optionally may substantially exclude binding to non-target sequences.

Stringent conditions are sequence-dependent and will vary under different circumstances. By controlling the stringency of the hybridization and/or washing conditions, target sequences can be identified that can be up to 100% complementary to the reference nucleotide sequence. Alternatively, conditions of moderate or even low stringency can be used to allow some mismatching in sequences so that lower degrees of sequence similarity are detected. For example, those skilled in the art will appreciate that to function as a primer or probe, a nucleic acid sequence only needs to be sufficiently complementary to the target sequence to substantially bind thereto so as to form a stable double-stranded structure under the conditions employed. Thus, primers or probes can be used under conditions of high, moderate or even low stringency. Likewise, conditions of low or moderate stringency can be advantageous to detect homolog, ortholog and/or paralog sequences having lower degrees of sequence identity than would be identified under highly stringent conditions. Typically, stringent conditions are those in which the salt concentration is less than about 1.5 M Na ion, typically about 0.01 to 1.0 M Na ion concentration (or other salts) at about pH 7.0 to pH 8.3 and the temperature is at least about 30° C. for short probes (e.g., 10 to 50 nucleotides) and at least about 60° C. for longer probes (e.g., greater than 50 nucleotides). Stringent conditions may also be achieved with the addition of destabilizing agents such as formamide or Denhardt's (5 g Ficoll, 5 g polyvinylpyrrolidone, 5 g bovine serum albumin in 500 ml of water). Exemplary low stringency conditions include hybridization with a buffer solution of 30% to 35% formamide, 1 M NaCl, 1% SDS (sodium dodecyl sulfate) at 3TC and a wash in 1× to 2×SSC (20×SSC=3.0 M NaCl/0.3 M trisodium citrate) at 50° C. to 55° C. Exemplary moderate stringency conditions include hybridization in 40% to 45% formamide, 1 M NaCl, 1% SDS at 37° C. and a wash in 0.5× to 1×SSC at 55° C. to 60° C. Exemplary high stringency conditions include hybridization in 50% formamide, 1 M NaCl, 1% SDS at 3TC and a wash in 0.1×SSC at 60° C. to 65° C. A further non-limiting example of high stringency conditions include hybridization in 4×SSC, 5×Denhardt's, 0.1 mg/ml boiled salmon sperm DNA, and 25 mM Na phosphate at 65° C. and a wash in 0.1×SSC, 0.1% SDS at 65° C. Another illustration of high stringency hybridization conditions includes hybridization in 7% SDS, 0.5 M NaPO4, 1 mM EDTA at 50° C. with washing in 2×SSC, 0.1% SDS at 50° C., alternatively with washing in 1×SSC, 0.1% SDS at 50° C., alternatively with washing in 0.5×SSC, 0.1% SDS at 50° C., or alternatively with washing in 0.1×SSC, 0.1% SDS at 50° C., or even with washing in 0.1×SSC, 0.1% SDS at 65° C. Those skilled in the art will appreciate that specificity is typically a function of post-hybridization washes, the relevant factors being the ionic strength and temperature of the final wash solution.

"Stable transformation" or "stably transformed" as used herein means that a nucleic acid is introduced into a cell and integrates into the genome of the cell. As such, the integrated nucleic acid is capable of being inherited by the progeny thereof, more particularly, by the progeny of multiple successive generations. "Genome" as used herein also includes the nuclear and the plastid genome, and therefore includes integration of the nucleic acid into, for example, the chloroplast genome. Stable transformation as used herein can also refer to a transgene that is maintained extrachromasomally, for example, as a minichromosome.

As used herein, gene or trait "stacking" is combining desired genes or traits into one transgenic plant line. As one approach, plant breeders stack transgenic traits by making crosses between parents that each have a desired trait and then identifying offspring that have both of these desired traits (so-called "breeding stacks"). Another way to stack genes is by transferring two or more genes into the cell nucleus of a plant at the same time during transformation. Another way to stack genes is by re-transforming a transgenic plant with another gene of interest. For example, gene stacking can be used to combine two different insect resistance traits, an insect resistance trait and a disease resistance trait, or a herbicide resistance trait (such as, for example, Bt11). The use of a selectable marker in addition to a gene of interest would also be considered gene stacking.

"Synthetic" refers to a nucleotide sequence comprising bases or a structural feature(s) that is not present in the natural sequence. For example, an artificial sequence encoding a protein of the disclosure that resembles more closely the G+C content and the normal codon distribution of dicot or monocot plant genes is said to be synthetic.

As used herein, a protein of the disclosure that is "toxic" to an insect pest is meant that the protein functions as an orally active insect control agent to kill the insect pest, or the protein is able to disrupt or deter insect feeding, or causes growth inhibition to the insect pest, both of which may or may not cause death of the insect. When a toxic protein of the disclosure is delivered to an insect or an insect comes into oral contact with the toxic protein, the result is typically death of the insect, or the insect's growth is slowed, or the insect stops feeding upon the source that makes the toxic protein available to the insect.

The terms "toxin fragment" and "toxin portion" are used interchangeably herein to refer to a fragment or portion of a longer (e.g., full-length) insecticidal protein of the disclosure, where the "toxin fragment" or "toxin portion" retains insecticidal activity. For example, it is known in the art that native Cry proteins are expressed as protoxins that are processed at the N-terminal and C-terminal ends to produce a mature toxin. In embodiments, the "toxin fragment" or "toxin portion" of a chimeric insecticidal protein of the disclosure is truncated at the N-terminus and/or C-terminus. In embodiments, the "toxin fragment" or "toxin portion" is truncated at the N-terminus to remove part or all of the N-terminal peptidyl fragment, and optionally comprises at least about 400, 425, 450, 475, 500, 510, 520, 530, 540, 550, 560, 570, 580 or 590 contiguous amino acids of insecticidal protein specifically described herein or an amino acid sequence that is substantially identical thereto. Thus, in embodiments, a "toxin fragment" or "toxin portion" of an insecticidal protein is truncated at the N-terminus (e.g., to omit part or all of the peptidyl fragment), for example, an N-terminal truncation of one amino acid or more than one amino acid, e.g., up to 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60 or more amino acids. In embodiments, a "toxin fragment" or "toxin portion" of an insecticidal protein is truncated at the C-terminus (e.g., to omit part or all of the protoxin tail), for example, a C-terminal truncation of one amino acid or more than one amino acid, e.g., up to 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 70, 80, 90, 100, 125, 150, 175, 200, 225, 250, 275, 300, 325, 350, 375, 400, 425, 450, 475, 500, 525, 550, 560 or more amino acids. In embodiments, the "toxin fragment" or "toxin portion" comprises domains 1 and 2, and the core domain 3. In embodiments, the "toxin fragment" or "toxin portion" is the mature (i.e., processed) toxin (e.g., Cry toxin).

"Transformation" is a process for introducing heterologous nucleic acid into a host cell or organism. In particular embodiments, "transformation" means the stable integration of a DNA molecule into the genome (nuclear or plastid) of an organism of interest. In some particular embodiments, the introduction into a plant, plant part and/or plant cell is via bacterial-mediated transformation, particle bombardment transformation, calcium-phosphate-mediated transformation, cyclodextrin-mediated transformation, electroporation, liposome-mediated transformation, nanoparticle-mediated transformation, polymer-mediated transformation, virus-mediated nucleic acid delivery, whisker-mediated nucleic acid delivery, microinjection, sonication, infiltration, polyethylene glycol-mediated transformation, protoplast transformation, or any other electrical, chemical, physical and/or biological mechanism that results in the introduction of nucleic acid into the plant, plant part and/or cell thereof, or a combination thereof. Procedures for transforming plants are well known and routine in the art and are described throughout the literature. Non-limiting examples of methods for transformation of plants include transformation via bacterial-mediated nucleic acid delivery (e.g., via bacteria from the genus *Agrobacterium*), viral-mediated nucleic acid delivery, silicon carbide or nucleic acid whisker-mediated nucleic acid delivery, liposome mediated nucleic acid delivery, microinjection, microparticle bombardment, calcium-phosphate-mediated transformation, cyclodextrin-mediated transformation, electroporation, nanoparticle-mediated transformation, sonication, infiltration, PEG-mediated nucleic acid uptake, as well as any other electrical, chemical, physical (mechanical) and/or biological mechanism that results in the introduction of nucleic acid into the plant cell, including any combination thereof. General guides to various plant transformation methods known in the art include Miki et al. ("Procedures for Introducing Foreign DNA into Plants" in Methods in Plant Molecular Biology and Biotechnology, Glick, B. R. and Thompson, J. E., Eds. (CRC Press, Inc., Boca Raton, 1993), pages 67-88) and Rakowoczy-Trojanowska (2002, Cell Mol Biol Lett 7:849-858 (2002)).

"Transformed" and "transgenic" refer to a host organism such as a bacterium or a plant into which a heterologous nucleic acid molecule has been introduced. The nucleic acid molecule can be stably integrated into the genome of the host or the nucleic acid molecule can also be present as an extrachromosomal molecule. Such an extrachromosomal molecule can be auto-replicating. Transformed cells, tissues, or plants are understood to encompass not only the end product of a transformation process, but also transgenic progeny thereof. A "non-transformed", "non-transgenic", or "non-recombinant" host refers to a wild-type organism, e.g., a bacterium or plant, which does not contain the heterologous nucleic acid molecule.

The term "transgenic plant" includes reference to a plant into which a heterologous nucleic acid molecule has been introduced. Generally, the heterologous nucleic acid sequence is stably integrated within the genome such that the nucleic acid sequence is passed on to successive generations. The heterologous nucleic acid sequence may be integrated into the genome alone or as part of a recombinant expression cassette. "Transgenic" is used herein to include any cell, cell line, callus, tissue, plant part or plant, the genotype of which has been altered by the presence of a heterologous nucleic acid sequence, including those transgenics initially so altered as well as those created by sexual crosses or asexual propagation from the initial transgenic.

The term "vector" refers to a composition for transferring, delivering or introducing a nucleic acid (or nucleic acids) into a cell. A vector comprises a nucleic acid molecule comprising the nucleotide sequence(s) to be transferred, delivered or introduced. Example vectors include a plasmid, cosmid, phagemid, artificial chromosome, phage or viral vector.

The term "yield" may include reference to bushels per acre of a grain crop at harvest, as adjusted for grain moisture (15% typically for corn, for example), and the volume of biomass generated (for forage crops such as alfalfa and plant root size for multiple crops). Grain moisture is measured in the grain at harvest. The adjusted test weight of grain is determined to be the weight in pounds per bushel, adjusted for grain moisture level at harvest. Biomass is measured as the weight of harvestable plant material generated. Yield can be affected by many properties including without limitation, plant height, pod number, pod position on the plant, number of internodes, incidence of pod shatter, grain size, efficiency of nodulation and nitrogen fixation, efficiency of nutrient assimilation, carbon assimilation, plant architecture, percent seed germination, seedling vigor, and juvenile traits. Yield can also be affected by efficiency of germination (including germination in stressed conditions), growth rate (including growth rate in stressed conditions), ear number, seed number per ear, seed size, composition of seed (starch, oil, protein) and characteristics of seed fill. Yield of a plant of the can be measured in a number of ways, including test weight, seed number per plant, seed weight, seed number per unit area (i.e. seeds, or weight of seeds, per acre), bushels per acre, tons per acre, or kilo per hectare. For example, corn yield may be measured as production of shelled corn kernels per unit of production area, for example in bushels per acre or metric tons per hectare, often reported on a moisture adjusted basis, for example at 15.5 percent moisture. Moreover a bushel of corn is defined by law in the State of Iowa as 56 pounds by weight, a useful conversion factor for corn yield is: 100 bushels per acre is equivalent to 6.272 metric tons per hectare. Other measurements for yield are common practice in the art. In certain embodiments of the disclosure yield may be increased in stressed and/or non-stressed conditions.

Nucleic Acid Molecules

The present disclosure provides compositions and methods for controlling harmful plant pests. Particularly, the present disclosure provides a nucleic acid molecule that, when expressed in a cell, confers insecticidal properties on the cell, e.g., insecticidal activity against Lepidopteran pests such as *Spodoptera frugiperda* (fall armyworm).

Multiple different constructs were produced to determine the efficacy and agronomic impact of the expressed protein(s) in the context of different expression cassettes. Surprisingly, one vector, SEQ ID NO: 2, when transformed into maize plants conferred excellent insecticidal properties with no or minimal negative effects on the vegetative development or the fertility of the transgenic plant. The expression cassette from the vector is SEQ ID NO: 1.

A skilled person would recognize that during the insertion of a nucleic acid molecule, such as SEQ ID NO: 1, into a cell, the 5' and/or 3' ends of the inserted molecule may be deleted or rearranged. Such deletions or rearrangements may not affect the function of the inserted molecule, and these relatively small changes result in an inserted molecule that may be considered to be substantially identical to SEQ ID NO: 1. A skilled person would also recognize that the nucleic acid molecule, such as one comprising SEQ ID NO: 1, may undergo full or partial rearrangement or duplication during the insertion event, such that the inserted molecule is a full or partial rearrangement or duplication of the starting nucleic acid molecule. A skilled person would recognize that this inserted molecule may still have the same characteristics and/or traits as the starting molecule, such that the inserted molecule is substantially identical to SEQ ID NO: 1, and the transformed cell or resulting transformed plant may still be desirable.

A skilled person would recognize that a transgene for commercial use, such as a nucleic acid molecule that comprises SEQ ID NO: 1, may need relatively minor modifications to the nucleic acid sequence to comply with governmental regulatory standards. Such modifications should not affect the function of the resulting molecule, which would be substantially identical to SEQ ID NO: 1. A skilled person would recognize that the modified nucleic acid molecule would be essentially the same as the starting molecule.

Therefore, the disclosure also encompasses a nucleic acid molecule substantially identical to SEQ ID NO: 1, wherein certain nucleotides of SEQ ID NO: 1 are deleted, substituted or rearranged, resulting in a mutated SEQ ID NO:1 and wherein the functionality of the mutated SEQ ID NO:1 is the same as the starting molecule. Accordingly, in some aspects, the disclosure provides a nucleic acid molecule comprising a nucleic acid sequence that is at least 90% identical to SEQ ID NO: 1 (e.g., at least 90% identical to SEQ ID NO: 1, at least 91% identical to SEQ ID NO: 1, at least 92% identical to SEQ ID NO: 1, at least 93% identical to SEQ ID NO: 1, at least 94% identical to SEQ ID NO: 1, at least 95% identical to SEQ ID NO: 1, at least 96% identical to SEQ ID NO: 1, at least 97% identical to SEQ ID NO: 1, at least 98% identical to SEQ ID NO: 1, at least 99% identical to SEQ ID NO: 1, or at least 99.5% identical to SEQ ID NO: 1), or the complement thereof. In some embodiments, the nucleic acid molecule encodes the same protein(s) that are encoded by SEQ ID NO: 1. In some embodiments, the nucleic acid sequence comprises any one of SEQ ID NOs: 1 or 8 to 31 or any one or more of the variants in Table 3. In some embodiments, the nucleic acid molecule produces protein(s) that is/are insecticidal against one or more Lepidopteran pests, e.g., insecticidal against at least *Spodoptera frugiperda* (fall armyworm). In some embodiments, the nucleic acid molecule produces protein(s) that is/are insecticidal against at least two (e.g., 2, 3, or 4) of *Spodoptera frugiperda* (fall armyworm), *Mythimna separata* (oriental armyworm), *Spodoptera litura* (common cutworm/oriental leafworm), and *Ostrinia furnacalis* (Asian corn borer). In some embodiments, the nucleic acid molecule is isolated. In some embodiments, the nucleic acid molecule is present in a plant.

The disclosed insecticidal protein(s) encoded by a nucleic acid molecule of the disclosure (e.g., any one of SEQ ID NOs: 1 or 8 to 31 or any one or more of the variants in Table 3) have insecticidal activity against Lepidopteran pests. In some embodiments, the insecticidal protein(s) has/have activity against one or more of the following non-limiting examples of a Lepidopteran pest: *Spodoptera* spp. such as *S. frugiperda* (fall armyworm), *S. littoralis* (Egyptian cotton leafworm), *S. ornithogalli* (yellowstriped armyworm), *S. praefica* (western yellowstriped armyworm), *S. eridania* (southern armyworm), *S. litura* (Common cutworm/Oriental leafworm), *S. cosmioides* (black armyworm), *S. exempta* (African armyworm), *S. mauritia* (lawn armyworm) and/or *S. exigua* (beet armyworm); *Ostrinia* spp. such as *O. nubilalis* (European corn borer) and/or *O. furnacalis* (Asian corn borer); *Plutella* spp. such as *P. xylostella* (diamondback moth); *Agrotis* spp. such as *A. ipsilon* (black cutworm), *A. segetum* (common cutworm), *A. gladiaria* (claybacked cutworm), and/or *A. orthogonia* (pale western cutworm); *Striacosta* spp. such as *S. albicosta* (western bean cutworm); *Helicoverpa* spp. such as *H. zea* (corn earworm/soybean podworm), *H. punctigera* (native budworm), and/or *H. armigera* (cotton bollworm); *Heliothis* spp. such as *H. virescens* (tobacco budworm); *Diatraea* spp. such as *D. grandiosella* (southwestern corn borer) and/or D. saccharalis (sugarcane borer); *Trichoplusia* spp. such as *T. ni* (cabbage looper); Sesamia spp. such as *S. nonagroides* (Mediterranean corn borer), *S. inferens* (Pink stem borer) and/or *S. calamistis* (pink stem borer); *Pectinophora* spp. such as *P. gossypiella* (pink bollworm); *Cochylis* spp. such as *C. hospes* (banded sunflower moth); *Manduca* spp. such as *M. sexta* (tobacco hornworm) and/or *M. quinquemaculata* (tomato hornworm); *Elasmopalpus* spp. such as *E. lignosellus* (lesser cornstalk borer); *Pseudoplusia* spp. such as *P. includens* (soybean looper); *Anticarsia* spp. such as *A. gemmatalis* (velvetbean caterpillar); *Plathypena* spp. such as *P. scabra* (green cloverworm); *Pieris* spp. such as *P. brassicae* (cabbage butterfly), *Papaipema* spp. such as *P. nebris* (stalk borer); *Pseudaletia* spp. such as *P. unipuncta* (common armyworm); *Peridroma* spp. such as *P. saucia* (variegated cutworm); *Keiferia* spp. such as *K. lycopersicella* (tomato pinworm); *Artogeia* spp. such as *A. rapae* (imported cabbageworm); *Phthorimaea* spp. such as *P. operculella* (potato tuberworm); *Chrysodeixis* spp. such as *C. includens* (soybean looper); *Feltia* spp. such as *F. ducens* (dingy cutworm); *Chilo* spp. such as *C. suppressalis* (striped stem borer), *C. Agamemnon* (oriental corn borer), and *C. partellus* (spotted stalk borer), *Cnaphalocrocis* spp. such as *C. medinalis* (rice leaffolder), *Conogethes* spp. such as *C. punctiferalis* (Yellow peach moth), *Mythimna* spp. such as *M. separata* (Oriental armyworm), *Athetis* spp. such as *A. lepigone* (Two-spotted armyworm), *Busseola* spp. such as *B. fusca* (maize stalk borer), *Etiella* spp. such as *E. zinckenella* (pulse pod borer), *Leguminivora* spp. such as *L. glycinivorella* (soybean pod borer), *Matsumuraeses* spp. such as *M. phaseoli* (adzuki pod worm), *Omiodes* spp. such as *O. indicata* (Soybean leaffolder/Bean-leaf webworm), *Rachiplusia* spp. such as *R. nu* (sunflower Looper), or any combination of the foregoing. In some embodiments, at least one of the insecticidal protein(s) encoded by the nucleic acid molecule has/have insecticidal activity against fall armyworm (*Spodoptera frugiperda*). In some embodiments, at least one of the insecticidal protein(s) encoded by the nucleic acid molecule has/have insecticidal activity against at least two (e.g., 2, 3, or 4) of *Spodoptera frugiperda* (fall armyworm), *Mythimna separata* (oriental armyworm), *Spodoptera litura* (common cutworm/oriental leafworm), and *Ostrinia furnacalis* (Asian corn borer). In some embodiments, the insecticidal protein(s) can optionally have insecticidal activity against a fall armyworm insect pest or colony that has resistance to another insecticidal agent, including another insecticidal protein (such as, e.g., a Bt protein). In some embodiments, the insecticidal protein(s) has/have insecticidal activity against a fall armyworm colony that is resistant to a Vip3A protein (e.g., a Vip3Aa, including without limitation maize event MIR162), a Cry1F protein (e.g., Cry1Fa, including without limitation maize event TC1507 or DP-4114), a Cry1A protein (e.g., Cry1A.105, including without limitation maize event MON89034), or a Cry2 protein (e.g., Cry2Ab, including without limitation maize event MON89034).

The disclosed insecticidal protein(s) may also have insecticidal activity against Coleopteran, Hemipteran, Dipteran, *Lygus* spp., and/or other piercing and sucking insects, for example of the order Orthoptera or Thysanoptera. In some embodiments, the insecticidal protein(s) has/have activity against one or more of the following non-limiting examples of a Coleopteran pest: *Diabrotica* spp. such as *D. barberi* (northern corn rootworm), *D. virgifera virgifera* (western corn rootworm), *D. undecimpunctata howardii* (southern corn rootworm), *D. balteata* (banded cucumber beetle), *D. undecimpunctata undecimpunctata* (western spotted cucumber beetle), *D. significata* (3-spotted leaf beetle), *D. speciosa* (cucurbit beetle), *D. virgifera zeae* (Mexican corn rootworm), *D. beniensis, D. cristata, D. curviplustalata, D. dissimilis, D. elegantula, D. emorsitans, D. graminea, D.*

*hispanloe, D. lemniscata, D. linsleyi, D. milleri, D. nummularis, D. occlusal, D. porrecea, D. scutellata, D. tibialis, D. trifasciata* and/or *D. viridula; Leptinotarsa* spp. such as *L. decemlineata* (Colorado potato beetle); *Chrysomela* spp. such as *C. scripta* (cottonwood leaf beetle); *Hypothenemus* spp. such as *H. hampei* (coffee berry borer); *Sitophilus* spp. such as *S. zeamais* (maize weevil); *Epitrix* spp. such as *E. hirtipennis* (tobacco flea beetle) and/or *E. cucumeris* (potato flea beetle); *Phyllotreta* spp. such as *P. cruciferae* (crucifer flea beetle) and/or *P. pusilla* (western black flea beetle); *Anthonomus* spp. such as *A. eugenii* (pepper weevil); *Hemicrepidus* spp. such as *H. memnonius* (wireworms); *Melanotus* spp. such as *M. communis* (wireworm); *Ceutorhychus* spp. such as *C. assimilis* (cabbage seedpod weevil); *Phyllotreta* spp. such as *P. cruciferae* (crucifer flea beetle); *Aeolus* spp. such as *A. mellillus* (wireworm); *Aeolus* spp. such as *A. mancus* (wheat wireworm); *Horistonotus* spp. such as *H. uhlerii* (sand wireworm); *Sphenophorus* spp. such as *S. maidis* (maize billbug), *S. zeae* (timothy billbug), *S. parvulus* (bluegrass billbug), and *S. callosus* (southern corn billbug); *Phyllophaga* spp. (White grubs); *Chaetocnema* spp. such as *C. pulicaria* (corn flea beetle); *Popillia* spp. such as *P. japonica* (Japanese beetle); *Epilachna* spp. such as *E. varivestis* (Mexican bean beetle); *Cerotoma* spp. such as *C. trifurcate* (Bean leaf beetle); *Epicauta* spp. such as *E. pestifera* and *E. lemniscata* (Blister beetles); or any combination of the foregoing. Insects of the order Hemiptera include but are not limited to *Chinavia hilaris* (green stink bug); *Anasa tristis* De Geer (squash bug); *Blissus leucopterus* (chinch bug); *Corythuca gossypii* Fabricius (cotton lace bug); *Cyrtopeltis modesta* Distant (tomato bug); *Dysdercus suturellus* Hern ch-Schaffer (cotton stainer); *Euschistus servus* Say (brown stink bug); *E. variolarius* Palisot de Beauvois (one-spotted stink bug); *Graptostethus* spp. (complex of seed bugs); *Leptoglossus corculus* Say (leaf-footed pine seed bug); *Lygus lineolaris* Palisot de Beauvois (tarnished plant bug); *L. Hesperus* Knight (Western tarnished plant bug); *L. pratensis* Linnaeus (common meadow bug); *L. rugulipennis* Poppius (European tarnished plant bug); *Lygocoris pabulinus* Linnaeus (common green capsid); *Nezara viridula* Linnaeus (southern green stink bug); *Oebalus pugnax* Fabricius (rice stink bug); *Oncopeltus fasciatus* Dallas (large milkweed bug); *Pseudatomoscelis seriatus* Reuter (cotton fleahopper), Calocoris *norvegicus* Gmelin (strawberry bug); Orthops *campestris* Linnaeus; Plesiocoris *rugicollis* Fallen (apple capsid); *Cyrtopeltis modestus* Distant (tomato bug); *Cyrtopeltis notatus* Distant (suckfly); *Spanagonicus albofasciatus* Reuter (whitemarked fleahopper); *Diaphnocoris chlorionis* Say (honeylocust plant bug); *Labopidicola allii* Knight (onion plant bug); *Pseudatomoscelis seriatus* Reuter (cotton fleahopper); *Adelphocoris rapidus* Say (rapid plant bug); *Poecilocapsus lineatus* Fabricius (four-lined plant bug); *Nysius ericae* Schilling (false chinch bug); *Nysius raphanus* Howard (false chinch bug); *Nezara viridula* Linnaeus (Southern green stink bug); *Eurygaster* spp.; *Coreidae* spp.; *Pyrrhocoridae* spp.; *Tinidae* spp.; *Blostomatidae* spp.; *Reduviidae* spp. and *Cimicidae* spp. Insects in the order Diptera include but are not limited *Liriomyza* spp. such as *L. trifolii* (leafminer) and *L. sativae* (vegetable leafminer); *Scrobipalpula* spp. such as *S. absoluta* (tomato leafminer); *Delia* spp. such as *D. platura* (seedcom maggot), *D. brassicae* (cabbage maggot) and *D. radicum* (cabbage root fly); *Psilia* spp. such as *P. rosae* (carrot rust fly); *Tetanops* spp. such as *T. myopaeformis* (sugarbeet root maggot); and any combination of the foregoing. Insects in the order Orthoptera include but are not limited *Melanoplus* spp. such as *M. diferentialis* (Differential grasshopper), *M. femurrubrum* (Redlegged grasshopper), *M. bivittatus* (Twostriped grasshopper); and any combination thereof. Insects in the order Thysanoptera include but are not limited *Frankliniella* spp. such as *F. occidentalis* (western flower *thrips*) and *F. fusca* (tobacco *thrips*); and *Thrips* spp. such as *T. tabaci* (onion *thrips*), *T. palmi* (melon *thrips*); and any combination of the foregoing.

The disclosed insecticidal protein(s) may also have insecticidal activity against any one or more of the following: *Phyllophaga* spp., *Rhopalosiphum maidis, Pratylenchus penetrans, Melanotus cribulosus, Cyclocephala lurida, Limonius calfornicus, Tetranychus urticae, Haplothrips aculeatus, Tetranychus truncates, Anomala corpulenta, Oedaleus infernalis, Frankliniella tenuicornis, Tetranychus cinnabarinus, Aiolopus thalassinus tamulus, Trachea tokionis, Laodelphax striatellus, Holotrichia oblita, Dichelops furcatus, Diloboderus abderu, Dalbulus maidis, Astylus variegathus, Scaptocoris castanea, Locusta migratoria manilensis, Agriotes lineatus, Peregrinus maidis, Oscinella frit, Frankliniella williamsi, Zyginidia manaliensis, Atherigona soccata, Nicentrites testaceipes, Myllocerus undecimpustulatus, Atherigona naquii, Amsecta albistriga, Plodia interpuctella, Melanotus caudex, Microtermes* spp., *Atherigona oryzae, Tanymecus dilaticollis, Delphacodes kuschelli, Lepidiota stigma, Phyllophaga hellery, Tribolium castaneum, Pelopidas mathias, Oxya chinensis* (Thunberg), *Stenocranus pacificus, Scutigerella immaculata, Chrysodeixis chalcites, Euproctis* sp. (Lymantriidae), *Phyllotreata* spp. (*undulata*), *Reptalus panzer, Cyrtacanthacris tartarica Linnaeus, Orgyfa postica, Dactylispa lameyi, Patanga succincta Johanson, Tetranychus* spp., *Calomycterus* sp., *Adoretus compressus Weber*, and *Paratetranychus stickney.*

In some aspects, the disclosure provides vectors that comprise the nucleic acid molecules of the disclosure. Examples of a vector include a plasmid, cosmid, phagemid, artificial chromosome, phage or viral vector. In embodiments, the vector is plant vector, e.g., for use in transformation of plants. In embodiments, the vector is a bacterial vector, e.g., for use in transformation of bacteria. Suitable vectors for plants, bacteria and other organisms are known in the art.

In some embodiments, a nucleic acid molecule or vector of the disclosure can also include sequences that encode other desired traits in addition to the insecticidal protein(s). Such expression cassettes comprising the stacked traits may be used to create plants, plant parts or plant cells having a desired phenotype with the stacked traits (i.e., molecular stacking). Such stacked combinations in plants can also be created by other methods including, but not limited to, cross breeding plants by any conventional methodology. If stacked by genetically transforming the plants, the nucleotide sequences of interest can be combined at any time and in any order. For example, a transgenic plant comprising one or more desired traits can be used as the target to introduce further traits by subsequent transformation. The additional nucleotide sequences can be introduced simultaneously in a co-transformation protocol with a nucleic acid molecule or vector of this disclosure. For example, if two nucleotide sequences will be introduced, they can be incorporated in separate cassettes (trans) or can be incorporated on the same cassette (cis). Expression of polynucleotides can be driven by the same promoter or by different promoters. It is further recognized that polynucleotides can be stacked at a desired genomic location using a site-specific nuclease or recombination system (e.g., FRT/Flp, Cre/Lox, TALE-endonucleases, zinc finger nucleases, CRISPR/Cas and related technologies). See U.S. Pat. Nos. 7,214,536, 8,921,332, 8,765,448, 5,527,695, 5,744,336, 5,910,415, 6,110,736, 6,175,058, 6,720,475, 6,455,315, 6,458,594 and US Patent Publication Nos. US2019093090, US2019264218, US2018327785, US2017240911, US2016208272, US2019062765.

In some embodiments, a nucleic acid molecule or vector of the disclosure can include an additional coding sequence for one or more polypeptides or double stranded RNA molecules (dsRNA) of interest for agronomic traits that primarily are of benefit to a seed company, grower or grain processor. A polypeptide of interest can be any polypeptide encoded by a nucleotide sequence of interest. Non-limiting examples of polypeptides of interest that are suitable for production in plants include those resulting in agronomically important traits such as herbicide resistance (also sometimes referred to as "herbicide tolerance"), virus resistance, bacterial pathogen resistance, insect resistance, nematode resistance, or fungal resistance. See, e.g., U.S. Pat. Nos. 5,569,823; 5,304,730; 5,495,071; 6,329,504; and 6,337,431. The polypeptide also can be one that increases plant vigor or yield (including traits that allow a plant to grow at different temperatures, soil conditions and levels of sunlight and precipitation), or one that allows identification of a plant exhibiting a trait of interest (e.g., a selectable marker, seed coat color, etc.). Various polypeptides of interest, as well as methods for introducing these polypeptides into a plant, are described, for example, in U.S. Pat. Nos. 4,761,373; 4,769,061; 4,810,648; 4,940,835; 4,975,374; 5,013,659; 5,162,602; 5,276,268; 5,304,730; 5,495,071; 5,554,798; 5,561,236; 5,569,823; 5,767,366; 5,879,903, 5,928,937; 6,084,155; 6,329,504 and 6,337,431; as well as US Patent Publication No. 2001/0016956.

Polynucleotides conferring resistance/tolerance to an herbicide that inhibits the growing point or meristem, such as an imidazalinone or a sulfonylurea can also be suitable in some embodiments. Exemplary polynucleotides in this category code for mutant ALS and AHAS enzymes as described, e.g., in U.S. Pat. Nos. 5,767,366 and 5,928,937. U.S. Pat. Nos. 4,761,373 and 5,013,659 are directed to plants resistant to various imidazalinone or sulfonamide herbicides. U.S. Pat. No. 4,975,374 relates to plant cells and plants containing a nucleic acid encoding a mutant glutamine synthetase (GS) resistant to inhibition by herbicides that are known to inhibit GS, e.g., phosphinothricin and methionine sulfoximine. U.S. Pat. No. 5,162,602 discloses plants resistant to inhibition by cyclohexanedione and aryloxyphenoxypropanoic acid herbicides. The resistance is conferred by an altered acetyl coenzyme A carboxylase (ACCase).

Polypeptides encoded by nucleotides sequences conferring resistance to glyphosate are also suitable for the disclosure. See, e.g., U.S. Pat. Nos. 4,940,835 and 4,769,061. U.S. Pat. No. 5,554,798 discloses transgenic glyphosate resistant maize plants, which resistance is conferred by an altered 5-enolpyruvyl-3-phosphoshikimate (EPSP) synthase gene.

Polynucleotides coding for resistance to phosphono compounds such as glufosinate ammonium or phosphinothricin, and pyridinoxy or phenoxy propionic acids and cyclohexones are also suitable. See, European Patent Application No. 0 242 246. See also, U.S. Pat. Nos. 5,879,903, 5,276,268 and 5,561,236.

Other suitable polynucleotides include those coding for resistance to herbicides that inhibit photosynthesis, such as a triazine and a benzonitrile (nitrilase) See, U.S. Pat. No. 4,810,648. Additional suitable polynucleotides coding for herbicide resistance include those coding for resistance to 2,2-dichloropropionic acid, sethoxydim, haloxyfop, imidazolinone herbicides, sulfonylurea herbicides, triazolopyrimidine herbicides, s-triazine herbicides and bromoxynil. Also suitable are polynucleotides conferring resistance to a protox enzyme, or that provide enhanced resistance to plant diseases; enhanced tolerance of adverse environmental conditions (abiotic stresses) including but not limited to drought, excessive cold, excessive heat, or excessive soil salinity or extreme acidity or alkalinity; and alterations in plant architecture or development, including changes in developmental timing. See, e.g., U.S. Patent Publication No. 2001/0016956 and U.S. Pat. No. 6,084,155.

Additional suitable polynucleotides include those coding for insecticidal polypeptides. These polypeptides may be produced in amounts sufficient to control, for example, insect pests (i.e., insect controlling amounts). It is recognized that the amount of production of an insecticidal polypeptide in a plant necessary to control insects or other pests may vary depending upon the cultivar, type of pest, environmental factors and the like. Polynucleotides useful for additional insect or pest resistance include, for example, those that encode toxins identified in *Bacillus* organisms. Polynucleotides comprising nucleotide sequences encoding *Bacillus thuringiensis* (Bt) Cry proteins from several subspecies have been cloned and recombinant clones have been found to be toxic to lepidopteran, dipteran and/or coleopteran insect larvae. Examples of such Bt insecticidal proteins include the Cry proteins such as Cry1Aa, Cry1Ab, Cry1Ac, Cry1B, Cry1C, Cry1D, Cry1Ea, Cry1Fa, Cry3A, Cry9A, Cry9B, Cry9C, and the like, as well as vegetative insecticidal proteins such as Vip1, Vip2, Vip3, and the like. A full list of Bt-derived proteins can be found on the worldwide web at *Bacillus thuringiensis* Toxin Nomenclature Database maintained by the University of Sussex (see also, Crickmore et al. (1998) Microbiol. Mol. Biol. Rev. 62:807-813).

In embodiments, an additional polypeptide is an insecticidal polypeptide derived from a non-Bt source, including without limitation, an alpha-amylase, a peroxidase, a cholesterol oxidase, a patatin, a protease, a protease inhibitor, a urease, an alpha-amylase inhibitor, a pore-forming protein, a chitinase, a lectin, an engineered antibody or antibody fragment, a *Bacillus cereus* insecticidal protein, a *Xenorhabdus* spp. (such as *X. nematophila* or *X. bovienii*) insecticidal protein, a *Photorhabdus* spp. (such as *P. luminescens* or *P. asymobiotica*) insecticidal protein, a *Brevibacillus* spp. (such as *B. laterosporous*) insecticidal protein, a *Lysinibacillus* spp. (such as *L. sphearicus*) insecticidal protein, a *Chromobacterium* spp. (such as *C. subtsugae* or *C. piscinae*) insecticidal protein, a *Yersinia* spp. (such as *Y. entomophaga*) insecticidal protein, a *Paenibacillus* spp. (such as *P. propylaea*) insecticidal protein, a *Clostridium* spp. (such as *C. bifermentans*) insecticidal protein, a *Pseudomonas* spp. (such as *P. fluorescens*) and a lignin.

Polypeptides that are suitable for production in plants further include those that improve or otherwise facilitate the conversion of harvested plants or plant parts into a commercially useful product, including, for example, increased or altered carbohydrate content or distribution, improved fermentation properties, increased oil content, increased protein content, improved digestibility, and increased nutraceutical content, e.g., increased phytosterol content, increased tocopherol content, increased stanol content or increased vitamin content. Polypeptides of interest also include, for example, those resulting in or contributing to a reduced content of an unwanted component in a harvested crop, e.g., phytic acid, or sugar degrading enzymes. By "resulting in" or "contributing to" is intended that the polypeptide of interest can directly or indirectly contribute to the existence of a trait of interest (e.g., increasing cellulose degradation by the use of a heterologous cellulase enzyme).

In some embodiments, the polypeptide contributes to improved digestibility for food or feed. Xylanases are hemicellulolytic enzymes that improve the breakdown of plant cell walls, which leads to better utilization of the plant nutrients by an animal. This leads to improved growth rate and feed conversion. Also, the viscosity of the feeds containing xylan can be reduced. Heterologous production of xylanases in plant cells also can facilitate lignocellulosic conversion to fermentable sugars in industrial processing.

Numerous xylanases from fungal and bacterial microorganisms have been identified and characterized (see, e.g., U.S. Pat. No. 5,437,992; Coughlin et al. (1993) "Proceedings of the Second TRICEL Symposium on *Trichoderma reesei* Cellulases and Other Hydrolases" Espoo; Souminen and Reinikainen, eds. (1993) Foundation for Biotechnical and Industrial Fermentation Research 8:125-135; U.S. Patent Publication No. 2005/0208178; and PCT Publication No. WO 03/16654). In particular, three specific xylanases (XYL-I, XYL-II, and XYL-III) have been identified in *T. reesei* (Tenkanen et al. (1992) Enzyme Microb. Technol. 14:566; Torronen et al. (1992) Bio/Technology 10:1461; and Xu et al. (1998) Appl. Microbiol. Biotechnol. 49:718).

In other embodiments, a polypeptide useful for the disclosure can be a polysaccharide degrading enzyme. Plants of this disclosure producing such an enzyme may be useful for generating, for example, fermentation feedstocks for bioprocessing. In some embodiments, enzymes useful for a fermentation process include alpha amylases, proteases, pullulanases, isoamylases, cellulases, hemicellulases, xylanases, cyclodextrin glycotransferases, lipases, phytases, laccases, oxidases, esterases, cutinases, granular starch hydrolyzing enzyme and other glucoamylases.

Polysaccharide-degrading enzymes include: starch degrading enzymes such as α-amylases (EC 3.2.1.1), glucuronidases (E.C. 3.2.1.131); exo-1,4-α-D glucanases such as amyloglucosidases and glucoamylase (EC 3.2.1.3), β-amylases (EC 3.2.1.2), α-glucosidases (EC 3.2.1.20), and other exo-amylases; starch debranching enzymes, such as a) isoamylase (EC 3.2.1.68), pullulanase (EC 3.2.1.41), and the like; b) cellulases such as exo-1,4-3-cellobiohydrolase (EC 3.2.1.91), exo-1,3-β-D-glucanase (EC 3.2.1.39), β-glucosidase (EC 3.2.1.21); c) L-arabinases, such as endo-1,5-α-L-arabinase (EC 3.2.1.99), α-arabinosidases (EC 3.2.1.55) and the like; d) galactanases such as endo-1,4-β-D-galactanase (EC 3.2.1.89), endo-1,3-β-D-galactanase (EC 3.2.1.90), α-galactosidase (EC 3.2.1.22), β-galactosidase (EC 3.2.1.23) and the like; e) mannanases, such as endo-1,4-β-D-mannanase (EC 3.2.1.78), β-mannosidase (EC 3.2.1.25), α-mannosidase (EC 3.2.1.24) and the like; f) xylanases, such as endo-1,4-β-xylanase (EC 3.2.1.8), β-D-xylosidase (EC 3.2.1.37), 1,3-β-D-xylanase, and the like; and g) other enzymes such as α-L-fucosidase (EC 3.2.1.51), α-L-rhamnosidase (EC 3.2.1.40), levanase (EC 3.2.1.65), inulanase (EC 3.2.1.7), and the like. In one embodiment, the α-amylase is the synthetic α-amylase, Amy797E, described is U.S. Pat. No. 8,093,453, herein incorporated by reference in its entirety.

Further enzymes which may be used with the disclosure include proteases, such as fungal and bacterial proteases. Fungal proteases include, but are not limited to, those obtained from *Aspergillus. Trichoderma. Mucor* and *Rhizopus*, such as *A. niger. A. awamori. A. orywae* and *M. miehei*. In some embodiments, the polypeptides of this disclosure can be cellobiohydrolase (CBH) enzymes (EC 3.2.1.91). In one embodiment, the cellobiohydrolase enzyme can be CBH1 or CBH2.

Other enzymes useful with the disclosure include, but are not limited to, hemicellulases, such as mannases and arabinofuranosidases (EC 3.2.1.55); ligninases; lipases (e.g., E.C. 3.1.1.3), glucose oxidases, pectinases, xylanases, transglucosidases, alpha 1,6 glucosidases (e.g., E.C. 3.2.1.20); esterases such as ferulic acid esterase (EC 3.1.1.73) and acetyl xylan esterases (EC 3.1.1.72); and cutinases (e.g. E.C. 3.1.1.74).

Double stranded RNA molecules useful with the disclosure include but are not limited to those that suppress target insect genes. As used herein the words "gene suppression", when taken together, are intended to refer to any of the well-known methods for reducing the levels of protein produced as a result of gene transcription to mRNA and subsequent translation of the mRNA. Gene suppression is also intended to mean the reduction of protein expression from a gene or a coding sequence including posttranscriptional gene suppression and transcriptional suppression. Posttranscriptional gene suppression is mediated by the homology between of all or a part of a mRNA transcribed from a gene or coding sequence targeted for suppression and the corresponding double stranded RNA used for suppression, and refers to the substantial and measurable reduction of the amount of available mRNA available in the cell for binding by ribosomes. The transcribed RNA can be in the sense orientation to effect what is called co-suppression, in the anti-sense orientation to effect what is called anti-sense suppression, or in both orientations producing a dsRNA to effect what is called RNA interference (RNAi). Transcriptional suppression is mediated by the presence in the cell of a dsRNA, a gene suppression agent, exhibiting substantial sequence identity to a promoter DNA sequence or the complement thereof to effect what is referred to as promoter trans suppression. Gene suppression may be effective against a native plant gene associated with a trait, e.g., to provide plants with reduced levels of a protein encoded by the native gene or with enhanced or reduced levels of an affected metabolite. Gene suppression can also be effective against target genes in plant pests that may ingest or contact plant material containing gene suppression agents, specifically designed to inhibit or suppress the expression of one or more homologous or complementary sequences in the cells of the pest. Such genes targeted for suppression can encode an essential protein, the predicted function of which is selected from the group consisting of muscle formation, juvenile hormone formation, juvenile hormone regulation, ion regulation and transport, digestive enzyme synthesis, maintenance of cell membrane potential, amino acid biosynthesis, amino acid degradation, sperm formation, pheromone synthesis, pheromone sensing, antennae formation, wing formation, leg formation, development and differentiation, egg formation, larval maturation, digestive enzyme formation, hemolymph synthesis, hemolymph maintenance, neurotransmission, cell division, energy metabolism, respiration, and apoptosis.

Transgenic Cells, Plants, Plant Parts

In some aspects, the disclosure further provides transgenic cells, plants, plant parts, and the like comprising a nucleic acid molecule or vector of the disclosure (e.g., comprising any one of SEQ ID NOs: 1 or 8 to 31 or any one or more of the variants in Table 3). In some embodiments, the disclosure provides a non-human host cell comprising a nucleic acid molecule or vector of the disclosure. The transgenic non-human host cell can include, but is not limited to, a plant cell (including a monocot cell and/or a dicot cell), a yeast cell, a bacterial cell or an insect cell. Accordingly, in some embodiments, a bacterial cell is provided which is selected from the genera *Bacillus, Brevibacillus, Clostridium, Xenorhabdus, Photorhabdus, Pasteuria, Escherichia, Pseudomonas, Erwinia, Serratia, Klebsiella, Salmonella, Pasteurella, Xanthomonas, Streptomyces, Rhizobium, Rhodopseudomonas, Methylophilius, Agrobacterium, Acetobacter, Lactobacillus, Arthrobacter, Azotobacter, Leuconostoc*, or *Alcaligenes*.

In some embodiments, the transgenic plant cell is a dicot plant cell or a monocot plant cell. In additional embodiments, the dicot plant cell is a soybean cell, sunflower cell, tomato cell, cole crop cell, cotton cell, sugar beet cell or a tobacco cell. In further embodiments, the monocot cell is a barley cell, maize cell, oat cell, rice cell, sorghum cell, sugar cane cell or wheat cell. In preferred embodiments, the monocot cell is a maize cell. In some embodiments, the disclosure provides a plurality of dicot cells or monocot cells comprising a nucleic acid molecule or vector of the disclosure (e.g., a plurality of maize cells comprising a nucleic acid molecule or vector of the disclosure). In embodiments, the plurality of cells is juxtaposed to form an apoplast and are grown in natural sunlight. In embodiments, the transgenic plant cell cannot regenerate a whole plant.

In other embodiments of the disclosure, the nucleic acid molecule of the disclosure is expressed in a higher organism, for example, a plant. Such transgenic plants express effective amounts of the insecticidal protein(s) encoded by the nucleic acid molecule to control plant pests such as insect pests. When an insect starts feeding on such a transgenic plant, it ingests the expressed insecticidal protein(s). This can deter the insect from further biting into the plant tissue or may even harm or kill the insect. In some embodiments, the nucleic acid molecule of the disclosure is stably integrated in the genome of the plant. In other embodiments, the nucleic acid molecule of the disclosure is included in a non-pathogenic self-replicating virus.

In some embodiments, the transgenic plant is insecticidal against at least *Spodoptera frugiperda* (fall armyworm). In some embodiments, the transgenic plant is insecticidal against at least two (e.g., 2, 3, or 4) of *Spodoptera frugiperda* (fall armyworm), *Mythimna separata* (oriental armyworm), *Spodoptera litura* (common cutworm/oriental leafworm), and *Ostrinia furnacalis* (Asian corn borer). In some embodiments, the transgenic plant has enhanced insecticidal properties, e.g., against at least *Spodoptera frugiperda* (fall armyworm), relative to a control plant, e.g., that does not comprise the nucleic acid molecule.

In some embodiments of the disclosure, a transgenic plant cell comprising a nucleic acid molecule of the disclosure is a cell of a plant part, a plant organ or a plant culture (each as described herein) including, but not limited to, a root, a leaf, a seed, a flower, a fruit, a pollen cell, organ or plant culture, and the like, or a callus cell or culture.

A transgenic plant or plant cell transformed in accordance with the disclosure may be a monocot or dicot plant or plant cell and includes, but is not limited to, corn (maize), soybean, rice, wheat, barley, rye, oats, sorghum, millet, sunflower, safflower, sugar beet, cotton, sugarcane, oilseed rape, alfalfa, tobacco, peanuts, vegetables, including, sweet potato, bean, pea, chicory, lettuce, cabbage, cauliflower, broccoli, turnip, carrot, eggplant, cucumber, radish, spinach, potato, tomato, asparagus, onion, garlic, melons, pepper, celery, squash, pumpkin, zucchini, fruits, including, apple, pear, quince, plum, cherry, peach, nectarine, apricot, strawberry, grape, raspberry, blackberry, pineapple, avocado, *papaya*, mango, banana, and specialty plants, such as *Arabidopsis*, and woody plants such as coniferous and deciduous trees. Preferably, plants of the of the disclosure are crop plants such as maize, sorghum, wheat, sunflower, tomato, crucifers, peppers, potato, cotton, rice, soybean, sugar beet, sugarcane, tobacco, barley, oilseed rape, and the like.

Once a desired nucleic acid molecule has been transformed into a particular plant species, it may be propagated in that species or moved into other varieties of the same species, particularly including commercial varieties, using any appropriate technique including traditional breeding techniques.

The insecticidal protein(s) encoded by a nucleic acid molecule of the disclosure can function in the plant part, plant cell, plant organ, seed, harvested product, processed product or extract, and the like, as an insect control agent. In other words, the insecticidal protein(s) can continue to perform the insecticidal function it had in the transgenic plant. The nucleic acid molecule can function to express the insecticidal protein. As an alternative to expressing the insecticidal protein of the disclosure, in some embodiments the nucleic acid molecule can function to identify a transgenic plant part, plant cell, plant organ, seed, harvested product, processed product or extract of the disclosure comprising the nucleic acid molecule.

In embodiments, a transgenic plant, plant part, plant cell, plant organ, or seed of the disclosure is hemizygous for a nucleic acid molecule of the disclosure. In embodiments, a transgenic plant, plant part, plant cell, plant organ, or seed of the disclosure is homozygous for a nucleic acid molecule of the disclosure.

Additional embodiments of the disclosure include harvested products produced from the transgenic plants or parts thereof of the disclosure, as well as a processed product produced from the harvested products. A harvested product can be a whole plant or any plant part, as described herein. Thus, in some embodiments, non-limiting examples of a harvested product include a seed, a fruit, a flower or part thereof (e.g., an anther, a stigma, and the like), a leaf, a stem, and the like. In other embodiments, a processed product includes, but is not limited to, a flour, meal, oil, starch, syrup, cereal, and the like produced from a harvested seed or other plant part of the disclosure, wherein said seed or other plant part comprises a nucleic acid molecule of the disclosure.

In other embodiments, the disclosure provides an extract from a transgenic seed or a transgenic plant of the disclosure, wherein the extract comprises a nucleic acid molecule of the disclosure. Extracts from plants or plant parts can be made according to procedures well known in the art (See, de la Torre et al., Food, Agric. Environ. 2(1):84-89 (2004); Guidet, Nucleic Acids Res. 22(9): 1772-1773 (1994); Lipton et al., Food Agric. Immun. 12:153-164 (2000)). Such extracts may be used, e.g., in methods to detect the presence of a nucleic acid molecule of the disclosure.

In some embodiments, a transgenic plant, plant part, plant cell, plant organ, seed, harvested product, processed product or extract has increased insecticidal activity to one or more insect pests (e.g., a lepidopteran pest) as compared with a suitable control that does not comprise a nucleic acid molecule of the disclosure. In some embodiments, a transgenic plant, plant part, plant cell, plant organ, seed, harvested product, processed product or extract has increased insecticidal activity to at least *Spodoptera frugiperda* (fall armyworm). In some embodiments, a transgenic plant, plant part, plant cell, plant organ, seed, harvested product, processed product or extract has increased insecticidal activity to at least two (e.g., 2, 3, or 4) of *Spodoptera frugiperda* (fall armyworm), *Mythimna separata* (oriental armyworm), *Spodoptera litura* (common cutworm/oriental leafworm), and *Ostrinia furnacalis* (Asian corn borer).

Plant Transformation and Breeding

Procedures for transforming plants are well known and routine in the art and are described throughout the literature. Non-limiting examples of methods for transformation of plants include transformation via bacterial-mediated nucleic acid delivery (e.g., via *Agrobacterium*), viral-mediated nucleic acid delivery, silicon carbide or nucleic acid whisker-mediated nucleic acid delivery, liposome mediated nucleic acid delivery, microinjection, microparticle bombardment, calcium-phosphate-mediated transformation, cyclodextrin-mediated transformation, electroporation, nanoparticle-mediated transformation, sonication, infiltration, PEG-mediated nucleic acid uptake, as well as any other electrical, chemical, physical (mechanical) or biological mechanism that results in the introduction of a nucleic acid molecule into the plant cell, including any combination thereof. General guides to various plant transformation methods known in the art include Miki et al. ("Procedures for Introducing Foreign DNA into Plants" in Methods in Plant Molecular Biology and Biotechnology, Glick, B. R. and Thompson, J. E., Eds. (CRC Press, Inc., Boca Raton, 1993), pages 67-88) and Rakowoczy-Trojanowska (Cell. Mol. Biol. Lett. 7:849-858 (2002)).

For *Agrobacterium*-mediated transformation, binary vectors or vectors carrying at least one T-DNA border sequence are generally suitable, whereas for direct gene transfer (e.g., particle bombardment and the like) any vector is suitable and linear DNA containing only the construction of interest can be used. In the case of direct gene transfer, transformation with a single DNA species or co-transformation can be used (Schocher et al., Biotechnology 4:1093-1096 (1986)). For both direct gene transfer and *Agrobacterium*-mediated transfer, transformation is usually (but not necessarily) undertaken with a selectable marker that may be a positive selection (e.g., Phosphomannose Isomerase), provide resistance to an antibiotic (e.g., kanamycin, hygromycin or methotrexate) or a herbicide (e.g., glyphosate or glufosinate). However, the choice of selectable marker is not critical to the disclosure.

*Agrobacterium*-mediated transformation is a commonly used method for transforming plants because of its high efficiency of transformation and because of its broad utility with many different species. *Agrobacterium*-mediated transformation typically involves transfer of the binary vector carrying the foreign DNA of interest to an appropriate *Agrobacterium* strain that may depend on the complement of vir genes carried by the host *Agrobacterium* strain either on a co-resident Ti plasmid or chromosomally (Uknes et al. (1993) Plant Cell 5:159-169). The transfer of the recombinant binary vector to *Agrobacterium* can be accomplished by a triparental mating procedure using *Escherichia coli* carrying the recombinant binary vector, a helper *E. coli* strain that carries a plasmid that is able to mobilize the recombinant binary vector to the target *Agrobacterium* strain. Alternatively, the recombinant binary vector can be transferred to *Agrobacterium* by nucleic acid transformation (Höfgen & Willmitzer (1988) Nucleic Acids Res. 16:9877).

Dicots as well as monocots may be transformed using *Agrobacterium*. Methods for *Agrobacterium*-mediated transformation of rice include well known methods for rice transformation, such as those described in any of the following: European patent application EP 1198985 A1, Aldemita and Hodges (Planta 199: 612-617, 1996); Chan et al. (Plant Mol Biol 22 (3): 491-506, 1993), Hiei et al. (Plant J 6 (2): 271-282, 1994), which disclosures are incorporated by reference herein as if fully set forth. In the case of maize transformation, methods include those as described in either Ishida et al. (Nat. Biotechnol 14(6): 745-50, 1996) or Frame et al. (Plant Physiol 129(1): 13-22, 2002), which disclosures are incorporated by reference herein as if fully set forth. Said methods are further described by way of example in B. Jenes et al., Techniques for Gene Transfer, in: Transgenic Plants, Vol. 1, Engineering and Utilization, eds. S. D. Kung and R. Wu, Academic Press (1993) 128-143 and in Potrykus Annu. Rev. Plant Physiol. Plant Molec. Biol. 42 (1991) 205-225). The nucleic acid or the construct to be expressed is preferably cloned into a vector, which is suitable for transforming *Agrobacterium tumefaciens*, for example pBin19 (Bevan et al., Nucl. Acids Res. 12 (1984) 8711). *Agrobacteria* transformed by such a vector can then be used in known manner for the transformation of plants, such as plants used as a model, like *Arabidopsis* or crop plants such as, by way of example, tobacco plants, for example by immersing bruised leaves or chopped leaves in an Agrobacterial solution and then culturing them in suitable media. The transformation of plants by means of *Agrobacterium tumefaciens* is described, for example, by Hagen and Willmitzer in Nucl. Acid Res. (1988) 16, 9877 or is known inter alia from F. F. White, Vectors for Gene Transfer in Higher Plants; in Transgenic Plants, Vol. 1, Engineering and Utilization, eds. S. D. Kung and R. Wu, Academic Press, 1993, pp. 15-38.

Soybean plant material can be suitably transformed, and fertile plants regenerated by many methods which are well known to one of skill in the art. Examples of soybean transformation methods can be found in U.S. Pat. No. 5,024,944; Finer and McMullen (1991) In Vitro Cell Dev. Biol. 27P:175-182; McCabe et al. (1988) Bio/technology 6:923-926; Khalafalla et al. (2006) African J. of Biotechnology 5:1594-1599; U.S. Pat. No. 7,001,754; Hinchee et al. (1988) Bio/Technology 6:915-922; U.S. Pat. No. 7,002,058; U.S. Patent Application Publication No. 20040034889; U.S. Patent Application Publication No. 20080229447; and Paz et al. (2006) Plant Cell Report 25:206-213.

Transgenic plants can be generated with the heretofore described binary vectors containing selectable marker genes with different transformation methods. For example, a vector is used to transform immature seed targets as described (see e.g., U.S. Patent Application Publication No. 20080229447) to generate transgenic HPPD plants directly using HPPD inhibitor, such as mesotrione, as selection agent. Optionally, other herbicide tolerance genes can be present in the polynucleotide alongside other sequences which provide additional means of selection/identification of transformed tissue including, for example, the known genes which provide resistance to kanamycin, hygromycin, phosphinothricin, butafenacil, or glyphosate. For example, different binary vectors containing PAT or EPSPS selectable marker genes are transformed using *Agrobacterium*-mediated transformation and glufosinate or glyphosate selection as described (see e.g., U.S. Patent Application Publication No. 20080229447).

Transformation of a plant by recombinant *Agrobacterium* usually involves co-cultivation of the *Agrobacterium* with explants from the plant and follows methods well known in the art. Transformed tissue is regenerated on selection medium carrying an antibiotic or herbicide resistance marker between the binary plasmid T-DNA borders.

As discussed previously, another method for transforming plants, plant parts and plant cells involves propelling inert or biologically active particles at plant tissues and cells. See, e.g., U.S. Pat. Nos. 4,945,050; 5,036,006 and 5,100,792. Generally, this method involves propelling inert or biologically active particles at the plant cells under conditions effective to penetrate the outer surface of the cell and afford incorporation within the interior thereof. When inert particles are utilized, the vector can be introduced into the cell by coating the particles with the vector containing the nucleic acid of interest. Alternatively, a cell or cells can be surrounded by the vector so that the vector is carried into the cell by the wake of the particle. Biologically active particles (e.g., a dried yeast cell, a dried bacterium or a bacteriophage, each containing one or more nucleic acids sought to be introduced) also can be propelled into plant tissue.

In other embodiments, a nucleic acid molecule of the disclosure can be directly transformed into the plastid genome. Plastid transformation technology is extensively described in U.S. Pat. Nos. 5,451,513, 5,545,817, and 5,545,818, in PCT application no. WO 95/16783, and in McBride et al. (1994) Proc. Natl. Acad. Sci. USA 91, 7301-7305.

Methods of selecting for transformed, transgenic plants, plant cells or plant tissue culture are routine in the art and can be employed in the methods of the disclosure provided herein. For example, a nucleic acid molecule or vector of the disclosure also can include an expression cassette comprising a nucleotide sequence for a selectable marker, which can be used to select a transformed plant, plant part or plant cell.

Examples of selectable markers include, but are not limited to, a nucleotide sequence encoding neo or nptII, which confers resistance to kanamycin, G418, and the like (Potrykus et al. (1985) Mol. Gen. Genet. 199:183-188); a nucleotide sequence encoding bar, which confers resistance to phosphinothricin; a nucleotide sequence encoding an altered 5-enolpyruvylshikimate-3-phosphate (EPSP) synthase, which confers resistance to glyphosate (Hinchee et al. (1988) Biotech. 6:915-922); a nucleotide sequence encoding a nitrilase such as bxn from *Klebsiella ozaenae* that confers resistance to bromoxynil (Stalker et al. (1988) Science 242:419-423); a nucleotide sequence encoding an altered acetolactate synthase (ALS) that confers resistance to imidazolinone, sulfonylurea or other ALS-inhibiting chemicals (EP Patent Application No. 154204); a nucleotide sequence encoding a methotrexate-resistant dihydrofolate reductase (DHFR) (Thillet et al. (1988) J. Biol. Chem. 263:12500-12508); a nucleotide sequence encoding a dalapon dehalogenase that confers resistance to dalapon; a nucleotide sequence encoding a mannose-6-phosphate isomerase (also referred to as phosphomannose isomerase (PMI)) that confers an ability to metabolize mannose (U.S. Pat. Nos. 5,767,378 and 5,994,629); a nucleotide sequence encoding an altered anthranilate synthase that confers resistance to 5-methyl tryptophan; or a nucleotide sequence encoding hph that confers resistance to hygromycin. One of skill in the art is capable of choosing a suitable selectable marker for use in an expression cassette of this disclosure.

Additional selectable markers include, but are not limited to, a nucleotide sequence encoding β-glucuronidase or uidA (GUS) that encodes an enzyme for which various chromogenic substrates are known; an R-locus nucleotide sequence that encodes a product that regulates the production of anthocyanin pigments (red color) in plant tissues (Dellaporta et al., "Molecular cloning of the maize R-nj allele by transposon-tagging with Ac" 263-282 In: Chromosome Structure and Function: Impact of New Concepts, 18th Stadler Genetics Symposium (Gustafson & Appels eds., Plenum Press 1988)); a nucleotide sequence encoding β-lactamase, an enzyme for which various chromogenic substrates are known (e.g., PADAC, a chromogenic cephalosporin) (Sutcliffe (1978) Proc. Natl. Acad. Sci. USA 75:3737-3741); a nucleotide sequence encoding xylE that encodes a catechol dioxygenase (Zukowsky et al. (1983) Proc. Natl. Acad. Sci. USA 80:1101-1105); a nucleotide sequence encoding tyrosinase, an enzyme capable of oxidizing tyrosine to DOPA and dopaquinone, which in turn condenses to form melanin (Katz et al. (1983) J. Gen. Microbiol. 129:2703-2714); a nucleotide sequence encoding β-galactosidase, an enzyme for which there are chromogenic substrates; a nucleotide sequence encoding luciferase (lux) that allows for bioluminescence detection (Ow et al. (1986) Science 234:856-859); a nucleotide sequence encoding aequorin which may be employed in calcium-sensitive bioluminescence detection (Prasher et al. (1985) Biochem. Biophys. Res. Comm. 126:1259-1268); or a nucleotide sequence encoding green fluorescent protein (Niedz et al. (1995) Plant Cell Reports 14:403-406) or other fluorescent protein such as dsRed or mCherry. One of skill in the art is capable of choosing a suitable selectable marker for use in an expression cassette of this disclosure.

Further, as is well known in the art, intact transgenic plants can be regenerated from transformed plant cells, plant tissue culture or cultured protoplasts using any of a variety of known techniques. Plant regeneration from plant cells, plant tissue culture or cultured protoplasts is described, for example, in Evans et al. (Handbook of Plant Cell Cultures, Vol. 1, MacMilan Publishing Co. New York (1983)); and Vasil I. R. (ed.) (Cell Culture and Somatic Cell Genetics of Plants, Acad. Press, Orlando, Vol. I (1984), and Vol. II (1986)).

Additionally, the genetic properties engineered into the transgenic seeds and plants, plant parts, or plant cells of the disclosure described above can be passed on by sexual reproduction or vegetative growth and therefore can be maintained and propagated in progeny plants. Generally, maintenance and propagation make use of known agricultural methods developed to fit specific purposes such as harvesting, sowing or tilling.

A nucleic acid molecule of the disclosure therefore can be introduced into the plant, plant part or plant cell in any number of ways that are well known in the art, as described above. Therefore, no particular method for introducing a nucleic acid molecule into a plant is relied upon, rather any method that allows the nucleic acid molecule to be stably integrated into the genome of the plant can be used. Where more than one polynucleotide is to be introduced, the respective polynucleotides can be assembled as part of a single nucleic acid molecule, or as separate nucleic acid molecules, and can be located on the same or different nucleic acid molecules. Accordingly, the polynucleotides can be introduced into the cell of interest in a single transformation event, in separate transformation events, or, for example, in plants, as part of a breeding protocol.

Once a desired nucleic acid molecule has been transformed into a particular plant species, it may be propagated in that species or moved into other varieties of the same species, particularly including commercial varieties, using traditional breeding techniques.

In some embodiments, a transgenic plant, plant part, plant cell, plant organ, seed, harvested product, processed product or extract of the disclosure can comprise one or more other nucleic acids of interest that provide one or more input traits (e.g., insect resistance, herbicide resistance, fungal resistance, virus resistance, stress tolerance, disease resistance, male sterility, stalk strength, and the like) and/or output traits (e.g., increased yield, modified starches, improved oil profile, balanced amino acids, high lysine or methionine, increased digestibility, improved fiber quality, drought resistance, and the like). In some embodiments, a transgenic plant of the disclosure can bred be with another transgenic plant comprising one or more other nucleic acids of interest.

In some embodiments, one or more other nucleic acids of interest encode one or more second pest control agents, e.g., a *Bacillus thuringiensis* (Bt) insecticidal protein, and/or a non-Bt insecticidal agent including without limitation a *Xenorhabdus* insecticidal protein, a *Photorhabdus* insecticidal protein, a *Brevibacillus laterosporus* insecticidal protein, a *Bacillus sphaericus* insecticidal protein, a protease inhibitor (both serine and cysteine types), a lectin, an alpha-amylase, a peroxidase, a cholesterol oxidase, or a double stranded RNA (dsRNA) molecule. In additional embodiments, the second pest control agent can be one or more of any number of *Bacillus thuringiensis* insecticidal proteins including but not limited to a Cry protein, a vegetative insecticidal protein (VIP) and insecticidal chimeras of any of the preceding insecticidal proteins. In some embodiments, the second pest control agent can be non-proteinaceous, for example, an interfering RNA molecule such as a dsRNA.

In some embodiments, the second pest control agent comprises any one or more of the insecticidal proteins or dsRNAs present in any of the following events: the Bt11 event (see U.S. Pat. No. 6,114,608), the MIR604 event (see U.S. Pat. No. 8,884,102), the MIR162 event (see U.S. Pat. No. 8,232,456), the 5307 event (see U.S. Pat. No. 10,428,393), the MZIR098 event (see US Patent Application No. US20200190533), the TC1507 event (see U.S. Pat. No. 7,288,643), the DAS-59122-7 event (see U.S. Pat. No. 7,323,556), the MON810 event (see U.S. Pat. No. 6,713,259), the MON863 event (see U.S. Pat. No. 7,705,216), the MON89034 event (see U.S. Pat. No. 8,062,840), the MON88017 event (see U.S. Pat. No. 9,556,492), the DP-4114 event (see U.S. Pat. No. 9,725,772), the MON87411 event (see U.S. Pat. No. 9,441,240), the DP-032218-9 event (see US Patent Application No. US2015361447), the DP-033121-3 event (see US Patent Application No. US2015361446), the DP-023211-2 event (see PCT Publication No. WO2019209700), the MON95379 event (see US Patent Application No. US2020032289), the DBN9936 event (see PCT Publication No. WO2016173361), the DBN9501 event (see PCT Publication No. WO20207125), the GH5112E-117C event (see PCT Publication No. WO17/088480), LP007-1 (see Chinese Patent Application No. CN112852801), LP007-2 (Chinese Patent Application No. CN112831584), LP007-3 (Chinese Patent Application No. CN112877454), LP007-4 (Chinese Patent Application No. CN112831585), LP007-5 (Chinese Patent Application No. CN113151534), LP007-6 (Chinese Patent Application No. CN113151533), LP007-7 (Chinese Patent Application No. CN112852991), LP007-8 (CN113980958), Ruifeng8, ND207, or the Ruifeng125 event (see Chinese Patent Application No. CN105017391). In some embodiments, the second pest control agent comprises any one or more of the following events: the Bt11 event (see U.S. Pat. No. 6,114,608), the MIR604 event (see U.S. Pat. No. 8,884,102), the MIR162 event (see U.S. Pat. No. 8,232,456), the 5307 event (see U.S. Pat. No. 10,428,393), the MZIR098 event (see US Patent Application No. US20200190533), the TC1507 event (see U.S. Pat. No. 7,288,643), the DAS-59122-7 event (see U.S. Pat. No. 7,323,556), the MON810 event (see U.S. Pat. No. 6,713,259), the MON863 event (see U.S. Pat. No. 7,705,216), the MON89034 event (see U.S. Pat. No. 8,062,840), the MON88017 event (see U.S. Pat. No. 9,556,492), the DP-4114 event (see U.S. Pat. No. 9,725,772), the MON87411 event (see U.S. Pat. No. 9,441,240), the DP-032218-9 event (see US Patent Application No. US2015361447), the DP-033121-3 event (see US Patent Application No. US2015361446), the DP-023211-2 event (see PCT Publication No. WO2019209700), the MON95379 event (see US Patent Application No. US2020032289), the DBN9936 event (see PCT Publication No. WO2016173361), the DBN9501 event (see PCT Publication No. WO20207125), the GH5112E-117C event (see PCT Publication No. WO17/088480), LP007-1 (see Chinese Patent Application No. CN112852801), LP007-2 (Chinese Patent Application No. CN112831584), LP007-3 (Chinese Patent Application No. CN112877454), LP007-4 (Chinese Patent Application No. CN112831585), LP007-5 (Chinese Patent Application No. CN113151534), LP007-6 (Chinese Patent Application No. CN113151533), LP007-7 (Chinese Patent Application No. CN112852991), LP007-8 (CN113980958), Ruifeng8, ND207, or the Ruifeng125 event (see Chinese Patent Application No. CN105017391).

In embodiments, the second pest control agent may be derived from sources other than *B. thuringiensis*. For example, the second pest control agent can be an alpha-amylase, a peroxidase, a cholesterol oxidase, a patatin, a protease, a protease inhibitor, a urease, an alpha-amylase inhibitor, a pore-forming protein, a chitinase, a lectin, an engineered antibody or antibody fragment, a *Bacillus cereus* insecticidal protein, a *Xenorhabdus* spp. (such as *X. nematophila* or *X. bovienii*) insecticidal protein, a *Photorhabdus* spp. (such as *P. luminescens* or *P. asymobiotica*) insecticidal protein, a *Brevibacillus* spp. (such as *B. laterosporous*) insecticidal protein, a *Lysinibacillus* spp. (such as *L. sphearicus*) insecticidal protein, a *Chromobacterium* spp. (such as *C. subtsugae* or *C. piscinae*) insecticidal protein, a *Yersinia* spp. (such as *Y. entomophaga*) insecticidal protein, a *Paenibacillus* spp. (such as *P. propylaea*) insecticidal protein, a *Clostridium* spp. (such as *C. bifermentans*) insecticidal protein, a *Pseudomonas* spp. (such as *P. fluorescens*) and a lignin. In other embodiments, the second agent may be at least one insecticidal protein derived from an insecticidal toxin complex (Tc) from *Photorhabdus, Xenorhabus, Serratia*, or *Yersinia*. In other embodiments, the insecticidal protein may be an ADP-ribosyltransferase derived from an insecticidal bacteria, such as *Photorhabdus* ssp. In other embodiments, the insecticidal protein may be a VIP protein, such as VIP1 and/or VIP2 from *B. cereus*. In still other embodiments, the insecticidal protein may be a binary toxin derived from an insecticidal bacterium, such as ISP1A and ISP2A from *B. laterosporous* or BinA and BinB from *L. sphaericus*. In still other embodiments, the insecticidal protein may be engineered or may be a hybrid or chimera of any of the preceding insecticidal proteins.

In some embodiments, one or more other nucleic acids of interest encode one or more herbicide tolerance agents, e.g., PAT (phosphinothricin N-acetyltransferase), AAD-1 (aryloxyalkanoate dioxygenase 1), EPSPS (5-enolpyruvulshikimate-3-phosphate synthase), or inhibitors of protoporphyrinogen oxidase (PPO, see, e.g., US Patent Application No. US2019185873). In some embodiments, the herbicide tolerance agent comprises any one or more of the following events: GA21 (see PCT Publication No. WO98/44140), NK603 (see U.S. Pat. No. 6,825,400), DAS40278 (see PCT Publication No. WO2011/022469), DBN9858 (see PCT Publication No. WO2016173508), MON87429 (see PCT Publication No. WO19/152316), LW2-2 (see Chinese Patent Application No. CN113278721) and T25 (see USDA/APHIS Petition 94-357-01 for Determination of Nonregulated Status for Glufosinate Resistant Corn Transformation Events T14 and T25, June 1995).

In some embodiments, one or more other nucleic acids of interest encode one or more enzymes, e.g., an alpha-amylase. In some embodiments, the enzyme comprises the 3272 event (see U.S. Pat. No. 7,635,799).

In some embodiments, one or more other nucleic acids of interest comprise one or more of the following events: MZDT09Y (see U.S. Pat. No. 9,121,033), LY038 (see U.S. Pat. No. 7,157,281), BT176 (see Koziel et al. (1993) Biotechnology 11: 194-200), and DP202216-6 (see US Patent Application No US2019320607).

Transgenic plants or seed comprising a nucleic acid molecule of the disclosure can also be treated with an insecticide or insecticidal seed coating as described, e.g., in U.S. Pat. Nos. 5,849,320 and 5,876,739. In some embodiments, both the insecticide or insecticidal seed coating and the transgenic plant or seed of the disclosure are active against the same target insect, for example a lepidopteran pest (e.g., fall armyworm). Thus, in some embodiments, a method is provided of enhancing control of a lepidopteran insect population comprising providing a transgenic plant or seed of the disclosure and applying to the plant or the seed an insecticide or insecticidal seed coating.

Even where the insecticide or insecticidal seed coating is active against a different insect, the insecticide or insecticidal seed coating is useful to expand the range of insect control, for example by adding an insecticide or insecticidal seed coating that has activity against coleopteran insects to a transgenic seed of the disclosure, which, in some embodiments, has activity against lepidopteran insects, the coated transgenic seed produced controls both lepidopteran and coleopteran insect pests.

Methods of Using Nucleic Acid Molecules and Transgenic Plants

In some aspects, the disclosure also provides methods of producing and using a nucleic acid molecule of the disclosure and related compositions such as cells and plants comprising the nucleic acid molecule and uses thereof.

In some embodiments, the methods of the disclosure provide control of at least one lepidopteran insect pest, including without limitation, one or more of the following: *Spodoptera* spp. such as *S. frugiperda* (fall armyworm), *S. littoralis* (Egyptian cotton leafworm), *S. ornithogalli* (yellowstriped armyworm), *S. praefica* (western yellowstriped armyworm), *S. eridania* (southern armyworm), *S. litura* (Common cutworm/Oriental leafworm), *S. cosmioides* (black armyworm), *S. exempta* (African armyworm), *S. mauritia* (lawn armyworm) and/or *S. exigua* (beet armyworm); *Ostrinia* spp. such as *O. nubilalis* (European corn borer) and/or *O. furnacalis* (Asian corn borer); *Plutella* spp. such as *P. xylostella* (diamondback moth); *Agrotis* spp. such as *A. ipsilon* (black cutworm), *A. segetum* (common cutworm), *A. gladiaria* (claybacked cutworm), and/or *A. orthogonia* (pale western cutworm); *Striacosta* spp. such as *S. albicosta* (western bean cutworm); *Helicoverpa* spp. such as *H. zea* (corn earworm/soybean podworm), *H. punctigera* (native budworm), and/or *H. armigera* (cotton bollworm); *Heliothis* spp. such as *H. virescens* (tobacco budworm); *Diatraea* spp. such as *D. grandiosella* (southwestern corn borer) and/or *D. saccharalis* (sugarcane borer); *Trichoplusia* spp. such as *T. ni* (cabbage looper); Sesamia spp. such as *S. nonagroides* (Mediterranean corn borer), *S. inferens* (Pink stem borer) and/or *S. calamistis* (pink stem borer); *Pectinophora* spp. such as *P. gossypiella* (pink bollworm); *Cochylis* spp. such as *C. hospes* (banded sunflower moth); *Manduca* spp. such as *M. sexta* (tobacco hornworm) and/or *M. quinquemaculata* (tomato hornworm); *Elasmopalpus* spp. such as *E. lignosellus* (lesser cornstalk borer); *Pseudoplusia* spp. such as *P. includens* (soybean looper); *Anticarsia* spp. such as *A. gemmatalis* (velvetbean caterpillar); *Plathypena* spp. such as *P. scabra* (green cloverworm); *Pieris* spp. such as *P. brassicae* (cabbage butterfly), *Papaipema* spp. such as *P. nebris* (stalk borer); *Pseudaletia* spp. such as *P. unipuncta* (common armyworm); *Peridroma* spp. such as *P. saucia* (variegated cutworm); *Keiferia* spp. such as *K. lycopersicella* (tomato pinworm); *Artogeia* spp. such as *A. rapae* (imported cabbageworm); *Phthorimaea* spp. such as *P. operculella* (potato tuberworm); *Chrysodeixis* spp. such as *C. includens* (soybean looper); *Feltia* spp. such as *F. ducens* (dingy cutworm); *Chilo* spp. such as *C. suppressalis* (striped stem borer), C. *Agamemnon* (oriental corn borer), and *C. partellus* (spotted stalk borer), *Cnaphalocrocis* spp. such as *C. medinalis* (rice leaffolder), *Conogethes* spp. such as *C. punctiferalis* (Yellow peach moth), *Mythimna* spp. such as *M. separata* (Oriental armyworm), *Athetis* spp. such as *A. lepigone* (Two-spotted armyworm), *Busseola* spp. such as *B. fusca* (maize stalk borer), *Etiella* spp. such as *E. zinckenella* (pulse pod borer), *Leguminivora* spp. such as *L. glycinivorella* (soybean pod borer), *Matsumuraeses* spp. such as *M. phaseoli* (adzuki pod worm), *Omiodes* spp. such as *O. indicata* (Soybean leaffolder/Bean-leaf webworm), *Rachiplusia* spp. such as *R. nu* (sunflower Looper), or any combination of the foregoing. In some embodiments, the lepidopteran pest is at least *S. frugiperda* (fall armyworm). In some embodiments, the lepidopteran pest is at least two (e.g., 2, 3, or 4) of *Spodoptera frugiperda* (fall armyworm), *Mythimna separata* (oriental armyworm), *Spodoptera litura* (common cutworm/oriental leafworm), and *Ostrinia furnacalis* (Asian corn borer).

In some embodiments, the methods provide control of a fall armyworm insect pest or colony that is resistant to another insecticidal protein such as a Vip3A protein (e.g., a Vip3Aa, including without limitation maize event MIR162), a Cry1F protein (e.g., Cry1Fa, including without limitation maize event TC1507 or DP-4114), a Cry1A protein (e.g., Cry1A.105, including without limitation maize event MON89034), and/or a Cry2 protein (e.g., Cry2Ab, including without limitation maize event MON89034).

In further embodiments, a method of controlling a lepidopteran pest is provided, the method comprising delivering to the pest an effective amount of a plant or plant part comprising a nucleic acid molecule of the disclosure. To be effective, the insecticidal protein(s) expressed by the nucleic acid molecule of the disclosure is/are orally ingested by the pest. In some embodiments, the insecticidal protein(s) are delivered to the pest in a transgenic plant, wherein the pest eats (ingests) one or more parts of the transgenic plant, thereby ingesting the insecticidal protein(s) that is/are expressed in the transgenic plant.

Also encompassed are methods of producing a transgenic plant with enhanced insecticidal properties. In representative embodiments, the method comprises: introducing into a plant a nucleic acid molecule of the disclosure, wherein the nucleotide acid molecule is expressed in the plant to produce insecticidal protein(s), thereby conferring to the plant enhanced insecticidal properties.

In some embodiments, the method of introducing the nucleic acid molecule of the disclosure into the plant comprises first transforming a plant cell with the nucleic acid molecule of the disclosure and regenerating a transgenic plant therefrom, where the transgenic plant comprises the nucleic acid molecule of the disclosure. In some embodiments, the method comprises introducing into a plant, tissue culture, or a plant cell the nucleic acid molecule of the disclosure to obtain a transformed plant, transformed tissue culture, or a transformed cell having enhanced insecticidal properties; and growing the transformed plant or regenerating a transformed plant from the transformed tissue culture or transformed plant cell, so a transgenic plant with enhanced insecticidal properties is produced.

Alternatively, or additionally, the introducing step can comprise crossing a first plant comprising the nucleic acid molecule of the disclosure with a second plant (e.g., a different plant from the first plant, for example, a plant that does not comprise the nucleic acid molecule of the disclosure) and, optionally, producing a progeny plant that comprises the nucleic acid molecule of the disclosure. Thus, a transgenic plant encompasses a plant that is the direct result of a transformation event and the progeny thereof (of any generation) that comprise the nucleic acid molecule of the disclosure.

The disclosure further provides a method of identifying a transgenic plant of the disclosure, the method comprising detecting the presence of a nucleic acid molecule of the disclosure in a plant (or a plant cell, plant part, and the like derived therefrom), and thereby identifying the plant as a transgenic plant of the disclosure based on the presence of the nucleic acid molecule of the disclosure.

Some embodiments further provide a method of producing a transgenic plant with increased resistance to at least one insect pest (e.g., a least one lepidopteran pest), the method comprising: planting a seed comprising a nucleic acid molecule of the disclosure or vector of the disclosure, and growing a transgenic plant from the seed, where the transgenic plant comprises the nucleic acid molecule of the disclosure.

The methods of producing a transgenic plant described herein optionally comprise a further step of harvesting a seed from the transgenic plant, where the seed comprises the nucleic acid molecule of the disclosure. Optionally, the seed produces a further transgenic plant that comprises the nucleic acid molecule of the disclosure.

The disclosure further provides plant parts, plant cells, plant organs, plant cultures, seed, plant extracts, harvested products and processed products of the transgenic plants produced by the methods of the disclosure.

As a further aspect, the disclosure also provides a method of producing seed, the method comprising: providing a transgenic plant that comprises a nucleic acid molecule of the disclosure, and harvesting a seed from the transgenic plant, wherein the seed comprises the nucleic acid molecule of the disclosure. Optionally, the seed produces a further transgenic plant that comprises the nucleic acid molecule of the disclosure. In representative embodiments, the step of providing the transgenic plant comprises planting a seed that produces the transgenic plant.

Further provided is a method of producing a hybrid plant seed, the method comprising: crossing a first inbred plant, which is a transgenic plant comprising a nucleic acid molecule of the disclosure of the disclosure with a different inbred plant (e.g., an inbred plant that does not comprise a nucleic acid molecule of the disclosure) and allowing hybrid seed to form. Optionally, the method further comprises harvesting a hybrid seed. In some embodiments, the hybrid seed comprises the nucleic acid molecule of the disclosure. In some embodiments, the hybrid seed produces a transgenic plant that comprises the nucleic acid molecule of the disclosure.

In some embodiments, the disclosure provides a method of producing a commodity plant product, the method comprising using a transgenic plant comprising a nucleic acid molecule of the disclosure to produce said commodity plant product therefrom. Example commodity plant products include grain, starch, seed oil, syrup, flour, meal, starch, cereal, protein and the like. Methods of producing such commodity plant products are well known in the art.

In some aspects, the disclosure provides a method of detecting the presence of a nucleic acid molecule in a sample, the method comprising: (a) contacting the sample with a pair of primers that, when used in a nucleic-acid amplification reaction with DNA comprising the nucleic acid molecule of any of the above-mentioned embodiments or any other embodiment described herein (e.g., comprising any one of SEQ ID NOs: 1 or 8 to 31 or any one or more of the variants in Table 3), produces an amplicon that is diagnostic for the nucleic acid molecule; (b) performing a nucleic acid amplification reaction, thereby producing the amplicon; and (c) detecting the amplicon. In some embodiments, the pair of primers is a first primer and a second primer wherein the first primer comprises at least 10 (e.g., at least 10, at least 15 or at least 20) contiguous nucleotides that are complementary to any one of SEQ ID NOs: 1 or 8 to 31 or any one or more of the variants in Table 3 and the second primer comprises at least 10 contiguous nucleotides that are complementary to the reverse complement of any one of SEQ ID NOs: 1 or 8 to 31 or any one or more of the variants in Table 3. In some embodiments, the first and second primer are between 10-50, 10-40, 10-30, or 10-20 nucleotides in length. In some embodiments, the sample is a sample obtained from a maize plant part or cell.

In some aspects, the disclosure provides a method of detecting the presence of a nucleic acid molecule in a sample, the method comprising: (a) contacting the sample with a probe that hybridizes under high stringency conditions with DNA comprising the nucleic acid molecule of any of the above-mentioned embodiments or any other embodiment described herein (e.g., comprising any one of SEQ ID NOs: 1 or 8 to 31 or any one or more of the variants in Table 3) and does not hybridize under high stringency conditions with DNA of a control maize plant not comprising the nucleic acid molecule; (b) subjecting the sample and probe to high stringency hybridization conditions; and (c) detecting hybridization of the probe to the nucleic acid molecule. In some embodiments, the probe comprises at least 10 (e.g., at least 10, at least 15 or at least 20) contiguous nucleotides that are complementary to any one of SEQ ID NOs: 1 or 8 to 31 or any one or more of the variants in Table 3 or the reverse complement thereof. In some embodiments, the probe is between 10-50, 10-40, 10-30, or 10-20 nucleotides in length. In some embodiments, the sample is a sample obtained from a maize plant part or cell.

In some aspects, the disclosure provides a pair of polynucleotide primers comprising a first polynucleotide primer and a second polynucleotide primer which function together in the presence of the nucleic acid molecule of any of the above-mentioned embodiments or any other embodiment described herein (e.g., comprising any one of SEQ ID NOs: 1 or 8 to 31 or any one or more of the variants in Table 3) in a sample to produce an amplicon diagnostic for the presence of the nucleic acid molecule in a sample. In some embodiments, the sample is a sample obtained from a maize plant part or cell. In some embodiments, the first polynucleotide primer comprises at least 10 contiguous nucleotides that are complementary to any one of SEQ ID NOs: 1 or 8 to 31 or any one or more of the variants in Table 3 and the second polynucleotide primer comprises at least 10 (e.g., at least 10, at least 15 or at least 20) contiguous nucleotides that are complementary to the reverse complement of any one of SEQ ID NOs: 1 or 8 to 31 or any one or more of the variants in Table 3. In some embodiments, the first and second primer are between 10-50, 10-40, 10-30, or 10-20 nucleotides in length.

In some aspects, the disclosure provides a kit for detecting the nucleic acid molecule of any of the above-mentioned embodiments or any other embodiment described herein (e.g., comprising any one of SEQ ID NOs: 1 or 8 to 31 or any one or more of the variants in Table 3), the kit comprising at least one nucleic acid molecule of sufficient length of contiguous nucleotides to function as a primer or probe in a nucleic acid detection method, and which upon amplification of or hybridization to a target nucleic acid sequence in a sample followed by detection of the amplicon or hybridization to the target sequence, are diagnostic for the presence of the nucleic acid molecule. In some embodiments, the at least one nucleic acid molecule comprises at least 10 (e.g., at least 10, at least 15 or at least 20) contiguous nucleotides that are complementary to any one of SEQ ID NOs: 1 or 8 to 31 or any one or more of the variants in Table 3. In some embodiments, the at least one nucleic acid molecule comprises a pair of primers, wherein the first polynucleotide primer comprises at least 10 (e.g., at least 10, at least 15 or at least 20) contiguous nucleotides that are complementary to any one of SEQ ID NOs: 1 or 8 to 31 or any one or more of the variants in Table 3 and the second polynucleotide primer comprises at least 10 (e.g., at least 10, at least 15 or at least 20) contiguous nucleotides that are complementary to the reverse complement of any one of SEQ ID NOs: 1 or 8 to 31 or any one or more of the variants in Table 3. In some embodiments, the first and second primer are between 10-50, 10-40, 10-30, or 10-20 nucleotides in length. In some embodiments, the at least one nucleic acid molecule comprises a probe that comprises at least 10 contiguous nucleotides that are complementary to any one of SEQ ID NOs: 1 or 8 to 31 or any one or more of the variants in Table 3 or the reverse complement thereof. In some embodiments, the probe is between 10-50, 10-40, 10-30, or 10-20 nucleotides in length. Kits of the disclosure may optionally also comprise reagents and/or instructions for performing the detection as described herein.

In some aspects, the disclosure provides methods of modifying a nucleic acid molecule of the disclosure, e.g., in a cell or plant. In some embodiments, the modification is a deletion, an insertion (e.g., of a heterologous nucleic acid sequence), a substitution, a duplication, or inversion, or a combination thereof. In some embodiments, the modification comprises deletion of a portion or all of a selectable marker coding sequence present in the nucleic acid molecule, e.g., a PMI or EPSPS coding sequence. In some embodiments, the modification is introduced using a nuclease, such as a CRISPR-Cas nuclease, a Zinc finger nuclease, a meganuclease, a TAL effector nuclease (TALEN), or a combination thereof.

In some embodiments, the modification is made in a host cell or plant of the disclosure, e.g., a maize cell or maize plant, to produce a modified transgenic cell or modified transgenic plant. In some embodiments, the modification is made by expressing the nuclease in the host cell or plant (e.g., by transforming the host cell or plant with an expression cassette encoding the nuclease or by crossing the plant with another plant containing such an expression cassette). In some embodiments, the modification is made by directly introducing the nuclease into the host cell or plant, e.g., using reagents that transfer the nuclease into the host cell or plant such as through physical methods such as biolistics/particle bombardment, protoplast transfection, nanoparticle-mediated delivery, aerosol bean injection, or whisker-mediated delivery. In some embodiments, the method further comprises producing a plant from the modified transgenic host cell to produce a modified transgenic plant. In some embodiments, the method further comprises selfing or crossing the modified transgenic plant with another plant for at least one generation (e.g., one, two, three, four or more generations), thereby producing a modified transgenic progeny plant. In some embodiments, the disclose provides such a modified transgenic cell, modified transgenic plant, or modified transgenic progeny plant, e.g., produced by a method herein.

In certain embodiments, the nucleic acid modification is affected by a (modified) zinc-finger nuclease (ZFN) system. The ZFN system uses artificial restriction enzymes generated by fusing a zinc finger DNA-binding domain to a DNA-cleavage domain that can be engineered to target desired DNA sequences. Non-limiting examples of methods of using ZFNs can be found for example in U.S. Pat. Nos. 6,534,261; 6,607,882; 6,746,838; 6,794,136; 6,824,978; 6,866,997; 6,933,113; and 6,979,539.

In certain embodiments, the nucleic acid modification is affected by a meganuclease, which are endodeoxyribonucleases characterized by a large recognition site (double-stranded DNA sequences of 12 to 40 base pairs). Non-limiting examples of methods of using meganucleases can be found in U.S. Pat. Nos. 8,163,514; 8,133,697; 8,021,867; 8,119,361; 8,119,381; 8,124,369; and 8,129,134

In certain embodiments, the nucleic acid modification is affected by a CRISPR/Cas complex or system. In certain embodiments, the CRISPR/Cas system or complex is a class 2 CRISPR/Cas system. In certain embodiments, said CRISPR/Cas system or complex is a type II, type V, or type VI CRISPR/Cas system or complex. The CRISPR/Cas system does not require the generation of customized proteins to target specific sequences but rather a Cas nuclease can be programmed by an RNA guide (gRNA) to recognize a specific nucleic acid target, in other words the Cas nuclease can be recruited to a specific nucleic acid target locus of interest using said short RNA guide.

In general, the CRISPR/Cas or CRISPR system as used herein refers collectively to the elements involved in the expression of or directing the activity of CRISPR-associated ("Cas") nuclease, including sequences encoding a Cas gene and one or more of, a tracr (transactivating CRISPR) sequence (e.g. tracrRNA or an active partial tracrRNA), a tracr-mate sequence (encompassing a "direct repeat" and a tracrRNA-processed partial direct repeat in the context of an endogenous CRISPR system), a guide sequence (also referred to as a"spacer" in the context of an endogenous CRISPR system), or "RNA(s)" as that term is herein used (e.g., RNA (s) to guide Cas, such as Cas9, e.g. CRISPR RNA and, where applicable, transactivating (tracr) RNA or a single guide RNA (sgRNA) (chimeric RNA)) or other sequences and transcripts from a CRISPR locus. In general, a CRISPR system is characterized by elements that promote the formation of a CRISPR complex at the site of a target sequence (also referred to as a protospacer in the context of an endogenous CRISPR system). In the context of formation of a CRISPR complex, "target sequence" refers to a sequence to which a guide sequence is designed to have complementarity, where hybridization between a target sequence and a guide sequence promotes the formation of a CRISPR complex.

In certain embodiments, the gRNA is a chimeric guide RNA or single guide RNA (sgRNA). In certain embodiments, the gRNA comprises a guide sequence and a tracr mate sequence (or direct repeat). In certain embodiments, the gRNA comprises a guide sequence, a tracr mate sequence (or direct repeat), and a tracr sequence. In certain embodiments, the CRISPR/Cas system or complex as described herein does not comprise and/or does not rely on the presence of a tracr sequence (e.g. if the Cas nuclease is Cas12a).

The CRISPR-Cas nuclease can be any such nuclease known in the art, such as a Cas9, Cas12a, Cas12b, Cas12i, Cas13a (formerly referred to as C2c2), C2c3, Cas13b or a modified version of any of the foregoing. CRISPR-Cas nucleases are well known in the art (see, e.g., Dong et al. Efficient Targeted Mutagenesis Mediated by CRISPR-Cas12a Ribonucleoprotein Complexes in Maize. Front. Genome Ed. (2021), vol. 3, article 670529; Wei et al. TALEN or Cas9—Rapid, Efficient and Specific Choices for Genome Modifications. J. of Genetics and Genomics (2013), vol. 40, pp. 281-289; Sedeek et al. Plant Genome Engineering for Targeted Improvement of Crop Traits. Frontiers in Plant Science (2019), vol. 10, article 114; and Zhang et al. Applications and potential of genome editing in crop improvement. Genome Biology (2018), vol. 19, article 210).

EXAMPLES

Example 1: Constructs Synthesized

Binary vector constructs were constructed containing differing combinations of transcriptional enhancers, promoters, transit peptides, and terminators, and variants of these genetic elements, driving expression of variants of eCry1Gb.1Ig. These genetic elements were synthesized and ligated into each binary vector through a restriction enzyme based cloning method. All promoters used were medium or strong constitutive promoters or viral promoters. Versions of eCry1Gb.1Ig genes were created with differing codon preferences to test desired expression level and efficacy. Table 1 shows the constructs created and lists the genetic elements with each coding sequence (CDS). Table 2 describes each of the genetic elements named in Table 1.

TABLE 1

Composition of Binary Constructs

| Construct ID | Cassette position | Promoter | Transit Peptide | CDS | Terminator |
|---|---|---|---|---|---|
| 24795 | 1 | prSoUbi4-02 | | eCry1Gb.1Ig-03 | tZmUbi361-05 |
| | 2 | prUbi1-43 | | cPMI-15 | tUbi1-04 |
| 23698 | 1 | prUbi1-18 | | eCry1Gb.1Ig-01 | tZmUbi361-01 |
| | 2 | prUbi1-18 | | cPMI-01 | tUbi1-04 |
| 24530 | 1 | prScBv-05 | | eCry1Gb.1Ig-02 | tNOS-05-01 |
| | 2 | prUbi1-18 | | cPMI-01 | tUbi1-04 |
| 24534 | 1 | pr35S-12 | | eCry1Gb.1Ig-02 | tNOS-05-01 |
| | 2 | prUbi1-43 | | cPMI-15 | tUbi1-04 |
| 25628 | 1 | prSoUbi4-02 | xOTPSSUct-02 | eCry1Gb.1Ig-03 | tZmUbi361-05 |
| | 2 | prUbi1-43 | | cPMI-15 | tUbi1-04 |

TABLE 2

Description of Genetic Elements

| Element | Name | Description with relevant references |
|---|---|---|
| promoter | SoUbi4-02 | Constitutive *Saccharum officinarum* Ubiquitin 4 promoter containing the first intron (NCBI accession number AF093504.1). |
| promoter | ScBv-05 | Modified promoter from sugarcane Bacilliform IM Badnavirus isolate Ireng Maleng (ScBVIM) (Davies et. al. 2014). |
| promoter | Ubi1-18 | Promoter region from *Zea mays* polyubiquitin gene which contains the first intron (NCBI accession number S94464.1). Provides constitutive expression in monocots (Christensen et al. 1992). |
| promoter | Ubi1-43 | Promoter region from *Zea mays* polyubiquitin gene containing the first intron (NCBI accession number S94464.1). Provides constitutive expression in monocots (Christensen et al. 1992). |
| promoter | 35S-12 | Modified promoter from cauliflower mosaic virus (Odell et al. 1985, Nature 313: 810-812). |
| transit peptide | xOTPSSUct-02 | Optimized chimeric sunflower and maize rubisco small subunit transit peptide similar to pDPG434 (U.S. Pat. No. 6,040,497). |
| coding sequence | eCry1Gb.1Ig-01 | Codon-optimized gene encoding the engineered protein eCry1Gb.1Ig, which is a chimera of Cry1Gb and Cry1Ig. Both Cry1Gb and Cry1Ig proteins are derived from sequenced genomes of the soil bacterium *Bacillus thuringiensis* and are active against several lepidopteran pest species. The eCry1Gb.1Ig protein was engineered to have improved insecticidal activity against fall armyworm (*Spodoptera frugiperda*) (see, e.g., International Patent Publication Number |

TABLE 2-continued

Description of Genetic Elements

| Element | Name | Description with relevant references |
|---|---|---|
| | | WO2018111553). The eCry1Gb.1Ig protein also has activity against other pest species including, e.g., oriental armyworm (*Mythimna separata*), common cutworm/oriental leafworm (*Spodoptera litura*), and Asian corn borer (*Ostrinia furnacalis*) (see, e.g., International Patent Application Number PCT/CN2021/073190). |
| coding sequence | eCry1Gb.1Ig-02 | Codon-optimized gene encoding the engineered protein eCry1Gb.1Ig, which is a chimera of Cry1Gb and Cry1Ig. This version encodes the same protein but differs from eCry1Gb.1Ig-01 by four base pairs to remove unintended open reading frames. |
| coding sequence | eCry1Gb.1Ig-03 | Sequence encoding the engineered protein eCry1Gb.1Ig, which is a chimera of Cry1Gb and Cry1Ig. Silent mutations were introduced to optimize codon usage. |
| coding sequence | PMI-01 | *Escherichia coli* gene pmi encoding the enzyme phosphomannose isomerase (PMI) (NCBI accession number M15380.1); this gene is also known as manA. Catalyzes the isomerization of mannose-6-phosphate to fructose-6-phosphate (Negrotto et al. 2000). |
| coding sequence | PMI-15 | *Escherichia coli* gene pmi encoding the enzyme phosphomannose isomerase (PMI) (NCBI accession umber M15380.1); this gene is also known as manA. Catalyzes the isomerization of mannose-6-phosphate to fructose-6-phosphate (Negrotto et al. 2000). Silent mutations were introduced as compared to PMI-01. |
| terminator | ZmUbi361-01 | Terminator derived from the maize Ubiquitin gene (Nuccio 2018). |
| terminator | ZmUbi361-05 | Terminator derived from the maize Ubiquitin gene (Nuccio 2018) with mutations to removed unintended open reading frames compared to ZmUbi361-01 terminator. |
| terminator | NOS-05-01 | Terminator sequence from the nopaline synthase (NOS) gene of *A. tumefaciens* (NCBI accession number V00087.1). Provides a polyadenylation site (Bevan et al. 1983). |
| terminator | Ubi1-04 | Terminator from the ubiquitin 1 gene from *Z. mays*. One bp mutation to remove an internal restriction site compared to Ubi1-01 terminator. |

Example 2: *Agrobacterium*-Mediated Transformation with Phosphomannose Isomerase (PMI) Selection Each of the binary vector constructs was used to create maize transgenic events. Transformation of *Zea mays* to produce genetically modified maize was accomplished using immature embryos via *Agrobacterium tumefaciens*-mediated transformation, as described in Zhong et al. (2018) (Advances in *Agrobacterium*-mediated Maize Transformation. In: Lagrimini L. (eds) Maize. Methods in Molecular Biology, vol 1676. Humana Press, New York, NY). *A. tumefaciens* strain LBA4404 (recA−) harboring disarmed pTi plasmid pAL4404 and helper plasmid pVGW7 was used for maize transformation. Detailed information about the pAL4404 and pVGW7 plasmids is described by Hoekema et al. (Nature. (1983) 303:179-189), Ishida et al. (Nat Biotechnol (1996) 14:745-750) and Imayama et al. (U.S. Ser. No. 10/266,835). *A. tumefaciens* strain LBA4404 (recA$^-$) containing individual binary vectors was prepared as described by Li et al. (Plant Physiol (2003) 133:736-47). For maize transformation, immature embryos from greenhouse grown maize inbred line NP2222 were harvested approximately 9 days after pollination and used as explants (Zhong et al., 2018). Immature embryo isolation, *Agrobacterium* inoculation and co-cultivation of *Agrobacterium* with the immature embryos were performed as described in Zhong et al. (2018) using the bulk extraction method described therein. Using this method, genetic elements within the left and right border regions of the transformation plasmid were efficiently transferred and integrated into the genome of the plant cell, while genetic elements outside these border regions were not transferred.

Transformed tissues and putative transgenic events were regenerated and rooted as described earlier (Zhong et al., 2018) using media with mannose selection for events containing a phosphomannose isomerase (PMI) selectable marker (Negrotto et al., (2000) *Plant Cell Rep.* 19:789-803.) or using 2 mM N-(Phosphonomethyl)-Glycine (TouchDown®) herbicide as the selection agent for events containing a modified version of a 5-enol pyruvylshikimate-3-phosphate synthase (EPSPS) enzyme.

Regenerated plantlets were tested for the presence of the target genes and plant selectable marker gene (PMI or EPSPS) by real-time TAQMAN® PCR analysis developed by Ingham et al. (Biotechniques 31(1):132-4, 136-40, 2001). Plants positive for target genes and selectable marker, also referred to as events, were transferred to the greenhouse for further propagation. In one plant transformed with binary vector 24795 (SEQ ID NO: 2), the expression cassette (SEQ ID NO:1) was found to contain a silent mutation in the coding sequence of cPMI-15 (SEQ ID NO: 7), creating a slightly modified expression cassette sequence in the plant (SEQ ID NO: 8). Upon further sequencing, additional mutations were found as shown in Table 3 (see also SEQ ID NOs: 9-31). The plants from which the sequencing results were obtained did not appear to have any significant negative impact on efficacy relative to the pool of other plants containing SEQ ID NO: 1.

TABLE 3

Additional variants identified by sequencing

| Position in SEQ ID NO 1 | Reference | Variant | Reference Sequence | Variant sequence |
|---|---|---|---|---|
| 324 | TC | T | CTCCCTCCTCCCCCGTTA (SEQ ID NO: 32) | CTCCCTCCTCCCCGTTA (SEQ ID NO: 33) |
| 711 | G | T | TGATTCTGCGGGTTGGC (SEQ ID NO: 34) | TGATTCTGCTGGTTGGC (SEQ ID NO: 35) |
| 7271 | A | AC | TAATAAATAGACACCCCC TCCACACCCTCTT (SEQ ID NO: 36) | TAATAAATAGACACCCCCCT CCACACCCTCTT (SEQ ID NO: 37) |
| 7387 | T | TC | CTCGTCCTCCCCCCCCCC CCCTC (SEQ ID NO: 38) | CTCGTCCTCCCCCCCCCCCC CTC (SEQ ID NO: 39) |
| 7989 | A | AT | CGGTCGTTCATTCGTTCT A (SEQ ID NO: 40) | CGGTCGTTCATTTCGTTCTA (SEQ ID NO: 41) |
| 6015 | C | CT | AGACTAGTGGCTTGCTTT TTCGTATGTCT (SEQ ID NO: 42) | AGACTAGTGGCTTGCTTTTT TCGTATGTCT (SEQ ID NO: 43) |
| 6470 | AT | A | AAAAAATTACCACATATT TTTTTGTCACA (SEQ ID NO: 44) | AAAAAATTACCACATATTTTT TTGTCACA (SEQ ID NO: 45) |
| 6683 | CT | C | TAGTGTGCATGTGTTCTC CTTTTTTTTTGCAAA (SEQ ID NO: 46) | TAGTGTGCATGTGTTCTCCT TTTTTTTGCAAA (SEQ ID NO: 47) |
| 7387 | T | TC | GTACGCCGCTCGTCCTCC CCCCCCCCCCCTCT (SEQ ID NO: 48) | GTACGCCGCTCGTCCTCCCC CCCCCCCCCCTCT (SEQ ID NO: 49) |
| 8397 | C | CA | GATCTCCGATCATGCAAA AACTCATTAACTCAGT (SEQ ID NO: 50) | GATCTCCGATCATGCAAAAA ACTCATTAACTCAGT (SEQ ID NO: 51) |
| 5944 | CT | C | CTTATGCAGAACCTTTTT TTTTG (SEQ ID NO: 52) | CTTATGCAGAACCTTTTTTTT G (SEQ ID NO: 53) |
| 6015 | CT | C | GGAGACTAGTGGCTTGC TTTTTCGTATGTCT (SEQ ID NO: 54) | GGAGACTAGTGGCTTGCTTT TCGTATGTCT (SEQ ID NO: 55) |
| 7387 | T | TC | ACGCCGCTCGTCCTCCCC CCCCCCCCCTCT (SEQ ID NO: 56) | ACGCCGCTCGTCCTCCCCCC CCCCCCCCTCT (SEQ ID NO: 57) |
| 7576 | TG | T | GCCAGTGTTTCTCTTTGG GGAATCCTGGGAT (SEQ ID NO: 58) | GCCAGTGTTTCTCTTTGGGA ATCCTGGGAT (SEQ ID NO: 59) |
| 10055 | G | GT | ACTAACAATTAGTTTCAG TGCATTCAAACA (SEQ ID NO: 60) | ACTAACAATTAGTTTCAGT GCATTCAAACA (SEQ ID NO: 61) |
| 347 | TC | T | TTATAAATTGGCTTCATC CCCTCCTTGCCTCAT (SEQ ID NO: 62) | TTATAAATTGGCTTCATCCCT CCTTGCCTCAT (SEQ ID NO: 63) |
| 1579 | A | AT | CATATATCATGTATTTTTT TTTGG (SEQ ID NO: 64) | CATATATCATGTATTTTTTTT TTGG (SEQ ID NO: 65) |
| 7387 | T | TC | TACGCCGCTCGTCCTCCC CCCCCCCCCCT (SEQ ID NO: 66) | TACGCCGCTCGTCCTCCCCC CCCCCCCCCT (SEQ ID NO: 67) |
| 7720 | CT | C | CATCTTTTCATGCTTTTTT TTGTCTTGGTTGTGATG (SEQ ID NO: 68) | CATCTTTTCATGCTTTTTTTG TCTTGGTTGTGATG (SEQ ID NO: 69) |

TABLE 3-continued

| Additional variants identified by sequencing | | | | |
|---|---|---|---|---|
| Position in SEQ ID NO 1 | Reference | Variant | Reference Sequence | Variant sequence |
| 8656 | A | G | CCTGTTCAAAGTATTATG CGCAGCACAGCCA (SEQ ID NO: 70) | CCTGTTCAAAGTATTGTGCG CAGCACAGCCA (SEQ ID NO: 71) |
| 8870 | GC | G | GTCTCCCTACTCCAGCCG GTCGCAGGTGCAC (SEQ ID NO: 72) | GTCTCCCTACTCCAGCGGTC GCAGGTGCAC (SEQ ID NO: 73) |
| 9064 | AC | A | AATTTCTGAATTTTACCC GGAAGACAGCGG (SEQ ID NO: 74) | AATTTCTGAATTTTACCGGA AGACAGCGG (SEQ ID NO: 75) |

Example 3: Quantitative ELISA for Detection of Trait Proteins

Detection of the different trait proteins used two monoclonal antibodies produced against each protein. Samples were taken from the leaves of transgenic events and extracted in phosphate buffered saline pH 7.3 (PBS) containing 0.05% Tween-20 (PBST). Total soluble protein (TSP) of the extract was measured using the Pierce BCA Protein Assay (Thermo Scientific, Rockford, IL). High-binding polystyrene plates (Nunc Maxisorp #430341) were coated at 4° C. overnight with 1 sg/ml of the specific monoclonal antibody (MAb) in 25 mM borate, 75 mM NaCl, pH 8.5. Plates were washed five times with PBST. Samples or standards in ELISA diluent (PBST containing 1% bovine serum albumin) were added to the plate (100 μl/well), incubated for 1 hr at room temperature (RT) with shaking, and washed five times. HRP-labeled secondary MAb (100 μl/well) diluted 1/10,000 in ELISA diluent was then added to the plate, incubated for 1 hr at ambient temperature with shaking, and washed as before. Substrate Tetramethylbenzidine (SurModics, Eden Prairie, MN) was added (100 μl/well) and allowed to develop for 15-30 min at room temperature with shaking. The reaction was stopped using 1 N HCl (100 μl/well). The absorbance was measured at 450 nm using a microplate reader (BioTek Powerwave XS2, Winooski, VT). The standard curve used a four-parameter curve fit to plot the concentrations versus the absorbance. To normalize for extraction efficiency, the concentration of each analyte was divided by the concentration of the total soluble protein (TSP).

TABLE 4

| Summary of ELISA expression data | | | |
|---|---|---|---|
| Construct ID | # of events | ng eCry1Gb.1Ig/mg TSP (average) | ng eCry1Gb.1Ig/mg TSP (range) |
| 24795 | 257 | 23 | 1-121 |
| 23698 | 43 | 57 | 30-125 |
| 24530 | 13 | 0.4 | 0.1-0.8 |
| 24534 | 29 | 0.9 | 0.3-2.3 |
| 25628 | 16 | 0 | NA |

Constructs 24530, 24534 and 25628 surprisingly only produced events with very low or no expression of the trait protein, even though the trait protein sequence was paired with a promoter that was expected to be a medium or strong promoter.

Example 4: Greenhouse Efficacy Testing 279 transgenic corn events from construct 24795 were confirmed to have single copy tDNA insertion and expression of trait protein via ELISA analysis as described in Example 3.

From this population, 45 transgenic corn events from construct 24795 as well transgenic corn events from the other constructs mentioned in Table 4 were selected for bioassay testing. The events selected represented a range of eCry1Gb.1Ig expression, comprising a mixture of low, medium, and high expressors. The bioassay sampling consisted of a detached leaf bioassay, where a portion of the leaf was excised from the plant, placed into a petri dish with a sterile water moistened filter pad, and infested with approximately 10 fall armyworm (*Spodoptera frugiperda*) neonate larvae. The assays were incubated at ambient laboratory temperature and scored 5 days after infestation. Each sample was scored for percentage of leaf protection (scale 1-5) and insect mortality (scale 1-3). Events which received a percentage of leaf protection rating of 1 or 2 (i.e., less than 5% damage to the excised leaf disk) and achieved 100% mortality of the neonate larvae were considered efficacious and used as a benchmark for the construct's performance. The bioassay data for the 45 events tested was extrapolated to those events whose trait gene expression was similar, resulting in a total of 65 24795 events meeting the efficacy and expression criteria and progressing for further characterization. Events from constructs 23698, 24530, 24534, and 25628 did not meet the efficacy and expression criteria; those constructs were not selected for further progression.

Example 5: Field Efficacy Trials 24 transgenic corn events from construct 24795 were tested in field cycles in Argentina. Events were planted in one plot rows with 3 replications each. Ratings for foliar fall armyworm (*Spodoptera frugiperda*) were assessed from eight plants for each row. The foliar leaf damage was evaluated using the Davis Scale of 0-9, (Davis, F. M. & Williams, W. P. 1992. Visual rating scales for screening whorl-stage corn for resistance to fall armyworm. Mississippi Agricultural & Forestry Experiment Station, Technical Bulletin 186, Mississippi State University, MS39762, USA.). 14 of 24 events from the above construct had acceptable efficacy against fall armyworm.

What is claimed is:

1. A recombinant nucleic acid molecule comprising a nucleic acid sequence that is at least 99% identical to SEQ ID NO: 1, wherein the nucleic acid sequence encodes a polypeptide comprising the sequence of SEQ ID NO: 4.

2. A transgenic host cell comprising the nucleic acid molecule of claim 1.

3. The transgenic host cell of claim 2, wherein the cell is a bacterial cell or a plant cell.

4. The transgenic host cell of claim 3, wherein the cell is a bacterial cell and the bacterial cell is an *Escherichia coli, Bacillus thuringiensis, Bacillus subtilis, Bacillus megaterium, Bacillus cereus, Agrobacterium* spp. or *Pseudomonas* spp. cell.

5. The transgenic host cell of claim 3, wherein the cell is a plant cell and the plant cell is a maize, sorghum, wheat, sunflower, tomato, crucifers, oat, turf grass, pasture grass, peppers, potato, cotton, rice, soybean, sugarcane, sugar beet, tobacco, barley, or oilseed rape cell.

6. The transgenic host cell of claim 5, wherein the plant cell is a maize cell.

7. A transgenic plant or plant part comprising the nucleic acid molecule of claim 1.

8. The transgenic plant of claim 7, wherein the plant is a monocot plant.

9. The transgenic plant of claim 7, wherein the plant is a dicot plant.

10. The transgenic plant or plant part of claim 7, wherein:

a) the plant is selected from the group consisting of maize, sorghum, wheat, sunflower, tomato, crucifers, oat, turf grass, pasture grass, peppers, potato, cotton, rice, soybean, sugarcane, sugar beet, tobacco, barley, and oilseed rape, or b) the plant part is a seed.

11. A progeny or propagule of any generation of the plant of claim 7, wherein the progeny or propagule comprises the nucleic acid molecule.

12. A method of producing a transgenic plant with enhanced insecticidal properties, comprising introducing the nucleic acid molecule of claim 1 into a plant thereby producing a transgenic plant, wherein the nucleic acid molecule expresses effective insect-controlling amounts of protein.

13. A method of producing a transgenic plant with enhanced insecticidal properties, comprising the steps of:

a) providing the nucleic acid molecule of claim 1;

b) introducing into a plant, tissue culture, or a plant cell the nucleic acid molecule of step (a) to obtain a transformed plant, transformed tissue culture, or a transformed cell having enhanced insecticidal properties; and c) growing the transformed plant or regenerating a transformed plant from the transformed tissue culture or transformed plant cell, so a transgenic plant with enhanced insecticidal properties is produced.

14. A method of producing transgenic seed, comprising the steps of:

a) obtaining a fertile transgenic plant of claim 11; and b) growing the plant under appropriate conditions to produce the transgenic seed.

15. A method of producing progeny of any generation of a fertile transgenic plant with enhanced insecticidal properties, comprising the steps of:

a) obtaining a fertile transgenic plant with enhanced insecticidal properties comprising the nucleic acid molecule of claim 1;

b) collecting transgenic seed from the transgenic plant;

c) planting the collected transgenic seed; and d) growing the progeny transgenic plants from the seed, wherein the progeny has enhanced insecticidal properties relative to a non- transformed plant.

16. A method for producing a transgenic plant with enhanced insecticidal properties, comprising the steps of sexually crossing a first parent plant with a second parent plant, wherein the first or second parent plant is the plant of claim 7, to produce a first generation progeny plant that comprises the nucleic acid molecule.

17. A method for producing a transgenic plant with enhanced insecticidal properties, comprising the steps of:

a) sexually crossing a first parent plant with a second parent plant, wherein the first or second parent plant is the plant of claim 7; and b) selecting a first generation progeny plant with enhanced insecticidal properties, wherein the selected progeny plant comprises the nucleic acid molecule.

18. The method of claim 17, further comprising the steps of:

a) selfing the first generation progeny plant, thereby producing a plurality of second generation progeny plants; and b) selecting from the second generation progeny plants one or more plants with enhanced insecticidal properties, wherein the selected second generation progeny plants comprise the nucleic acid molecule.

19. A method of controlling a lepidopteran pest comprising feeding the pest a plant or plant part comprising the nucleic acid molecule of claim 1.

20. The method of claim 19, wherein the lepidopteran pest is a *Spodoptera frugiperda* (fall armyworm) pest.

21. A method of producing a commodity plant product, the method comprising using the plant of claim 7 to produce said commodity plant product therefrom.

22. The method of claim 21, wherein the commodity plant product is a grain, starch, seed oil, syrup, flour, meal, starch, cereal, or protein.

23. A method comprising introducing a modification into the nucleic acid molecule present in a transgenic host cell of any one of claims 6 to 10 or a transgenic plant of claim 7, thereby producing a modified transgenic host cell or a modified transgenic plant, wherein said modified transgenic host cell or said modified transgenic plant has insecticidal activity against a lepidopteran pest.

24. The method of claim 23, wherein the modification is a deletion, an insertion, a substitution, a duplication, or inversion or a combination thereof.

25. The method of claim 24, wherein the modification comprises deletion of a portion or all of a selectable marker coding sequence present in the nucleic acid molecule.

26. The method of claim 23, wherein the modification is introduced using a nuclease or homologous recombination, or a combination thereof.

27. The method of claim 26, wherein the nuclease is a CRISPR-Cas nuclease.

28. The method of claim 23, wherein the method further comprises producing a plant from the modified transgenic host cell and selfing or crossing the plant with another plant, thereby producing a modified transgenic progeny plant.

29. The method of claim 23, wherein the method further comprises selfing or crossing the modified transgenic plant with another plant, thereby producing a modified transgenic progeny plant.

30. The method of claim 28, wherein the method further comprises selfing or outcrossing the modified transgenic progeny plant for at least one additional generation.

* * * * *